United States Patent
Emmitte et al.

(10) Patent No.: US 9,550,778 B2
(45) Date of Patent: Jan. 24, 2017

(54) SUBSTITUTED 6-ARYL-IMIDAZOPYRIDINE AND 6-ARYL-TRIAZOLOPYRIDINE CARBOXAMIDE ANALOGS AS NEGATIVE ALLOSTERIC MODULATORS OF MGLUR5

(71) Applicant: Vanderbilt University, Nashville, TN (US)

(72) Inventors: Kyle A. Emmitte, Aledo, TX (US); Craig W. Lindsley, Brentwood, TN (US); P. Jeffrey Conn, Nashville, TN (US); Andrew S. Felts, Brentwood, TN (US); Katrina A. Smith, Murfreesboro, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/873,869

(22) Filed: Oct. 2, 2015

(65) Prior Publication Data
US 2016/0096833 A1  Apr. 7, 2016

Related U.S. Application Data

(60) Provisional application No. 62/059,813, filed on Oct. 3, 2014.

(51) Int. Cl.
C07D 471/04 (2006.01)

(52) U.S. Cl.
CPC .................... C07D 471/04 (2013.01)

(58) Field of Classification Search
USPC .................... 514/217.07, 218, 303
See application file for complete search history.

(56) References Cited

U.S. PATENT DOCUMENTS

| | | | |
|---|---|---|---|
| 6,638,953 B2 | 10/2003 | Gaster et al. | |
| 6,846,827 B1 | 1/2005 | Cumming | |
| 7,414,060 B2 | 8/2008 | Jaeschke et al. | |
| 8,501,757 B2 | 8/2013 | Conn et al. | |
| 8,569,308 B2 | 10/2013 | Conn et al. | |
| 8,598,345 B2 | 12/2013 | Conn et al. | |
| 8,796,295 B2 | 8/2014 | Conn et al. | |
| 9,085,562 B2 | 7/2015 | Conn et al. | |
| 2003/0134843 A1* | 7/2003 | Lubisch | C07D 471/04 514/217.07 |
| 2006/0199828 A1 | 9/2006 | Jaeschke et al. | |
| 2006/0199858 A1 | 9/2006 | Durst et al. | |
| 2006/0235035 A1 | 10/2006 | Hogberg et al. | |
| 2006/0235069 A1 | 10/2006 | Duggan et al. | |
| 2007/0149547 A1 | 6/2007 | Bonnefous et al. | |
| 2007/0293457 A1 | 12/2007 | Baker et al. | |
| 2009/0042855 A1 | 2/2009 | Conn et al. | |
| 2009/0047296 A1 | 2/2009 | Doronina et al. | |
| 2009/0124625 A1 | 5/2009 | Bessis et al. | |
| 2009/0197883 A1 | 8/2009 | Armstrong et al. | |
| 2010/0179121 A1 | 7/2010 | Chen et al. | |
| 2010/0227887 A1 | 9/2010 | Jaeschke et al. | |
| 2010/0317643 A1 | 12/2010 | Goodacre et al. | |
| 2011/0152299 A1 | 6/2011 | Conn et al. | |
| 2011/0166158 A1 | 7/2011 | Conn et al. | |
| 2011/0172247 A1 | 7/2011 | Conn et al. | |
| 2011/0172248 A1 | 7/2011 | Conn et al. | |
| 2012/0129812 A1 | 5/2012 | Kawata et al. | |
| 2012/0178742 A1 | 7/2012 | Henrich et al. | |

FOREIGN PATENT DOCUMENTS

| | | |
|---|---|---|
| EP | 2447630 A2 | 5/2012 |
| EP | 2477629 A1 | 7/2012 |
| FR | 1472619 A | 3/1967 |
| JP | 2007-524682 A | 8/2007 |
| JP | 5792173 B2 | 10/2015 |
| WO | WO-03/059258 A2 | 7/2003 |
| WO | WO-2004/037789 A2 | 5/2004 |
| WO | WO-2005/004863 A1 | 1/2005 |
| WO | WO-2005/079802 A1 | 9/2005 |
| WO | WO-2006/091639 A2 | 8/2006 |
| WO | WO-2006/094691 A1 | 9/2006 |
| WO | WO-2006/115895 A2 | 11/2006 |
| WO | WO-2008/092072 A2 | 7/2008 |
| WO | WO-2009/010454 A2 | 1/2009 |
| WO | WO-2009/047296 A2 | 4/2009 |
| WO | WO-2009/135758 A1 | 11/2009 |
| WO | WO-2010/142752 A1 | 12/2010 |
| WO | WO-2011/035186 A1 | 3/2011 |
| WO | WO-2011/035209 A1 | 3/2011 |
| WO | WO-2011/035214 A1 | 3/2011 |

OTHER PUBLICATIONS

U.S. Appl. No. 62/059,813, filed Oct. 3, 2014, Kyle A. Emmitte.
Adams et al. (2010) *Br. J. Pharmacol.* 159: 534.
Amato et al. (2013) *ACS Chem. Neurosci.* 4: 1217.
Awad et al. (2000) "Activation of Metabotropic Glutamate Recept 5 Has Direct Excitatory Effects and Potentiates NMDA Receptor Currents in Neurons of the Subthalamic Nucleus." *J. Neurosci.* 20: 7871-7879.
Besheer et al. (2009) *J. Neurosci.* 29: 9582.
Busse et al. (2004) *Neuropsychopharmacology* 29: 1971.
Chiamulera et al. (2001) "Reinforcing and locomotor stimulant effects of cocaine are absent in mGluR5 null mutant mice." *Nature Neurosci.* 4: 873-874.
Cosford et al. (2003) *Bioorg. Med. Chem. Lett.* 13: 351.
De Vrij et al. (2008) "Rescue of behavioral phenotype and neuronal protrusion morphology." *Neurobiol. Dis.* 31: 127-132.
Frisby et al. (2005) *Gastroenterology* 129: 995.

(Continued)

*Primary Examiner* — Pancham Bakshi
(74) *Attorney, Agent, or Firm* — Ballard Spahr LLP

(57) ABSTRACT

Disclosed are negative allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

14 Claims, No Drawings

(56) References Cited

OTHER PUBLICATIONS

Gass et al. (2009) "mGluR5 antagonism attenuates methamphetamine reinforcement and prevents reinstatement of methamphetamine-seeking behavior in rats." *Neuropsychopharmacology* 34: 820-833.
Hamilton et al. (2014) "Metabotropic glutamate receptor 5 knockout reduces cognitive impairment and pathogenesis in a mouse model of Alzheimer's disease." *Molecular Brain* 7: 40.
Hughes et al. (2013) "Negative allosteric modulation of metabotropic glutamate receptor 5 results in broad spectrum activity relevant to treatment resistant depression." *Neuropharmacology* 66: 202-214.
Jensen et al. (2005) "Transient lower esophageal sphincter relaxations in dogs are inhibited by a metabotropic glutamate receptor 5 antagonist." *Eur. J. Pharmacol.* 519: 154-157.
Klodzinska et al. (2004) "Anxiolytic-like effects of MTEP, a potent and selective mGlu5 receptor agonist does not involve GABA(A) signaling." *Neuropharmacology* 47: 342.
Kotlinska and Bochenski (2007) "Comparison of the effects of mGluR1 and mGluR5 antagonists on the expression of behavioral sensitization to the locomotor effect of morphine and the morphine withdrawal jumping in mice." *Eur. J. Pharmacol.* 558: 113-118.
Kumaresan et al. (2009) "Metabotropic glutamate receptor 5 (mGluR5) antagonists attenuate cocaine priming- and cue-induced reinstatement of cocaine seeking." *Behav. Brain Res.* 202: 238-244.
Lindsley et al. (2011) "(3-Cyano-5-fluorophenyl)biaryl negative allosteric modulators of mGlu(5): Discovery of a new tool compound with activity in the OSS mouse model of addiction." *ACS Chem. Neurosci.* 2: 471.
Lominac et al. (2006) "Behavioral and neurpchemical interactions between Group 1 mGluR antagonists and ethanol: Potential insight into their anti-addictive properties." *Drug Alcohol Depend.* 85: 142-156.
Mannaioni et al. (2001) "Metabotropic Glutamate Receptors 1 and 5 Differentially Regulate CA1 Pyramidal Cell Function." *J. Neurosci.* 21: 5925-5934.
Martin-Fardon et al. (2009) "Dissociation of the effects of MTEP [3-[(2-methyl-1,3-thiazol-4-yl)ethynyl]piperidine] on conditioned reinstatement and reinforcement: comparison between cocaine and a conventional reinforce." *J. Pharmacol. Exp. Ther.* 329: 1084.
Michalon et al. (2012) "Chronic Pharmacological mGlu5 Inhibition Corrects Fragile X in Adult Mice." *Neuron* 74: 49-56.
Morin et al. (2010) "Effect of the metabotropic glutamate receptor type 5 antagonists MPEP and MTEP in parkinsonian monkeys." *Neuropharmacology* 58: 981-986.
Nicolas et al. (2006) "A combined marble burying-locomotor activity test in mice: A practical screening test with sensitivity to different classes of anxiolytics and antidepressants." *Eur. J. Pharmacol.* 547: 106-115.
Niswender et al. (2008) "A Novel Assay of $G_{i/o}$-Linked G Protein-Coupled Receptor Coupling to Potassium Channels Provides New Insights into the Pharmacology of the Group III Metabotropic Glutamate Receptors." *Mol. Pharmacol.* 73: 1213-1224.
Ossowska et al. (2001) "Blockade of the metabotropic glutamate receptor subtype 5 (mGluR5) produces antiparkinsonian-like effects in rats." *Neurophmaracol.* 41: 413-420.
Pietraszek et al. (2005) "Anxiolytic-like effects of mGlu1 and mGlu5 receptor antagonists in rats." *Eur. J. Pharmacol.* 514: 25.
Rodriguez et al. (2005) "A Close Structural Analog of 2-Methyl-6-(phenylethynyl)-pyridine Acts as a Neutral Allosteric Site Ligand on Metabotropic Glutamate Receptor Subtype 5 and Blocks the Effects of Multiple Allosteric Modulators." *Mol. Pharmacol.* 68: 1793-1802.
Romano et al. (1996) "Metabotropic Glutamate Receptor 5 is a Disulfide-linked Dimer" *J. Biol. Chem.* 271: 28612-28616.
Salt and Binns (2001) "Contributions of mGlu1 and mGlu5 Receptors to Interactions with N-Methyl-D-Aspartate Receptor-Mediated Responses and Nociceptive Sensory Responses of Rat Thalamic Neurons." *Neurosci.* 100: 375-380.

Silverman et al. (2010) "Repetitive Self-Grooming Behavior in the BTBR Mouse Model of Autism is Blocked by the mGluR5 Antagonist MPEP." *Neuropsychopharmacology* 35: 976-989.
Silverman et al. (2012) "Negative Allosteric Modulation of the mGluR5 Receptor Reduces Repetitive Behaviors and Rescues Social Deficits in Mouse Models of Autism." *Sci. Transl. Med.* 4: 131ra51.
Spooren et al. (2000) "Anxiolytic-Like Effects of the Prototypical Metabotropic Glutamate Receptor 5 Antagonist 2-Methyl-6-(phenylethynylpyridine in Rodents." *J. Pharmacol. Exp. Therapeut.* 295: 1267-1275.
Tatarczynska et al. (2001) "Potential anxiolytic- and antidepressant-like effects of MPEP, a potent, selective and systemically active mGlu5 receptor antagonist." *Br. J. Pharmacol.* 132: 1423-1430.
Tronci et al. (2010) "The effects of the mGluR5 receptor antagonist 6-methyl-2-(phenylethynyl)-pyridine (MPEP) on behavioral responses to nicotine." *Psychopharmacology* 211: 33-42.
Vrig et al. (2008) "Rescue of behavioral phenotype and neuronal protrusion morphology in Fmr1 KO mice." *Neurobiol. Disease* 31(1): 127-132.
Yan et al. (2005) "Suppression of two major Fragile X Syndrome mouse model phenotypes by the mGluR5 antagonist MPEP." *Neuropharmacol.* 49(7): 1053-1066.
Abdel-Magid et al. (1996) Reductive Amination of Aldehydes and Ketones with Sodium Triacetoxyborohydride. Studies on Direct and Indirect Reductive Amination Procedures(1). J. Org. Chem. 61: 3849-3862.
Almarasson O, et al. (2004) Crystal engineering of the composition of pharmaceutical phases. Do Pharmaceutical co-crystals represent a new path to improved medicines? The Royal Society of Chemistry, 1889-1896.
Bloch, R. (1998) Additions of Organometallic Reagents to C=N Bonds: Reactivity and Selectivity. Chem. Rev. 98: 1407-1438.
Bonnefous C, et al. (2005) Dipyridyl amides: potent metabotropic glutamate subtype 5 (mGlu5) receptor antagonists. Biorganic & Medicinal ; Chemistry Letters, 15: 1197-1200.
Botteghi et al. (2001) Rhodium catalyzed hydroformylation of 1,1-bis(p-fluorophenyl)allyl or propargyl alcohol: a key step in the synthesis of Fluspirilen and Penfluridol. Tetrahedron 57: 1631-1637.
Broekkamp CL, et al. (1986) Major tranquilizers can be distinguished from minor tranquillizers on the basis of effects on marble burying and swim-induced grooming in mice. Eur. J. Pharmacol. 126: 223-229.
Brookhart and Studabaker (1987) Cyclopropanes from reactions of transition metal carbene complexes with olefins. Chem. Rev. 87: 411-432.
Burkhard et al. (2010) Synthesis and structural analysis of a new class of azaspiro[3.3]heptanes as building blocks for medicinal chemistry. Org. Lett. 12: 1944-1947.
Burkhard et al. (2010) Synthesis of azaspirocycles and their evaluation ind rug discovery. Angew. Chem. Int. Ed. 49: 3524-3527.
Caron S, et al. (2000) A practical, effecient, and rapid method for the oxidation of electron deficient pyridines using trifluoroacetic anhydride and hydrogen peroxide-urea complex. Tetrahedron Lett. 41: 2299-2302.
Ceccarelli, et al., "Rational design, synthesis, and structure-activity relationship of benzoxazolones: New potent mglu5 receptor antagonists based on the fenobam structure", Bioorganic & Medicinal Chemistry Letters, vol. 17, No. 5, Feb. 14, 2007 (Feb. 14, 2007), pp. 1302-1306.
Cella, J. A. (1982) Reductive alkylation/arylation of arylcarbinols and ketonsd with organosilicon compounds. J. Org. Chem. 47: 2125-2130.
Chiamulera et al. (2001) Reinforcing and locomotor stimulant effects of cocaine are absent in mGluR5 null mutant mice. Nature Neurosci. 4: 873-874.
Christlieb et al. (2001) The stereoselective synthesis of oxetanes; exploration of a new, Mitsonobu-style procedure for the cyclisation of 1,3-diols. J. Chem. Soc. Perkin Trans. 1: 2983-2996.
Ciaccio et al. (2003) "Instant Methylide" Modification of the Corey-Chaykovsky Epoxide Synthesis. Synthetic Comm. 33: 2135-2143.

(56) References Cited

OTHER PUBLICATIONS

Communication enclosing the Extended European Search Report for European Patent Application No. 10817928.4, dated Apr. 4, 2013.
Communication pursuant to Rules 70(2) and 70a(2) EPC issued by the European Patent Office on Apr. 23, 2013 for Application No. 10817950.8 filed ; on Sep. 17, 2010 (Applicants—Vanderbilt University; Inventors—Conn, et al.) (1 page).
Conn PJ, et al. (2009) Allosteric modulators of GPCRs: a novel approach for the treatment of CNS disorders. Nature Reviews, 8: 41-54.
Conn, et al., "Allosteric modulators of GPCRs: a novel approach for the treatment of CNS disorders", Nature Reviews Drug Discovery, vol. 8, No. 1, Jan. 1, 2009 (Jan. 1, 2009), pp. 41-54.
Cosford ND, et al. (2003a) 3-[(2-Methyl-1,3-thiazol-4-yl)ethynyl]-pyridine: a potent and highly selective metabotropic glutamate subtype 5 receptor antagonist with anxiolytic activity. J. Med. Chem. 46: 204-206.
De and Gibbs (2005) Bismuth(III) Chloride-Catalyzed Direct Deoxygenative Allylation of Substituted Benzylic Alcohols with Allyltrimethylsilane. Tetrahedron Lett. 46: 8345-8350.
De Kimpe and De Smaele (1994) Synthesis of aziridines and azetidines from N-(?-haloalkyl). Tetrahedron Lett. 35: 8023-8026.
Deacon, RMJ. (2006) Digging and marble burying in mice: simple methods for in vivo identification of biological impacts. Nature Protocols 1: 122-124.
Dolbier et al. (2004) Trimethylsilyl fluorosulfonyldifluoroacetate (TFDA): a new, highly efficient difluorocarbene reagent. J. Fluorine Chem. 125: 459-469.
European Search Report issued Jan. 13, 2015 for Application No. 12752374.4 (Applicant—Vanderbilt University//Inventor—P. Jeffrey Conn//) (8 pages).
Extended European Search Report issued by the European Patent Office on Apr. 4, 2013 for Application No. 10817950.8 filed on Sep. 17, 2010 ; (Applicants—Vanderbilt University; Inventors—Conn, et al.; (13 pages).
Extended European Search Report issued on Apr. 9, 2013 for application EP 10817954.0, filed on Sep. 17, 2010 and published as EP 2477631 on Jul. 25, 2012 (Applicant—Vanderbilt University // Inventor—Conn, et al.) (14 pages).
Felts, et al., "3-Cyano-5-fluoro-N-arylbenzamides as negative allosteric modulators of mGiu5: Identification of easily prepared tool compounds with CNS exposure in rats", Bioorganic & Medicinal Chemistry Letters, vol. 20, No. 15, Aug. 1, 2010 (Aug. 1, 2010), pp. 4390-4394.
Fife WK. (1983) Regioselective cyanation of pyridine 1-oxides with trimethylsilanecarbonitrile: a modified Reissert-Henze reaction. J. Org. Chem. 48: 1375-1377.
Final Official Action issued by the JPO on Feb. 22, 2016 for application JP 2013-556618, filed on Mar. 5, 2012 and published as Jp 2014-515008 on Jun. 26, 2014 (Applicant—Vanderbilt University // Inventor—Conn, et al.) (2 pages).
Fleming and Urch (1985) Stereospecific cyclopropane synthesis from ?-stannyl alcohols. J. Organomet. Chem. 285: 173-191.
Groundwater et al. (2001) A novel synthesis of imidazoles via the cycloaddition of nitrile ylides to their imidoyl chloride precursors. J. Chem. Soc., Perkin Trans. 1: 2781-2787.
International Preliminary Report on Patentability and Written Opinion from International Application No. PCT/US10/49373, issued Mar. 20, 2012.
International Preliminary Report on Patentability from International Application No. PCT/US10/049400, issued on Mar. 20, 2012.
International Preliminary Report on Patentability from International Application No. PCT/US10/049407, issued on Mar. 20, 2012 (6 pp).
International Preliminary Report on Patentability issued Feb. 27, 2012 by the International Searching Authority for International Patent Application PCT/US2012/000119 filed Jul. 9, 2011 and which published as WO 2012/118563 on Sep. 7, 202(Inventor—Jeffrey Conn // Applicant—Vanderbilt University) (9 pages).

International Preliminary Report on Patentability issued in corresponding International Application No. PCT/US201 0/049358 on Mar. 20, 2012.
International Preliminary Report on Patentability issued on May 24, 2016 for application PCT/US14/066207, filed on Nov. 18, 2014 and published as WO 2015/077246 on May 28, 2015 (Applicant—Vanderbilt Univ. // Inventor—Emmitt, et al.) (7 pages).
International Search Report and Written Opinion issued in corresponding International Application No. PCT/US2010/049358 mailed Oct. 25, 2010 (7 pages).
International Search Report and Written Opinion issued on Jan. 27, 2015 for application PCT/US14/066207, filed on Nov. 18, 2014 and published as WO 2015/077246 on May 28, 2015 (Applicant—Vanderbilt Univ. // Inventor—Emmitt, et al.) (15 pages).
International Search Report from International Application No. PCT/US1 0/049400, mailed Nov. 9, 2010.
International Search Report from International Application No. PCT/US10/049407, mailed Nov. 1, 2010 (1 page).
International Search Report from International Application No. PCT/US10/49373, dated Nov. 9, 2010.
International Search Report issued Feb. 27, 2012 by the International Searching Authority for International Patent Application PCT/US2012/000119 filed Jul. 9, 2011 and which published as WO 2012/118563 on Sep. 7, 2012 (Inventor—Jeffrey Conn //Applicant—Vanderbilt University) (5 pages).
Jaeschke, et al., "mG1u5 receptor antagonists and their therapeutic potential," Expert Opinion, Informa Healthcare, 2008 (20 pages).
Jingami, et al., "Structure of the metabotropic glutamate receptor," Current Opinions in Neurobiology, 2003, vol. 13 pp. 271-287.
Kew JNC, et al. (2004) Positive and negative allosteric modulation of metabotropic glutamate receptors: emerging therapeutic potential. Pharmacology & Therapeutics, 104: 233-244.
Kew, et al., "Positive and negative allosteric modulation of metabotropic glutamate receptors: emerging therapeutic potential", Pharmacology and Therapeutics, vol. 104, No. 3, Dec. 1, 2004 (Dec. 1, 2004), pp. 233-244.
Kulkarni et al., "Design and Synthesis of Novel Heterobiaryl Amides as Metabotropic Glutamate Receptor Subtype 5 Antagonists," Bioorg. Med. Chem. Lett.vol. 17(7), pp. 2074-2079, 2007 (From NIH Public Access pp. 1-16).
Li F, et al. (2005) Synthesis of Diaryl Ethers, Diaryl Sulfides, Heteroaryl Ethers and heteroaryl Sulfides under Mircrowave Dielectric Heating. ; Synthesis, 8: 1305-1313.
Lindsley CW, et al. (2008) Recent progress in the discovery and development of negative allosteric modulators of mGluR5. Current Opinion in Drug Discovery & Development 12(4): 440-452.
Njung'e K.and Handley SL. (1991) Effects of 5-HT uptake inhibitors, agonists and antagonists on the burying of harmless objects by mice; a putative test for anxiolytic agents. 20 Brit. J. Pharmacol. 104: 105-112.
Non-Final Office Action issued on Apr. 24, 2013 for U.S. Appl. No. 12/885,378, filed on Sep. 17, 2010 and granted as U.S. Pat. No. 8,796,295 on Aug. 5, 2014 (Applicant—Vanderbilt University // Inventor—Conn, et al.) (7 pages).
Non-Final Office Action issued on Apr. 28, 2016 for U.S. Appl. No. 14/664,792, filed on Mar. 20, 2015 and published as US 2015-0266866 A1 on Sep. 24, 2015 (Applicant—Vanderbilt Univ. // Inventor—Conn, et al.) (11 pages).
Non-Final Office Action issued on Nov. 13, 2012 for U.S. Appl. No. 12/885,289, filed on Sep. 17, 2010 and granted as U.S. Pat. No. 8,598,345 on Dec. 3, 2013 (Applicant—Vanderbilt Univ. // Inventor—Conn, et al.) (58 pages).
Non-Final Office Action issued on Nov. 8, 2012 for U.S. Appl. No. 12/885,245, filed on Sep. 17, 2010 and granted as U.S. Pat. No. 8,569,308 on Oct. 29, 2013 (Applicant—Vanderbilt Univ. // Inventor—Conn, et al.) (8 pages).
Non-Final Office Action issued on Sep. 17, 2014 for U.S. Appl. No. 14/002,309, filed on Mar. 17, 2014 and granted as U.S. Pat. No. 9,085,562 on Jul. 21, 2015 (Applicant—Vanderbilt University // Inventor—Conn, et al.) (33 pages).

(56) References Cited

OTHER PUBLICATIONS

Notice of Allowance issued on Jul. 31, 2013 for U.S. Appl. No. 12/885,289, filed on Sep. 17, 2010 and granted as U.S. Pat. No. 8,598,345 on Dec. 3, 2013 (Applicant—Vanderbilt Univ. // Inventor—Conn, et al.) (6 pages).
Notice of Allowance issued on Jun. 20, 2013 for U.S. Appl. No. 12/885,245, filed on Sep. 17, 2010 and granted as U.S. Pat. No. 8,569,308 on Oct. 29, 2013 (Applicant—Vanderbilt Univ. // Inventor—Conn, et al.) (10 pages).
Notice of Allowance issued on Mar. 16, 2015 for U.S. Appl. No. 14/002,309, filed on Mar. 17, 2014 and granted as U.S. Pat. No. 9,085,562 on Jul. 21, 2015 (Applicant—Vanderbilt University // Inventor—Conn, et al.) (5 pages).
Notice of Allowance issued on May 23, 2013 for U.S. Appl. No. 12/885,420, filed on Sep. 17, 2010 and granted as U.S. Pat. No. 8,501,757 on Aug. 6, 2013 (Applicant—Vanderbilt University // Inventor—Conn, et al.) (14 pages).
Notice of Allowance issued on Nov. 20, 2013 for U.S. Appl. No. 12/885,378, filed on Sep. 17, 2010 and granted as U.S. Pat. No. 8,796,295 on Aug. 5, 2014 (Applicant—Vanderbilt University // Inventor—Conn, et al.) (7 pages).
Official Action issued by the JPO on Aug. 19, 2015 for application JP 2013-556618, filed on Mar. 5, 2012 and published as JP 2014-515008 on Jun. 26, 2014 (Applicant—Vanderbilt University // Inventor—Conn, et al.) (3 pages).
Requirement for Restriction or Election issued on Feb. 24, 2016 for U.S. Appl. No. 14/664,792, filed on Mar. 20, 2015 and published as US 2015-0266866 A1 on Sep. 24, 2015 (Applicant—Vanderbilt Univ. // Inventor—Conn, et al.) (9 pages).
Response to Non-Final Office Action filed on May 13, 2013 for U.S. Appl. No. 12/885,289, filed on Sep. 17, 2010 and granted as U.S. Pat. No. 8,598,345 on Dec. 3, 2013 (Applicant—Vanderbilt Univ. // Inventor—Conn, et al.) (6 pages).
Response to Non-Final Office Action filed on May 7, 2013 for U.S. Appl. No. 12/885,245, filed on Sep. 17, 2010 and granted as U.S. Pat. No. 8,569,308 on Oct. 29, 2013 (Applicant—Vanderbilt Univ. // Inventor—Conn, et al.) (4 pages).
Response to Non-Final Office Action filed on Oct. 20, 2015 for U.S. Appl. No. 14/002,309, filed on Mar. 17, 2014 and granted as U.S. Pat. No. 9,085,562 on Jul. 21, 2015 (Applicant—Vanderbilt University // Inventor—Conn, et al.) (23 pages).
Response to Non-Final Office Action filed on Oct. 24, 2013 for U.S. Appl. No. 12/885,378, filed on Sep. 17, 2010 and granted as U.S. Pat. No. 8,796,295 on Aug. 5, 2014 (Applicant—Vanderbilt University // Inventor—Conn, et al.) (9 pages).
Response to Requirement for Restriction or Election filed on Apr. 19, 2016 for U.S. Appl. No. 14/664,792, filed on Mar. 20, 2015 and published as US 2015-0266866 A1 on Sep. 24, 2015 (Applicant—Vanderbilt Univ. // Inventor—Conn, et al.) (29 pages).
Ross and Bartsch (2003) High-Intensity Ultrasound-Promoted Reformatsky Reactions. J. Org. Chem. 68: 360-366.
Saidi and Nazari (2004) Aminoalkylation with Aldehydes Mediated by Solkid Lithium Perchlorate. Monatshefte fur Chem. 135: 309-312.
Singh et al. (1997) Catalytic Enantioselective Cyclopropanation of Olefins Using Carbenoid Chemistry. Synthesis 137-149.
Singh et al. (1999) Cesium Fluoride Catalyzed Trifluoromethylation of Esters, Aldehydes, and Ketones with (Trifluoromethyl)trimethylsilane. J. Org. Chem. 64: 2873-2876.
Sorensen et al. (2003) Synthesis and Structure-Activity Relationship Studies of Novel 2-Diarylethyl Substituted (2-Carboxycycloprop-1-yl)glycines as Hih-Affinity Group II Metabotropic Glutamate Receptor Ligands. Bioorg. Med. Chem. 11: 197-205.
Srivastava RR, et al. (2007) Application of polymer-supported triphenylphospine and microwave irradiation to the palladium-catalyzed cyanation of aryl triflates. Synthetic Comm. 37: 431-438.
Stafford and McMurry (1988) An efficient method for the preparation of alkylidenecyclopropanes. Tetrahedron Lett. 29: 2531-2534.
Suh and Rieke (2004) Synthesis of β-hydroxy esters using highly active manganese. Tetrahedron Lett. 45: 1807-1809.
Suri et al. (2005) New Application of Bromotrimethylsilane: Elaboration of Aldehydes/Ketones into Homologous a, β-Unsaturated Esters via β-Hydroxy Esters. Synth. Comm. 37: 379-387.
Tanaka and Shishido (2007) Synthesis of aromatic compounds containing a 1,1-dialkyl-2-trifluoromethyl group, a bioisostere of the tert-alkyl moiety. Bioorg. Med. Chem. Lett. 17: 6079-6085.
Taylor EC and Crovetti AJ. (1956) 3-Methyl-4-nitropyridine-1-oxide. Organic Syntheses, 36: 53.
Ulrich, Crystallization, Kirk-Othmer Encyclopedia of Chemical Technology, pp. 1-7, 2002.
Vippagunta et al., Crystalline Solids, Advanced Drug Delivery Reviews 48 (2001), pp. 3-26.
Virender and Sain (2005) Indium-mediated, highly efficient cyclopropanation of olefins using CH2I2 as methylene transfer reagent. Tetrahedron Lett. 46: 37-38.
Winter, B. (2004) Spirocyclic Ethers Related to Ambrox®: Synthesis and Structure-Odor Relationships. Helv. Chim. Acta 87: 1616-1627.
Written Opinion issued Feb. 27, 2012 by the International Searching Authority for International Patent Application PCT/US2012/000119 filed Jul. 9, 2011 and which published as WO 2012/118563 on Sep. 7, 2012 (Inventor—Jeffrey Conn //Applicant—Vanderbilt University) (8 pages).
Written Opinion of the International Searching Authority from International Application No. PCT/US1 0/049400, mailed Nov. 9, 2010.
Written Opinion of the International Searching Authority from International Application No. PCT/US10/049400, mailed Nov. 1, 2010 (5 pp).
Yoshida et al. (1997) J. Chem. Soc., Perkin Trans 1 643-648.
Zhou, et al., "Synthesis and SAR of novel, non-MPEP chemotype mGiuR5 NAMs identified by functional HTS", Bioorganic & Medicinal Chemistry Letters,vol. 19, No. 23, Dec. 1, 2009 (Dec. 1, 2009), pp. 6502-6506.

* cited by examiner

SUBSTITUTED 6-ARYL-IMIDAZOPYRIDINE AND 6-ARYL-TRIAZOLOPYRIDINE CARBOXAMIDE ANALOGS AS NEGATIVE ALLOSTERIC MODULATORS OF MGLUR5

CROSS-REFERENCE TO RELATED APPLICATIONS

This application claims the benefit of U.S. Provisional Application No. 62/059,813, filed on Oct. 3, 2014, which is incorporated herein by reference in its entirety.

STATEMENT REGARDING FEDERALLY SPONSORED RESEARCH OR DEVELOPMENT

This invention was made with government support under Grant no. 2R01-MH062646-12 awarded by the National Institute of Mental Health (NIMH), under Grant no. 5R01-MH073676-04 awarded by the National Institute of Mental Health (NIMH), under Grant no. 5R01-NS031373-15 awarded by the National Institute of Neurological Disorders and Stroke (NINDS), under Grant no. 1R0-DA023947-01 awarded by the National Institute of Drug Abuse (NIDA), and under Grant no. 1U19-MH097056-01 awarded by the National Institute of Mental Health (NIMH). The United States government has certain rights in the Invention.

BACKGROUND

Glutamate (L-glutamic acid) is the major excitatory transmitter in the mammalian central nervous system, exerting its effects through both ionotropic and metabotropic glutamate receptors. The metabotropic glutamate receptors (mGluRs) belong to family C (also known as family 3) of the G-protein-coupled receptors (GPCRs). They are characterized by a seven transmembrane (7TM) α-helical domain connected via a cysteine rich-region to a large bi-lobed extracellular amino-terminal domain. While the orthosteric binding site is contained in the amino-terminal domain, currently known allosteric binding sites reside in the 7TM domain. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c. The family has been classified into three groups based on their structure, preferred signal transduction mechanisms, and pharmacology. Group I receptors (mGluR1 and mGluR5) are coupled to Gαq, a process that results in stimulation of phospholipase C and an increase in intracellular calcium and inositol phosphate levels. Group II receptors (mGluR2 and mGluR3) and group III receptors (mGluR4, mGluR6, mGluR7, and mGluR8) are coupled to Gαi, which leads to decreases in cyclic adenosine monophosphate (cAMP) levels. While the Group I receptors are predominately located postsynaptically and typically enhance postsynaptic signaling, the group II and III receptors are located presynaptically and typically have inhibitory effects on neurotransmitter release. Without wishing to be bound by theory, increasing evidence indicates mGluRs play an important role in lasting changes in synaptic transmission, and studies of synaptic plasticity in the Fmr1 knockout mouse have identified a connection between the fragile X phenotype and mGluR signaling.

The identification of small molecule mGluR antagonists that bind at the orthosteric site has greatly increased the understanding of the roles played by these receptors and their corresponding relation to disease. Because the majority of these antagonists were designed as analogs of glutamate, they typically lack desired characteristics for drugs targeting mGluRs such as oral bioavailability and/or distribution to the central nervous system (CNS). Moreover, because of the highly conserved nature of the glutamate binding site, most orthosteric antagonists lack selectivity among the various mGluRs.

A more recent strategy that has been able to successfully deal with the aforementioned issues has been the design of compounds that bind the mGluR at a site that is topographically distinct from the orthosteric binding site, or an allosteric binding site. Selective negative allosteric modulators (NAMs) are compounds that do not directly deactivate receptors by themselves, but decrease the affinity of a glutamate-site agonist at its extracellular N-terminal binding site. Negative allosteric modulation is thus an attractive mechanism for inhibiting appropriate physiological receptor activation. Among the most studied and characterized small molecules are the mGluR5 NAMs, 2-methyl-6-(phenylethynyl)pyridine (MPEP) and 3-[(2-methyl-1,3-thiazol-4-yl)ethynyl]pyridine (MTEP). Both MPEP and MTEP have proven efficacious in numerous rodent models of disease, including those for drug addiction and pain as well as anxiety. The compounds were also able to inhibit transient lower esophageal sphincter relaxation (TLESD), the major cause of gastroesophageal reflux disease (GERD), in dogs and ferrets. In addition, MPEP was efficacious in mouse models of fragile X syndrome (FXS) and Parkinson's disease (PD) as well as a baboon model of binge-eating disorder.

Although the utility of MPEP and MTEP as tool compounds has been clearly demonstrated, both molecules have issues that complicate or prevent their further development as therapeutic molecules. MPEP has been shown to directly inhibit the N-methyl-D-aspartate (NMDA) receptor activity at higher concentrations and is a positive allosteric modulator of mGluR4. While these selectivity issues are mitigated with MTEP, it is a potent inhibitor of cytochrome P450 1A2 and is efficiently cleared following intravenous administration to rhesus monkeys.

Potential adverse effects of known mGluR5 NAMs, however, could reduce their ultimate therapeutic utility. Further, conventional mGluR5 receptor modulators which target the orthosteric binding site can lack satisfactory aqueous solubility, exhibit poor oral bioavailability, and/or exhibit adverse effects. Therefore, there remains a need for methods and compositions that overcome these deficiencies and that effectively provide selective negative allosteric modulators for the mGluR5 receptor.

SUMMARY

In accordance with the purpose(s) of the invention, as embodied and broadly described herein, the invention, in one aspect, relates to compounds useful as negative allosteric modulators of the metabotropic glutamate receptor subtype 5 (mGluR5), methods of making same, pharmaceutical compositions comprising same, and methods of treating disorders associated with glutamate dysfunction using same.

Disclosed are compounds having a structure represented by a formula:

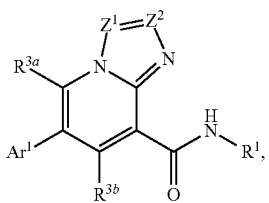

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein $R^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein each occurrence of $R^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl, and —$NR^{64a}R^{64b}$; wherein each occurrence of each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{3a}$ and $R^{3b}$ is independently selected from hydrogen and fluoro; wherein $Ar^1$ is selected from aryl and heteroaryl, and wherein $Ar^1$ is substituted with 0, 1, 2, or 3 groups independently selected from halogen, —CN, C1-C3 alkyl, C1-C3 monohaloalkyl, C1-C3 polyhaloalkyl, —$OR^{30}$, —$NR^{31a}R^{31b}$, —$SO_2R^{32}$, —(C=O)$R^{33}$, and cyclopropyl; wherein each occurrence of $R^{30}$, when present, is independently selected from hydrogen, C1-C3 alkyl, C1-C3 monohaloalkyl, C1-C3 polyhaloalkyl, and cyclopropyl; wherein each occurrence of each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with the nitrogen atom to which they are attached, comprise a 3- to 6-membered heterocycle; wherein each occurrence of $R^{32}$, when present, is independently selected from C1-C3 alkyl, C1-C3 monohaloalkyl, C1-C3 polyhaloalkyl, cyclopropyl, and —$NR^{34a}R^{34b}$; wherein each occurrence of each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with the nitrogen atom to which they are attached, comprise a 3- to 6-membered heterocycle; wherein each occurrence of $R^{33}$, when present, is independently from C1-C3 alkyl, C1-C3 monohaloalkyl, C1-C3 polyhaloalkyl, cyclopropyl, and —$NR^{35a}R^{35b}$; wherein each occurrence of each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; or a pharmaceutically acceptable salt thereof.

Also disclosed are pharmaceutical compositions comprising an effective amount of at least one disclosed compound, or a pharmaceutically acceptable salt thereof, and a pharmaceutically acceptable carrier.

Also disclosed are methods for manufacturing a medicament comprising combining at least one disclosed compound with a pharmaceutically acceptable carrier or diluent.

Also disclosed are methods for the treatment of a disorder associated with metabotropic glutamate receptor activity in a subject, the method comprising the step of administering to the subject an effective amount of at least one disclosed compound, or a pharmaceutically acceptable salt thereof, thereby treating the disorder associated with metabotropic glutamate receptor activity in the subject.

Also disclosed are methods for modulating metabotropic glutamate receptor activity in a subject, the method comprising the step of administering to the subject an effective amount of at least one disclosed compound, or a pharmaceutically acceptable salt thereof, thereby modulating the metabotropic glutamate receptor activity in the subject.

Also disclosed are methods for modulating metabotropic glutamate receptor activity in at least one cell, the method comprising the step of contacting the at least one cell with an effective amount of at least one disclosed compound, or a pharmaceutically acceptable salt thereof, thereby modulating the metabotropic glutamate receptor activity in the at least one cell.

Also disclosed are kits comprising at least one disclosed compound, or a pharmaceutically acceptable salt thereof; and one or more of: (a) at least one agent known to increase mGluR5 activity; (b) at least one agent known to decrease mGluR5 activity; (c) at least one agent known to treat a neurological and/or psychiatric disorder; or (d) instructions for treating a disorder associated with glutamate dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples and Figures included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mGluR5 receptor is the site that glutamate binds.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for negative allosteric modulation of metabotropic glutamate receptor activity prior to the administering step. In some aspects of the disclosed method, the subject has been diagnosed with a need for partial antagonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mGluR5" means having been subjected to a physical examination by a person of skill, for example, a physician, and found to have a condition that can be diagnosed or treated by a compound or composition that can modulate mGluR5. As a further example, "diagnosed with a need for modulation of mGluR5" refers to having been subjected to a physical examination by a person of skill, for example, a physician, and found to have a condition characterized by mGluR5 activity. Such a diagnosis can be in reference to a disorder, such as a neurodegenerative disease, and the like, as discussed herein. For example, the term "diagnosed with a need for negative allosteric modulation of metabotropic glutamate receptor activity" refers to having been subjected to a physical examination by a person of skill, for example, a physician, and found to have a condition that can be diagnosed or treated by negative allosteric modulation of metabotropic glutamate receptor activity. For example, "diagnosed with a need for partial antagonism of metabotropic glutamate receptor activity" means having been subjected to a physical examination by a person of skill, for example, a physician, and found to have a condition that can be diagnosed or treated by partial antagonism of metabotropic glutamate receptor activity. For example, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "(ECs," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refer to the concentration of agonist that provokes a response halfway between the baseline and maximum response. In a yet further aspect, the response is in vitro. In a still further aspect, the response is in a human embryonic kidney cell transfected with human mGluR5. In a yet further aspect, the response is a human embryonic kidney cell transfected with rat mGluR5. In an even further aspect, the response is in a human embryonic kidney cell transfected with a mammalian mGluR5.

As used herein, "(IC$_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refer to the half maximal (50%) inhibitory concentration (IC) of a substance. In a yet further aspect, the inhibition is measured in vitro. In a still further aspect, the inhibition is measured in a human embryonic kidney cell transfected with human mGluR5. In a yet further aspect, the inhibition is measured in a human embryonic kidney cell transfected with rat mGluR5. In an even further aspect, the inhibition is measured in a human embryonic kidney cell transfected with a mammalian mGluR5.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The terms "aliphatic" and "aliphatic group," as used herein, denote a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl," as used herein, refers to a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification, "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl," as used herein, is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group," as used herein, is a group having two or more $CH_2$ groups linked to one another. The polyalkylene group can be represented by the formula $—(CH_2)_a—$, where "a" is an integer of from 2 to 500.

The terms "alkoxy" and "alkoxyl," as used herein, refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The term "alkenyl," as used herein, is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl," as used herein, is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl," as used herein, is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl," as used herein, is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group," as used herein, refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl," as used herein, is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde," as used herein, is represented by the formula —C(O)H. Throughout this specification "C(O)" is a short hand notation for a carbonyl group, i.e., C=O.

The terms "amine" or "amino," as used herein, are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino," as used herein, is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino," as used herein, is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid," as used herein, is represented by the formula —C(O)OH.

The term "ester," as used herein, is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether," as used herein, is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," and "halide", as used herein, can be used interchangeably and refer to F, C, Br, or I.

The terms "pseudohalide," "pseudohalogen," and "pseudohalo," as used herein, can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein, refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein, refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "hydroxy" and "hydroxyl," as used herein, are represented by the formula —OH.

The term "ketone," as used herein, is represented by the formula $A^1C(O)A^2$ where $A^1$ and $A^2$ can be, independently, an alkyl, cycloalkyl, alkenyl, cycloalkenyl, alkynyl, cycloalkynyl, aryl, or heteroaryl group as described herein.

The terms "azide" and "azido," as used herein, are represented by the formula —$N_3$.

The term "nitro," as used herein, is represented by the formula —$NO_2$—.

The terms "nitrile" and "cyano," as used herein, are represented by the formula —CN.

The term "silyl," as used herein, is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo," as used herein, is represented by the formula —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol," as used herein, is represented by the formula —SH.

"$R^1$," "$R^2$," "$R^3$,", ... "$R^n$," where n is an integer, as used herein, can independently possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group is independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}OC(O)R^\circ$; $C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ Straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), is independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-N_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ is independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, trifate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

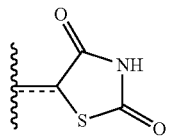

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thioha-loalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but are not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

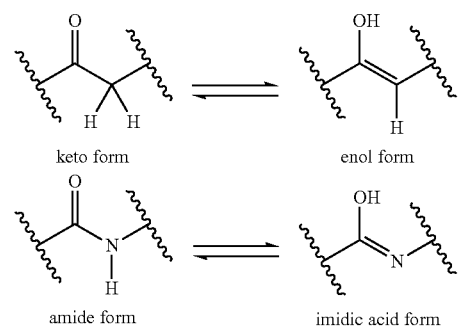

keto form    enol form amide form    imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

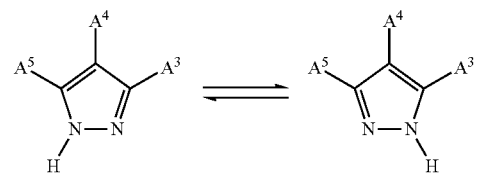

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

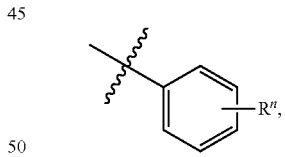

which is understood to be equivalent to a formula:

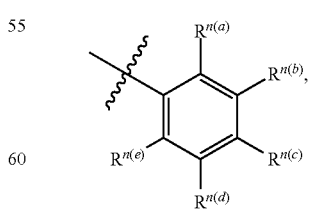

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. mGluR5 Negative Allosteric Modulators

In one aspect, the invention relates to compounds useful as negative allosteric modulators of the metabotropic glutamate receptor subtype 5 (mGluR5). Negative allosteric modulators are noncompetitive antagonists and can include a range of maximal antagonist activity from partial antagonists to inverse agonists. In one aspect, the present invention relates to compounds that allosterically modulate mGluR5 receptor activity, affecting the sensitivity of mGluR5 receptors to agonists without acting as orthosteric agonists themselves. The compounds can, in one aspect, exhibit subtype selectivity. The compounds of the invention can be useful in the treatment of neurological and psychiatric disorders associated with glutamate dysfunction and other diseases in which metabotropic glutamate receptors are involved, as further described herein. Generally, the disclosed compounds exhibit negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, the human embryonic kidney cells are transfected with human mGluR5. In yet a further aspect, human embryonic kidney cells are transfected with mGluR5 of a mammal.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds, or pharmaceutically acceptable salts thereof, having a structure represented by a formula:

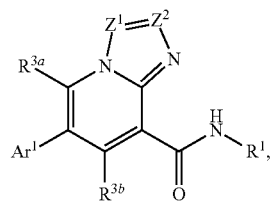

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein $R^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein each occurrence of $R^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl, and —$NR^{64a}R^{64b}$; wherein each occurrence of each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{3a}$ and $R^{3b}$ is independently selected from hydrogen and fluoro; wherein $Ar^1$ is selected from aryl and heteroaryl, and wherein $Ar^1$ is substituted with 0, 1, 2, or 3 groups independently selected from halogen, —CN, C1-C3 alkyl, C1-C3 monohaloalkyl, C1-C3 polyhaloalkyl, —$OR^{30}$, —$NR^{31a}R^{31b}$, —$SO_2R^{32}$, —(C=O)$R^{33}$, and cyclopropyl; wherein each occurrence of $R^{30}$, when present, is independently selected from hydrogen, C1-C3 alkyl, C1-C3 monohaloalkyl, C1-C3 polyhaloalkyl, and cyclopropyl; wherein each occurrence of each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with the nitrogen atom to which they are attached, comprise a 3- to 6-membered heterocycle; wherein each occurrence of $R^{32}$, when present, is independently selected from C1-C3 alkyl, C1-C3 monohaloalkyl, C1-C3 polyhaloalkyl, cyclopropyl, and —$NR^{34a}R^{34b}$; wherein each occurrence of each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with the nitrogen atom to which they are attached, comprise a 3- to 6-membered heterocycle; wherein each occurrence of $R^{33}$, when present, is independently from C1-C3 alkyl, C1-C3 monohaloalkyl, C1-C3 polyhaloalkyl, cyclopropyl, and —$NR^{35a}R^{35b}$; wherein each occurrence of each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; or a pharmaceutically acceptable salt thereof.

In a further aspect, the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound. In an even further aspect, the human embryonic kidney cells are transfected with rat mGluR5. In a still further aspect, the human embryonic kidney cells are transfected with human mGluR5.

In a further aspect, the compound exhibits partial inhibition of mGluR5 response. In a still further aspect, the compound exhibits total inhibition of mGluR5 response.

In a further aspect, the compound exhibits noncompetitive antagonism. In a still further aspect, the compound exhibits negative allosteric modulation. In a yet further aspect, the compound exhibits noncompetitive inhibition. In an even further aspect, the compound exhibits allosteric antagonism.

In a further aspect, the compounds exhibit negative allosteric modulation with an $IC_{50}$ of less than about $30\times10^{-6}$ M. In a still further aspect, the compounds exhibit negative allosteric modulation with an $IC_{50}$ of less than about $25\times10^{-6}$ M. In yet a further aspect, the compounds exhibit negative allosteric modulation with an $IC_{50}$ of less than about $20\times10^{-6}$ M. In an even further aspect, the compounds exhibit negative allosteric modulation with an $IC_{50}$ of less than about $15\times10^{-6}$ M. In a still further aspect, the compounds exhibit negative allosteric modulation with an $IC_{50}$ of less than about $10\times10^{-6}$ M. In yet a further aspect, the compounds exhibit negative allosteric modulation with an $IC_{50}$ of less than about $5\times10^{-6}$ M. In an even further aspect, the compounds exhibit negative allosteric modulation with an $IC_{50}$ of less than about $1\times10^{-6}$ M.

In a further aspect, the compounds exhibit negative allosteric modulation with an $IC_{50}$ of less than about $30\times10^{-7}$ M. In a still further aspect, the compounds exhibit negative allosteric modulation with an $IC_{50}$ of less than about $25\times10^{-7}$ M. In yet a further aspect, the compounds exhibit negative allosteric modulation with an $IC_{50}$ of less than about $20\times10^{-7}$ M. In an even further aspect, the compounds exhibit negative allosteric modulation with an $IC_{50}$ of less than about $15\times10^{-7}$ M. In a still further aspect, the compounds exhibit negative allosteric modulation with an $IC_{50}$ of less than about $10\times10^{-7}$ M. In yet a further aspect, the compounds exhibit negative allosteric modulation with an $IC_{50}$ of less than about $5\times10^{-7}$ M. In an even further aspect, the compounds exhibit negative allosteric modulation with an $IC_{50}$ of less than about $1\times10^{-7}$ M.

In a further aspect, the invention relates to a pharmaceutical composition comprising a therapeutically effective amount of a disclosed compound or product of a disclosed method of making and a pharmaceutically acceptable carrier.

In a further aspect, a compound has a structure represented by a formula selected from:

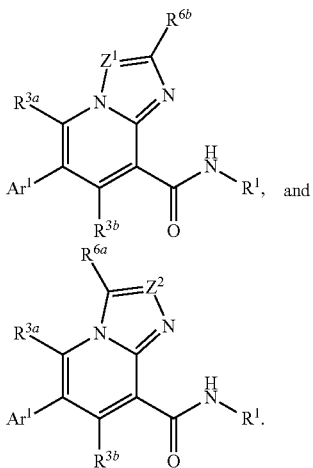

In a still further aspect, a compound has a structure represented by a formula selected from:

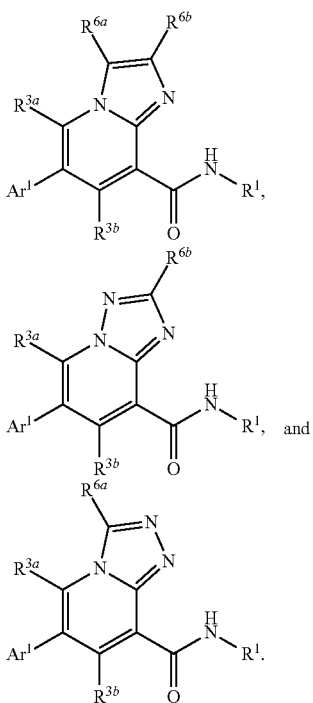

In a further aspect, a compound has a structure represented by a formula:

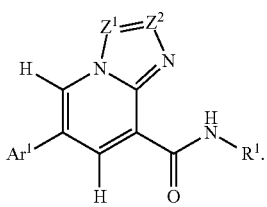

In a still further aspect, a compound has a structure represented by a formula selected from:

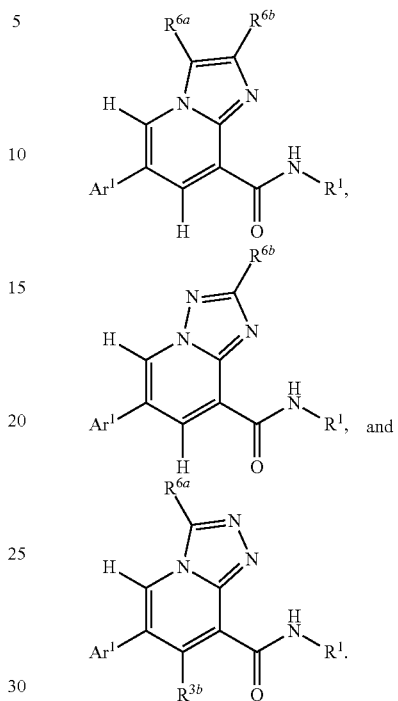

In yet a further aspect, a compound has a structure represented by a formula

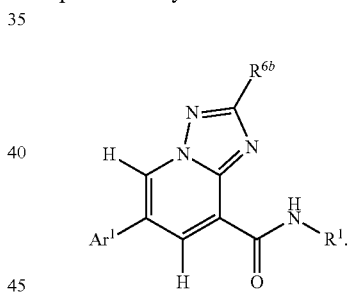

In a further aspect, a compound has a structure represented by a formula selected from:

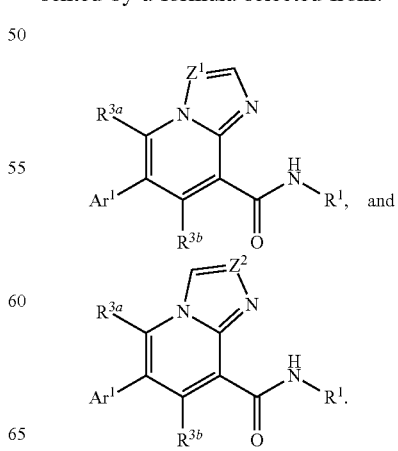

In a still further aspect, a compound has a structure represented by a formula selected from:

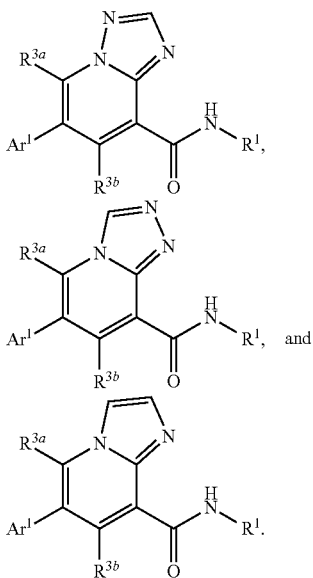

In yet a further aspect, a compound has a structure represented by a formula selected from:

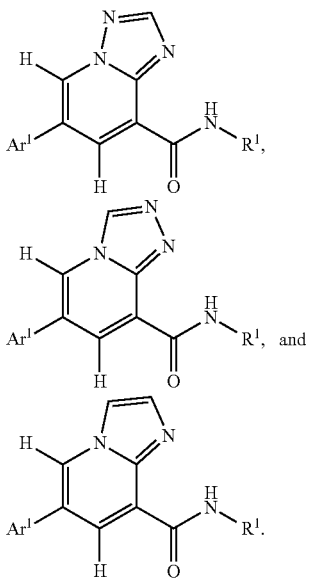

In a further aspect, a compound has a structure represented by a formula

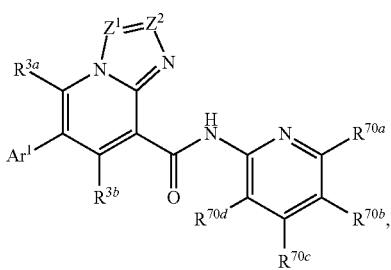

wherein each of $R^{70a}$, $R^{70b}$, $R^{70c}$, and $R^{70d}$ is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$, provided that at least one of $R^{70a}$, $R^{70b}$, $R^{70c}$, and $R^{70d}$ is hydrogen.

In a still further aspect, a compound has a structure represented by a formula selected from:

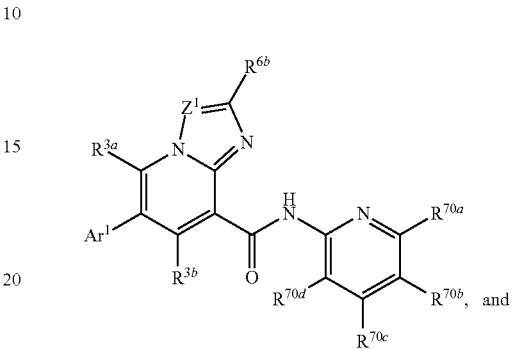

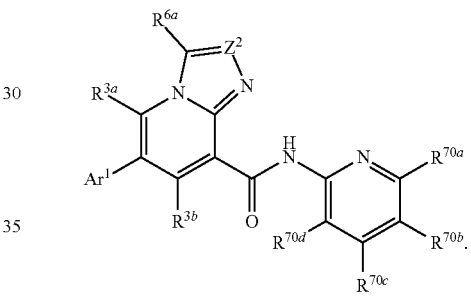

In yet a further aspect, a compound has a structure represented by a formula selected from:

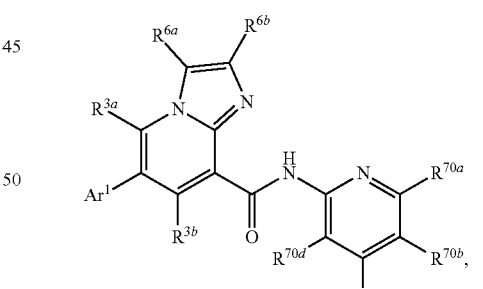

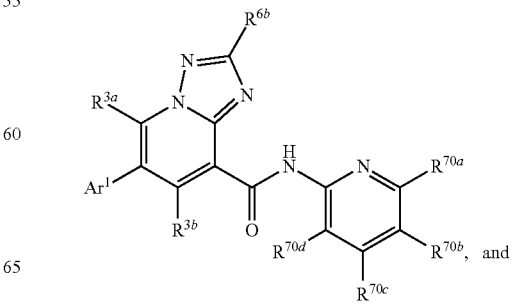

-continued

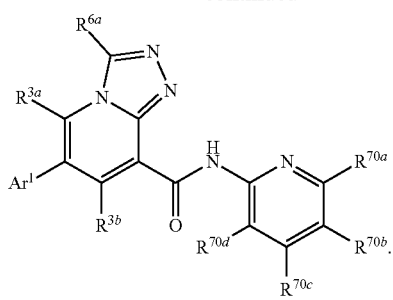

In as further aspect, a compound has a structure represented by a formula:

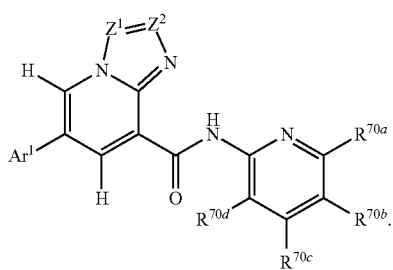

In a still further aspect, a compound has a structure represented by a formula selected from:

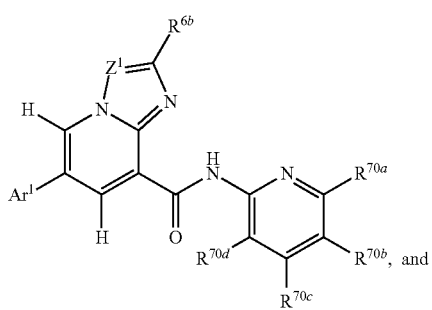

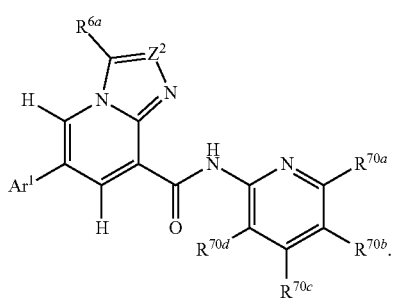

In yet a further aspect, a compound has a structure represented by a formula selected from:

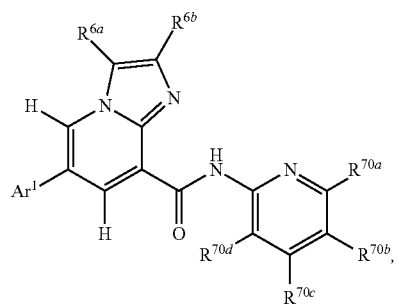

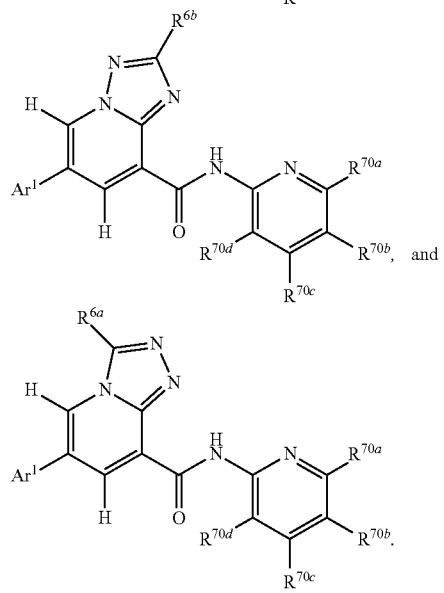

In a still further aspect, a compound has a structure represented by a formula:

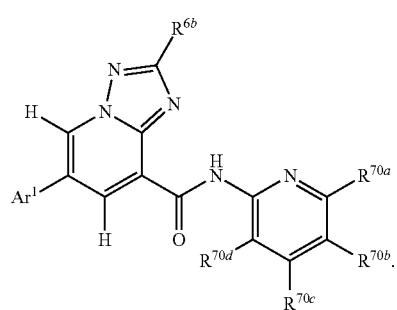

In yet a further aspect, a compound has a structure represented by a formula selected from:

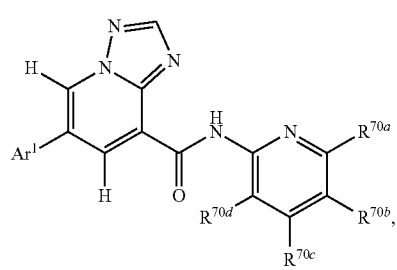

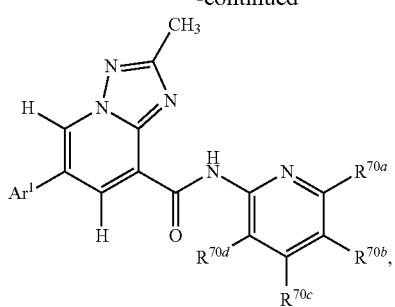
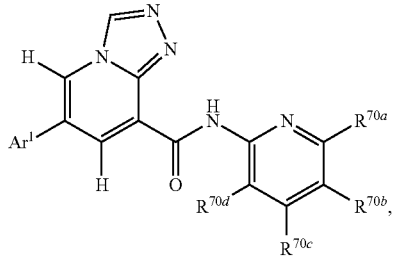
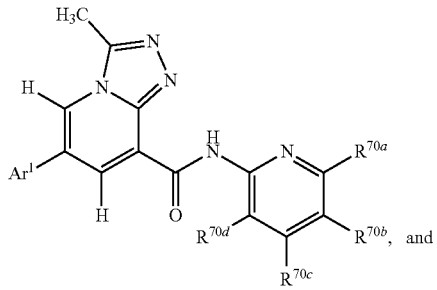
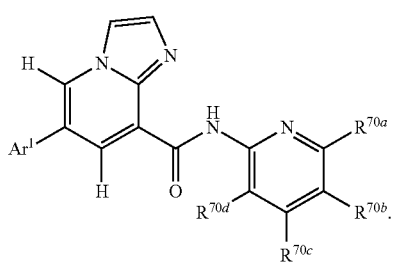
In a further aspect, a compound has a structure represented by a formula:
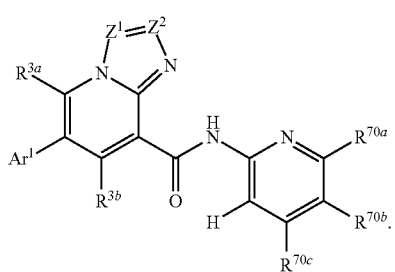
In a still further aspect, a compound has a structure represented by a formula selected from:
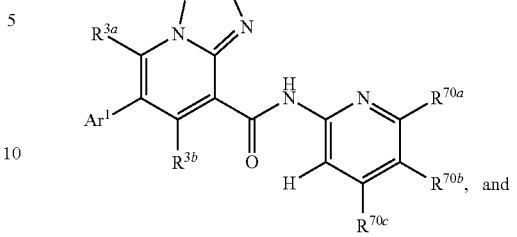
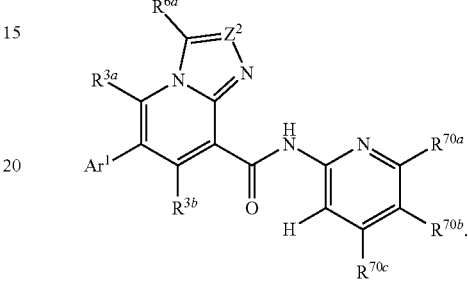
In yet a further aspect, a compound has a structure represented by a formula selected from:
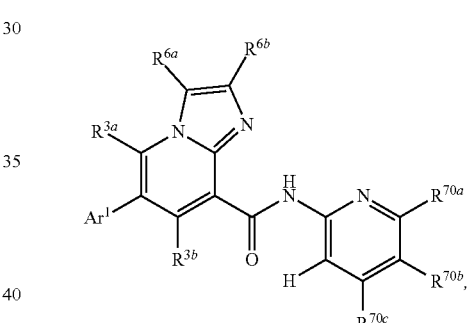
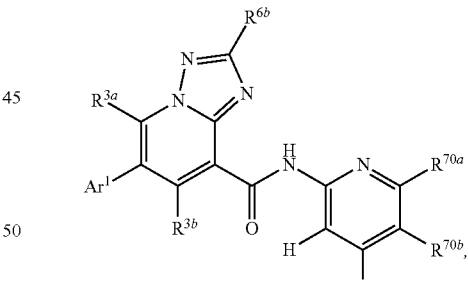
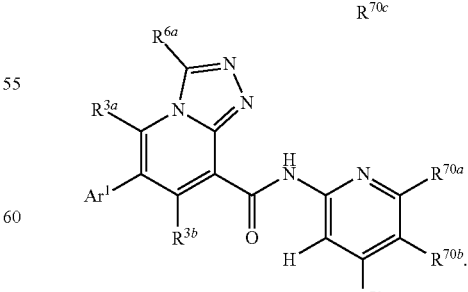
In a further aspect, a compound has a structure represented by a formula

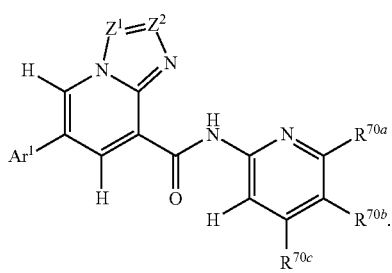
In a further aspect, a compound has a structure represented by a formula selected from:
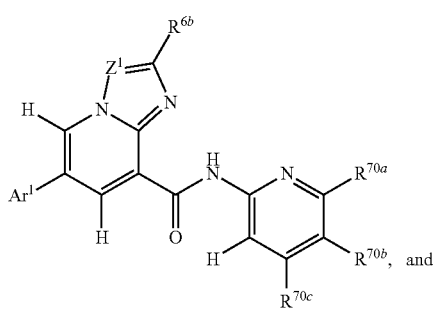
In yet a further aspect, a compound has a structure represented by a formula selected from:
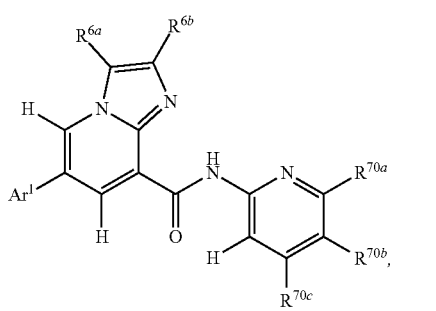
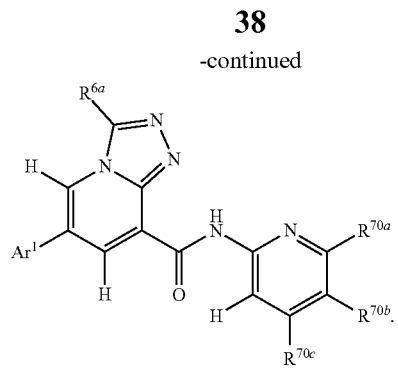
In an even further aspect, a compound has a structure represented by a formula:
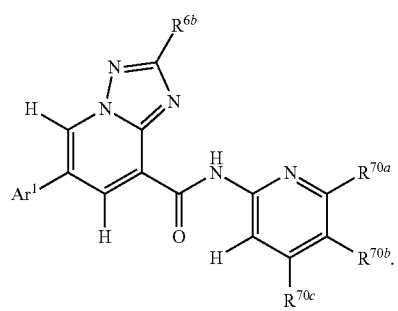
In an sill further aspect, a compound has a structure represented by a formula selected from:
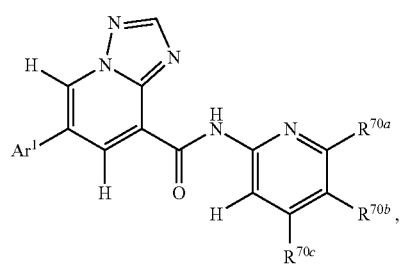
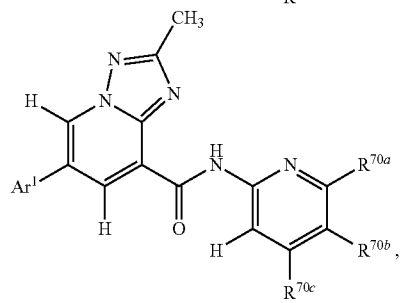
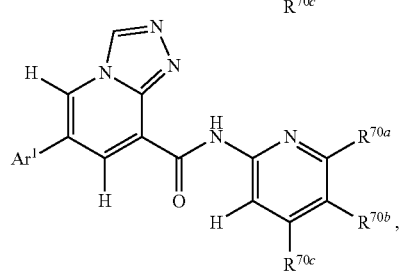

-continued

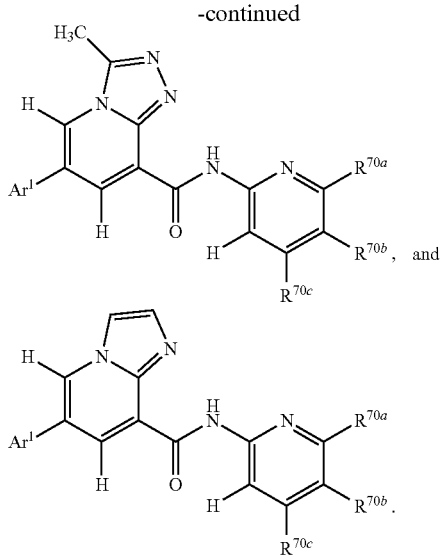

In a further aspect, a compound has a structure represented by a formula:

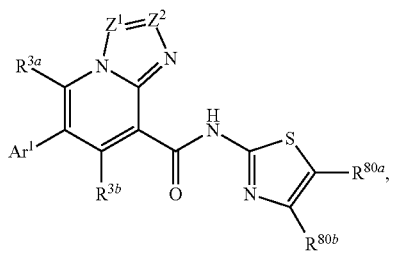

wherein each of $R^{80a}$ and $R^{80b}$ is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$.

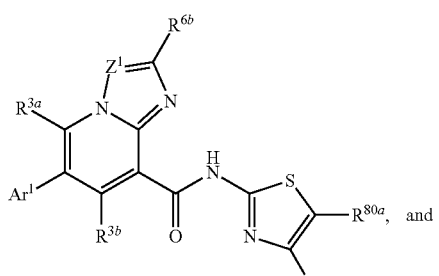

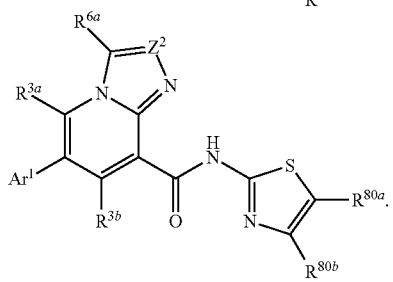

In yet a further aspect, a compound has a structure represented by a formula selected from:

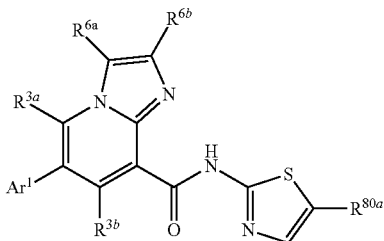

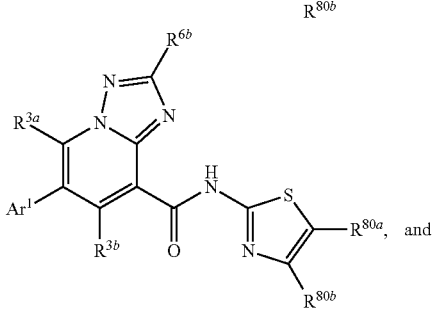

In a further aspect, a compound has a structure represented by a formula:

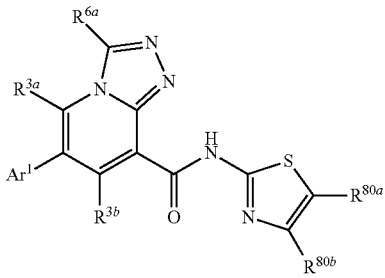

In a still further aspect, a compound has a structure represented by a formula selected from:

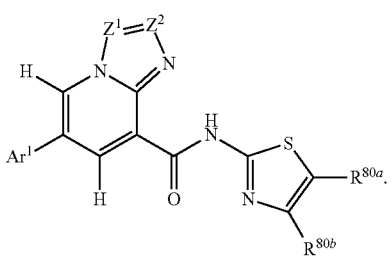

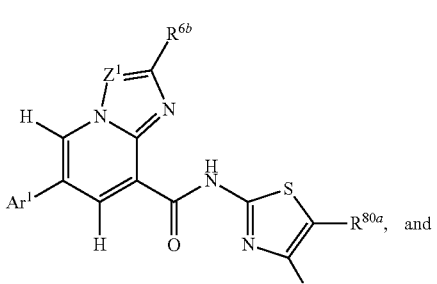

-continued
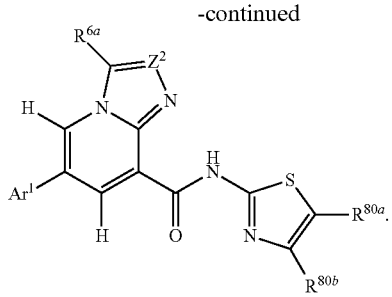
In yet a further aspect, a compound has a structure represented by a formula selected from:
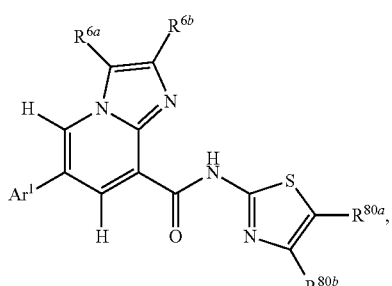
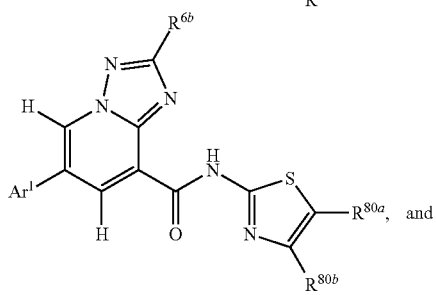
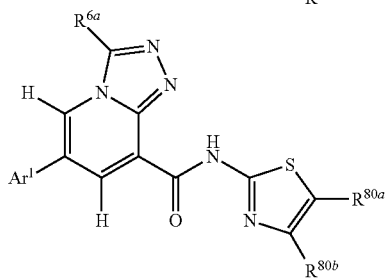
In an even further aspect, a compound has a structure represented by a formula:
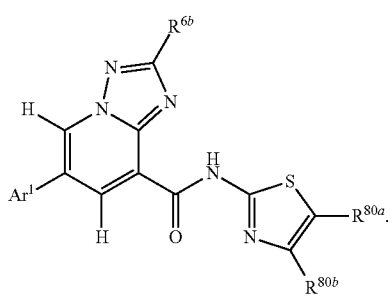
In a still further aspect, a compound has a structure represented by a formula selected from:
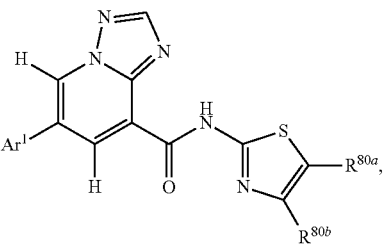
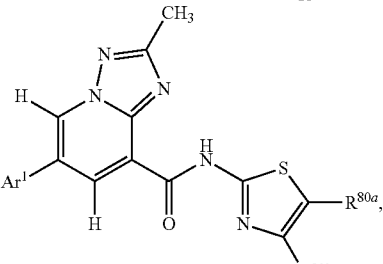
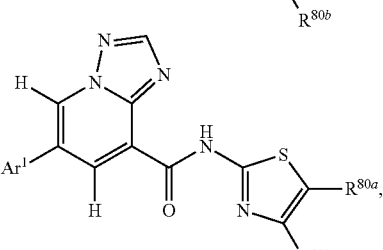
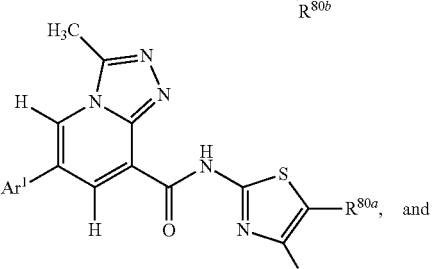
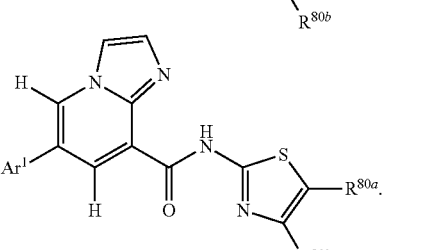
In a further aspect, a compound has a structure represented by a formula:
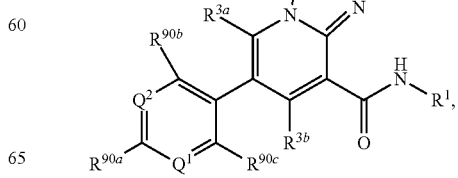

wherein $Q^1$ is selected from N and $CR^{5a}$; and wherein $Q^2$ is selected from N and $CR^{5b}$; wherein each of $R^{5a}$ and $R^{5b}$, when present, is independently selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein each of $R^{90a}$, $R^{90b}$, and $R^{90c}$ is independently selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(CO)$R^{33}$, provided that at least one of $R^{90a}$, $R^{90b}$, and $R^{90c}$ is hydrogen.

In a still further aspect, a compound has a structure represented by a formula selected from:

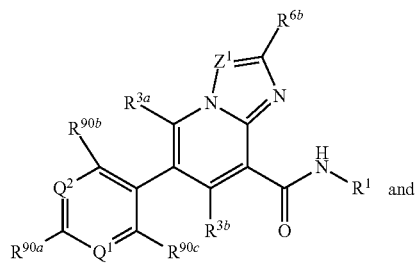

In yet a further aspect, a compound has a structure represented by a formula selected from:

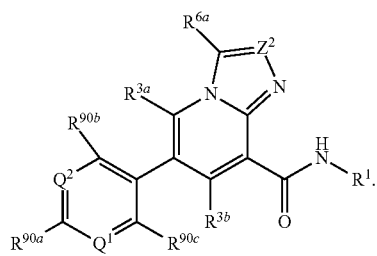

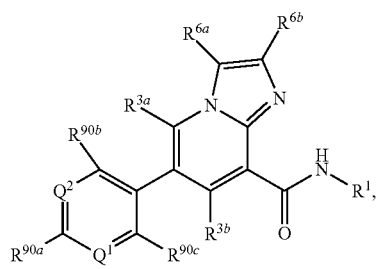

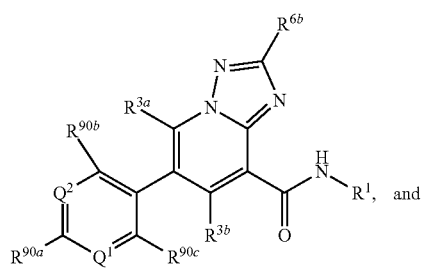

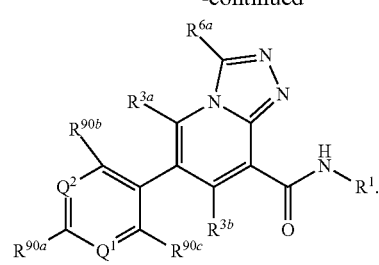

In a further aspect, a compound has a structure represented by a formula:

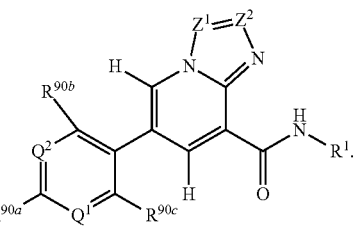

In a still further aspect, a compound has a structure represented by a formula selected from:

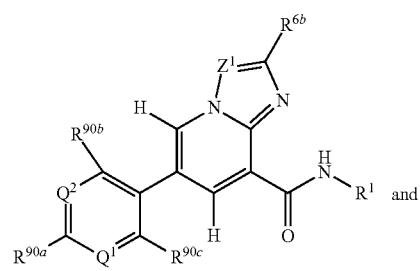

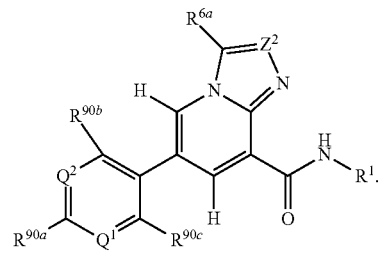

In yet a further aspect, a compound has a structure represented by a formula selected from:

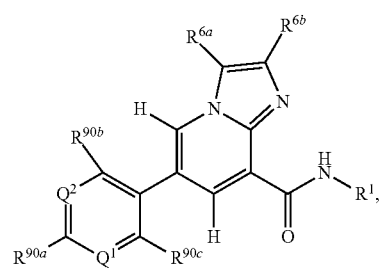

-continued

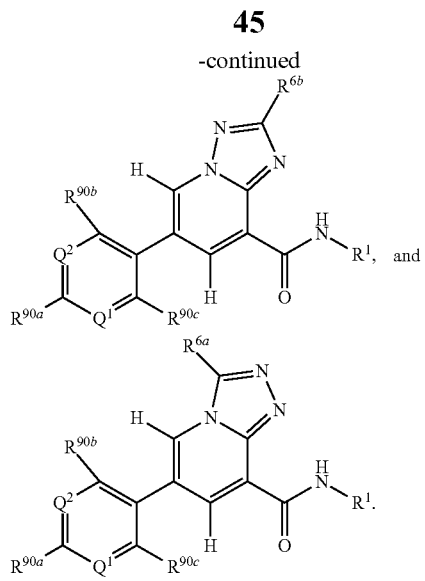

and

In an even further aspect, a compound has a structure represented by a formula:

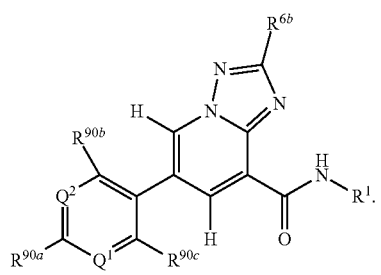

In a further aspect, a compound has a structure represented by a formula:

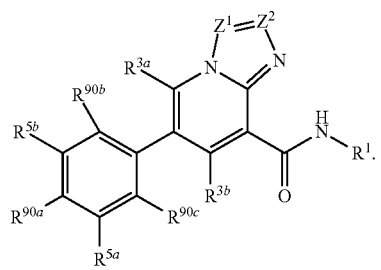

In a still further aspect, a compound has a structure represented by a formula selected from:

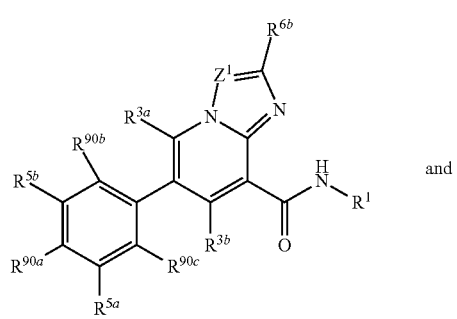

and

-continued

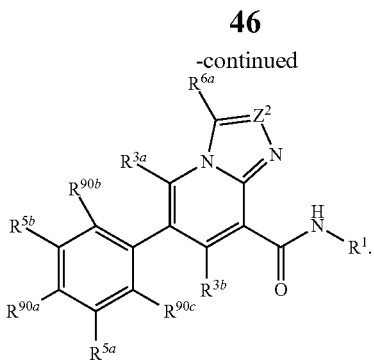

In yet a further aspect, a compound has a structure represented by a formula selected from:

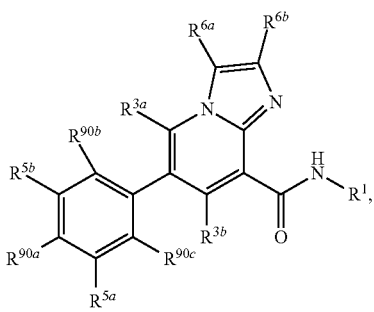

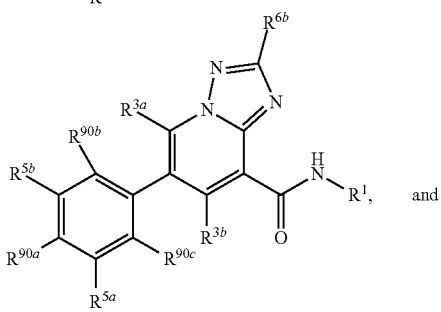

and

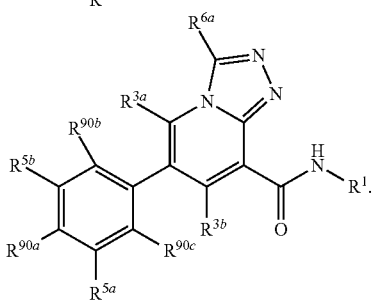

In a further aspect, a compound has a structure represented by a formula:

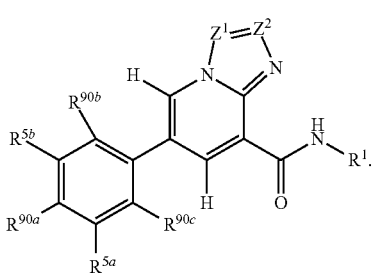

In a still further aspect, a compound has a structure represented by a formula selected from:

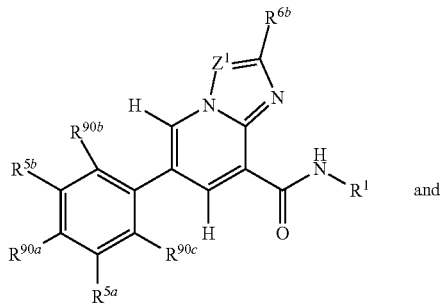

and

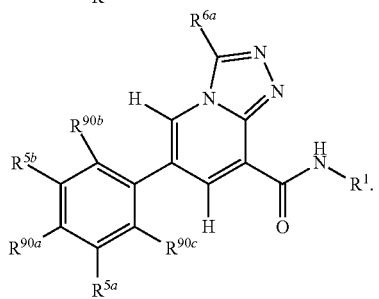

In yet a further aspect, a compound has a structure represented by a formula selected from:

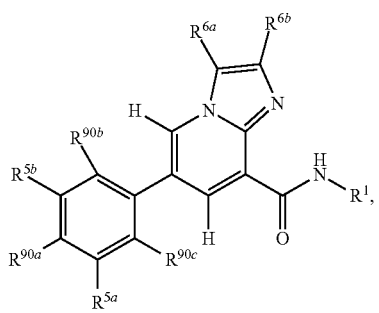

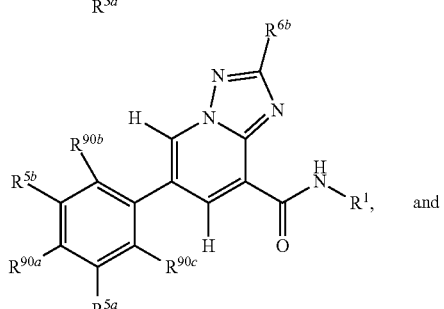

and

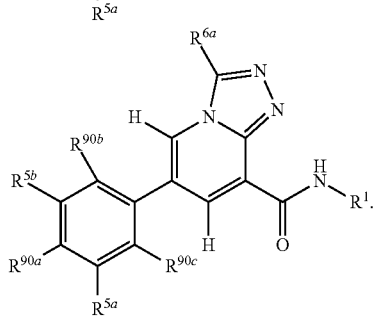

In an even further aspect, a compound has a structure represented by a formula:

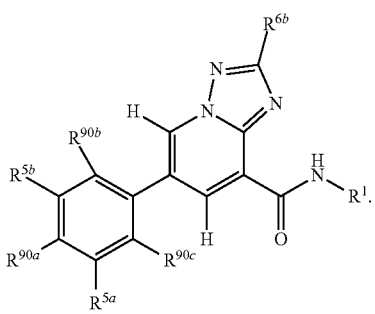

In a further aspect, a compound has a structure represented by a formula:

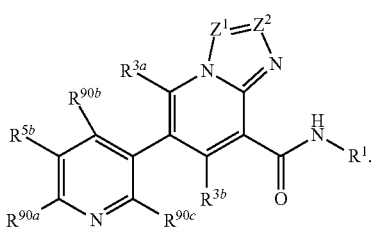

In a still further aspect, a compound has a structure represented by a formula selected from:

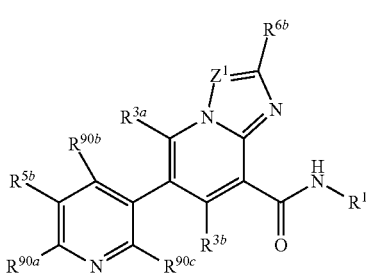

and

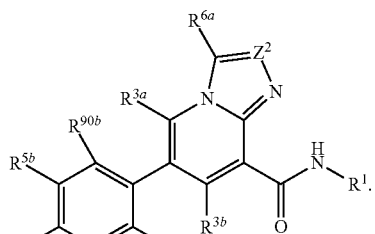

In yet a further aspect, a compound has a structure represented by a formula selected from:

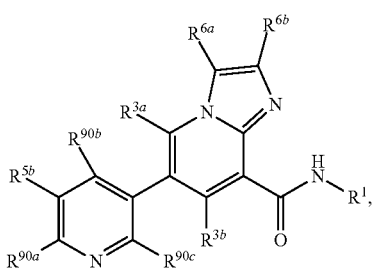

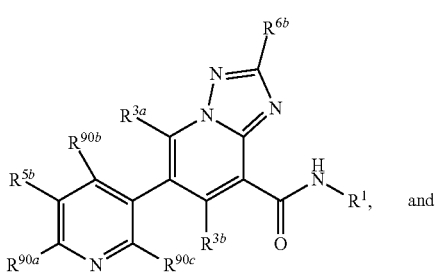

and

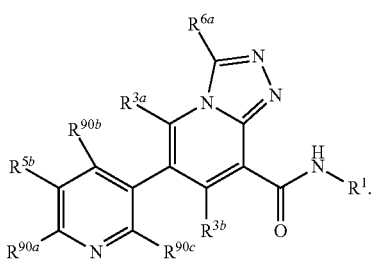

In a further aspect, a compound has a structure represented by a formula:

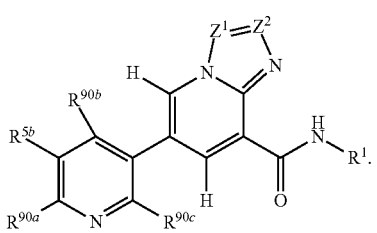

In a still further aspect, a compound has a structure represented by a formula selected from:

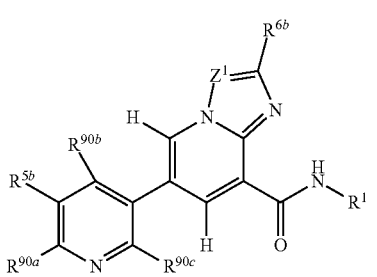

and

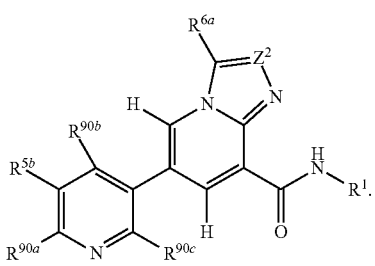

In yet a further aspect, a compound has a structure represented by a formula selected from:

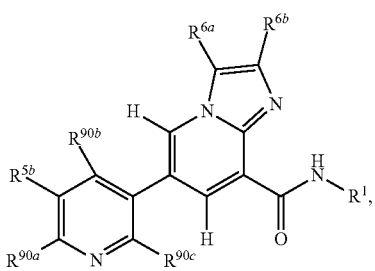

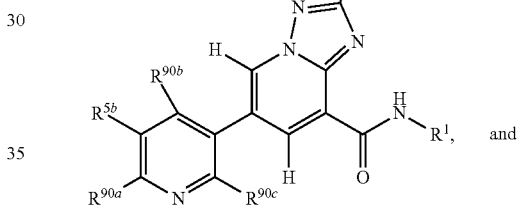

and

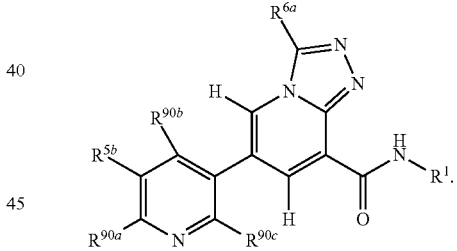

In an even further aspect, a compound has a structure represented by a formula:

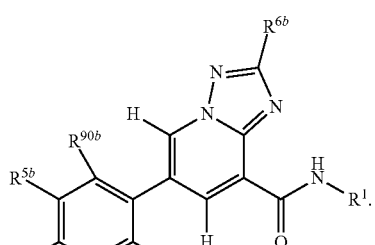

In a further aspect, a compound has a structure represented by a formula:

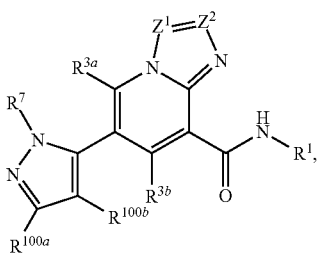

wherein R[7] is selected from hydrogen, C1-C4 alkyl, C1-C4 monohaloalkyl C1-C4 polyhaloalkyl, and —(C═O)R[33]; and wherein each of R[100a] and R[100b] is independently selected from hydrogen, halogen, —CN, C1-C3 alkyl, C1-C3 monohaloalkyl, C1-C3 polyhaloalkyl, cyclopropyl, —OR[30], —NR[31a]R[31b], —SO$_2$R[32], and —(C═O)R[33].

In a still further aspect, a compound has a structure represented by a formula selected from:

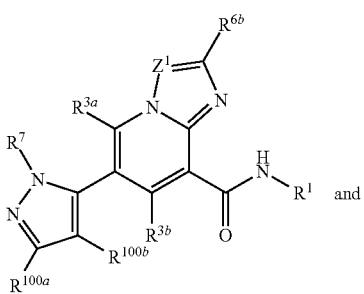

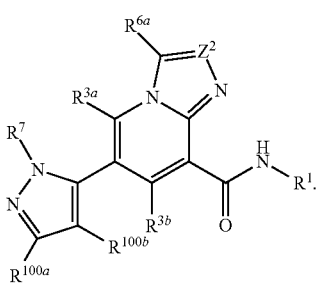

In yet a further aspect, a compound has a structure represented by a formula selected from:

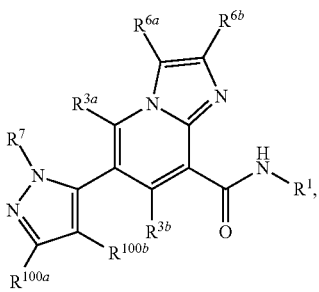

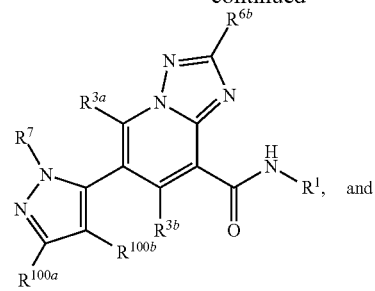

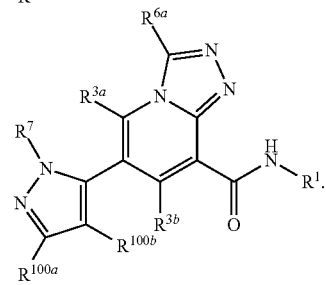

In a further aspect, a compound has a structure represented by a formula:

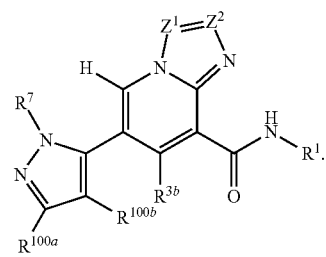

In a still further aspect, a compound has a structure represented by a formula selected from:

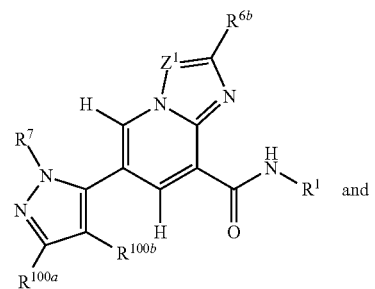

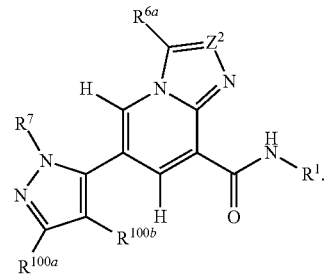

In yet a further aspect, a compound has a structure represented by a formula selected from:

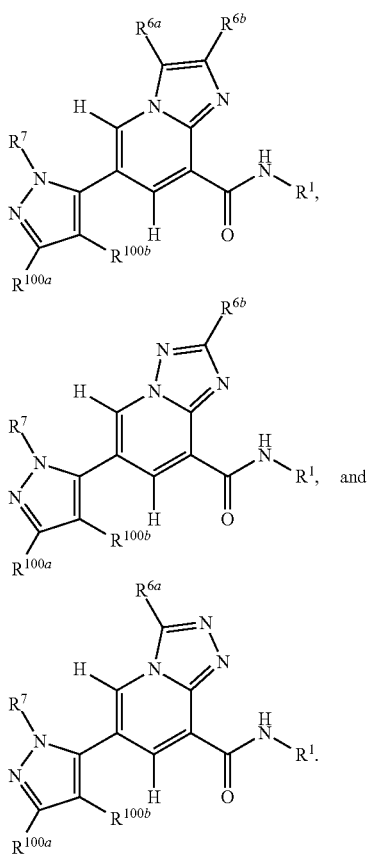

In an even further aspect, a compound has a structure represented by a formula:

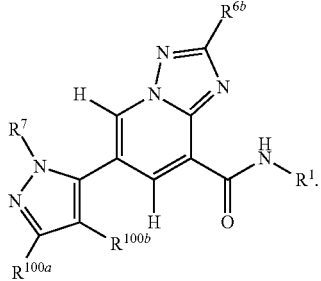

a. Q¹ and Q² Groups

In one aspect, $Q^1$ is selected from N and $CR^{5a}$ and $Q^2$ is selected from N and $CR^{5b}$. In a still further aspect, $Q^1$ is N and $Q^2$ is selected from N and $CR^{5b}$. In yet a further aspect, $Q^1$ is N and $Q^2$ is $CR^{5b}$. In an even further aspect, $Q^1$ is selected from N and $CR^{5a}$ and $Q^2$ is N. In a still further aspect, $Q^1$ is $CR^{5a}$ and $Q^2$ is N. In yet a further aspect, $Q^1$ is $CR^{5a}$ and $Q^2$ is $CR^{5b}$. In an even further aspect, each of $Q^1$ and $Q^2$ is N.

b. Z¹ and Z² Groups

In one aspect, $Z^1$ is selected from N and $CR^{6a}$ and $Z^2$ is selected from N and $CR^{6b}$, provided that $Z^1$ and $Z^2$ are not simultaneously N. In a further aspect, $Z^1$ is N and $Z^2$ is $CR^{6b}$. In a still further aspect, $Z^1$ is $CR^{6a}$ and $Z^2$ is N. In yet a further aspect, $Z^1$ is $CR^{6a}$ and $Z^2$ is $CR^{6b}$.

c. R¹ Groups

In one further aspect, $R^1$ is heteroaryl substituted with 0, 1, 2, or 3 groups independently selected from halogen, —N, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a further aspect, $R^1$ is heteroaryl substituted with 0, 1, or 2 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a still further aspect, $R^1$ is heteroaryl substituted with 0 or 1 group selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In yet a further aspect, $R^1$ is heteroaryl monosubstituted with a group selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In an even further aspect, $R^1$ is unsubstituted heteroaryl.

In a further aspect, $R^1$ is pyridinyl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a still further aspect, $R^1$ is pyridinyl substituted with 0, 1, or 2 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In yet a further aspect, $R^1$ is pyridinyl substituted with 0 or 1 group selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In an even further aspect, $R^1$ is pyridinyl monosubstituted with a group selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a still further aspect, $R^1$ is unsubstituted pyridinyl.

In a further aspect, $R^1$ is thiazolyl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a still further aspect, $R^1$ is thiazolyl substituted with 0, 1 or 2 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In yet a further aspect, $R^1$ is thiazole substituted with 0 or 1 group selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a even further aspect, $R^1$ is thiazolyl monosubstituted with a group selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$. In a still further aspect, $R^1$ is unsubstituted thiazolyl.

In a further aspect, $R^1$ is pyridinyl substituted with 0, 1, 2, or 3 groups independently selected from —F, —Cl, —CN, methyl, ethyl, —$CH_2F$, —$CH_2CH_2F$, —$CHF_2$, —$CF_3$, cyclopropyl, —OH, —$OCH_3$, —$OCH_2F$, —$OCHF_2$, —$OCF_3$, —O-cyclopropyl, —$NH_2$, —$NHCH_3$, —$N(CH_3)_2$, —$SO_2CH_3$, —$SO_2CH_2F$, —$SO_2CHF_2$, —$SO_2CF_3$, —$SO_2$-cyclopropyl, —$SO_2$—$NH_2$, —$SO_2$—$NHCH_3$, —$SO_2$—$N(CH_3)_2$, —$(C=O)CH_3$, —$(C=O)CH_2CH_3$, —$(C=O)CH_2F$, —$(C=O)CH_2CH_2F$, —$(C=O)CHF_2$, —$(C=O)CF_3$, —$(C=O)NH_2$, —$(C=O)NHCH_3$, and —$(C=O)N(CH_3)_2$. In a still further aspect, $R^1$ is pyridinyl substituted with 0, 1, 2, or 3 groups independently selected from —F, —Cl, —CN, methyl, —$CH_2F$, —$CHF_2$, —$CF_3$, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C=O)CH₃, —(C=O)CF₃, —(C=O)NH₂, —(C=O)NHCH₃, and —(C=O)N(CH₃)₂. In yet a further aspect, R¹ is pyridinyl substituted with 0, 1, 2, or 3 groups independently selected from —F, —Cl, methyl, —CF₃, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, R¹ is pyridinyl substituted with 0, 1, 2, or 3 groups selected from —F, —Cl, methyl, —CF₃, —OH, —OCH₃, —OCF₃, —NH₂, —NHCH₃, and —N(CH₃)₂. In a still further aspect, R¹ is pyridinyl substituted with 0, 1, 2, or 3 groups selected from —F, —Cl, methyl, and —CF₃. In yet a further aspect, R¹ is pyridinyl substituted with 0, 1, 2, or 3 groups independently selected from —F and methyl.

In a further aspect, R¹ is pyridinyl substituted with 0, 1, or 2 groups independently selected from —F, —Cl, —CN, methyl, ethyl, —CH₂F, —CH₂CH₂F, —CHF₂, —CF₃, cyclopropyl, —OH, —OCH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, —SO₂—N(CH₃)₂, —(C=O)CH₃, —(C=O)CH₂CH₃, —(C=O)CH₂F, —(C=O)CH₂CH₂F, —(C=O)CHF₂, —(C=O)CF₃, —(C=O)NH₂, —(C=O)NHCH₃, and —(C=O)N(CH₃)₂. In a still further aspect, R¹ is pyridinyl substituted with 0, 1, or 2 groups independently selected from —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C=O)CH₃, —(C=O)CF₃, —(C=O)NH₂, —(C=O)NHCH₃, and —(C=O)N(CH₃)₂. In yet a further aspect, R¹ is pyridinyl substituted with 0, 1, or 2 groups independently selected from —F, —Cl, methyl, —CF₃, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, R¹ is pyridinyl substituted with 0, 1, or 2 groups independently selected from —F, —Cl, methyl, —CF₃, —OH, —OCH₃, —OCF₃, —NH₂, —NHCH₃, and —N(CH₃)₂. In a still further aspect, R¹ is pyridinyl substituted with 0, 1, or 2 groups independently selected from —F, —Cl, methyl, and —CF₃. In yet a further aspect, R¹ is pyridinyl substituted with 0, 1, or 2 groups independently selected from —F and methyl.

In a further aspect, R¹ is pyridinyl substituted with 0 or 1 group selected from —F, —Cl, —CN, methyl, ethyl, —CH₂F, —CH₂CH₂F, —CHF₂, —CF₃, cyclopropyl, —OH, —OCH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, —SO₂—N(CH₃)₂, —(C=O)CH₃, —(C=O)CH₂CH₃, —(C=O)CH₂F, —(C=O)CH₂CH₂F, —(C=O)CHF₂, —(C=O)CF₃, —(C=O)NH₂, —(C=O)NHCH₃, and —(C=O)N(CH₃)₂. In a still further aspect, R¹ is pyridinyl substituted with 0 or 1 group selected from —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C=O)CH₃, —(C=O)CF₃, —(C=O)NH₂, —(C=O)NHCH₃, and —(C=O)N(CH₃)₂. In yet a further aspect, R¹ is pyridinyl substituted with 0 or 1 group selected from —F, —Cl, methyl, —CF₃, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, R¹ is pyridinyl substituted with 0 or 1 group selected from —F, —Cl, methyl, —CF₃, —OH, —OCH₃, —OCF₃, —NH₂, —NHCH₃, and —N(CH₃)₂. In a still further aspect, R¹ is pyridinyl substituted with 0 or 1 group selected from —F, —Cl, methyl, and —CF₃. In yet a further aspect, R¹ is pyridinyl substituted with 0 or 1 group selected from —F and methyl.

In a further aspect, R¹ is pyridinyl monosubstituted with a group selected from —F, —Cl, —CN, methyl, ethyl, —CH₂F, —CH₂CH₂F, —CHF₂, —CF₃, cyclopropyl, —OH, —OCH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, —SO₂—N(CH₃)₂, —(C=O)CH₃, —(C=O)CH₂CH₃, —(C=O)CH₂F, —(C=O)CH₂CH₂F, —(C=O)CHF₂, —(C=O)CF₃, —(C=O)NH₂, —(C=O)NHCH₃, and —(C=O)N(CH₃)₂. In a still further aspect, R¹ is pyridinyl monosubstituted with a group selected from —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C=O)CH₃, —(C=O)CF₃, —(C=O)NH₂, —(C=O)NHCH₃, and —(C=O)N(CH₃)₂. In yet a further aspect, R¹ is pyridinyl monosubstituted with a group selected from —F, —Cl, methyl, —CF₃, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, R¹ is pyridinyl monosubstituted with a group selected from —F, —Cl, methyl, —CF₃, —OH, —OCH₃, —OCF₃, —NH₂, —NHCH₃, and —N(CH₃)₂. In a still further aspect, R¹ is pyridinyl monosubstituted a group selected from —F, —Cl, methyl, and —CF₃. In yet a further aspect, R¹ is pyridinyl monosubstituted a group selected from —F and methyl. In an even further aspect, R¹ is pyridinyl monosubstituted with —F. In a still further aspect, R¹ is pyridinyl monosubstituted with methyl.

In a further aspect, R¹ is pyridinyl substituted with 2 groups independently selected from —F, —Cl, —CN, methyl, ethyl, —CH₂F, —CH₂CH₂F, —CHF₂, —CF₃, cyclopropyl, —OH, —OCH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, —SO₂—N(CH₃)₂, —(C=O)CH₃, —(C=O)CH₂CH₃, —(C=O)CH₂F, —(C=O)CH₂CH₂F, —(C=O)CHF₂, —(C=O)CF₃, —(C=O)NH₂, —(C=O)NHCH₃, and —(C=O)N(CH₃)₂. In a still further aspect, R¹ is pyridinyl substituted with 2 groups independently selected from —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C=O)CH₃, —(C=O)CF₃, —(C=O)NH₂, —(C=O)NHCH₃, and —(C=O)N(CH₃)₂. In yet a further aspect, R¹ is pyridinyl substituted with 2 groups independently selected from —F, —Cl, methyl, —CF₃, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, R¹ is pyridinyl substituted with 2 groups independently selected from —F, —Cl, methyl, —CF₃, —OH, —OCH₃, —OCF₃, —NH₂, —NHCH₃, and —N(CH₃)₂. In a still further aspect, R¹ is pyridinyl substituted with 2 groups independently selected from —F, —Cl, methyl, and —CF₃. In yet a further aspect, R¹ is pyridinyl substituted with 2 groups independently selected from —F and methyl. In an even further aspect, $R^1$ is pyridinyl disubstituted with —F. In a still further aspect, $R^1$ is pyridinyl disubstituted with -methyl.

In a further aspect, thiazolyl substituted with 0, 1, 2, or 3 groups independently selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, $R^1$ is thiazolyl substituted with 0, 1, 2, or 3 groups independently selected from —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, $R^1$ is thiazolyl substituted with 0, 1, 2, or 3 groups independently selected from —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^1$ is thiazolyl substituted with 0, 1, 2, or 3 groups independently selected from —F, —Cl, methyl, —CF$_3$, —OH, —OCH$_3$, —OCF$_3$, —NH$_2$, —NHCH$_3$, and —N(CH$_3$)$_2$. In a still further aspect, $R^1$ is thiazolyl substituted with 0, 1, 2, or 3 groups independently selected from —F, —Cl, methyl, and —CF$_3$. In yet a further aspect, $R^1$ is thiazolyl substituted with 0, 1, 2, or 3 groups independently selected from —F and methyl.

In a further aspect, $R^1$ is thiazolyl substituted with 0, 1, or 2 groups independently selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, $R^1$ is thiazolyl substituted with 0, 1, or 2 groups independently selected from —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, $R^1$ is thiazolyl substituted with 0, 1, or 2 groups independently selected from —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^1$ is thiazolyl substituted with 0, 1, or 2 groups independently selected from —F, —Cl, methyl, —CF$_3$, —OH, —OCH$_3$, —OCF$_3$, —NH$_2$, —NHCH$_3$, and —N(CH$_3$)$_2$. In a still further aspect, $R^1$ is thiazolyl substituted with 0, 1, or 2 groups independently selected from —F, —Cl, methyl, and —CF$_3$. In yet a further aspect, $R^1$ is thiazolyl substituted with 0, 1, or 2 groups independently selected from —F and methyl.

In a further aspect, $R^1$ is thiazolyl substituted with 0 or 1 group selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, $R^1$ is thiazolyl substituted with 0 or 1 group selected from —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, $R^1$ is thiazolyl substituted with 0 or 1 group selected from —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^1$ is thiazolyl substituted with 0 or 1 group selected from —F, —Cl, methyl, —CF$_3$, —OH, —OCH$_3$, —OCF$_3$, —NH$_2$, —NHCH$_3$, and —N(CH$_3$)$_2$. In a still further aspect, $R^1$ is thiazolyl substituted with 0 or 1 group selected from —F, —Cl, methyl, and —CF$_3$. In yet a further aspect, $R^1$ is thiazolyl substituted with 0 or 1 group selected from —F and methyl.

In a further aspect, $R^1$ is thiazolyl monosubstituted with a group selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, $R^1$ is thiazolyl monosubstituted with a group selected from —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, $R^1$ is thiazolyl monosubstituted with a group selected from —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^1$ is thiazolyl monosubstituted with a group selected from —F, —Cl, methyl, —CF$_3$, —OH, —OCH$_3$, —OCF$_3$, —NH$_2$, —NHCH$_3$, and —N(CH$_3$)$_2$. In a still further aspect, $R^1$ is thiazolyl monosubstituted with a group selected from —F, —Cl, methyl, and —CF$_3$. In yet a further aspect, $R^1$ is thiazolyl monosubstituted with a group selected from —F and methyl. In an even further aspect, $R^1$ is thiazolyl monosubstituted with —F. In a still further aspect, $R^1$ is thiazolyl monosubstituted with methyl.

In a further aspect, $R^1$ is thiazolyl substituted with 2 groups independently selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, $R^1$ is thiazolyl substituted with 2 groups independently selected from —F, —Cl, —CN, methyl, —CH$_2$F, —CHF$_2$, —CF$_3$, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂. In yet a further aspect, R¹ is thiazolyl substituted with 2 groups independently selected from —F, —Cl, methyl, —CF₃, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, R¹ is thiazolyl substituted with 2 groups independently selected from —F, —Cl, methyl, —CF₃, —OH, —OCH₃, —OCF₃, —NH₂, —NHCH₃, and —N(CH₃)₂. In a still further aspect, R¹ is thiazolyl substituted with 2 groups independently selected from —F, —Cl, methyl, and —CF₃. In yet a further aspect, R¹ is thiazolyl substituted with 2 groups independently selected from —F and methyl. In an even further aspect, R¹ is thiazolyl disubstituted with —F. In a still further aspect, R¹ is thiazolyl disubstituted with -methyl.

d. $R^{3a}$ and $R^{3b}$ Groups

In one aspect, each of $R^{3a}$ and $R^{3b}$ is independently selected from hydrogen and fluoro. In a further aspect, $R^{3a}$ is hydrogen and $R^{3b}$ is fluoro. In a still further aspect, $R^{3b}$ is hydrogen and $R^{3a}$ is fluoro. In yet a further aspect, each of $R^{3a}$ and $R^{3b}$ is fluoro. In an even further aspect, each of $R^{3a}$ and $R^{3b}$ is hydrogen.

e. $R^{5a}$ and $R^{5b}$ Groups

In one aspect, each of $R^{5a}$ and $R^{5b}$, when present, is independently selected from hydrogen, halogen, —CN, C1-C3 alkyl, C1-C3 monohaloalkyl, C1-C3 polyhaloalkyl, cyclopropyl, —OR³⁰, —NR³¹ᵃR³¹ᵇ, —SO₂R³², and —(C═O)R³³. In a further aspect, each of $R^{5a}$ and $R^{5b}$, when present, is independently selected from hydrogen, —F, —Cl, —CN, methyl, ethyl, —CH₂F, —CH₂CH₂F, —CHF₂, —CF₃, cyclopropyl, —OH, —OCH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, —SO₂—N(CH₃)₂, —(C═O)CH₃, —(C═O)CH₂CH₃, —(C═O)CH₂F, —(C═O)CH₂CH₂F, —(C═O)CHF₂, —(C═O)CF₃, —(C═O)NH₂, —(C═O)NHCH₃, and —(C═O)N(CH₃)₂. In a still further aspect, each of $R^{5a}$ and $R^{5b}$, when present, is independently selected from hydrogen, —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂. In a yet further aspect, each of $R^{5a}$ and $R^{5b}$, when present, is independently selected from hydrogen, —F, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂. In an even further aspect, each of $R^{5a}$ and $R^{5b}$, when present, is independently selected from hydrogen, —F, —CN, methyl, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂.

In a further aspect, each of $R^{5a}$ and $R^{5b}$, when present, is independently selected from halogen, —CN, C1-C3 alkyl, C1-C3 monohaloalkyl, C1-C3 polyhaloalkyl, cyclopropyl, —OR³⁰, —NR³¹ᵃR³¹ᵇ, —SO₂R³², and —(C═O)R³³. In a yet further aspect, each of $R^{5a}$ and $R^{5b}$ when present, is independently selected from —F, —Cl, —CN, methyl, ethyl, —CH₂F, —CH₂CH₂F, —CHF₂, —CF₃, cyclopropyl, —OH, —CH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, —SO₂—N(CH₃)₂, —(C═O)CH₃, —(C═O)CH₂CH₃, —(C═O)CH₂F, —(C═O)CH₂CH₂F, —(C═O)CHF₂, —(C═O)CF₃, —(C═O)NH₂, —(C═O)NHCH₃, and —(C═O)N(CH₃)₂. In an even further aspect, each of $R^{5a}$ and $R^{5b}$, when present, is independently selected from —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂. In a still further aspect, each of $R^{5a}$ and $R^{5b}$, when present, is independently selected from —F, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂. In a yet further aspect, each of $R^{5a}$ and $R^{5b}$, when present, is independently selected from —F, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, —SO₂—N(CH₃)₂, —(C═O)CH₃, —(C═O)CF₃, —(C═O)NH₂, —(C═O)NHCH₃, and —(C═O)N(CH₃)₂.

In a further aspect, each of $R^{5a}$ and $R^{5b}$, when present, is independently selected from hydrogen, halogen, —CN, C1-C3 alkyl, C1-C3 monohaloalkyl, C1-C3 polyhaloalkyl, cyclopropyl, —OR³⁰, —NR³¹ᵃR³¹ᵇ, and —SO₂R³². In a yet further aspect, each of $R^{5a}$ and $R^{5b}$ when present, is independently selected from hydrogen, —F, —Cl, —CN, methyl, ethyl, —CH₂F, —CH₂Cl, —CH₂CH₂F, —CHF₂, —CF₃, cyclopropyl, —OH, —OCH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, and —SO₂—N(CH₃)₂. In an even further aspect, each of $R^{5a}$ and $R^{5b}$, when present, is independently selected from hydrogen, —F, —Cl, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In a still further aspect, each of $R^{5a}$ and $R^{5b}$, when present, is independently selected from hydrogen, —F, —CN, methyl, —CH₂F, —CHF₂, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂. In an even further aspect, each of $R^{5a}$ and $R^{5b}$, when present, is independently selected from hydrogen, —F, —CN, methyl, —CF₃, cyclopropyl, —OH, —OCH₃, —OCF₃, —NH₂, —NHCH₃, —N(CH₃)₂, —SO₂CH₃, —SO₂CF₃, —SO₂—NH₂, —SO₂—NHCH₃, and —SO₂—N(CH₃)₂.

In a further aspect, each of $R^{5a}$ and $R^{5b}$, when present, is independently selected from hydrogen, halogen, —CN, C1-C3 alkyl, C1-C3 monohaloalkyl, C1-C3 polyhaloalkyl, cyclopropyl, —OR³⁰, —NR³¹ᵃR³¹ᵇ, and —SO₂R³². In a still further aspect, each of $R^{5a}$ and $R^{5b}$ when present, is independently selected from hydrogen, —F, —Cl, methyl, ethyl, —CH₂F, —CH₂CH₂F, —CHF₂, —CF₃, cyclopropyl, —OH, —CH₃, —OCH₂F, —OCHF₂, —OCF₃, —O-cyclopropyl, —NH₂, —NHCH₃, —N(CH₃)₂, —SO₂CH₃, —SO₂CH₂F, —SO₂CHF₂, —SO₂CF₃, —SO₂-cyclopropyl, —SO₂—NH₂, —SO₂—NHCH₃, and —SO₂—N(CH₃)₂. In an even further aspect, each of $R^{5a}$ and $R^{5b}$, when present, is independently selected from hydrogen, —F, —Cl, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a yet further aspect, each of $R^{5a}$ and $R^{5b}$, when present, is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of $R^{5a}$ and $R^{5b}$, when present, is independently selected from hydrogen, —F, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of $R^{5a}$ and $R^{5b}$, when present, is independently selected from hydrogen, halogen, C1-C3 alkyl, C1-C3 monohaloalkyl, C1-C3 polyhaloalkyl, —OR$^{30}$, —NR$^{31a}$R$^{31b}$, and —SO$_2$R$^{32}$. In yet further aspect, each of $R^{5a}$ and $R^{5b}$, when present, is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a still further aspect, each of $R^{5a}$ and $R^{5b}$, when present, is independently selected from hydrogen, —F, —Cl, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of $R^{5a}$ and $R^{5b}$, when present, is independently selected from hydrogen, —F, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of $R^{5a}$ and $R^{5b}$, when present, is independently selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of $R^{5a}$ and $R^{5b}$, when present, is independently selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of $R^{5a}$ and $R^{5b}$, when present, is independently selected from hydrogen, halogen, —CN, C1-C3 alkyl, C1-C3 monohaloalkyl, C1-C3 polyhaloalkyl, cyclopropyl, —OR$^{30}$, and —NR$^{31a}$R$^{31b}$. In a yet further aspect, each of $R^{5a}$ and $R^{5b}$, when present, is independently selected from hydrogen, —F, —Cl, —CN, methyl, ethyl, —CH$_2$F, —CH$_2$CH$_2$F, —CHF$_2$, —CF$_3$, cyclopropyl, —OH, —CH$_3$, —OCH$_2$F, —OCHF$_2$, —OCF$_3$, —O-cyclopropyl, —NH$_2$, —NHCH$_3$, and —N(CH$_3$)$_2$. In a still further aspect, each of $R^{5a}$ and $R^{5b}$, when present, is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In an even further aspect, each of $R^{5a}$ and $R^{5b}$, when present, is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$.

In a further aspect, each of $R^{5a}$ and $R^{5b}$, when present, is independently selected from hydrogen, halogen, C1-C3 alkyl, C1-C3 monohaloalkyl, C1-C3 polyhaloalkyl, cyclopropyl, —OR$^{30}$, and —NR$^{31a}$R$^{31b}$. In a yet further aspect, each of $R^{5a}$ and $R^{5b}$, when present, is independently selected from hydrogen, —F, —Cl, methyl, ethyl, —CH$_2$F, —CH$_2$CH$_2$F, —CHF$_2$, —CF$_3$, cyclopropyl, —OH, —CH$_3$, —OCH$_2$F, —OCHF$_2$, —OCF$_3$, —O-cyclopropyl, —NH$_2$, —NHCH$_3$, and —N(CH$_3$)$_2$. In an even further aspect, each of $R^{5a}$ and $R^{5b}$, when present, is independently selected from hydrogen, —F, —Cl, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a yet further aspect, each of $R^{5a}$ and $R^{5b}$, when present, is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, each of $R^{5a}$ and $R^{5b}$, when present, is independently selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, each of $R^{5a}$ and $R^{5b}$, when present, is independently selected from hydrogen, halogen, C1-C3 alkyl, C1-C3 monohaloalkyl, C1-C3 polyhaloalkyl, —OR$^{30}$ and —NR$^{31a}$R$^{31b}$. In an even further aspect, each of $R^{5a}$ and $R^{5b}$, when present, is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, each of $R^{5a}$ and $R^{5b}$, when present, is independently selected from hydrogen, —F, —Cl, methyl, —CH$_2$F, —CHF$_2$, —CF$_3$, —OH, —OCH$_3$, —OCF$_3$, —NH$_2$, —NHCH$_3$, and —N(CH$_3$)$_2$. In a still further aspect, each of $R^{5a}$ and $R^{5b}$, when present, is independently selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In an even further aspect, each of $R^{5a}$ and $R^{5b}$ when present, is independently selected from hydrogen, —F, —Cl, methyl, —CF$_3$, —OH, —OCH$_3$, —OCF$_3$, —NH$_2$, —NHCH$_3$, and —N(CH$_3$)$_2$. In a yet further aspect, each of $R^{5a}$ and $R^{5b}$, when present, is independently selected from hydrogen, —F, methyl, —CF$_3$, —OH, —OCH$_3$, —OCF$_3$, —NH$_2$, —NHCH$_3$, and —N(CH$_3$)$_2$.

In a further aspect, each of $R^{5a}$ and $R^{5b}$, when present, is independently selected from hydrogen, halogen, C1-C3 alkyl, C1-C3 monohaloalkyl, C1-C3 polyhaloalkyl, and cyclopropyl. In an even further aspect, each of $R^{5a}$ and $R^{5b}$, when present, is independently selected from hydrogen, —F, —Cl, methyl, ethyl, —CH$_2$F, —CH$_2$CH$_2$F, —CHF$_2$, —CF$_3$, and cyclopropyl. In a yet further aspect, each of $R^{5a}$ and $R^{5b}$, when present, is independently selected from hydrogen, —F, —Cl, methyl, —CH$_2$F, —CHF$_2$, —CF$_3$, and cyclopropyl. In a still further aspect, each of $R^{5a}$ and $R^{5b}$, when present, is independently selected from hydrogen, —F, methyl, —CH$_2$F, —CHF$_2$, —CF$_3$, and cyclopropyl. In an even further aspect, each of $R^{5a}$ and $R^{5b}$, when present, is independently selected from hydrogen, —F, methyl, —CF$_3$, and cyclopropyl.

In a further aspect, each of $R^{5a}$ and $R^{5b}$, when present, is independently selected from hydrogen, halogen, C1-C3 alkyl, C1-C3 monohaloalkyl, and C1-C3 polyhaloalkyl. In a still further aspect, each of $R^{5a}$ and $R^{5b}$, when present, is independently selected from hydrogen, —F, —Cl, methyl, ethyl, —CH$_2$F, —CH$_2$CH$_2$F, —CHF$_2$, and —CF$_3$. In an even further aspect, each of $R^{5a}$ and $R^{5b}$, when present, is independently selected from hydrogen, —F, —Cl, methyl, —CH$_2$F, —CHF$_2$, and —CF$_3$. In a yet further aspect, each of R$^{5a}$ and R$^{5b}$ when present, is independently selected from hydrogen, —F, methyl, —CH$_2$F, —CHF$_2$, and —CF$_3$. In a still further aspect, each of R$^{5a}$ and R$^{5b}$, when present, is independently selected from hydrogen, —F, —Cl, methyl, and —CF$_3$. In an even further aspect, each of R$^{5a}$ and R$^{5b}$ when present, is independently selected from hydrogen, —F, methyl, and —CF$_3$.

In a further aspect, each of R$^{5a}$ and R$^{5b}$, when present, is independently selected from hydrogen, halogen, and C1-C3 alkyl. In a still further aspect, each of R$^{5a}$ and R$^{5b}$, when present, is independently selected from hydrogen, —F, —Cl, methyl, and ethyl. In an even further aspect, each of R$^{5a}$ and R$^{5b}$, when present, is independently selected from hydrogen, —F, —Cl, and methyl. In a yet further aspect, each of R$^{5a}$ and R$^{5b}$, when present, is independently selected from hydrogen, —F, and methyl.

In a further aspect, each of R$^{5a}$ and R$^{5b}$, when present, is independently selected from hydrogen and C1-C3 alkyl. In a still further aspect, each of R$^{5a}$ and R$^{5b}$, when present, is independently selected from hydrogen, methyl, and ethyl. In an even further aspect, each of R$^{5a}$ and R$^{5b}$, when present, is independently selected from hydrogen and methyl.

In a further aspect, each of R$^{5a}$ and R$^{5b}$, when present, is —F. In a still further aspect, each of R$^{5a}$ and R$^{5b}$, when present, is —Cl. In an even further aspect, each of R$^{5a}$ and R$^{5b}$, when present, is methyl. In a still further aspect, each of R$^{5a}$ and R$^{5b}$, when present, is —CF$_3$. In a yet further aspect, each of R$^{5a}$ and R$^{5b}$, when present, is hydrogen.

In a further aspect, each of R$^{3a}$, R$^{3b}$, R$^{5a}$, and R$^{5b}$, when present, is hydrogen.

In a further aspect, each of R$^{5a}$ and R$^{5b}$, when present, is —F and each of R$^{3a}$ and R$^{3b}$, when present, is hydrogen.

f. R$^{6a}$ and R$^{6b}$ Groups

In one aspect, each of R$^{6a}$ and R$^{6b}$, when present, is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$. In a further aspect, each of R$^{6a}$ and R$^{6b}$, when present is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, each of R$^{6a}$ and R$^{6b}$, when present, is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a yet further aspect, each of R$^{6a}$ and R$^{6b}$, when present, is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, each of R$^{6a}$ and R$^{6b}$, when present, is independently selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, each of R$^{6a}$ and R$^{6b}$, when present, is independently selected from halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$. In a still further aspect, each of R$^{6a}$ and R$^{6b}$ when present, is independently selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$.

In a yet further aspect, each of R$^{6a}$ and R$^{6b}$, when present, is independently selected from —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, each of R$^{6a}$ and R$^{6b}$, when present, is independently selected from —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a still further aspect, each of R$^{6a}$ and R$^{6b}$, when present, is independently selected from —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —(C=O)N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, each of R$^{6a}$ and R$^{6b}$, when present, is independently selected from halogen, —CN, C1-C3 alkyl, C1-C3 monohaloalkyl, C1-C3 polyhaloalkyl, cyclopropyl, —OR$^{40}$, —NR$^{41a}$R$^{41b}$, and —SO$_2$R$^{42}$. In a still further aspect, each of R$^{6a}$ and R$^{6b}$ when present, is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, each of R$^{6a}$ and R$^{6b}$, when present, is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{6a}$ and R$^{6b}$, when present, is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{6a}$ and R$^{6b}$, when present, is independently selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{6a}$ and R$^{6b}$, when present, is independently selected from hydrogen, halogen, C1-C3 alkyl, C1-C3 monohaloalkyl, C1-C3 polyhaloalkyl, cyclopropyl, —OR$^{40}$, —NR$^{41a}$R$^{41b}$, and —SO$_2$R$^{42}$. In a still further aspect, each of R$^{6a}$ and R$^{6b}$ when present, is independently selected from hydrogen, —F, —Cl, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, each of R$^{6a}$ and R$^{6b}$, when present, is independently selected from hydrogen, —F, —Cl, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{6a}$ and R$^{6b}$, when present, is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{6a}$ and R$^{6b}$, when present, is independently selected from hydrogen, —F, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{6a}$ and R$^{6b}$, when present, is independently selected from hydrogen, halogen, C1-C3 alkyl, C1-C3 monohaloalkyl, C1-C3 polyhaloalkyl, —OR$^{40}$, —NR$^{41a}$R$^{41b}$, and —SO$_2$R$^{42}$. In a still further aspect, each of R$^{6a}$ and R$^{6b}$, when present, is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, each of R$^{6a}$ and R$^{6b}$, when present, is independently selected from hydrogen, —F, —Cl, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{6a}$ and R$^{6b}$, when present, is independently selected from hydrogen, —F, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{6a}$ and R$^{6b}$, when present, is independently selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a yet further aspect, each of R$^{6a}$ and R$^{6b}$, when present, is independently selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{6a}$ and R$^{6b}$, when present, is independently selected from hydrogen, halogen, —CN, C1-C3 alkyl, C1-C3 monohaloalkyl, C1-C3 polyhaloalkyl, cyclopropyl, OR$^{40}$ and —NR$^{41a}$R$^{41b}$. In a still further aspect, each of R$^{6a}$ and R$^{6b}$, when present, is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, each of R$^{6a}$ and R$^{6b}$, when present, is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In an even further aspect, each of R$^{6a}$ and R$^{6b}$, when present, is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, each of R$^{6a}$ and R$^{6b}$, when present, is independently selected from hydrogen, —F, —CN, methyl, —CF$_3$, cyclopropyl, —OH, —OCH$_3$, —OCF$_3$, —NH$_2$, —NHCH$_3$, and —N(CH$_3$)$_2$.

In a further aspect, each of R$^{6a}$ and R$^{6b}$, when present, is independently selected from hydrogen, halogen, C1-C3 alkyl, C1-C3 monohaloalkyl, C1-C3 polyhaloalkyl, cyclopropyl, —OR$^{40}$, and —NR$^{41a}$R$^{41b}$. In a still further aspect, each of R$^{6a}$ and R$^{6b}$, when present, is independently selected from hydrogen, —F, —Cl, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, each of R$^{6a}$ and R$^{6b}$, when present, is independently selected from hydrogen, —F, —Cl, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In an even further aspect, each of R$^{6a}$ and R$^{6b}$, when present, is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, each of R$^{6a}$ and R$^{6b}$, when present, is independently selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, each of R$^{6a}$ and R$^{6b}$, when present, is independently selected from hydrogen, halogen, C1-C3 alkyl, C1-C3 monohaloalkyl, C1-C3 polyhaloalkyl, —OR$^{40}$ and —NR$^{41a}$R$^{41b}$. In a still further aspect, each of R$^{6a}$ and R$^{6b}$, when present, is independently selected from hydrogen, —F, —Cl, methyl, ethyl, —CH$_2$F, —CH$_2$CH$_2$F, —CF$_2$, —CF$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, each of R$^{6a}$ and R$^{6b}$, when present, is independently selected from hydrogen, —F, —Cl, methyl, —CH$_2$F, —CHF$_2$, —CF$_3$, —OH, —OCH$_3$, —OCF$_3$, —NH$_2$, —NHCH$_3$, and —N(CH$_3$)$_2$. In an even further aspect, each of R$^{6a}$ and R$^{6b}$, when present, is independently selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In a still further aspect, each of R$^{6a}$ and R$^{6b}$, when present, is independently selected from hydrogen, —F, —Cl, methyl, —CF$_3$, —OH, —OCH$_3$, —OCF$_3$, —NH$_2$, —NHCH$_3$, and —N(CH$_3$)$_2$. In a yet further aspect, each of R$^{6a}$ and R$^{6b}$, when present, is independently selected from hydrogen, —F, methyl, —CF$_3$, —OH, —OCH$_3$, —OCF$_3$, —NH$_2$, —NHCH$_3$, and —N(CH$_3$)$_2$.

In a further aspect, each of R$^{6a}$ and R$^{6b}$, when present, is independently selected from hydrogen, halogen, C1-C3 alkyl, C1-C3 monohaloalkyl, C1-C3 polyhaloalkyl, and cyclopropyl. In a still further aspect, each of R$^{6a}$ and R$^{6b}$, when present, is independently selected from hydrogen, —F, —Cl, methyl, ethyl, —CH$_2$F, —CH$_2$CH$_2$F, —CF$_2$, —CF$_3$, and cyclopropyl. In a yet further aspect, each of R$^{6a}$ and R$^{6b}$, when present, is independently selected from hydrogen, —F, —Cl, methyl, —CH$_2$F, —CHF$_2$, —CF$_3$, and cyclopropyl. In an even further aspect, each of R$^{6a}$ and R$^{6b}$, when present, is independently selected from hydrogen, —F, methyl, —CH$_2$F, —CHF$_2$, —CF$_3$, and cyclopropyl. In a still further aspect, each of R$^{6a}$ and R$^{6b}$, when present, is independently selected from hydrogen, —F, methyl, —CF$_3$, and cyclopropyl.

In a further aspect, each of R$^{6a}$ and R$^{6b}$, when present, is independently selected from hydrogen, halogen, C1-C3 alkyl, C1-C3 monohaloalkyl, and C1-C3 polyhaloalkyl. In a still further aspect, each of $R^{6a}$ and $R^{6b}$, when present, is independently selected from hydrogen, —F, —Cl, methyl, ethyl, —CH$_2$F, —CH$_2$CH$_2$F, —CHF$_2$, and —CF$_3$. In yet a further aspect, each of $R^{6a}$ and $R^{6b}$, when present, is independently selected from hydrogen, —F, —Cl, methyl, —CH$_2$F, —CHF$_2$, and —CF$_3$. In an even further aspect, each of $R^{6a}$ and $R^{6b}$, when present, is independently selected from hydrogen, —F, methyl, —CH$_2$F, —CHF$_2$, and —CF$_3$. In a still further aspect, each of $R^{6a}$ and $R^{6b}$, when present, is independently selected from hydrogen, —F, —Cl, methyl, and —CF$_3$. In a yet further aspect, each of $R^{6a}$ and $R^{6b}$, when present, is independently selected from hydrogen, —F, methyl, and —CF$_3$.

In a further aspect, each of $R^{6a}$ and $R^{6b}$, when present, is independently selected from hydrogen, halogen, and C1-C3 alkyl. In a still further aspect, each of $R^{6a}$ and $R^{6b}$, when present, is independently selected from hydrogen, —F, —Cl, methyl, and ethyl. In yet a further aspect, each of $R^{6a}$ and $R^{6b}$, when present, is independently selected from hydrogen, —F, —Cl, and methyl. In an even further aspect, each of $R^{6a}$ and $R^{6b}$, when present, is independently selected from hydrogen, —F, and methyl.

In a further aspect, each of $R^{6a}$ and $R^{6b}$, when present, is independently selected from hydrogen and C1-C3 alkyl. In a still further aspect, each of $R^{6a}$ and $R^{6b}$, when present, is independently selected from hydrogen, methyl, and ethyl. In yet a further aspect, each of $R^{6a}$ and $R^{6b}$, when present, is independently selected from hydrogen and methyl.

In a further aspect, each of $R^{6a}$ and $R^{6b}$, when present, is —F. In a still further aspect, each of $R^{6a}$ and $R^{6b}$, when present, is —Cl. In yet a further aspect, each of $R^{6a}$ and $R^{6b}$, when present, is methyl. In an even further aspect, each of $R^{6a}$ and $R^{6b}$, when present, is —CF$_3$. In still a further aspect, each of $R^{6a}$ and $R^{6b}$, when present, is hydrogen.

In a further aspect, each of $R^{3a}$, $R^{3b}$, $R^{6a}$, and $R^{6b}$, when present, is hydrogen.

g. $R^7$ Groups

In one aspect, $R^7$ is selected from hydrogen, C1-C4 alkyl, C1-C4 monohaloalkyl, C1-C4 polyhaloalkyl, and —(C=O)R$^{33}$. In a further aspect, $R^7$ is hydrogen. In a further aspect, $R^7$ is selected from hydrogen, methyl, ethyl, propyl, isopropyl, n-butyl, sec-butyl, isobutyl, tert-butyl, —CH$_2$F, —CHF$_2$, —CF$_3$, —CH$_2$CH$_2$F, —CH$_2$CHF$_2$, —CH$_2$CF$_3$, and —(C=O)R$^{33}$. In a still further aspect, $R^7$ is selected from hydrogen, methyl, ethyl, propyl, isopropyl, —CH$_2$F, —CHF$_2$, —CF$_3$, —CH$_2$CH$_2$F, —CH$_2$CHF$_2$, —CH$_2$CF$_3$, and —C=R$^{33}$. In yet a further aspect, $R^7$ is selected from hydrogen, methyl, ethyl, —CH$_2$F, —CHF$_2$, —CF$_3$, —CH$_2$CH$_2$F, —CH$_2$CHF$_2$, —CH$_2$CF$_3$, and —(C=O)R$^{33}$. In an even further aspect, $R^7$ is selected from hydrogen, methyl, —CH$_2$F, —CHF$_2$, —CF$_3$, and —(C=O)R$^{33}$.

In a further aspect, $R^7$ is selected from hydrogen and C1-C4 alkyl. In a yet further aspect, $R^7$ is selected from hydrogen, methyl, ethyl, propyl, isopropyl, n-butyl, sec-butyl, isobutyl, and tert-butyl. In a still further aspect, $R^7$ is selected from hydrogen, methyl, ethyl, propyl, and isopropyl. In yet a further aspect, $R^7$ is selected from hydrogen, methyl, and ethyl. In an even further aspect, $R^7$ is selected from hydrogen and ethyl. In a still further aspect, $R^7$ is selected from hydrogen and methyl.

In a further aspect, $R^7$ is C1-C4 alkyl. In a yet further aspect, $R^7$ is selected from methyl, ethyl, propyl, isopropyl, n-butyl, sec-butyl, isobutyl, and tert-butyl. In a still further aspect, $R^7$ is selected from methyl, ethyl, propyl, and isopropyl. In yet a further aspect, $R^7$ is selected from methyl and ethyl. In an even further aspect, $R^7$ is ethyl. In a still further aspect, $R^7$ is and methyl.

In a further aspect, $R^7$ is selected from hydrogen, C1-C4 monohaloalkyl, and C1-C4 polyhaloalkyl. In a still further aspect, $R^7$ is selected from hydrogen, —CH$_2$F, —CHF$_2$, —CF$_3$, —CH$_2$CH$_2$F, —CH$_2$CHF$_2$, and —CH$_2$CF$_3$. In yet a further aspect, $R^7$ is selected from hydrogen, —CH$_2$F, —CHF$_2$, and —CF$_3$. In an even further aspect, $R^7$ is selected from hydrogen and —CH$_2$F. In a still further aspect, $R^7$ is selected from hydrogen and —CHF$_2$. In yet a further aspect, $R^7$ is selected from hydrogen and —CF$_3$.

In a further aspect, $R^7$ is selected from hydrogen and —(C=O)R$^{33}$. In a still further aspect, $R^7$ is selected from hydrogen, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)CH$_2$CHF$_2$, —(C=O)CH$_2$CF$_3$, —(C=O)CH$_2$CHCl$_2$, —(C=O)CH$_2$CCl$_3$, —(C=O)-cyclopropyl, —(C=O)NHCH$_3$, —(C=O)NHCH$_2$CH$_3$, —(C=O)NH(CH$_2$)$_2$CH$_3$, —(C=O)NHCH(CH$_3$)$_2$, —(C=O)N(CH$_3$)$_2$, —(C=O)N(CH$_3$)CH$_2$CH$_3$, —(C=O)N(CH$_3$)(CH$_2$)$_2$CH$_3$, —(C=O)N(CH$_3$)CH(CH$_3$)$_2$, and —(C=O)N(CH$_2$CH$_3$)$_2$. In a yet further aspect, $R^7$ is selected from hydrogen, —(C=O)CH$_3$, —(C=O)CH$_2$F, —(C=O)CHF$_2$, —(C=O)CF$_3$, —(C=O)-cyclopropyl, —(C=O)NHCH$_3$, and —(C=O)N(CH$_3$)$_2$. In an even further aspect, $R^7$ is selected from hydrogen, —(C=O)CH$_3$, —(C=O)CH$_2$F, —(C=O)CHF$_2$, —(C=O)CF$_3$, —(C=O)-cyclopropyl, —(C=O)NHCH$_3$, and —(C=O)N(CH$_3$)$_2$. In a still further aspect, R is selected from hydrogen, —(C=O)CH$_3$, —(C=O)CF$_3$, —(C=O)-cyclopropyl, and —(C=O)NHCH$_3$.

In a further aspect, $R^7$ is —(C=O)R$^{33}$. In a still further aspect, $R^7$ is selected from —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)CH$_2$CHF$_2$, —(C=O)CH$_2$CF$_3$, —(C=O)-cyclopropyl, —(C=O)NHCH$_3$, —(C=O)NHCH$_2$CH$_3$, —(C=O)NH(CH$_2$)$_2$CH$_3$, —(C=O)NHCH(CH$_3$)$_2$, —(C=O)N(CH$_3$)$_2$, —(C=O)N(CH$_3$)CH$_2$CH$_3$, —(C=O)N(CH$_3$)(CH$_2$)$_2$CH$_3$, —(C=O)N(CH$_3$)CH(CH$_3$)$_2$, and —(C=O)N(CH$_2$CH$_3$)$_2$. In a yet further aspect, R is selected from —(C=O)CH$_3$, —(C=O)CH$_2$F, —(C=O)CHF$_2$, —(C=O)CF$_3$, —(C=O)-cyclopropyl, —(C=O)NHCH$_3$, and —(C=O)N(CH$_3$)$_2$. In an even further aspect, R is selected from —(C=O)CH$_3$, —(C=O)CH$_2$F, —(C=O)CHF$_2$, —(C=O)CF$_3$, —(C=O)-cyclopropyl, —(C=O)NHCH$_3$, and —(C=O)N(CH$_3$)$_2$. In a still further aspect, $R^7$ is selected from —(C=O)CH$_3$, —(C=O)CF$_3$, —(C=O)-cyclopropyl, and —(C=O)NHCH$_3$.

h. $R^{30}$ Groups

In one aspect, $R^{30}$, when present, is selected from hydrogen, C1-C3 alkyl, C1-C3 monohaloalkyl, C1-C3 polyhaloalkyl, and cyclopropyl. In a further aspect, $R^{30}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, $R^{30}$, when present, is selected from hydrogen, methyl, —CH$_2$F, —CHF$_2$, —CF$_3$, and cyclopropyl. In a yet further aspect, $R^{30}$, when present, is selected from hydrogen, methyl, —CH$_2$F, —CHF$_2$, —CF$_3$, and cyclopropyl. In an even further aspect, $R^{30}$, when present, is selected from hydrogen, methyl, —CF$_3$, and cyclopropyl.

In a further aspect, $R^{30}$, when present, is selected from hydrogen, C1-C3 monohaloalkyl, C1-C3 polyhaloalkyl, and cyclopropyl. In a still further aspect, $R^{30}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In a yet further aspect, $R^{30}$, when present, is selected from hydrogen, —CH$_2$F, —CH$_2$Cl, —CHF$_2$, —CF$_3$, and cyclopropyl. In a still further aspect, R$^{30}$ when present, is selected from hydrogen, —CH$_2$F, —CHF$_2$, —CF$_3$, and cyclopropyl. In a yet further aspect, R$^{30}$, when present, is selected from hydrogen, —CF$_3$ and cyclopropyl.

In a further aspect, R$^{30}$, when present, is selected from hydrogen, C1-C3 alkyl, and cyclopropyl. In a still further aspect, R$^{30}$, when present, is selected from hydrogen, methyl, ethyl, and cyclopropyl. In a yet further aspect, R$^{30}$, when present, is selected from hydrogen, methyl, and cyclopropyl.

In a further aspect, R$^{30}$, when present, is selected from hydrogen, C1-C3 alkyl, C1-C3 monohaloalkyl, and C1-C3 polyhaloalkyl. In a still further aspect, R$^{30}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In a yet further aspect, R$^{30}$, when present, is selected from hydrogen, methyl, —CH$_2$F, —CHF$_2$, and —CF$_3$. In an even further aspect, R$^{30}$, when present, is selected from hydrogen, methyl, and —CF$_3$.

In a further aspect, R$^{30}$, when present, is selected from hydrogen, C1-C3 monohaloalkyl, and C1-C3 polyhaloalkyl. In a still further aspect, R$^{30}$, when present, is selected from hydrogen, —CH$_2$F, —CH$_2$CH$_2$F, —CHF$_2$, —CF$_3$, —CH$_2$CHF$_2$, and —CH$_2$CF$_3$. In a yet further aspect, R$^{30}$, when present, is selected from hydrogen, —CH$_2$F, —CHF$_2$, and —CF$_3$. In an even further aspect, R$^{30}$, when present, is selected from hydrogen and —CF$_3$.

In a further aspect, R$^{30}$, when present, is selected from hydrogen and C1-C3 alkyl. In a still further aspect, R$^{30}$, when present, is selected from hydrogen, methyl, and ethyl. In a yet further aspect, R$^{30}$, when present, is selected from hydrogen and methyl. In an even further aspect, R$^{30}$, when present, is hydrogen.

i. R$^{31a}$ and R$^{31b}$ Groups

In one aspect, each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with the nitrogen atom to which they are attached, comprise a 3- to 6-membered heterocycle.

In a further aspect, each of R$^{31a}$ and R$^{31b}$, when present, is independently selected from hydrogen, C1-C3 alkyl, C1-C3 monohaloalkyl, C1-C3 polyhaloalkyl, and cyclopropyl. In a still further aspect, each of R$^{31a}$ and R$^{31b}$, when present, is independently selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of R$^{31a}$ and R$^{31b}$, when present, is independently selected from hydrogen, methyl, —CH$_2$F, —CHF$_2$, —CF$_3$, and cyclopropyl. In an even aspect, each of R$^{31a}$ and R$^{31b}$, when present, is independently selected from hydrogen, methyl, —CF$_3$, and cyclopropyl.

In a further aspect, each of R$^{31a}$ and R$^{31b}$, when present, is independently selected from hydrogen, C1-C3 monohaloalkyl, C1-C3 polyhaloalkyl, and cyclopropyl. In a still further aspect, each of R$^{31a}$ and R$^{31b}$, when present, is independently selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of R$^{31a}$ and R$^{31b}$, when present, is independently selected from hydrogen, —CH$_2$F, —CHF$_2$, —CF$_3$, and cyclopropyl. In an even further aspect, each of R$^{31a}$ and R$^{31b}$, when present, is independently selected from hydrogen, —CF$_3$ and cyclopropyl.

In a further aspect, each of R$^{31a}$ and R$^{31b}$, when present, is independently selected from hydrogen, C1-C3 alkyl, and cyclopropyl. In a still further aspect, each of R$^{31a}$ and R$^{31b}$, when present, is independently selected from hydrogen, methyl, ethyl, and cyclopropyl. In yet a further aspect, each of R$^{31a}$ and R$^{31b}$, when present, is independently selected from hydrogen, methyl, and cyclopropyl.

In a further aspect, each of R$^{31a}$ and R$^{31b}$, when present, is independently selected from hydrogen, C1-C3 alkyl, C1-C3 monohaloalkyl, and C1-C3 polyhaloalkyl. In a still further aspect, each of R$^{31a}$ and R$^{31b}$, when present, is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, each of R$^{31a}$ and R$^{31b}$, when present, is independently selected from hydrogen, methyl, —CH$_2$F, —CHF$_2$, and —CF$_3$. In an even further aspect, each of R$^{31a}$ and R$^{31b}$, when present, is independently selected from hydrogen, methyl, and —CF$_3$.

In a further aspect, each of R$^{31a}$ and R$^{31b}$, when present, is independently selected from hydrogen, C1-C3 monohaloalkyl, and C1-C3 polyhaloalkyl. In a still further aspect, each of R$^{31a}$ and R$^{31b}$, when present, is independently selected from hydrogen, —CH$_2$F, —CH$_2$CH$_2$F, —CHF$_2$, —CF$_3$, —CH$_2$CHF$_2$, and —CH$_2$CF$_3$. In yet a further aspect, each of R$^{31a}$ and R$^{31b}$, when present, is independently selected from hydrogen, —CH$_2$F, —CHF$_2$, and —CF$_3$. In an even further aspect, each of R$^{31a}$ and R$^{31b}$, when present, is independently selected from hydrogen and —CF$_3$.

In a further aspect, each of R$^{31a}$ and R$^{31b}$, when present, is independently selected from hydrogen and C1-C3 alkyl. In a still further aspect, each of R$^{31a}$ and R$^{31b}$, when present, is independently selected from hydrogen, methyl, and ethyl. In yet a further aspect, each of R$^{31a}$ and R$^{31b}$, when present, is independently selected from hydrogen and methyl. In an even further aspect, R$^{31a}$, when present, is hydrogen and R$^{31b}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, R$^{31a}$, when present, is hydrogen R$^{31b}$, when present, is selected from hydrogen, methyl, —CH$_2$F, —CHF$_2$, —CF$_3$, and cyclopropyl. In yet a further aspect, R$^{31a}$, when present, is hydrogen and R$^{31b}$, when present, is selected from hydrogen, methyl, —CF$_3$, and cyclopropyl.

In a further aspect, R$^{31a}$, when present, is hydrogen and R$^{31b}$, when present, is selected from hydrogen, C1-C3 monohaloalkyl, C1-C3 polyhaloalkyl, and cyclopropyl. In a still further aspect, R$^{31a}$, when present, is hydrogen and R$^{31b}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, R$^{31a}$, when present, is hydrogen and R$^{31b}$, when present, is selected from hydrogen, —CH$_2$F, —CHF$_2$, —CF$_3$, and cyclopropyl. In yet a further aspect, R$^{31a}$, when present, is hydrogen and R$^{31b}$, when present, is selected from hydrogen, —CF$_3$ and cyclopropyl.

In a further aspect, R$^{31a}$, when present, is hydrogen and R$^{31b}$, when present, is selected from hydrogen, C1-C3 alkyl, and cyclopropyl. In a still further aspect, R$^{31a}$, when present, is hydrogen and R$^{31b}$, when present, is selected from hydrogen, methyl, ethyl, and cyclopropyl. In yet a further aspect, R$^{31a}$, when present, is hydrogen and R$^{31b}$, when present, is selected from hydrogen, methyl, and cyclopropyl.

In a further aspect, R$^{31a}$, when present, is hydrogen and R$^{31b}$, when present, is selected from hydrogen, C1-C3 alkyl, C1-C3 monohaloalkyl, and C1-C3 polyhaloalkyl. In a still further aspect, R$^{31a}$, when present, is hydrogen and R$^{31b}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, R$^{31a}$, when present, is hydrogen and $R^{31b}$, when present, is selected from hydrogen, methyl, —CH$_2$F, —CHF$_2$, and —CF$_3$. In an even further aspect, $R^{31a}$, when present, is hydrogen and $R^{31b}$, when present, is selected from hydrogen, methyl, and —CF$_3$.

In a further aspect, $R^{31a}$, when present, is hydrogen and $R^{31b}$, when present, is selected from hydrogen, C1-C3 monohaloalkyl, and C1-C3 polyhaloalkyl. In a still further aspect, $R^{31a}$, when present, is hydrogen and $R^{31b}$, when present, is selected from hydrogen, —CH$_2$F, —CH$_2$CH$_2$F, —CHF$_2$, —CF$_3$, —CH$_2$CHF$_2$, and —CH$_2$CF$_3$. In yet a further aspect, $R^{31a}$, when present, is hydrogen and $R^{31b}$, when present, is selected from hydrogen, —CH$_2$F, —CHF$_2$, and —CF$_3$. In an even further aspect, $R^{31a}$, when present, is hydrogen and $R^{31b}$, when present, is selected from hydrogen and —CF$_3$.

In a further aspect, $R^{31a}$, when present, is hydrogen and $R^{31b}$, when present, is selected from hydrogen and C1-C3 alkyl. In a still further aspect, $R^{31a}$, when present, is hydrogen and $R^{31b}$, when present, is selected from hydrogen, methyl, and ethyl. In yet a further aspect, $R^{31a}$, when present, is hydrogen and $R^{31b}$, when present, is selected from hydrogen and methyl. In an even further aspect, each of $R^{31a}$ and $R^{31b}$, when present, is hydrogen.

In a further aspect, $R^{31a}$ and $R^{31b}$, when present, are optionally covalently bonded and, together with the nitrogen atom to which they are attached, comprise a 3- to 6-membered heterocycle. In a still further aspect, $R^{31a}$ and $R^{31b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{31a}$ and $R^{31b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, $R^{31a}$ and $R^{31b}$, when present, are covalently bonded, and together with the nitrogen atom to which they are attached, comprise a heterocycle selected from imidazolyl, pyrazolyl, and pyrrolyl. In a still further aspect, $R^{31a}$ and $R^{31b}$, when present, are covalently bonded, and together with the nitrogen atom to which they are attached, comprise a pyrrolidinyl. In yet a further aspect, $R^{31a}$ and $R^{31b}$, when present, are covalently bonded, and together with the nitrogen atom to which they are attached, comprise a piperidinyl.

j. $R^{32}$ Groups

In one aspect, $R^{32}$, when present, is selected from C1-C3 alkyl, C1-C3 monohaloalkyl, C1-C3 polyhaloalkyl, cyclopropyl, and, —NR$^{34a}$R$^{34b}$. In further aspect, $R^{32}$, when present, is selected from methyl, ethyl, —CH$_2$F, —CH$_2$CH$_2$F, —CHF$_2$, —CF$_3$, —CH$_2$CHF$_2$, —CH$_2$CF$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^{32}$, when present, is selected from methyl, —CH$_2$F, —CHF$_2$, —CF$_3$, cyclopropyl, —NHCH$_3$, and —N(CH$_3$)$_2$. In yet a further aspect, $R^{32}$, when present, is selected from methyl, —CH$_2$F, —CHF$_2$, —CF$_3$, cyclopropyl, —NHCH$_3$, and —N(CH$_3$)$_2$. In an even further aspect, $R^{32}$, when present, is selected from methyl, —CF$_3$, cyclopropyl, and —NHCH$_3$.

In a further aspect, $R^{32}$, when present, is selected from is selected from C1-C3 alkyl, C1-C3 monohaloalkyl, C1-C3 polyhaloalkyl, and, —NR$^{34a}$R$^{34b}$. In a still further aspect, $R^{32}$, when present, is selected from methyl, ethyl, —CH$_2$F, —CH$_2$CH$_2$F, —CHF$_2$, —CF$_3$, —CH$_2$CHF$_2$, —CH$_2$CF$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, $R^{32}$, when present, is selected from methyl, —CH$_2$F, —CHF$_2$, —CF$_3$, —NHCH$_3$, and —N(CH$_3$)$_2$. In an even further aspect, $R^{32}$, when present, is selected from methyl, —CH$_2$F, —CHF$_2$, —CF$_3$, —NHCH$_3$, and —N(CH$_3$)$_2$. In a still further aspect, $R^{32}$, when present, is selected from methyl, —CF$_3$, and —NHCH$_3$.

In a further aspect, $R^{32}$, when present, is selected from C1-C3 alkyl, C1-C3 monohaloalkyl, C1-C3 polyhaloalkyl, and cyclopropyl. In a still further aspect, $R^{32}$, when present, is selected from methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{32}$, when present, is selected from methyl, —CH$_2$F, —CHF$_2$, —CF$_3$, and cyclopropyl. In an even further aspect, $R^{32}$, when present, is selected from methyl, —CF$_3$, and cyclopropyl.

In a further aspect, $R^{32}$, when present, is selected from C1-C3 monohaloalkyl, C1-C3 polyhaloalkyl, and cyclopropyl. In a still further aspect, $R^{32}$, when present, is selected from —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{32}$, when present, is selected from —CH$_2$F, —CHF$_2$, —CF$_3$, and cyclopropyl. In an even further aspect, $R^{32}$, when present, is selected from —CF$_3$ and cyclopropyl.

In a further aspect, $R^{32}$, when present, is selected from C1-C3 alkyl, and cyclopropyl. In a still further aspect, $R^{32}$, when present, is selected from methyl, ethyl, and cyclopropyl. In yet a further aspect, $R^{32}$, when present, is selected from methyl, and cyclopropyl.

In a further aspect, $R^{32}$, when present, is selected from C1-C3 alkyl, C1-C3 monohaloalkyl, and C1-C3 polyhaloalkyl. In a still further aspect, $R^{32}$, when present, is selected from methyl, ethyl, —CH$_2$F, —CH$_2$CH$_2$F, —CHF$_2$, —CF$_3$, —CH$_2$CHF$_2$, and —CH$_2$CF$_3$. In a yet further aspect, $R^{32}$, when present, is selected from methyl, —CH$_2$F, —CHF$_2$, and —CF$_3$. In an even further aspect, $R^{32}$, when present, is selected from methyl and —CF$_3$.

In a further aspect, $R^{32}$, when present, is selected from C1-C3 monohaloalkyl, and C1-C3 polyhaloalkyl. In a still further aspect, $R^{32}$, when present, is selected from —CH$_2$F, —CH$_2$CH$_2$F, —CHF$_2$, —CF$_3$, —CH$_2$CHF$_2$, and —CH$_2$CF$_3$. In yet a further aspect, $R^{32}$, when present, is selected from —CH$_2$F, —CHF$_2$, and —CF$_3$. In an even further aspect, $R^{32}$, when present, is —CF$_3$.

In a further aspect, $R^{32}$, when present, is C1-C3 alkyl. In a still further aspect, $R^{32}$, when present, is selected from methyl, and ethyl. In yet a further aspect, $R^{32}$, when present, is methyl.

k. $R^{33}$ Groups

In one aspect, $R^{33}$, when present, is selected from C1-C3 alkyl, C1-C3 monohaloalkyl, C1-C3 polyhaloalkyl, cyclopropyl, and, —NR$^{35a}$R$^{35b}$. In a further aspect, $R^{33}$, when present, is selected from methyl, ethyl, —CH$_2$F, —CH$_2$CH$_2$F, —CHF$_2$, —CF$_3$, —CH$_2$CHF$_2$, —CH$_2$CF$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^{33}$, when present, is selected from methyl, —CH$_2$F, —CHF$_2$, —CF$_3$, cyclopropyl, —NHCH$_3$, and —N(CH$_3$)$_2$. In yet a further aspect, $R^{33}$, when present, is selected from methyl, —CF$_3$, cyclopropyl, and —NHCH$_3$.

In a further aspect, $R^{33}$, when present, is selected from is selected from C1-C3 alkyl, C1-C3 monohaloalkyl, C1-C3 polyhaloalkyl, and, —NR$^{34a}$R$^{34b}$. In a still further aspect, $R^{33}$, when present, is selected from methyl, ethyl, —CH$_2$F, —CH$_2$CH$_2$F, —CHF$_2$, —CF$_3$, —CH$_2$CHF$_2$, —CH$_2$CF$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, $R^{33}$, when present, is selected from methyl, —CH$_2$F, —CHF$_2$, —CF$_3$, —NHCH$_3$, and —N(CH$_3$)$_2$. In an even further aspect, $R^{33}$, when present, is selected from methyl, —CF$_3$, and —NHCH$_3$.

In a further aspect, $R^{33}$, when present, is selected from C1-C3 alkyl, C1-C3 monohaloalkyl, C1-C3 polyhaloalkyl, and cyclopropyl. In a still further aspect, $R^{33}$, when present, is selected from methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a yet further aspect, $R^{33}$, when present, is selected from methyl, —CH$_2$F, —CHF$_2$, —CF$_3$, and cyclopropyl. In an even further aspect, $R^{33}$, when present, is selected from methyl, —CF$_3$, and cyclopropyl.

In a further aspect, $R^{33}$, when present, is selected from C1-C3 monohaloalkyl, C1-C3 polyhaloalkyl, and cyclopropyl. In a still further aspect, $R^{33}$, when present, is selected from —CH$_2$F, —CH$_2$CH$_2$F, —CHF$_2$, —CF$_3$, —CH$_2$CHF$_2$, —CH$_2$CF$_3$, and cyclopropyl. In a yet further aspect, $R^{33}$, when present, is selected from —CH$_2$F, —CHF$_2$, —CF$_3$, and cyclopropyl. In an even further aspect, $R^{33}$, when present, is selected from —CF$_3$ and cyclopropyl.

In a further aspect, $R^{33}$, when present, is selected from C1-C3 alkyl, and cyclopropyl. In a still further aspect, $R^{33}$, when present, is selected from methyl, ethyl, and cyclopropyl. In a yet further aspect, $R^{33}$, when present, is selected from methyl, and cyclopropyl.

In a further aspect, $R^{33}$, when present, is selected from C1-C3 alkyl, C1-C3 monohaloalkyl, and C1-C3 polyhaloalkyl. In a still further aspect, $R^{33}$, when present, is selected from methyl, ethyl, —CH$_2$F, —CH$_2$CH$_2$F, —CHF$_2$, —CF$_3$, —CH$_2$CHF$_2$, and —CH$_2$CF$_3$. In a yet further aspect, $R^{33}$, when present, is selected from methyl, —CH$_2$F, —CHF$_2$, and —CF$_3$. In an even further aspect, $R^{33}$, when present, is selected from methyl and —CF$_3$.

In a further aspect, $R^{33}$, when present, is selected from C1-C3 monohaloalkyl, and C1-C3 polyhaloalkyl. In a still further aspect, $R^{33}$, when present, is selected from —CH$_2$F, —CH$_2$CH$_2$F, —CHF$_2$, —CF$_3$, —CH$_2$CHF$_2$, and —CH$_2$CF$_3$. In a yet further aspect, $R^{33}$, when present, is selected from —CH$_2$F, —CHF$_2$, and —CF$_3$. In an even further aspect, $R^{33}$, when present, is —CF$_3$.

In a further aspect, $R^{33}$, when present, is C1-C3 alkyl. In a still further aspect, $R^{33}$, when present, is selected from methyl, and ethyl. In a yet further aspect, $R^{33}$, when present, is methyl.

l. $R^{34a}$ and $R^{34b}$ Groups

In one aspect, each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with the nitrogen atom to which they are attached, comprise a 3- to 6-membered heterocycle.

In a further aspect, each of $R^{34a}$ and $R^{34b}$, when present, is independently selected from hydrogen, C1-C3 alkyl, C1-C3 monohaloalkyl, C1-C3 polyhaloalkyl, and cyclopropyl. In a still further aspect, each of $R^{34a}$ and $R^{34b}$, when present, is independently selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of $R^{34a}$ and $R^{34b}$, when present, is independently selected from hydrogen, methyl, —CH$_2$F, —CHF$_2$, —CF$_3$, and cyclopropyl. In an even further aspect, each of $R^{34a}$ and $R^{34b}$, when present, is independently selected from hydrogen, methyl, —CF$_3$, and cyclopropyl.

In a further aspect, each of $R^{34a}$ and $R^{34b}$, when present, is independently selected from hydrogen, C1-C3 monohaloalkyl, C1-C3 polyhaloalkyl, and cyclopropyl. In a still further aspect, each of $R^{34a}$ and $R^{34b}$, when present, is independently selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of $R^{34a}$ and $R^{34b}$, when present, is independently selected from hydrogen, —CH$_2$F, —CHF$_2$, —CF$_3$, and cyclopropyl. In an even further aspect, each of $R^{34a}$ and $R^{34b}$ when present, is independently selected from hydrogen, —CF$_3$ and cyclopropyl.

In a further aspect, each of $R^{34a}$ and $R^{34b}$, when present, is independently selected from hydrogen, C1-C3 alkyl, and cyclopropyl. In a still further aspect, each of $R^{34a}$ and $R^{34b}$ when present, is independently selected from hydrogen, methyl, ethyl, and cyclopropyl. In yet a further aspect, each of $R^{34a}$ and $R^{34b}$, when present, is independently selected from hydrogen, methyl, and cyclopropyl.

In a further aspect, each of $R^{34a}$ and $R^{34b}$, when present, is independently selected from hydrogen, C1-C3 alkyl, C1-C3 monohaloalkyl, and C1-C3 polyhaloalkyl. In a still further aspect, each of $R^{34a}$ and $R^{34b}$, when present, is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, each of $R^{34a}$ and $R^{34b}$, when present, is independently selected from hydrogen, methyl, —CH$_2$F, —CHF$_2$, and —CF$_3$. In an even further aspect, each of $R^{34a}$ and $R^{34b}$, when present, is independently selected from hydrogen, methyl, and —CF$_3$.

In a further aspect, each of $R^{34a}$ and $R^{34b}$, when present, is independently selected from hydrogen, C1-C3 monohaloalkyl, and C1-C3 polyhaloalkyl. In a still further aspect, each of $R^{34a}$ and $R^{34b}$, when present, is independently selected from hydrogen, —CH$_2$F, —CH$_2$CH$_2$F, —CHF$_2$, —CF$_3$, —CH$_2$CHF$_2$, and —CH$_2$CF$_3$. In yet a further aspect, each of $R^{34a}$ and $R^{34b}$, when present, is independently selected from hydrogen, —CH$_2$F, —CHF$_2$, and —CF$_3$. In an even further aspect, each of $R^{34a}$ and $R^{34b}$, when present, is independently selected from hydrogen and —CF$_3$.

In a further aspect, each of $R^{34a}$ and $R^{34b}$, when present, is independently selected from hydrogen and C1-C3 alkyl. In a still further aspect, each of $R^{34a}$ and $R^{34b}$, when present, is independently selected from hydrogen, methyl, and ethyl. In yet a further aspect, each of $R^{34a}$ and $R^{34b}$, when present, is independently selected from hydrogen and methyl. In an even further aspect, $R^{34a}$, when present, is hydrogen and $R^{34b}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, $R^{34a}$, when present, is hydrogen and $R^{34b}$, when present, is selected from hydrogen, methyl, —CH$_2$F, —CHF$_2$, —CF$_3$, and cyclopropyl. In yet a further aspect, $R^{34a}$, when present, is hydrogen and $R^{34b}$, when present, is selected from hydrogen, methyl, —CF$_3$, and cyclopropyl.

In a further aspect, $R^{34a}$, when present, is hydrogen and $R^{34b}$, when present, is selected from hydrogen, C1-C3 monohaloalkyl, C1-C3 polyhaloalkyl, and cyclopropyl. In a still further aspect, $R^{34a}$, when present, is hydrogen and $R^{34b}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{34a}$, when present, is hydrogen and $R^{34b}$, when present, is selected from hydrogen, —CH$_2$F, —CHF$_2$, —CF$_3$, and cyclopropyl. In yet a further aspect, $R^{34a}$, when present, is hydrogen and $R^{34b}$, when present, is selected from hydrogen, —$CF_3$ and cyclopropyl.

In a further aspect, $R^{34a}$, when present, is hydrogen and $R^{34b}$, when present, is selected from hydrogen, C1-C3 alkyl, and cyclopropyl. In a still further aspect, $R^{34a}$, when present, is hydrogen and $R^{34b}$, when present, is selected from hydrogen, methyl, ethyl, and cyclopropyl. In yet a further aspect, $R^{34a}$, when present, is hydrogen and $R^{34b}$, when present, is selected from hydrogen, methyl, and cyclopropyl.

In a further aspect, $R^{34a}$, when present, is hydrogen and $R^{34b}$, when present, is selected from hydrogen, C1-C3 alkyl, C1-C3 monohaloalkyl, and C1-C3 polyhaloalkyl. In a still further aspect, $R^{34a}$, when present, is hydrogen and $R^{34b}$, when present, is selected from hydrogen, methyl, ethyl, —$CH_2F$, —$CH_2CH_2F$, —$CHF_2$, —$CF_3$, —$CH_2CHF_2$, and —$CH_2CF_3$. In yet a further aspect, $R^{34a}$, when present, is hydrogen and $R^{34b}$, when present, is selected from hydrogen, methyl, —$CH_2F$, —$CHF_2$, and —$CF_3$. In an even further aspect, $R^{34a}$, when present, is hydrogen and $R^{34b}$, when present, is selected from hydrogen, methyl, and —$CF_3$.

In a further aspect, $R^{34a}$, when present, is hydrogen and $R^{34b}$, when present, is selected from hydrogen, C1-C3 monohaloalkyl, and C1-C3 polyhaloalkyl. In a still further aspect, $R^{34a}$, when present, is hydrogen and $R^{34b}$, when present, is selected from hydrogen, —$CH_2F$, —$CH_2CH_2F$, —$CHF_2$, —$CF_3$, —$CH_2CHF_2$, and —$CH_2CF_3$. In yet a further aspect, $R^{34a}$, when present, is hydrogen and $R^{34b}$, when present, is selected from hydrogen, —$CH_2F$, —$CHF_2$, and —$CF_3$. In an even further aspect, $R^{34a}$, when present, is hydrogen and $R^{34b}$, when present, is selected from hydrogen and —$CF_3$.

In a further aspect, $R^{34a}$, when present, is hydrogen and $R^{34b}$, when present, is selected from hydrogen and C1-C3 alkyl. In a still further aspect, $R^{34a}$, when present, is hydrogen and $R^{34b}$, when present, is selected from hydrogen, methyl, and ethyl. In yet a further aspect, $R^{34a}$, when present, is hydrogen and $R^{34b}$, when present, is selected from hydrogen and methyl. In an even further aspect, each of $R^{34a}$ and $R^{34b}$, when present, is hydrogen.

In a further aspect, $R^{34a}$ and $R^{34b}$, when present, are optionally covalently bonded and, together with the nitrogen atom to which they are attached, comprise a 3- to 6-membered heterocycle. In a still further aspect, $R^{34a}$ and $R^{34b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{34a}$ and $R^{34b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, $R^{34a}$ and $R^{34b}$, when present, are covalently bonded, and together with the nitrogen atom to which they are attached, comprise a heterocycle selected from imidazolyl, pyrazolyl, and pyrrolyl. In a still further aspect, $R^{34a}$ and $R^{34b}$, when present, are covalently bonded, and together with the nitrogen atom to which they are attached, comprise a pyrrolidinyl. In yet a further aspect, $R^{34a}$ and $R^{34b}$, when present, are covalently bonded, and together with the nitrogen atom to which they are attached, comprise a piperidinyl.

m. $R^{35a}$ and $R^{35b}$ Groups

In one aspect, each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with the nitrogen atom to which they are attached, comprise a 3- to 6-membered heterocycle.

In a further aspect, each of $R^{35a}$ and $R^{35b}$, when present, is independently selected from hydrogen, C1-C3 alkyl, C1-C3 monohaloalkyl, C1-C3 polyhaloalkyl, and cyclopropyl. In a still further aspect, each of $R^{35a}$ and $R^{35b}$, when present, is independently selected from hydrogen, methyl, ethyl, —$CH_2F$, —$CH_2CH_2F$, —$CHF_2$, —$CF_3$, —$CH_2CHF_2$, —$CH_2CF_3$, and cyclopropyl. In a yet further aspect, each of $R^{35a}$ and $R^{35b}$, when present, is independently selected from hydrogen, methyl, —$CH_2F$, —$CHF_2$, —$CF_3$, and cyclopropyl. In an even further aspect, each of $R^{35a}$ and $R^{35b}$, when present, is independently selected from hydrogen, methyl, —$CF_3$, and cyclopropyl.

In a further aspect, each of $R^{35a}$ and $R^{35b}$, when present, is independently selected from hydrogen, C1-C3 monohaloalkyl, C1-C3 polyhaloalkyl, and cyclopropyl. In a still further aspect, each of $R^{35a}$ and $R^{35b}$, when present, is independently selected from hydrogen, —$CH_2F$, —$CH_2CH_2F$, —$CHF_2$, —$CF_3$, —$CH_2CHF_2$, —$CH_2CF_3$, and cyclopropyl. In a yet further aspect, each of $R^{35a}$ and $R^{35b}$, when present, is independently selected from hydrogen, —$CH_2F$, —$CHF_2$, —$CF_3$, and cyclopropyl. In an even further aspect, each of $R^{35a}$ and $R^{35b}$ when present, is independently selected from hydrogen, —$CF_3$ and cyclopropyl.

In a further aspect, each of $R^{35a}$ and $R^{35b}$, when present, is independently selected from hydrogen, C1-C3 alkyl, and cyclopropyl. In a still further aspect, each of $R^{35a}$ and $R^{35b}$ when present, is independently selected from hydrogen, methyl, ethyl, and cyclopropyl. In a yet further aspect, each of $R^{35a}$ and $R^{35b}$, when present, is independently selected from hydrogen, methyl, and cyclopropyl.

In a further aspect, each of $R^{35a}$ and $R^{35b}$, when present, is independently selected from hydrogen, C1-C3 alkyl, C1-C3 monohaloalkyl, and C1-C3 polyhaloalkyl. In a still further aspect, each of $R^{35a}$ and $R^{35b}$, when present, is independently selected from hydrogen, methyl, ethyl, —$CH_2F$, —$CH_2CH_2F$, —$CHF_2$, —$CF_3$, —$CH_2CHF_2$, and —$CH_2CF_3$. In a yet further aspect, each of $R^{35a}$ and $R^{35b}$, when present, is independently selected from hydrogen, methyl, —$CH_2F$, —$CHF_2$, and —$CF_3$. In an even further aspect, each of $R^{35a}$ and $R^{35b}$, when present, is independently selected from hydrogen, methyl, and —$CF_3$.

In a further aspect, each of $R^{35a}$ and $R^{35b}$, when present, is independently selected from hydrogen, C1-C3 monohaloalkyl, and C1-C3 polyhaloalkyl. In a still further aspect, each of $R^{35a}$ and $R^{35b}$, when present, is independently selected from hydrogen, —$CH_2F$, —$CH_2CH_2F$, —$CHF_2$, —$CF_3$, —$CH_2CHF_2$, and —$CH_2CF_3$. In a yet further aspect, each of $R^{35a}$ and $R^{35b}$, when present, is independently selected from hydrogen, —$CH_2F$, —$CHF_2$, and —$CF_3$. In an even further aspect, each of $R^{35a}$ and $R^{35b}$, when present, is independently selected from hydrogen and —$CF_3$.

In a further aspect, each of $R^{35a}$ and $R^{35b}$, when present, is independently selected from hydrogen and C1-C3 alkyl. In a still further aspect, each of $R^{35a}$ and $R^{35b}$, when present, is independently selected from hydrogen, methyl, and ethyl. In a yet further aspect, each of $R^{35a}$ and $R^{35b}$, when present, is independently selected from hydrogen and methyl. In an even further aspect, $R^{35a}$ is hydrogen and $R^{35b}$, when present, is selected from hydrogen, methyl, ethyl, —$CH_2F$, —$CH_2CH_2F$, —$CHF_2$, —$CF_3$, —$CH_2CHF_2$, —$CH_2CF_3$, and cyclopropyl. In a still further aspect, $R^{35a}$, when present, is hydrogen and $R^{35b}$, when present, is selected from hydrogen, methyl, —$CH_2F$, —$CHF_2$, —$CF_3$, and cyclopropyl. In yet a further aspect, $R^{35a}$, when present, is hydrogen and $R^{35b}$, when present, is selected from hydrogen, methyl, —CF$_3$, and cyclopropyl.

In a further aspect, $R^{35a}$, when present, is hydrogen and $R^{35b}$, when present, is selected from hydrogen, C1-C3 monohaloalkyl, C1-C3 polyhaloalkyl, and cyclopropyl. In a still further aspect, $R^{35a}$, when present, is hydrogen and $R^{35b}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In a yet further aspect, $R^{35a}$, when present, is hydrogen and $R^{35b}$, when present, is selected from hydrogen, —CH$_2$F, —CHF$_2$, —CF$_3$, and cyclopropyl. In an even further aspect, $R^{35a}$, when present, is hydrogen and $R^{35b}$, when present, is selected from hydrogen, —CF$_3$ and cyclopropyl.

In a further aspect, $R^{35a}$, when present, is hydrogen and $R^{35b}$, when present, is selected from hydrogen, C1-C3 alkyl, and cyclopropyl. In a still further aspect, $R^{35a}$, when present, is hydrogen and $R^{35b}$, when present, is selected from hydrogen, methyl, ethyl, and cyclopropyl. In a yet further aspect, $R^{35a}$, when present, is hydrogen and $R^{35b}$, when present, is selected from hydrogen, methyl, and cyclopropyl.

In a further aspect, $R^{35a}$, when present, is hydrogen and $R^{35b}$, when present, is selected from hydrogen, C1-C3 alkyl, C1-C3 monohaloalkyl, and C1-C3 polyhaloalkyl. In a still further aspect, $R^{35a}$, when present, is hydrogen and $R^{35b}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In a yet further aspect, $R^{35a}$, when present, is hydrogen and $R^{35b}$, when present, is selected from hydrogen, methyl, —CH$_2$F, —CHF$_2$, and —CF$_3$. In an even further aspect, $R^{35a}$, when present, is hydrogen and $R^{35b}$, when present, is selected from hydrogen, methyl, and —CF$_3$.

In a further aspect, $R^{35a}$, when present, is hydrogen and $R^{35b}$, when present, is selected from hydrogen, C1-C3 monohaloalkyl, and C1-C3 polyhaloalkyl. In a still further aspect, $R^{35a}$, when present, is hydrogen and $R^{35b}$, when present, is selected from hydrogen, —CH$_2$F, —CH$_2$CH$_2$F, —CHF$_2$, —CF$_3$, —CH$_2$CHF$_2$, and —CH$_2$CF$_3$. In a yet further aspect, $R^{35a}$, when present, is hydrogen and $R^{35b}$, when present, is selected from hydrogen, —CH$_2$F, —CHF$_2$, and —CF$_3$. In an even further aspect, $R^{35a}$, when present, is hydrogen and $R^{35b}$, when present, is selected from hydrogen and —CF$_3$.

In a further aspect, $R^{35a}$, when present, is hydrogen and $R^{35b}$, when present, is selected from hydrogen and C1-C3 alkyl. In a still further aspect, $R^{35a}$, when present, is hydrogen and $R^{35b}$, when present, is selected from hydrogen, methyl, and ethyl. In a yet further aspect, $R^{35a}$, when present, is hydrogen and $R^{35b}$, when present, is selected from hydrogen and methyl. In an even further aspect, each of $R^{35a}$ and $R^{35b}$, when present, is hydrogen.

In a further aspect, $R^{35a}$ and $R^{35b}$, when present, are optionally covalently bonded and, together with the nitrogen atom to which they are attached, comprise a 3- to 6-membered heterocycle. In a still further aspect, $R^{35a}$ and $R^{35b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{35a}$ and $R^{35b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, $R^{35a}$ and $R^{35b}$, when present, are covalently bonded, and together with the nitrogen atom to which they are attached, comprise a heterocycle selected from imidazolyl, pyrazolyl, and pyrrolyl. In a still further aspect, $R^{35a}$ and $R^{35b}$, when present, are covalently bonded, and together with the nitrogen atom to which they are attached, comprise a pyrrolidinyl. In yet a further aspect, $R^{35a}$ and $R^{35b}$, when present, are covalently bonded, and together with the nitrogen atom to which they are attached, comprise a piperidinyl.

n. $R^{40}$ Groups

In one aspect, $R^{40}$, when present, is selected from is selected from hydrogen, C1-C3 alkyl, C1-C3 monohaloalkyl, C1-C3 polyhaloalkyl, and cyclopropyl. In a further aspect, $R^{40}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{40}$, when present, is selected from hydrogen, methyl, —CH$_2$F, —CHF$_2$, —CF$_3$, and cyclopropyl. In an even further aspect, $R^{40}$, when present, is selected from hydrogen, methyl, —CF$_3$, and cyclopropyl.

In a further aspect, $R^{40}$, when present, is selected from hydrogen, C1-C3 monohaloalkyl, C1-C3 polyhaloalkyl, and cyclopropyl. In a still further aspect, $R^{40}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{40}$, when present, is selected from hydrogen, —CH$_2$F, —CHF$_2$, —CF$_3$, and cyclopropyl. In an even further aspect, $R^{40}$, when present, is selected from hydrogen, —CF$_3$ and cyclopropyl.

In a further aspect, $R^{40}$, when present, is selected from hydrogen, C1-C3 alkyl, and cyclopropyl. In a still further aspect, $R^{40}$, when present, is selected from hydrogen, methyl, ethyl, and cyclopropyl. In yet a further aspect, $R^{40}$, when present, is selected from hydrogen, methyl, and cyclopropyl.

In a further aspect, $R^{40}$, when present, is selected from hydrogen, C1-C3 alkyl, C1-C3 monohaloalkyl, and C1-C3 polyhaloalkyl. In a still further aspect, $R^{40}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, $R^{40}$, when present, is selected from hydrogen, methyl, —CH$_2$F, —CHF$_2$, and —CF$_3$. In an even further aspect, $R^{40}$, when present, is selected from hydrogen, methyl, and —CF$_3$.

In a further aspect, $R^{40}$, when present, is selected from hydrogen, C1-C3 monohaloalkyl, and C1-C3 polyhaloalkyl. In a still further aspect, $R^{40}$, when present, is selected from hydrogen, —CH$_2$F, —CH$_2$CH$_2$F, —CHF$_2$, —CF$_3$, —CH$_2$CHF$_2$, and —CH$_2$CF$_3$. In yet a further aspect, $R^{40}$, when present, is selected from hydrogen, —CH$_2$F, —CHF$_2$, and —CF$_3$. In an even further aspect, $R^{40}$, when present, is selected from hydrogen and —CF$_3$.

In a further aspect, $R^{40}$, when present, is selected from hydrogen and C1-C3 alkyl. In a still further aspect, $R^{40}$, when present, is selected from hydrogen, methyl, and ethyl. In yet a further aspect, $R^{40}$, when present, is selected from hydrogen and methyl. In an even further aspect, $R^{40}$, when present, is hydrogen.

o. $R^{41a}$ and $R^{41b}$ Groups

In one aspect, each of $R^{41a}$ and $R^{41b}$, when present, is independently selected from is selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle.

In a further aspect, each of $R^{41a}$ and $R^{41b}$, when present, is independently selected from hydrogen, C1-C3 alkyl, C1-C3 monohaloalkyl, C1-C3 polyhaloalkyl, and cyclopropyl. In a still further aspect, each of $R^{41a}$ and $R^{41b}$, when present, is independently selected from hydrogen, methyl, ethyl, —$CH_2F$, —$CH_2CH_2F$, —$CHF_2$, —$CF_3$, —$CH_2CHF_2$, —$CH_2CF_3$, and cyclopropyl. In yet a further aspect, each of $R^{41a}$ and $R^{41b}$, when present, is independently selected from hydrogen, methyl, —$CH_2F$, —$CHF_2$, —$CF_3$, and cyclopropyl. In an even further aspect, each of $R^{41a}$ and $R^{41b}$, when present, is independently selected from hydrogen, methyl, —$CF_3$, and cyclopropyl.

In a further aspect, each of $R^{41a}$ and $R^{41b}$, when present, is independently selected from hydrogen, C1-C3 monohaloalkyl, C1-C3 polyhaloalkyl, and cyclopropyl. In a still further aspect, each of $R^{41a}$ and $R^{41b}$, when present, is independently selected from hydrogen, —$CH_2F$, —$CH_2CH_2F$, —$CHF_2$, —$CF_3$, —$CH_2CHF_2$, —$CH_2CF_3$, and cyclopropyl. In yet a further aspect, each of $R^{41a}$ and $R^{41b}$, when present, is independently selected from hydrogen, —$CH_2F$, —$CHF_2$, —$CF_3$, and cyclopropyl. In an even further aspect, each of $R^{41a}$ and $R^{41b}$ when present, is independently selected from hydrogen, —$CF_3$ and cyclopropyl.

In a further aspect, each of $R^{41a}$ and $R^{41b}$, when present, is independently selected from hydrogen, C1-C3 alkyl, and cyclopropyl. In a still further aspect, each of $R^{41a}$ and $R^{41b}$ when present, is independently selected from hydrogen, methyl, ethyl, and cyclopropyl. In yet a further aspect, each of $R^{41a}$ and $R^{41b}$, when present, is independently selected from hydrogen, methyl, and cyclopropyl.

In a further aspect, each of $R^{41a}$ and $R^{41b}$, when present, is independently selected from hydrogen, C1-C3 alkyl, C1-C3 monohaloalkyl, and C1-C3 polyhaloalkyl. In a still further aspect, each of $R^{41a}$ and $R^{41b}$, when present, is independently selected from hydrogen, methyl, ethyl, —$CH_2F$, —$CH_2CH_2F$, —$CHF_2$, —$CF_3$, —$CH_2CHF_2$, and —$CH_2CF_3$. In yet a further aspect, each of $R^{41a}$ and $R^{41b}$, when present, is independently selected from hydrogen, methyl, —$CH_2F$, —$CHF_2$, and —$CF_3$. In an even further aspect, each of $R^{41a}$ and $R^{41b}$, when present, is independently selected from hydrogen, methyl, and —$CF_3$.

In a further aspect, each of $R^{41a}$ and $R^{41b}$, when present, is independently selected from hydrogen, C1-C3 monohaloalkyl, and C1-C3 polyhaloalkyl. In a still further aspect, each of $R^{41a}$ and $R^{41b}$, when present, is independently selected from hydrogen, —$CH_2F$, —$CH_2Cl$, —$CH_2CH_2F$, —$CHF_2$, —$CF_3$, —$CH_2CHF_2$, and —$CH_2CF_3$. In yet a further aspect, each of $R^{41a}$ and $R^{41b}$, when present, is independently selected from hydrogen, —$CH_2F$, —$CHF_2$, and —$CF_3$. In an even further aspect, each of $R^{41a}$ and $R^{41b}$, when present, is independently selected from hydrogen and —$CF_3$.

In a further aspect, each of $R^{41a}$ and $R^{41b}$, when present, is independently selected from hydrogen and C1-C3 alkyl. In a still further aspect, each of $R^{41a}$ and $R^{41b}$, when present, is independently selected from hydrogen and methyl.

In a further aspect, $R^{41a}$ is hydrogen and $R^{41b}$, when present, is selected from hydrogen, methyl, ethyl, —$CH_2F$, —$CH_2CH_2F$, —$CHF_2$, —$CF_3$, —$CH_2CHF_2$, —$CH_2CF_3$, and cyclopropyl. In a still further aspect, $R^{41a}$, when present, is hydrogen and $R^{41b}$, when present, is selected from hydrogen, methyl, —$CH_2F$, —$CHF_2$, —$CF_3$, and cyclopropyl. In yet a further aspect, $R^{41a}$, when present, is hydrogen and $R^{41b}$, when present, is selected from hydrogen, methyl, —$CF_3$, and cyclopropyl.

In a further aspect, $R^{41a}$, when present, is hydrogen and $R^{41b}$, when present, is selected from hydrogen, C1-C3 monohaloalkyl, C1-C3 polyhaloalkyl, and cyclopropyl. In a still further aspect $R^{41a}$, when present, is hydrogen and $R^{41b}$, when present, is selected from hydrogen, —$CH_2F$, —$CH_2CH_2F$, —$CHF_2$, —$CF_3$, —$CH_2CHF_2$, —$CH_2CF_3$, and cyclopropyl. In yet further aspect, $R^{41a}$, when present, is hydrogen and $R^{41b}$, when present, is selected from hydrogen, —$CH_2F$, —$CHF_2$, —$CF_3$, and cyclopropyl. In yet a further aspect, $R^{41a}$, when present, is hydrogen and $R^{41b}$, when present, is selected from hydrogen, —$CF_3$ and cyclopropyl.

In a further aspect, $R^{41a}$, when present, is hydrogen and $R^{41b}$, when present, is selected from hydrogen, C1-C3 alkyl, and cyclopropyl. In a still further aspect, $R^{41a}$, when present, is hydrogen and $R^{41b}$, when present, is selected from hydrogen, methyl, ethyl, and cyclopropyl. In yet a further aspect, $R^{41a}$, when present, is hydrogen and $R^{41b}$, when present, is selected from hydrogen, methyl, and cyclopropyl.

In a further aspect, $R^{41a}$, when present, is hydrogen and $R^{41b}$, when present, is selected from hydrogen, C1-C3 alkyl, C1-C3 monohaloalkyl, and C1-C3 polyhaloalkyl. In a still further aspect, $R^{41a}$, when present, is hydrogen and $R^{41b}$, when present, is selected from hydrogen, methyl, ethyl, —$CH_2F$, —$CH_2CH_2F$, —$CHF_2$, —$CF_3$, —$CH_2CHF_2$, and —$CH_2CF_3$. In yet a further aspect, $R^{41a}$, when present, is hydrogen and $R^{41b}$, when present, is selected from hydrogen, methyl, —$CH_2F$, —$CHF_2$, and —$CF_3$. In an even further aspect, $R^{41a}$, when present, is hydrogen and $R^{41b}$, when present, is selected from hydrogen, methyl, and —$CF_3$.

In a further aspect, $R^{41a}$, when present, is hydrogen and $R^{41b}$, when present, is selected from hydrogen, C1-C3 monohaloalkyl, and C1-C3 polyhaloalkyl. In a still further aspect, $R^{41a}$, when present, is hydrogen and $R^{41b}$, when present, is selected from hydrogen, —$CH_2F$, —$CH_2CH_2F$, —$CHF_2$, —$CF_3$, —$CH_2CHF_2$, and —$CH_2CF_3$. In yet a further aspect, $R^{41a}$, when present, is hydrogen and $R^{41b}$, when present, is selected from hydrogen, —$CH_2F$, —$CHF_2$, and —$CF_3$. In an even further aspect, $R^{41a}$, when present, is hydrogen and $R^{41b}$, when present, is selected from hydrogen and —$CF_3$.

In a further aspect, $R^{41a}$, when present, is hydrogen and $R^{41b}$, when present, is selected from hydrogen and C1-C3 alkyl. In a still further aspect, $R^{41a}$, when present, is hydrogen and $R^{41b}$, when present, is selected from hydrogen, methyl, and ethyl. In yet a further aspect, $R^{41b}$, when present, is hydrogen and $R^{41b}$, when present, is selected from hydrogen and methyl. In an even further aspect, each of $R^{41a}$ and $R^{41b}$, when present, is hydrogen.

In a further aspect, $R^{41a}$ and $R^{41b}$, when present, are optionally covalently bonded and, together with the nitrogen atom to which they are attached, comprise a 3- to 6-membered heterocycle. In a still further aspect, $R^{41a}$ and $R^{41b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{41a}$ and $R^{41b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, $R^{41a}$ and $R^{41b}$, when present, are covalently bonded, and together with the nitrogen atom to which they are attached, comprise a heterocycle selected from imidazolyl, pyrazolyl, and pyrrolyl. In a still further aspect, $R^{41a}$ and $R^{41b}$, when present, are covalently bonded, and together with the nitrogen atom to which they are attached, comprise a pyrrolidinyl. In yet a further aspect, $R^{41a}$ and $R^{41b}$, when present, are covalently bonded, and together with the nitrogen atom to which they are attached, comprise a piperidinyl.

p. $R^{42}$ Groups

In one aspect, $R^{42}$, when present, is selected from C1-C3 alkyl, C1-C3 monohaloalkyl, C1-C3 polyhaloalkyl, cyclopropyl, and, $-NR^{44a}R^{44b}$. In a further aspect, $R^{42}$, when present, is selected from methyl, ethyl, $-CH_2F$, $-CH_2CH_2F$, $-CHF_2$, $-CF_3$, $-CH_2CHF_2$, $-CH_2CF_3$, cyclopropyl, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In a still further aspect, $R^{42}$, when present, is selected from methyl, $-CH_2F$, $-CHF_2$, $-CF_3$, cyclopropyl, $-NHCH_3$, and $-N(CH_3)_2$. In yet a further aspect, $R^{42}$, when present, is selected from methyl, $-CF_3$, cyclopropyl, and $-NHCH_3$.

In a further aspect, $R^{42}$, when present, is selected from is selected from C1-C3 alkyl, C1-C3 monohaloalkyl, C1-C3 polyhaloalkyl, and, $-NR^{44a}R^{44b}$. In a still further aspect, $R^{42}$, when present, is selected from methyl, ethyl, $-CH_2F$, $-CH_2CH_2F$, $-CHF_2$, $-CF_3$, $-CH_2CHF_2$, $-CH_2CF_3$, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In yet a further aspect, $R^{42}$, when present, is selected from methyl, $-CH_2F$, $-CHF_2$, $-CF_3$, $-NHCH_3$, and $-N(CH_3)_2$. In an even further aspect, $R^{42}$, when present, is selected from methyl, $-CF_3$, and $-NHCH_3$.

In a further aspect, $R^{42}$, when present, is selected from C1-C3 alkyl, C1-C3 monohaloalkyl, C1-C3 polyhaloalkyl, and cyclopropyl. In a still further aspect, $R^{42}$, when present, is selected from methyl, ethyl, $-CH_2F$, $-CH_2CH_2F$, $-CHF_2$, $-CF_3$, $-CH_2CHF_2$, $-CH_2CF_3$, and cyclopropyl. In yet a further aspect, $R^{42}$, when present, is selected from methyl, $-CH_2F$, $-CHF_2$, $-CF_3$, and cyclopropyl. In an even further aspect, $R^{42}$, when present, is selected from methyl, $-CF_3$, and cyclopropyl.

In a further aspect, $R^{42}$, when present, is selected from C1-C3 monohaloalkyl, C1-C3 polyhaloalkyl, and cyclopropyl. In a still further aspect, $R^{42}$, when present, is selected from $-CH_2F$, $-CH_2CH_2F$, $-CHF_2$, $-CF_3$, $-CH_2CHF_2$, $-CH_2CF_3$, and cyclopropyl. In yet a further aspect, $R^{42}$, when present, is selected from $-CH_2F$, $-CHF_2$, $-CF_3$, and cyclopropyl.

In an even further aspect, $R^{42}$, when present, is selected from $-CF_3$ and cyclopropyl. In a further aspect, $R^{42}$, when present, is selected from C1-C3 alkyl, and cyclopropyl. In a still further aspect, $R^{42}$, when present, is selected from methyl, ethyl, and cyclopropyl. In yet a further aspect, $R^{42}$, when present, is selected from methyl, and cyclopropyl.

In a further aspect, $R^{42}$, when present, is selected from C1-C3 alkyl, C1-C3 monohaloalkyl, and C1-C3 polyhaloalkyl. In a still further aspect, $R^{42}$, when present, is selected from methyl, ethyl, $-CH_2F$, $-CH_2CH_2F$, $-CHF_2$, $-CF_3$, $-CH_2CHF_2$, and $-CH_2CF_3$. In yet a further aspect, $R^{42}$, when present, is selected from methyl, $-CH_2F$, $-CHF_2$, and $-CF_3$. In an even further aspect, $R^{42}$, when present, is selected from methyl and $-CF_3$.

In a further aspect, $R^{42}$, when present, is selected from C1-C3 monohaloalkyl, and C1-C3 polyhaloalkyl. In a still further aspect, $R^{42}$, when present, is selected from $-CH_2F$, $-CH_2CH_2F$, $-CHF_2$, $-CF_3$, $-CH_2CHF_2$, $-CH_2CF_3$. In yet a further aspect, $R^{42}$, when present, is selected from $-CH_2F$, $-CHF_2$, and $-CF_3$. In an even further aspect, $R^{42}$, when present, is $-CF_3$.

In a further aspect, $R^{42}$, when present, is C1-C3 alkyl. In a still further aspect, $R^{42}$, when present, is selected from methyl, and ethyl. In yet a further aspect, $R^{42}$, when present, is methyl.

q. $R^{43}$ Groups

In one aspect, $R^{43}$, when present, is selected from C1-C3 alkyl, C1-C3 monohaloalkyl, C1-C3 polyhaloalkyl, cyclopropyl, and, $-NR^{45a}R^{45b}$. In a further aspect, $R^{43}$, when present, is selected from methyl, ethyl, $-CH_2F$, $-CH_2CH_2F$, $-CHF_2$, $-CF_3$, $-CH_2CHF_2$, $-CH_2CF_3$, cyclopropyl, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In a still further aspect, $R^{43}$, when present, is selected from methyl, $-CH_2F$, $-CHF_2$, $-CF_3$, cyclopropyl, $-NHCH_3$, and $-N(CH_3)_2$. In yet a further aspect, $R^{43}$, when present, is selected from methyl, $-CF_3$, cyclopropyl, and $-NHCH_3$.

In a further aspect, $R^{43}$, when present, is selected from is selected from C1-C3 alkyl, C1-C3 monohaloalkyl, C1-C3 polyhaloalkyl, and, $-NR^{44a}R^{44b}$. In a still further aspect, $R^{43}$, when present, is selected from methyl, ethyl, $-CH_2F$, $-CH_2CH_2F$, $-CHF_2$, $-CF_3$, $-CH_2CHF_2$, $-CH_2CF_3$, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In yet a further aspect, $R^{43}$, when present, is selected from methyl, $-CH_2F$, $-CHF_2$, $-CF_3$, $-NHCH_3$, and $-N(CH_3)_2$. In an even further aspect, $R^{43}$, when present, is selected from methyl, $-CF_3$, and $-NHCH_3$.

In a further aspect, $R^{43}$, when present, is selected from C1-C3 alkyl, C1-C3 monohaloalkyl, C1-C3 polyhaloalkyl, and cyclopropyl. In a still further aspect, $R^{43}$, when present, is selected from methyl, ethyl, $-CH_2F$, $-CH_2CH_2F$, $-CHF_2$, $-CF_3$, $-CH_2CHF_2$, $-CH_2CF_3$, and cyclopropyl. In yet a further aspect, $R^{43}$, when present, is selected from methyl, $-CH_2F$, $-CHF_2$, $-CF_3$, and cyclopropyl. In an even further aspect, $R^{43}$, when present, is selected from methyl, $-CF_3$, and cyclopropyl.

In a further aspect, $R^{43}$, when present, is selected from C1-C3 monohaloalkyl, C1-C3 polyhaloalkyl, and cyclopropyl. In a still further aspect, $R^{43}$, when present, is selected from $-CH_2F$, $-CH_2CH_2F$, $-CHF_2$, $-CF_3$, $-CH_2CHF_2$, $-CH_2CF_3$, and cyclopropyl. In yet a further aspect, $R^{43}$, when present, is selected from $-CH_2F$, $-CHF_2$, $-CF_3$, and cyclopropyl. In yet a further aspect, $R^{43}$, when present, is selected from $-CF_3$ and cyclopropyl.

In a further aspect, $R^{43}$, when present, is selected from C1-C3 alkyl, and cyclopropyl. In a still further aspect, $R^{43}$, when present, is selected from methyl, ethyl, and cyclopropyl. In yet a further aspect, $R^{43}$, when present, is selected from methyl, and cyclopropyl.

In a further aspect, $R^{43}$, when present, is selected from C1-C3 alkyl, C1-C3 monohaloalkyl, and C1-C3 polyhaloalkyl. In a still further aspect, $R^{43}$, when present, is selected from methyl, ethyl, $-CH_2F$, $-CH_2CH_2F$, $-CHF_2$, $-CF_3$, $-CH_2CHF_2$, and $-CH_2CF_3$. In yet a further aspect, $R^{43}$, when present, is selected from methyl, $-CH_2F$, $-CHF_2$, and $-CF_3$. In an even further aspect, $R^{43}$, when present, is selected from methyl and $-CF_3$.

In a further aspect, $R^{43}$, when present, is selected from C1-C3 monohaloalkyl, and C1-C3 polyhaloalkyl. In a still further aspect, $R^{43}$, when present, is selected from $-CH_2F$, $-CH_2CH_2F$, $-CHF_2$, $-CF_3$, $-CH_2CHF_2$, and $-CH_2CF_3$. In yet a further aspect, $R^{43}$, when present, is selected from $-CH_2F$, $-CHF_2$, and $-CF_3$. In an even further aspect, $R^{43}$, when present, is $-CF_3$.

In a further aspect, $R^{43}$, when present, is C1-C3 alkyl. In a still further aspect, $R^{43}$, when present, is selected from methyl, and ethyl. In yet a further aspect, $R^{43}$, when present, is methyl.

r. $R^{44a}$ and $R^{44b}$ Groups

In one aspect, each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle.

In a further aspect, each of $R^{44a}$ and $R^{44b}$, when present, is independently selected from hydrogen, C1-C3 alkyl, C1-C3 monohaloalkyl, C1-C3 polyhaloalkyl, and cyclopropyl. In a still further aspect, each of $R^{44a}$ and $R^{44b}$, when present, is independently selected from hydrogen, methyl, ethyl, $—CH_2F$, $—CH_2CH_2F$, $—CHF_2$, $—CF_3$, $—CH_2CHF_2$, $—CH_2CF_3$, and cyclopropyl. In yet a further aspect, each of $R^{44a}$ and $R^{44b}$, when present, is independently selected from hydrogen, methyl, $—CH_2F$, $—CHF_2$, $—CF_3$, and cyclopropyl. In an even further aspect, each of $R^{44a}$ and $R^{44b}$, when present, is independently selected from hydrogen, methyl, $—CF_3$, and cyclopropyl.

In a further aspect, each of $R^{44a}$ and $R^{44b}$, when present, is independently selected from hydrogen, C1-C3 monohaloalkyl, C1-C3 polyhaloalkyl, and cyclopropyl. In a still further aspect, each of $R^{44a}$ and $R^{44b}$, when present, is independently selected from hydrogen, $—CH_2F$, $—CH_2CH_2F$, $—CHF_2$, $—CF_3$, $—CH_2CHF_2$, $—CH_2CF_3$, and cyclopropyl. In yet a further aspect, each of $R^{44a}$ and $R^{44b}$, when present, is independently selected from hydrogen, $—CH_2F$, $—CHF_2$, $—CF_3$, and cyclopropyl. In an even further aspect, each of $R^{44a}$ and $R^{44b}$, when present, is independently selected from hydrogen, $—CF_3$ and cyclopropyl.

In a further aspect, each of $R^{44a}$ and $R^{44b}$, when present, is independently selected from hydrogen, C1-C3 alkyl, and cyclopropyl. In a still further aspect, each of $R^{44a}$ and $R^{44b}$, when present, is independently selected from hydrogen, methyl, ethyl, and cyclopropyl. In yet a further aspect, each of $R^{44a}$ and $R^{44b}$, when present, is independently selected from hydrogen, methyl, and cyclopropyl.

In a further aspect, each of $R^{44a}$ and $R^{44b}$, when present, is independently selected from hydrogen, C1-C3 alkyl, C1-C3 monohaloalkyl, and C1-C3 polyhaloalkyl. In a still further aspect, each of $R^{44a}$ and $R^{44b}$, when present, is independently selected from hydrogen, methyl, ethyl, $—CH_2F$, $—CH_2CH_2F$, $—CHF_2$, $—CF_3$, $—CH_2CHF_2$, and $—CH_2CF_3$. In yet a further aspect, each of $R^{44a}$ and $R^{44b}$, when present, is independently selected from hydrogen, methyl, $—CH_2F$, $—CHF_2$, and $—CF_3$. In an even further aspect, each of $R^{44a}$ and $R^{44b}$, when present, is independently selected from hydrogen, methyl, and $—CF_3$.

In a further aspect, each of $R^{44a}$ and $R^{44b}$, when present, is independently selected from hydrogen, C1-C3 monohaloalkyl, and C1-C3 polyhaloalkyl. In a still further aspect, each of $R^{44a}$ and $R^{44b}$, when present, is independently selected from hydrogen, $—CH_2F$, $—CH_2CH_2F$, $—CHF_2$, $—CF_3$, $—CH_2CHF_2$, and $—CH_2CF_3$. In yet a further aspect, each of $R^{44a}$ and $R^{44b}$, when present, is independently selected from hydrogen, $—CH_2F$, $—CHF_2$, and $—CF_3$. In an even further aspect, each of $R^{44a}$ and $R^{44b}$, when present, is independently selected from hydrogen and $—CF_3$.

In a further aspect, each of $R^{44a}$ and $R^{44b}$, when present, is independently selected from hydrogen and C1-C3 alkyl. In a still further aspect, each of $R^{44a}$ and $R^{44b}$, when present, is independently selected from hydrogen, methyl, and ethyl.

In yet a further aspect, each of $R^{44a}$ and $R^{44b}$, when present, is independently selected from hydrogen and methyl.

In a further aspect, $R^{44a}$ is hydrogen and $R^{44b}$, when present, is selected from hydrogen, methyl, ethyl, $—CH_2F$, $—CH_2CH_2F$, $—CHF_2$, $—CF_3$, $—CH_2CHF_2$, $—CH_2CF_3$, and cyclopropyl. In a still further aspect, $R^{44a}$, when present, is hydrogen and $R^{44b}$, when present, is selected from hydrogen, methyl, $—CH_2F$, $—CHF_2$, $—CF_3$, and cyclopropyl. In yet a further aspect, $R^{44a}$, when present, is hydrogen and $R^{44b}$, when present, is selected from hydrogen, methyl, $—CF_3$, and cyclopropyl.

In further aspect $R^{44a}$, when present, is hydrogen and $R^{44b}$, when present, is selected from hydrogen, C1-C3 monohaloalkyl, C1-C3 polyhaloalkyl, and cyclopropyl. In a still further aspect, $R^{44a}$, when present, is hydrogen and $R^{44b}$, when present, is selected from hydrogen, $—CH_2F$, $—CH_2CH_2F$, $—CHF_2$, $—CF_3$, $—CH_2CHF_2$, $—CH_2CF_3$, and cyclopropyl. In yet a further aspect, $R^{44a}$, when present, is hydrogen and $R^{44b}$, when present, is selected from hydrogen, $—CH_2F$, $—CHF_2$, $—CF_3$, and cyclopropyl. In an even further aspect, $R^{44a}$, when present, is hydrogen and $R^{44b}$, when present, is selected from hydrogen, $—CF_3$ and cyclopropyl.

In a further aspect, $R^{44a}$, when present, is hydrogen and $R^{44b}$, when present, is selected from hydrogen, C1-C3 alkyl, and cyclopropyl. In a still further aspect, $R^{44a}$, when present, is hydrogen and $R^{44b}$, when present, is selected from hydrogen, methyl, ethyl, and cyclopropyl. In yet a further aspect, $R^{44a}$, when present, is hydrogen and $R^{44b}$, when present, is selected from hydrogen, methyl, and cyclopropyl.

In a further aspect, $R^{44a}$, when present, is hydrogen and $R^{44b}$, when present, is selected from hydrogen, C1-C3 alkyl, C1-C3 monohaloalkyl, and C1-C3 polyhaloalkyl. In a still further aspect, $R^{44a}$, when present, is hydrogen and $R^{44b}$, when present, is selected from hydrogen, methyl, ethyl, $—CH_2F$, $—CH_2CH_2F$, $—CHF_2$, $—CF_3$, $—CH_2CHF_2$, and $—CH_2CF_3$. In yet a further aspect, $R^{44a}$, when present, is hydrogen and $R^{44b}$, when present, is selected from hydrogen, methyl, $—CH_2F$, $—CHF_2$, and $—CF_3$. In an even further aspect, $R^{44a}$, when present, is hydrogen and $R^{44b}$, when present, is selected from hydrogen, methyl, and $—CF_3$.

In a further aspect, $R^{44a}$, when present, is hydrogen and $R^{44b}$, when present, is selected from hydrogen, C1-C3 monohaloalkyl, and C1-C3 polyhaloalkyl. In a still further aspect, $R^{44a}$, when present, is hydrogen and $R^{44b}$, when present, is selected from hydrogen, $—CH_2F$, $—CH_2CH_2F$, $—CHF_2$, $—CF_3$, $—CH_2CHF_2$, and $—CH_2CF_3$. In yet a further aspect, $R^{44a}$, when present, is hydrogen and $R^{44b}$, when present, is selected from hydrogen, $—CH_2F$, $—CHF_2$, and $—CF_3$. In an even further aspect, $R^{44a}$, when present, is hydrogen and $R^{44b}$, when present, is selected from hydrogen and $—CF_3$.

In a further aspect, $R^{44a}$, when present, is hydrogen and $R^{44b}$, when present, is selected from hydrogen and C1-C3 alkyl. In a still further aspect, $R^{44a}$, when present, is hydrogen and $R^{44b}$, when present, is selected from hydrogen, methyl, and ethyl. In yet a further aspect, $R^{44a}$, when present, is hydrogen and $R^{44b}$, when present, is selected from hydrogen and methyl. In an even further aspect, each of $R^{44a}$ and $R^{44b}$, when present, is hydrogen.

In a further aspect, $R^{44a}$ and $R^{44b}$, when present, are optionally covalently bonded and, together with the nitrogen atom to which they are attached, comprise a 3- to 6-membered heterocycle. In a still further aspect, $R^{44a}$ and $R^{44b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{44a}$ and $R^{44b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, $R^{44a}$ and $R^{44b}$, when present, are covalently bonded, and together with the nitrogen atom to which they are attached, comprise a heterocycle selected from imidazolyl, pyrazolyl, and pyrrolyl. In a still further aspect, $R^{44a}$ and $R^{44b}$, when present, are covalently bonded, and together with the nitrogen atom to which they are attached, comprise a pyrrolidinyl. In yet a further aspect, $R^{44a}$ and $R^{44b}$, when present, are covalently bonded, and together with the nitrogen atom to which they are attached, comprise a piperidinyl.

s. $R^{45a}$ and $R^{45b}$ Groups

In one aspect, each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle.

In a further aspect, each of $R^{45a}$ and $R^{45b}$, when present, is independently selected from hydrogen, C1-C3 alkyl, C1-C3 monohaloalkyl, C1-C3 polyhaloalkyl, and cyclopropyl. In a still further aspect, each of $R^{45a}$ and $R^{45b}$, when present, is independently selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of $R^{45a}$ and $R^{45b}$, when present, is independently selected from hydrogen, methyl, —CH$_2$F, —CHF$_2$, —CF$_3$, and cyclopropyl. In an even further aspect, each of $R^{45a}$ and $R^{45b}$, when present, is independently selected from hydrogen, methyl, —CF$_3$, and cyclopropyl.

In a further aspect, each of $R^{45a}$ and $R^{45b}$, when present, is independently selected from hydrogen, C1-C3 monohaloalkyl, C1-C3 polyhaloalkyl, and cyclopropyl. In a still further aspect, each of $R^{45a}$ and $R^{45b}$, when present, is independently selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of $R^{45a}$ and $R^{45b}$, when present, is independently selected from hydrogen, —CH$_2$F, —CHF$_2$, —CF$_3$, and cyclopropyl. In an even further aspect, each of $R^{45a}$ and $R^{45b}$ when present, is independently selected from hydrogen, —CF$_3$ and cyclopropyl.

In a further aspect, each of $R^{45a}$ and $R^{45b}$, when present, is independently selected from hydrogen, C1-C3 alkyl, and cyclopropyl. In a still further aspect, each of $R^{45a}$ and $R^{45b}$ when present, is independently selected from hydrogen, methyl, ethyl, and cyclopropyl. In yet a further aspect, each of $R^{45a}$ and $R^{45b}$, when present, is independently selected from hydrogen, methyl, and cyclopropyl.

In a further aspect, each of $R^{45a}$ and $R^{45b}$, when present, is independently selected from hydrogen, C1-C3 alkyl, C1-C3 monohaloalkyl, and C1-C3 polyhaloalkyl. In a still further aspect, each of $R^{45a}$ and $R^{45b}$, when present, is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, each of $R^{45a}$ and $R^{45b}$, when present, is independently selected from hydrogen, methyl, —CH$_2$F, —CHF$_2$, and —CF$_3$. In an even further aspect, each of $R^{45a}$ and $R^{45b}$, when present, is independently selected from hydrogen, methyl, and —CF$_3$.

In a further aspect, each of $R^{45a}$ and $R^{45b}$, when present, is independently selected from hydrogen, C1-C3 monohaloalkyl, and C1-C3 polyhaloalkyl. In a still further aspect, each of $R^{45a}$ and $R^{45b}$, when present, is independently selected from hydrogen, —CH$_2$F, —CH$_2$CH$_2$F, —CHF$_2$, —CF$_3$, —CH$_2$CHF$_2$, and —CH$_2$CF$_3$. In yet a further aspect, each of $R^{45a}$ and $R^{45b}$, when present, is independently selected from hydrogen, —CH$_2$F, —CHF$_2$, and —CF$_3$. In an even further aspect, each of $R^{45a}$ and $R^{45b}$, when present, is independently selected from hydrogen and —CF$_3$.

In a further aspect, each of $R^{45a}$ and $R^{45b}$, when present, is independently selected from hydrogen and C1-C3 alkyl. In a still further aspect, each of $R^{45a}$ and $R^{45b}$, when present, is independently selected from hydrogen, methyl, and ethyl. In yet a further aspect, each of $R^{45a}$ and $R^{45b}$, when present, is independently selected from hydrogen and methyl.

In a further aspect, $R^{45a}$ is hydrogen and $R^{45b}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, $R^{45a}$, when present, is hydrogen and $R^{45b}$, when present, is selected from hydrogen, methyl, —CH$_2$F, —CHF$_2$, —CF$_3$, and cyclopropyl. In yet a further aspect, $R^{45a}$, when present, is hydrogen and $R^{45b}$, when present, is selected from hydrogen, methyl, —CF$_3$, and cyclopropyl.

In a further aspect, $R^{45a}$, when present, is hydrogen and $R^{45b}$, when present, is selected from hydrogen, C1-C3 monohaloalkyl, C1-C3 polyhaloalkyl, and cyclopropyl. In a still further aspect, $R^{45a}$, when present, is hydrogen and $R^{45b}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{45a}$, when present, is hydrogen and $R^{45b}$, when present, is selected from hydrogen, —CH$_2$F, —CHF$_2$, —CF$_3$, and cyclopropyl. In an even further aspect, $R^{45a}$, when present, is hydrogen and $R^{45b}$, when present, is selected from hydrogen, —CF$_3$ and cyclopropyl.

In a further aspect, $R^{45a}$, when present, is hydrogen and $R^{45b}$, when present, is selected from hydrogen, C1-C3 alkyl, and cyclopropyl. In a still further aspect, $R^{45a}$, when present, is hydrogen and $R^{45b}$, when present, is selected from hydrogen, methyl, ethyl, and cyclopropyl. In yet a further aspect, $R^{45a}$, when present, is hydrogen and $R^{45b}$, when present, is selected from hydrogen, methyl, and cyclopropyl.

In a further aspect, $R^{45a}$, when present, is hydrogen and $R^{45b}$, when present, is selected from hydrogen, C1-C3 alkyl, C1-C3 monohaloalkyl, and C1-C3 polyhaloalkyl. In a still further aspect, $R^{45a}$, when present, is hydrogen and $R^{45b}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet further aspect, $R^{45a}$, when present, is hydrogen and $R^{45b}$, when present, is selected from hydrogen, methyl, —CH$_2$F, —CHF$_2$, and —CF$_3$. In an even further aspect, $R^{45a}$, when present, is hydrogen and $R^{45b}$, when present, is selected from hydrogen, methyl, and —CF$_3$.

In a further aspect, $R^{45a}$, when present, is hydrogen and $R^{45b}$, when present, is selected from hydrogen, C1-C3 monohaloalkyl, and C1-C3 polyhaloalkyl. In a still further aspect, $R^{45a}$, when present, is hydrogen and $R^{45b}$, when present, is selected from hydrogen, —CH$_2$F, —CH$_2$CH$_2$F, —CHF$_2$, —CF$_3$, —CH$_2$CHF$_2$, and —CH$_2$CF$_3$. In yet a further aspect, $R^{45a}$, when present, is hydrogen and $R^{45b}$, when present, is selected from hydrogen, —CH$_2$F, —CHF$_2$, and —CF$_3$. In an even further aspect, $R^{45a}$, when present, is hydrogen and $R^{45b}$, when present, is selected from hydrogen and —CF$_3$.

In further aspect $R^{44a}$, when present, is hydrogen and $R^{45b}$, when present, is selected from hydrogen and C1-C3 alkyl. In a still further aspect, $R^{45a}$, when present, is hydrogen and $R^{45b}$, when present, is selected from hydrogen, methyl, and ethyl. In yet a further aspect, $R^{45a}$, when present, is hydrogen and $R^{45b}$, when present, is selected from hydrogen and methyl. In an even further aspect, each of $R^{45a}$ and $R^{45b}$, when present, is hydrogen.

In a further aspect, $R^{45a}$ and $R^{45b}$, when present, are optionally covalently bonded and, together with the nitrogen atom to which they are attached, comprise a 3- to 6-membered heterocycle. In a still further aspect, $R^{45a}$ and $R^{45b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{45a}$ and $R^{45b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, $R^{45a}$ and $R^{45b}$, when present, are covalently bonded, and together with the nitrogen atom to which they are attached, comprise a heterocycle selected from imidazolyl, pyrazolyl, and pyrrolyl. In a still further aspect, $R^{45a}$ and $R^{45b}$, when present, are covalently bonded, and together with the nitrogen atom to which they are attached, comprise a pyrrolidinyl. In yet a further aspect, $R^{45a}$ and $R^{45b}$, when present, are covalently bonded, and together with the nitrogen atom to which they are attached, comprise a piperidinyl.

t. $R^{60}$ Groups

In one aspect, $R^{60}$, when present, is selected from is selected from hydrogen, C1-C3 alkyl, C1-C3 monohaloalkyl, C1-C3 polyhaloalkyl, and cyclopropyl. In a further aspect, $R^{60}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, $R^{60}$, when present, is selected from hydrogen, methyl, —CH$_2$F, —CHF$_2$, —CF$_3$, and cyclopropyl. In yet a further aspect, $R^{60}$, when present, is selected from hydrogen, methyl, —CF$_3$, and cyclopropyl.

In a further aspect, $R^{60}$, when present, is selected from hydrogen, C1-C3 monohaloalkyl, C1-C3 polyhaloalkyl, and cyclopropyl. In a still further aspect, $R^{60}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, $R^{60}$, when present, is selected from hydrogen, —CH$_2$F, —CHF$_2$, —CF$_3$, and cyclopropyl. In an even further aspect, $R^{60}$, when present, is selected from hydrogen, —CF$_3$ and cyclopropyl.

In a further aspect, $R^{60}$, when present, is selected from hydrogen, C1-C3 alkyl, and cyclopropyl. In a still further aspect, $R^{60}$, when present, is selected from hydrogen, methyl, ethyl, and cyclopropyl. In yet a further aspect, $R^{60}$, when present, is selected from hydrogen, methyl, and cyclopropyl.

In a further aspect, $R^{60}$, when present, is selected from hydrogen, C1-C3 alkyl, C1-C3 monohaloalkyl, and C1-C3 polyhaloalkyl. In a still further aspect, $R^{60}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, $R^{60}$, when present, is selected from hydrogen, methyl, —CH$_2$F, —CHF$_2$, and —CF$_3$. In an even further aspect, $R^{60}$, when present, is selected from hydrogen, methyl, and —CF$_3$.

In a further aspect, $R^{60}$, when present, is selected from hydrogen, C1-C3 monohaloalkyl, and C1-C3 polyhaloalkyl. In a still further aspect, $R^{60}$, when present, is selected from hydrogen, —CH$_2$F, —CH$_2$CH$_2$F, —CHF$_2$, —CF$_3$, —CH$_2$CHF$_2$, and —CH$_2$CF$_3$. In yet a further aspect, $R^{60}$, when present, is selected from hydrogen, —CH$_2$F, —CHF$_2$, and —CF$_3$. In an even further aspect, $R^{60}$, when present, is selected from hydrogen and —CF$_3$.

In a further aspect, $R^{60}$, when present, is selected from hydrogen and C1-C3 alkyl. In a still further aspect, $R^{60}$, when present, is selected from hydrogen, methyl, and ethyl. In yet a further aspect, $R^{60}$, when present, is selected from hydrogen and methyl. In an even further aspect, $R^{60}$, when present, is hydrogen.

u. $R^{61a}$ and $R^{61b}$ Groups

In one aspect, each of $R^{61a}$ and $R^{61b}$, when present, is independently selected from is selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle.

In a further aspect, each of $R^{61a}$ and $R^{61b}$, when present, is independently selected from hydrogen, C1-C3 alkyl, C1-C3 monohaloalkyl, C1-C3 polyhaloalkyl, and cyclopropyl. In a still further aspect, each of $R^{61a}$ and $R^{61b}$, when present, is independently selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of $R^{61a}$ and $R^{61b}$, when present, is independently selected from hydrogen, methyl, —CH$_2$F, —CHF$_2$, —CF$_3$, and cyclopropyl. In an even further aspect, each of $R^{61a}$ and $R^{61b}$, when present, is independently selected from hydrogen, methyl, —CF$_3$, and cyclopropyl.

In a further aspect, each of $R^{61a}$ and $R^{61b}$, when present, is independently selected from hydrogen, C1-C3 monohaloalkyl, C1-C3 polyhaloalkyl, and cyclopropyl. In a still further aspect, each of $R^{61a}$ and $R^{61b}$, when present, is independently selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of $R^{61a}$ and $R^{61b}$, when present, is independently selected from hydrogen, —CH$_2$F, —CHF$_2$, —CF$_3$, and cyclopropyl. In an even further aspect, each of $R^{61a}$ and $R^{61b}$, when present, is independently selected from hydrogen, —CF$_3$ and cyclopropyl.

In a further aspect, each of $R^{61a}$ and $R^{61b}$, when present, is independently selected from hydrogen, C1-C3 alkyl, and cyclopropyl. In a still further aspect, each of $R^{61a}$ and $R^{61b}$ when present, is independently selected from hydrogen, methyl, ethyl, and cyclopropyl. In yet a further aspect, each of $R^{61a}$ and $R^{61b}$, when present, is independently selected from hydrogen, methyl, and cyclopropyl.

In a further aspect, each of $R^{61a}$ and $R^{61b}$, when present, is independently selected from hydrogen, C1-C3 alkyl, C1-C3 monohaloalkyl, and C1-C3 polyhaloalkyl. In a still further aspect, each of $R^{61a}$ and $R^{61b}$, when present, is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, each of $R^{61a}$ and $R^{61b}$, when present, is independently selected from hydrogen, methyl, —CH$_2$F, —CHF$_2$, and —CF$_3$. In an even further aspect, each of $R^{61a}$ and $R^{61b}$, when present, is independently selected from hydrogen, methyl, and —CF$_3$.

In a further aspect, each of $R^{61a}$ and $R^{61b}$, when present, is independently selected from hydrogen, C1-C3 monohaloalkyl, and C1-C3 polyhaloalkyl. In a still further aspect, each of $R^{61a}$ and $R^{61b}$, when present, is independently selected from hydrogen, —CH$_2$F, —CH$_2$CH$_2$F, —CHF$_2$, —CF$_3$, —CH$_2$CHF$_2$, and —CH$_2$CF$_3$. In yet a further aspect, each of $R^{61a}$ and $R^{61b}$, when present, is independently selected from hydrogen, —CH$_2$F, —CHF$_2$, and —CF$_3$. In an even further aspect, each of R$^{61a}$ and R$^{61b}$, when present, is independently selected from hydrogen and —CF$_3$.

In a further aspect, each of R$^{61a}$ and R$^{61b}$, when present, is independently selected from hydrogen and C1-C3 alkyl. In a still further aspect, each of R$^{61a}$ and R$^{61b}$, when present, is independently selected from hydrogen, methyl, and ethyl. In yet a further aspect, each of R$^{61a}$ and R$^{61b}$, when present, is independently selected from hydrogen and methyl.

In a further aspect, R$^{61a}$ is hydrogen and R$^{61b}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, R$^{61a}$, when present, is hydrogen and R$^{61b}$, when present, is selected from hydrogen, methyl, —CH$_2$F, —CHF$_2$, —CF$_3$, and cyclopropyl. In yet a further aspect, R$^{61a}$, when present, is hydrogen and R$^{61b}$, when present, is selected from hydrogen, methyl, —CF$_3$, and cyclopropyl.

In a further aspect, R$^{61a}$, when present, is hydrogen and R$^{61b}$, when present, is selected from hydrogen, C1-C3 monohaloalkyl, C1-C3 polyhaloalkyl, and cyclopropyl. In a still further aspect, R$^{61a}$, when present, is hydrogen and R$^{61b}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet further aspect, R$^{61a}$, when present, is hydrogen and R$^{61b}$, when present, is selected from hydrogen, —CH$_2$F, —CHF$_2$, —CF$_3$, and cyclopropyl. In an even further aspect, R$^{61a}$, when present, is hydrogen and R$^{61b}$, when present, is selected from hydrogen, —CF$_3$ and cyclopropyl.

In a further aspect, R$^{61a}$, when present, is hydrogen and R$^{61b}$, when present, is selected from hydrogen, C1-C3 alkyl, and cyclopropyl. In a still further aspect, R$^{61a}$, when present, is hydrogen and R$^{61b}$, when present, is selected from hydrogen, methyl, ethyl, and cyclopropyl. In yet a further aspect, R$^{61a}$, when present, is hydrogen and R$^{61b}$, when present, is selected from hydrogen, methyl, and cyclopropyl.

In a further aspect, R$^{61a}$, when present, is hydrogen and R$^{61b}$, when present, is selected from hydrogen, C1-C3 alkyl, C1-C3 monohaloalkyl, and C1-C3 polyhaloalkyl. In a still further aspect, R$^{61a}$, when present, is hydrogen and R$^{61b}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, R$^{61a}$, when present, is hydrogen and R$^{61b}$, when present, is selected from hydrogen, methyl, —CH$_2$F, —CHF$_2$, and —CF$_3$. In an even further aspect, R$^{61a}$, when present, is hydrogen and R$^{61b}$, when present, is selected from hydrogen, methyl, and —CF$_3$.

In a further aspect, R$^{61a}$, when present, is hydrogen and R$^{61b}$, when present, is selected from hydrogen, C1-C3 monohaloalkyl, and C1-C3 polyhaloalkyl. In a still further aspect, R$^{61a}$, when present, is hydrogen and R$^{61b}$, when present, is selected from hydrogen, —CH$_2$F, —CH$_2$CH$_2$F, —CHF$_2$, —CF$_3$, —CH$_2$CHF$_2$, and —CH$_2$CF$_3$. In yet a further aspect, R$^{61a}$, when present, is hydrogen and R$^{61b}$, when present, is selected from hydrogen, —CH$_2$F, —CHF$_2$, and —CF$_3$. In an even further aspect, R$^{61a}$, when present, is hydrogen R$^{61b}$, when present, is selected from hydrogen and —CF$_3$.

In a further aspect, R$^{61a}$, when present, is hydrogen and R$^{61b}$, when present, is selected from hydrogen and C1-C3 alkyl. In a still further aspect, R$^{61a}$, when present, is hydrogen and R$^{61b}$, when present, is selected from hydrogen, methyl, and ethyl. In yet a further aspect, R$^{61a}$, when present, is hydrogen and R$^{61b}$, when present, is selected from hydrogen and methyl. In an even further aspect, each of R$^{61a}$ and R$^{61b}$, when present, is hydrogen.

In a further aspect, R$^{61a}$ and R$^{61b}$, when present, are optionally covalently bonded and, together with the nitrogen atom to which they are attached, comprise a 3- to 6-membered heterocycle. In a still further aspect, R$^{61a}$ and R$^{61b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, R$^{61a}$ and R$^{61b}$, when present, are covalently bonded, and together with the nitrogen atom to which they are attached, comprise a heterocycle selected from pyrrolidinyl, piperidinyl, azepanyl, imidazolidinyl, and pyrazolidinyl. In an even further aspect, R$^{61a}$ and R$^{61b}$, when present, are covalently bonded, and together with the nitrogen atom to which they are attached, comprise a heterocycle selected from imidazolyl, pyrazolyl, and pyrrolyl. In a still further aspect, R$^{61a}$ and R$^{61b}$, when present, are covalently bonded, and together with the nitrogen atom to which they are attached, comprise a pyrrolidinyl. In yet a further aspect, R$^{61a}$ and R$^{61b}$, when present, are covalently bonded, and together with the nitrogen atom to which they are attached, comprise a piperidinyl.

v. R$^{62}$ Groups

In one aspect, R$^{62}$, when present, is selected from C1-C3 alkyl, C1-C3 monohaloalkyl, C1-C3 polyhaloalkyl, cyclopropyl, and —NR$^{64a}$R$^{64b}$. In a further aspect, R$^{62}$, when present, is selected from methyl, ethyl, —CH$_2$F, —CH$_2$CH$_2$F, —CHF$_2$, —CF$_3$, —CH$_2$CHF$_2$, —CH$_2$CF$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{62}$, when present, is selected from methyl, —CH$_2$F, —CHF$_2$, —CF$_3$, cyclopropyl, —NHCH$_3$, and —N(CH$_3$)$_2$. In yet a further aspect, R$^{62}$, when present, is selected from methyl, —CF$_3$, cyclopropyl, and —NHCH$_3$.

In a further aspect, R$^{62}$, when present, is selected from is selected from C1-C3 alkyl, C1-C3 monohaloalkyl, C1-C3 polyhaloalkyl, and —NR$^{64a}$R$^{64b}$. In a still further aspect, R$^{62}$, when present, is selected from methyl, ethyl, —CH$_2$F, —CH$_2$CH$_2$F, —CHF$_2$, —CF$_3$, —CH$_2$CHF$_2$, —CH$_2$CF$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, R$^{62}$, when present, is selected from methyl, —CH$_2$F, —CHF$_2$, —CF$_3$, —NHCH$_3$, and —N(CH$_3$)$_2$. In an even further aspect, R$^{62}$, when present, is selected from methyl, —CF$_3$, and —NHCH$_3$.

In a further aspect, R$^{62}$, when present, is selected from C1-C3 alkyl, C1-C3 monohaloalkyl, C1-C3 polyhaloalkyl, and cyclopropyl. In a still further aspect, R$^{62}$, when present, is selected from methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, R$^{62}$, when present, is selected from methyl, —CH$_2$F, —CHF$_2$, —CF$_3$, and cyclopropyl. In an even further aspect, R$^{62}$, when present, is selected from methyl, —CF$_3$, and cyclopropyl.

In a further aspect, R$^{62}$, when present, is selected from C1-C3 monohaloalkyl, C1-C3 polyhaloalkyl, and cyclopropyl. In a still further aspect, R$^{62}$, when present, is selected from —CH$_2$F, —CH$_2$CH$_2$F, —CHF$_2$, —CF$_3$, —CH$_2$CHF$_2$, —CH$_2$CF$_3$, and cyclopropyl. In yet a further aspect, R$^{62}$, when present, is selected from —CH$_2$F, —CHF$_2$, —CF$_3$, and cyclopropyl. In an even further aspect, R$^{62}$, when present, is selected from —CF$_3$ and cyclopropyl.

In a further aspect, $R^{62}$, when present, is selected from C1-C3 alkyl, and cyclopropyl. In a still further aspect, $R^{62}$, when present, is selected from methyl, ethyl, and cyclopropyl. In yet a further aspect, $R^{62}$, when present, is selected from methyl, and cyclopropyl.

In a further aspect, $R^{62}$, when present, is selected from C1-C3 alkyl, C1-C3 monohaloalkyl, and C1-C3 polyhaloalkyl. In a still further aspect, $R^{62}$, when present, is selected from meth 1, ethyl, —$CH_2F$, —$CH_2CH_2F$, —$CHF_2$, —$CF_3$, —$CH_2CHF_2$, and —$CH_2CF_3$. In yet a further aspect, $R^{62}$, when present, is selected from methyl, —$CH_2F$, —$CHF_2$, and —$CF_3$. In an even further aspect, $R^{62}$, when present, is selected from methyl and —$CF_3$.

In a further aspect, $R^{62}$, when present, is selected from C1-C3 monohaloalkyl, and C1-C3 polyhaloalkyl. In a still further aspect, $R^{62}$, when present, is selected from —$CH_2F$, —$CH_2CH_2F$, —$CHF_2$, —$CF_3$, —$CH_2CHF_2$, and —$CH_2CF_3$. In yet a further aspect, $R^{62}$, when present, is selected from —$CH_2F$, —$CHF_2$, and —$CF_3$. In an even further aspect, $R^{62}$, when present, is —$CF_3$.

In a further aspect, $R^{62}$, when present, is C1-C3 alkyl. In a still further aspect, $R^{62}$, when present, is selected from methyl, and ethyl. In yet a further aspect, $R^{62}$, when present, is methyl.

w. $R^{63}$ Groups

In one aspect, $R^{63}$, when present, is selected from C1-C3 alkyl, C1-C3 monohaloalkyl, C1-C3 polyhaloalkyl, cyclopropyl, and —$NR^{65a}R^{65b}$. In further aspect, $R^{63}$, when present, is selected from methyl, ethyl, —$CH_2F$, —$CH_2CH_2F$, —$CHF_2$, —$CF_3$, —$CH_2CHF_2$, —$CH_2CF_3$, cyclopropyl, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In a still further aspect, $R^{63}$, when present, is selected from methyl, —$CH_2F$, —$CHF_2$, —$CF_3$, cyclopropyl, —$NHCH_3$, and —$N(CH_3)_2$. In yet a further aspect, $R^{63}$, when present, is selected from methyl, —$CF_3$, cyclopropyl, and —$NHCH_3$.

In a further aspect, $R^{63}$, when present, is selected from is selected from C1-C3 alkyl, C1-C3 monohaloalkyl, C1-C3 polyhaloalkyl, and —$NR^{64a}R^{64b}$. In still further aspect, $R^{63}$, when present, is selected from methyl, ethyl, —$CH_2F$, —$CH_2CH_2F$, —$CHF_2$, —$CF_3$, —$CH_2CHF_2$, —$CH_2CF_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In yet a further aspect, $R^{63}$, when present, is selected from methyl, —$CH_2F$, —$CHF_2$, —$CF_3$, —$NHCH_3$, and —$N(CH_3)_2$. In an even further aspect, $R^{63}$, when present, is selected from methyl, —$CF_3$, and —$NHCH_3$.

In a further aspect, $R^{63}$, when present, is selected from C1-C3 alkyl, C1-C3 monohaloalkyl, C1-C3 polyhaloalkyl, and cyclopropyl. In a still further aspect, $R^{63}$, when present, is selected from methyl, ethyl, —$CH_2F$, —$CH_2CH_2F$, —$CHF_2$, —$CF_3$, —$CH_2CHF_2$, —$CH_2CF_3$, and cyclopropyl. In yet a further aspect, $R^{63}$, when present, is selected from methyl, —$CH_2F$, —$CHF_2$, —$CF_3$, and cyclopropyl. In an even further aspect, $R^{63}$, when present, is selected from methyl, —$CF_3$, and cyclopropyl.

In a further aspect, $R^{63}$, when present, is selected from C1-C3 monohaloalkyl, C1-C3 polyhaloalkyl, and cyclopropyl. In a still further aspect, $R^{63}$, when present, is selected from —$CH_2F$, —$CH_2CH_2F$, —$CHF_2$, —$CF_3$, —$CH_2CHF_2$, —$CH_2CF_3$, and cyclopropyl. In yet a further aspect, $R^{63}$, when present, is selected from —$CH_2F$, —$CHF_2$, —$CF_3$, and cyclopropyl. In an even further aspect, $R^{63}$, when present, is selected from —$CF_3$ and cyclopropyl.

In a further aspect, $R^{63}$, when present, is selected from C1-C3 alkyl, and cyclopropyl. In a still further aspect, $R^{63}$, when present, is selected from methyl, ethyl, and cyclopropyl. In yet a further aspect, $R^{63}$, when present, is selected from methyl, and cyclopropyl.

In a further aspect, $R^{63}$, when present, is selected from C1-C3 alkyl, C1-C3 monohaloalkyl, and C1-C3 polyhaloalkyl. In a still further aspect, $R^{63}$, when present, is selected from methyl, ethyl, —$CH_2F$, —$CH_2CH_2F$, —$CHF_2$, —$CF_3$, —$CH_2CHF_2$, and —$CH_2CF_3$. In yet a further aspect, $R^{63}$, when present, is selected from methyl, —$CH_2F$, —$CHF_2$, and —$CF_3$. In an even further aspect, $R^{63}$, when present, is selected from methyl and —$CF_3$.

In a further aspect, $R^{63}$, when present, is selected from C1-C3 monohaloalkyl, and C1-C3 polyhaloalkyl. In a still further aspect, $R^{63}$, when present, is selected from —$CH_2F$, —$CH_2CH_2F$, —$CHF_2$, —$CF_3$, —$CH_2CHF_2$, and —$CH_2CF_3$. In yet a further aspect, $R^{63}$, when present, is selected from —$CH_2F$, —$CHF_2$, and —$CF_3$. In an even further aspect, $R^{63}$, when present, is —$CF_3$.

In a further aspect, $R^{63}$, when present, is C1-C3 alkyl. In a still further aspect, $R^{63}$, when present, is selected from methyl, and ethyl. In yet a further aspect, $R^{63}$, when present, is methyl.

x. $R^{64a}$ and $R^{64b}$ Groups

In one aspect, each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle.

In a further aspect, each of $R^{64a}$ and $R^{64b}$, when present, is independently selected from hydrogen, C1-C3 alkyl, C1-C3 monohaloalkyl, C1-C3 polyhaloalkyl, and cyclopropyl. In a still further aspect, each of $R^{64a}$ and $R^{64b}$, when present, is independently selected from hydrogen, methyl, ethyl, —$CH_2F$, —$CH_2CH_2F$, —$CHF_2$, —$CF_3$, —$CH_2CHF_2$, —$CH_2CF_3$, and cyclopropyl. In yet a further aspect, each of $R^{64a}$ and $R^{64b}$, when present, is independently selected from hydrogen, methyl, —$CH_2F$, —$CHF_2$, —$CF_3$, and cyclopropyl. In an even further aspect, each of $R^{64a}$ and $R^{64b}$, when present, is independently selected from hydrogen, methyl, —$CF_3$, and cyclopropyl.

In a further aspect, each of $R^{64a}$ and $R^{64b}$, when present, is independently selected from hydrogen, C1-C3 monohaloalkyl, C1-C3 polyhaloalkyl, and cyclopropyl. In a still further aspect, each of $R^{64a}$ and $R^{64b}$, when present, is independently selected from hydrogen, —$CH_2F$, —$CH_2CH_2F$, —$CHF_2$, —$CF_3$, —$CH_2CHF_2$, —$CH_2CF_3$, and cyclopropyl. In yet a further aspect, each of $R^{64a}$ and $R^{64b}$, when present, is independently selected from hydrogen, —$CH_2F$, —$CHF_2$, —$CF_3$, and cyclopropyl. In an even further aspect, each of $R^{64a}$ and $R^{64b}$, when present, is independently selected from hydrogen, —$CF_3$ and cyclopropyl.

In a further aspect, each of $R^{64a}$ and $R^{64b}$, when present, is independently selected from hydrogen, C1-C3 alkyl, and cyclopropyl. In a still further aspect, each of $R^{64a}$ and $R^{64b}$, when present, is independently selected from hydrogen, methyl, ethyl, and cyclopropyl. In yet a further aspect, each of $R^{64a}$ and $R^{64b}$, when present, is independently selected from hydrogen, methyl, and cyclopropyl.

In a further aspect, each of $R^{64a}$ and $R^{64b}$, when present, is independently selected from hydrogen, C1-C3 alkyl, C1-C3 monohaloalkyl, and C1-C3 polyhaloalkyl. In a still further aspect, each of $R^{64a}$ and $R^{64b}$, when present, is independently selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, each of each of R$^{64a}$ and R$^{64b}$, when present, is independently selected from hydrogen, methyl, —CH$_2$F, —CHF$_2$, and —CF$_3$. In an even further aspect, each of R$^{64a}$ and R$^{64b}$, when present, is independently selected from hydrogen, methyl, and —CF$_3$.

In a further aspect, each of R$^{64a}$ and R$^{64b}$, when present, is independently selected from hydrogen, C1-C3 monohaloalkyl, and C1-C3 polyhaloalkyl. In a still further aspect, each of R$^{64a}$ and R$^{64b}$, when present, is independently selected from hydrogen, —CH$_2$F, —CH$_2$CH$_2$F, —CHF$_2$, —CF$_3$, —CH$_2$CHF$_2$, and —CH$_2$CF$_3$. In yet a further aspect, each of R$^{64a}$ and R$^{64b}$, when present, is independently selected from hydrogen, —CH$_2$F, —CHF$_2$, and —CF$_3$. In an even further aspect, each of R$^{64a}$ and R$^{64b}$, when present, is independently selected from hydrogen and —CF$_3$.

In a further aspect, each of R$^{64a}$ and R$^{64b}$, when present, is independently selected from hydrogen and C1-C3 alkyl. In a still further aspect, each of R$^{64a}$ and R$^{64b}$, when present, is independently selected from hydrogen, methyl, and ethyl. In yet a further aspect, each of R$^{64a}$ and R$^{64b}$, when present, is independently selected from hydrogen and methyl.

In a further aspect, R$^{64a}$ is hydrogen and R$^{64b}$, when present, is selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In a still further aspect, R$^{64a}$, when present, is hydrogen and R$^{64b}$, when present, is selected from hydrogen, methyl, —CH$_2$F, —CHF$_2$, —CF$_3$, and cyclopropyl. In yet a further aspect, R$^{64a}$, when present, is hydrogen and R$^{64b}$, when present, is selected from hydrogen, methyl, —CF$_3$, and cyclopropyl.

In a further aspect, R$^{64a}$, when present, is hydrogen and R$^{64b}$, when present, is selected from hydrogen, C1-C3 monohaloalkyl, C1-C3 polyhaloalkyl, and cyclopropyl. In a still further aspect, R$^{64a}$, when present, is hydrogen and R$^{64b}$, when present, is selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet further aspect, R$^{64a}$, when present, is hydrogen and R$^{64b}$, when present, is selected from hydrogen, —CH$_2$F, —CHF$_2$, —CF$_3$, and cyclopropyl. In an even further aspect, R$^{64a}$, when present, is hydrogen and R$^{64b}$, when present, is selected from hydrogen, —CF$_3$ and cyclopropyl.

In a further aspect, R$^{64a}$, when present, is hydrogen and R$^{64b}$, when present, is selected from hydrogen, C1-C3 alkyl, and cyclopropyl. In a still further aspect, R$^{64a}$, when present, is hydrogen and R$^{64b}$, when present, is selected from hydrogen, methyl, ethyl, and cyclopropyl. In yet a further aspect, R$^{64a}$, when present, is hydrogen and R$^{64b}$, when present, is selected from hydrogen, methyl, and cyclopropyl.

In a further aspect, R$^{64a}$, when present, is hydrogen and R$^{64b}$, when present, is selected from hydrogen, C1-C3 alkyl, C1-C3 monohaloalkyl, and C1-C3 polyhaloalkyl. In a still further aspect, R$^{64a}$, when present, is hydrogen and R$^{64b}$, when present, is selected from hydrogen, methyl, ethyl, —CH$_2$F, —CH$_2$CH$_2$F, —CHF$_2$, —CF$_3$, —CH$_2$CHF$_2$, and —CH$_2$CF$_3$. In yet a further aspect, R$^{64a}$, when present, is hydrogen and R$^{64b}$, when present, is selected from hydrogen, methyl, —CH$_2$F, —CHF$_2$, and —CF$_3$. In an even further aspect, R$^{64a}$, when present, is hydrogen and R$^{64b}$, when present, is selected from hydrogen, methyl, and —CF$_3$.

In a further aspect, R$^{64a}$, when present, is hydrogen and R$^{64b}$, when present, is selected from hydrogen, C1-C3 monohaloalkyl, and C1-C3 polyhaloalkyl. In a still further aspect, R$^{64a}$, when present, is hydrogen and R$^{64b}$, when present, is selected from hydrogen, —CH$_2$F, —CH$_2$CH$_2$F, —CHF$_2$, —CF$_3$, —CH$_2$CHF$_2$, and —CH$_2$CF$_3$. In yet a further aspect, R$^{64a}$, when present, is hydrogen and R$^{64b}$, when present, is selected from hydrogen, —CH$_2$F, —CHF$_2$, and —CF$_3$. In an even further aspect, R$^{64a}$, when present, is hydrogen R$^{64a}$, when present, is selected from hydrogen and —CF$_3$.

In a further aspect, R$^{64a}$, when present, is hydrogen and R$^{64b}$, when present, is selected from hydrogen and C1-C3 alkyl. In a still further aspect, R$^{64a}$, when present, is hydrogen and R$^{64b}$, when present, is selected from hydrogen, methyl, and ethyl. In yet a further aspect, R$^{64a}$, when present, is hydrogen and R$^{64b}$, when present, is selected from hydrogen and methyl. In an even further aspect, each of R$^{64a}$ and R$^{64b}$, when present, is hydrogen.

In a further aspect, R$^{64a}$ and R$^{64b}$, when present, are optionally covalently bonded and, together with nitrogen atom to which they are attached, comprise a 3- to 6-membered heterocycle. In a still further aspect, R$^{64a}$ and R$^{64b}$, when present, are covalently bonded, and together with nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, R$^{64a}$ and R$^{64b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, R$^{64a}$ and R$^{64b}$, when present, are covalently bonded, and together with nitrogen atom to which they are attached, comprise a heterocycle selected from imidazolyl, pyrazolyl, and pyrrolyl. In a still further aspect, R$^{64a}$ and R$^{64b}$, when present, are covalently bonded, and together with nitrogen atom to which they are attached, comprise a pyrrolidinyl. In yet a further aspect, R$^{64a}$ and R$^{64b}$, when present, are covalently bonded, and together with nitrogen atom to which they are attached, comprise a piperidinyl.

y. R$^{65a}$ and R$^{6b}$ Groups

In one aspect, each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with the nitrogen atom to which they are attached, comprise a 3- to 6-membered heterocycle.

In a further aspect, ach of R$^{65a}$ and R$^{65b}$, when present, is independently selected from hydrogen, C1-C3 alkyl, C1-C3 monohaloalkyl, C1-C3 polyhaloalkyl, and cyclopropyl. In a still further aspect, each of R$^{65a}$ and R$^{65b}$, when present, is independently selected from hydrogen, methyl, ethyl, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of R$^{65a}$ and R$^{65b}$, when present, is independently selected from hydrogen, methyl, —CH$_2$F, —CHF$_2$, —CF$_3$, and cyclopropyl. In an even further aspect, each of R$^{65a}$ and R$^{65b}$, when present, is independently selected from hydrogen, methyl, —CF$_3$, and cyclopropyl.

In a further aspect, each of R$^{65a}$ and R$^{65b}$, when present, is independently selected from hydrogen, C1-C3 monohaloalkyl, C1-C3 polyhaloalkyl, and cyclopropyl. In a still further aspect, each of R$^{65a}$ and R$^{65b}$, when present, is independently selected from hydrogen, —CH$_2$F, —CH$_2$CH$_2$F, —CHF$_2$, —CF$_3$, —CH$_2$CHF$_2$, —CH$_2$CF$_3$, and cyclopropyl. In yet a further aspect, each of R$^{65a}$ and R$^{65b}$, when present, is independently selected from hydrogen, —CH$_2$F, —CHF$_2$, —CF$_3$, and cyclopropyl. In an even further aspect, each of R$^{65a}$ and R$^{65b}$, when present, is independently selected from hydrogen, —CF$_3$ and cyclopropyl.

In a further aspect, each of $R^{65a}$ and $R^{65b}$, when present, is independently selected from hydrogen, C1-C3 alkyl, and cyclopropyl. In a still further aspect, each of $R^{65a}$ and $R^{65b}$ when present, is independently selected from hydrogen, methyl, ethyl, and cyclopropyl. In yet a further aspect, each of $R^{65a}$ and $R^{65b}$, when present, is independently selected from hydrogen, methyl, and cyclopropyl.

In a further aspect, each of $R^{65a}$ and $R^{65b}$, when present, is independently selected from hydrogen, C1-C3 alkyl, C1-C3 monohaloalkyl, and C1-C3 polyhaloalkyl. In a still further aspect, each of $R^{65a}$ and $R^{65b}$, when present, is independently selected from hydrogen, methyl, ethyl, $-CH_2F$, $-CH_2CH_2F$, $-CHF_2$, $-CF_3$, $-CH_2CHF_2$, and $-CH_2CF_3$. In yet a further aspect, each of $R^{65a}$ and $R^{65b}$, when present, is independently selected from hydrogen, methyl, $-CH_2F$, $-CHF_2$, and $-CF_3$. In an even further aspect, each of $R^{65a}$ and $R^{65b}$, when present, is independently selected from hydrogen, methyl, and $-CF_3$.

In a further aspect, each of $R^{65a}$ and $R^{65b}$, when present, is independently selected from hydrogen, C1-C3 monohaloalkyl, and C1-C3 polyhaloalkyl. In a still further aspect, each of $R^{65a}$ and $R^{65b}$, when present, is independently selected from hydrogen, $-CH_2F$, $-CH_2CH_2F$, $-CHF_2$, $-CF_3$, $-CH_2CHF_2$, and $-CH_2CF_{33}$. In yet a further aspect, each of $R^{65a}$ and $R^{65b}$, when present, is independently selected from hydrogen, $-CH_2F$, $-CHF_2$, and $-CF_3$. In an even further aspect, each of $R^{65a}$ and $R^{65b}$, when present, is independently selected from hydrogen and $-CF_3$.

In a further aspect, each of $R^{65a}$ and $R^{65b}$, when present, is independently selected from hydrogen and C1-C3 alkyl. In a still further aspect, each of $R^{65a}$ and $R^{65b}$, when present, is independently selected from hydrogen, methyl, and ethyl. In yet a further aspect, each of $R^{65a}$ and $R^{65b}$, when present, is independently selected from hydrogen and methyl.

In a further aspect, $R^{65a}$ is hydrogen and $R^{65b}$, when present, is selected from hydrogen, methyl, ethyl, $-CH_2F$, $-CH_2CH_2F$, $-CHF_2$, $-CF_3$, $-CH_2CHF_2$, $-CH_2CF_3$, and cyclopropyl. In a still further aspect, $R^{65a}$, when present, is hydrogen and $R^{65b}$, when present, is selected from hydrogen, methyl, $-CH_2F$, $-CHF_2$, $-CF_3$, and cyclopropyl. In yet a further aspect, $R^{65a}$, when present, is hydrogen and $R^{65b}$, when present, is selected from hydrogen, methyl, $-CF_3$, and cyclopropyl.

In a further aspect, $R^{65a}$, when present, is hydrogen and $R^{65b}$, when present, is selected from hydrogen, C1-C3 monohaloalkyl, C1-C3 polyhaloalkyl, and cyclopropyl. In a still further aspect, $R^{65a}$, when present, is hydrogen and $R^{65b}$, when present, is selected from hydrogen, $-CH_2F$, $-CH_2CH_2F$, $-CHF_2$, $-CF_3$, $-CH_2CHF_2$, $-CH_2CF_3$, and cyclopropyl. In yet further aspect, $R^{65a}$, when present, is hydrogen and $R^{65b}$, when present, is selected from hydrogen, $-CH_2F$, $-CHF_2$, $-CF_3$, and cyclopropyl. In an even further aspect, $R^{65a}$, when present, is hydrogen and $R^{65b}$, when present, is selected from hydrogen, $-CF_3$ and cyclopropyl.

In a further aspect, $R^{65a}$, when present, is hydrogen and $R^{65b}$, when present, is selected from hydrogen, C1-C3 alkyl, and cyclopropyl. In a still further aspect, $R^{65a}$, when present, is hydrogen and $R^{65b}$, when present, is selected from hydrogen, methyl, ethyl, and cyclopropyl. In yet a further aspect, $R^{65a}$, when present, is hydrogen and $R^{65b}$, when present, is selected from hydrogen, methyl, and cyclopropyl.

In a further aspect, $R^{65a}$, when present, is hydrogen and $R^{65b}$, when present, is selected from hydrogen, C1-C3 alkyl, C1-C3 monohaloalkyl, and C1-C3 polyhaloalkyl. In a still further aspect, $R^{65a}$, when present, is hydrogen and $R^{65b}$, when present, is selected from hydrogen, methyl, ethyl, $-CH_2F$, $-CH_2CH_2F$, $-CH_2CH_2Cl$, $-CHF_2$, $-CF_3$, $-CH_2CHF_2$, and $-CH_2CF_3$. In yet a further aspect, $R^{65b}$, when present, is hydrogen and $R^{65b}$, when present, is selected from hydrogen, methyl, $-CH_2F$, $-CHF_2$, and $-CF_3$. In an even further aspect, $R^{65a}$, when present, is hydrogen and $R^{65b}$, when present, is selected from hydrogen, methyl, and $-CF_3$.

In a further aspect, $R^{65a}$, when present, is hydrogen and $R^{65b}$, when present, is selected from hydrogen, C1-C3 monohaloalkyl, and C1-C3 polyhaloalkyl. In a still further aspect, $R^{65a}$, when present, is hydrogen and $R^{65b}$, when present, is selected from hydrogen, $-CH_2F$, $-CH_2CH_2F$, $-CHF_2$, $-CF_3$, $-CH_2CHF_2$, and $-CH_2CF_3$. In yet a further aspect, $R^{65a}$, when present, is hydrogen and $R^{65b}$, when present, is selected from hydrogen, $-CH_2F$, $-CHF_2$, and $-CF_3$. In an even further aspect, $R^{65a}$, when present, is hydrogen and $R^{65b}$, when present, is selected from hydrogen and $-CF_3$.

In a further aspect, $R^{65a}$, when present, is hydrogen and $R^{65b}$, when present, is selected from hydrogen and C1-C3 alkyl. In a still further aspect, $R^{65a}$, when present, is hydrogen and $R^{65b}$, when present, is selected from hydrogen, methyl, and ethyl. In yet a further aspect, $R^{65a}$, when present, is hydrogen and $R^{65b}$, when present, is selected from hydrogen and methyl. In an even further aspect, $R^{65a}$ and $R^{65b}$, when present, is hydrogen.

In a further aspect, $R^{65a}$ and $R^{65b}$, when present, are optionally covalently bonded and, together with nitrogen atom to which they are attached, comprise a 3- to 6-membered heterocycle. In a still further aspect, $R^{65a}$ and $R^{65b}$, when present, are covalently bonded, and together with nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{65a}$ and $R^{65b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, $R^{65a}$ and $R^{65b}$, when present, are covalently bonded, and together with nitrogen atom to which they are attached, comprise a heterocycle selected from imidazolyl, pyrazolyl, and pyrrolyl. In a still further aspect, $R^{65a}$ and $R^{65b}$, when present, are covalently bonded, and together with nitrogen atom to which they are attached, comprise a pyrrolidinyl. In yet a further aspect, $R^{65a}$ and $R^{65b}$, when present, are covalently bonded, and together with nitrogen atom to which they are attached, comprise a piperidinyl.

z. $R^{70a}$, $R^{70b}$, $R^{70c}$, and $R^{70d}$ Groups

In one aspect, each of $R^{70a}$, $R^{70b}$, $R^{70c}$, and $R^{70d}$ is independently selected from hydrogen, halogen, $-CN$, C1-C3 alkyl, C1-C3 monohaloalkyl, C1-C3 polyhaloalkyl, cyclopropyl, $-OR^{40}$, $-NR^{41a}R^{41b}$, $-SO_2R^{42}$, and $-(C=O)R^{43}$, provided that at least one of $R^{70a}$, $R^{70b}$, $R^{70c}$, and $R^{70d}$ is hydrogen. In a further aspect, each of $R^{70a}$, $R^{70b}$, $R^{70c}$, and $R^{70d}$ is independently selected from hydrogen, $-F$, $-Cl$, $-CN$, methyl, ethyl, $-CH_2F$, $-CH_2CH_2F$, $-CHF_2$, $-CF_3$, cyclopropyl, $-OH$, $-OCH_3$, $-OCH_2F$, $-OCHF_2$, $-OCF_3$, $-O$-cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2$-cyclopropyl, $-SO_2-NH_2$, $-SO_2-NHCH_3$, $-SO_2-N(CH_3)_2$, $-(C=O)CH_3$, $-(C=O)CH_2CH_3$, $-(C=O)CH_2F$, $-(C=O)CH_2CH_2F$, $-(C=O)CHF_2$, $-(C=O)CF_3$, $-(C=O)NH_2$, $-(C=O)NHCH_3$, and $-(C=O)N(CH_3)_2$. In a still further aspect, each of $R^{70a}$, $R^{70b}$, $R^{70c}$, and $R^{70d}$ is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In yet a further aspect, each of R$^{70a}$, R$^{70b}$, R$^{70c}$, and R$^{70d}$ is independently selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{70a}$, R$^{70b}$, R$^{70c}$, and R$^{70d}$ is independently selected from hydrogen, —F, —Cl, methyl, —CF$_3$, —OH, —OCH$_3$, —OCF$_3$, —NH$_2$, —NHCH$_3$, and —N(CH$_3$)$_2$. In a still further aspect, each of R$^{70a}$, R$^{70b}$, R$^{70c}$, and R$^{70d}$ is independently selected from hydrogen, —F, —Cl, methyl, and —CF$_3$. In yet a further aspect, each of R$^{70a}$, R$^{70b}$, R$^{70c}$, and R$^{70d}$ is independently selected from hydrogen, —F, —Cl, and methyl.

In a further aspect, each of R$^{70b}$, R$^{70c}$, and R$^{70d}$ is hydrogen and R$^{70a}$ is selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C═O)CH$_3$, —(C═O)CH$_2$CH$_3$, —(C═O)CH$_2$F, —(C═O)CH$_2$CH$_2$F, —(C═O)CHF$_2$, —(C═O)CF$_3$, —(C═O)NH$_2$, —(C═O)NHCH$_3$, and —(C═O)N(CH$_3$)$_2$. In a still further aspect, each of R$^{70b}$, R$^{70c}$, and R$^{70d}$ is hydrogen and R$^{70a}$ is selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In yet a further aspect, each of R$^{70b}$, R$^{70c}$, and R$^{70d}$ is hydrogen and R$^{70a}$ is selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{70b}$, R$^{70c}$, and R$^{70d}$ is hydrogen and R$^{70a}$ is selected from hydrogen, —F, —Cl, methyl, —CF$_3$, —OH, —OCH$_3$, —OCF$_3$, —NH$_2$, —NHCH$_3$, and —N(CH$_3$)$_2$. In a still further aspect, each of R$^{70b}$, R$^{70c}$, and R$^{70d}$ is hydrogen and R$^{70a}$ is selected from hydrogen, —F, —Cl, methyl, and —CF$_3$. In yet a further aspect, each of R$^{70b}$, R$^{70c}$, and R$^{70d}$ is hydrogen and R$^{70a}$ is selected from hydrogen, —F, —Cl, and methyl. In an even further aspect, each of R$^{70b}$, R$^{70c}$, and R$^{70d}$ is hydrogen and R$^{70a}$ is —F. In a still further aspect, each of R$^{70b}$, R$^{70c}$, and R$^{70d}$ is hydrogen and R$^{70a}$ is —Cl. In yet a further aspect, each of R$^{70b}$, R$^{70c}$, and R$^{70d}$ is hydrogen and R$^{70a}$ is methyl. In an even further aspect, each of R$^{70b}$, R$^{70c}$, and R$^{70d}$ is hydrogen and R$^{70a}$ is —CF$_3$.

In a further aspect, each of R$^{70a}$, R$^{70c}$, and R$^{70d}$ is hydrogen and R$^{70b}$ is selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C═O)CH$_3$, —(C═O)CH$_2$CH$_3$, —(C═O)CH$_2$F, —(C═O)CH$_2$CH$_2$F, —(C═O)CHF$_2$, —(C═O)CF$_3$, —(C═O)NH$_2$, —(C═O)NHCH$_3$, and —(C═O)N(CH$_3$)$_2$. In a still further aspect, each of R$^{70a}$, R$^{70c}$, and R$^{70d}$ is hydrogen and R$^{70b}$ is selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In yet a further aspect, each of R$^{70a}$, R$^{70c}$, and R$^{70d}$ is hydrogen and R$^{70b}$ is selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{70a}$, R$^{70c}$, and R$^{70d}$ is hydrogen and R$^{70b}$ is selected from hydrogen, —F, —Cl, methyl, —CF$_3$, —OH, —OCH$_3$, —OCF$_3$, —NH$_2$, —NHCH$_3$, and —N(CH$_3$)$_2$. In a still further aspect, each of R$^{70a}$, R$^{70c}$, and R$^{70d}$ is hydrogen and R$^{70b}$ is selected from hydrogen, —F, —Cl, methyl, and —CF$_3$. In yet a further aspect, each of R$^{70a}$, R$^{70c}$, and R$^{70d}$ is hydrogen and R$^{70b}$ is selected from hydrogen, —F, —Cl, and methyl. In an even further aspect, each of R$^{70a}$, R$^{70c}$, and R$^{70d}$ is hydrogen and R$^{70b}$ is —F. In a still further aspect, each of R$^{70a}$, R$^{70c}$, and R$^{70d}$ is hydrogen and R$^{70b}$ is —Cl. In yet a further aspect, each of R$^{70a}$, R$^{70c}$, and R$^{70d}$ is hydrogen and R$^{70b}$ is —CF$_3$. In an even further aspect, each of R$^{70a}$, R$^{70b}$, R$^{70c}$, and R$^{70d}$ is hydrogen.

aa. R$^{80a}$ and R$^{80b}$ Groups

In one aspect, each of R$^{80a}$ and R$^{80b}$ is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C═O)R$^{43}$. In a further aspect, each of R$^{80a}$ and R$^{80b}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a still further aspect, each of R$^{80a}$ and R$^{80b}$ is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In yet a further aspect, each of R$^{80a}$ and R$^{80b}$ is independently selected from hydrogen, —F, —Cl, methyl, —CF$_3$, —OH, —OCH$_3$, —OCF$_3$, —NH$_2$, —NHCH$_3$, and —N(CH$_3$)$_2$. In an even further aspect, each of R$^{80a}$ and R$^{80b}$ is independently selected from hydrogen, —F, —Cl, methyl, —CF$_3$, —OH, —OCH$_3$, —OCF$_3$, —NH$_2$, —NHCH$_3$, and —N(CH$_3$)$_2$. In a still further aspect, each of R$^{80a}$ and R$^{80b}$ is independently selected from hydrogen, —F, —Cl, and methyl.

In a further aspect, R$^{80b}$ is hydrogen and R$^{80a}$ is selected from hydrogen, methyl, ethyl, propyl, isopropyl, —CH$_2$F, —CH$_2$CH$_2$F, —CHF$_2$, —CF$_3$, and cyclopropyl. In a still further aspect, R$^{80b}$ is hydrogen and R$^{80a}$ is selected from hydrogen, methyl, ethyl, propyl, isopropyl, —CH$_2$F, —CHF$_2$, —CF$_3$, and cyclopropyl. In yet a further aspect, R$^{80b}$ is hydrogen and R$^{80a}$ is selected from hydrogen, methyl, and —CF$_3$. In an even further aspect, R$^{80b}$ is hydrogen and R$^{80a}$ is methyl. In a still further aspect, R$^{80b}$ is hydrogen and R$^{80a}$ is —CF$_3$. In yet a further aspect, each of R$^{80a}$ and R$^{80b}$ is hydrogen.

bb. R$^{90a}$, R$^{90b}$, and R$^{90c}$ Groups

In one aspect, each of R$^{90a}$, R$^{90b}$, and R$^{90c}$ is independently selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C═O)R$^{33}$, provided that at least one of R$^{90a}$, R$^{90b}$, and R$^{90c}$ is hydrogen. In a further aspect, each of R$^{90a}$, R$^{90b}$, and R$^{90c}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, each of R$^{90a}$, R$^{90b}$, and R$^{90c}$ is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a yet further aspect, each of R$^{90a}$, R$^{90b}$, and R$^{90c}$ is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, each of R$^{90a}$, R$^{90b}$, and R$^{90c}$ is independently selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, each of R$^{90a}$, R$^{90b}$, and R$^{90c}$ is independently selected from halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$. In a yet further aspect, R$^5$, when present, is selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In an even further aspect, each of R$^{90a}$, R$^{90b}$, and R$^{90c}$ is independently selected from —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a still further aspect, each of R$^{90a}$, R$^{90b}$, and R$^{90c}$ is independently selected from —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a yet further aspect, each of R$^{90a}$, R$^{90b}$, and R$^{90c}$ is independently selected from —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, each of R$^{90a}$, R$^{90b}$, and R$^{90c}$ is independently selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, and —SO$_2$R$^{32}$. In a yet further aspect, each of R$^{90a}$, R$^{90b}$, and R$^{90c}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —CH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In an even further aspect, each of R$^{90a}$, R$^{90b}$, and R$^{90c}$ is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{90a}$, R$^{90b}$, and R$^{90c}$ is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of R$^{90a}$, R$^{90b}$, and R$^{90c}$ is independently selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{90a}$, R$^{90b}$, and R$^{90c}$ is independently selected from hydrogen, halogen, C1-C3 alkyl, C1-C3 monohaloalkyl, C1-C3 polyhaloalkyl, cyclopropyl, —OR$^{30}$, —NR$^{31a}$R$^{31b}$, and —SO$_2$R$^{32}$. In a still further aspect, each of R$^{90a}$, R$^{90b}$, and R$^{90c}$ is independently selected from hydrogen, —F, —Cl, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a yet further aspect, each of R$^{90a}$, R$^{90b}$ and R$^{90c}$ is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{90a}$, R$^{90b}$, and R$^{90c}$ is independently selected from hydrogen, —F, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{90a}$, R$^{90b}$, and R$^{90c}$ is independently selected from hydrogen, halogen, C1-C3 alkyl, C1-C3 monohaloalkyl, C1-C3 polyhaloalkyl, —OR$^{30}$, —NR$^{31a}$R$^{31b}$, and —SO$_2$R$^{32}$. In yet further aspect, each of R$^{90a}$, R$^{90b}$, and R$^{90c}$ is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a still further aspect, each of R$^{90a}$, R$^{90b}$, and R$^{90c}$ is independently selected from hydrogen, —F, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{90a}$, R$^{90b}$, and R$^{90c}$ is independently selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{90a}$, R$^{90b}$, and R$^{90c}$ is independently selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{90a}$, R$^{90b}$, and R$^{90c}$ is independently selected from hydrogen, halogen, —CN, C1-C3 alkyl, C1-C3 monohaloalkyl, C1-C3 polyhaloalkyl, cyclopropyl, —OR$^{30}$, and —NR$^{31a}$R$^{31b}$. In a yet further aspect, each of R$^{90a}$, R$^{90b}$, and R$^{90c}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a still further aspect, each of R$^{90a}$, R$^{90b}$, and R$^{90c}$ is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In an even further aspect, each of R$^{90a}$, R$^{90b}$, and R$^{90c}$ is independently selected from hydrogen, —F, —CN, methyl, —CF$_3$, cyclopropyl, —OH, —OCH$_3$, —OCF$_3$, —NH$_2$, —NHCH$_3$, and —N(CH$_3$)$_2$.

In a further aspect, each of R$^{90a}$, R$^{90b}$, and R$^{90c}$ is independently selected from hydrogen, halogen, C1-C3 alkyl, C1-C3 monohaloalkyl, C1-C3 polyhaloalkyl, cyclopropyl, —OR$^{30}$, and —NR$^{31a}$R$^{31b}$. In a yet further aspect, each of R$^{90a}$, R$^{90b}$, and R$^{90c}$ is independently selected from hydrogen, —F, —Cl, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In an even further aspect, each of R$^{90a}$, R$^{90b}$, and R$^{90c}$ is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In yet a further aspect, each of R$^{90a}$, R$^{90b}$, and R$^{90c}$ is independently selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, each of R$^{90a}$, R$^{90b}$, and R$^{90c}$ is independently selected from hydrogen, halogen, C1-C3 alkyl, C1-C3 monohaloalkyl, C1-C3 polyhaloalkyl, —OR$^{30}$, and —NR$^{31a}$R$^{31b}$. In an even further aspect, each of R$^{90a}$, R$^{90b}$, and R$^{90c}$ is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, each of R$^{90a}$, R$^{90b}$, and R$^{90c}$ is independently selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In a still further aspect, each of R$^{90a}$, R$^{90b}$, and R$^{90c}$ is independently selected from hydrogen, —F, —Cl, methyl, —CF$_3$, —OH, —OCH$_3$, —OCF$_3$, —NH$_2$, —NHCH$_3$, and —N(CH$_3$)$_2$. In a yet further aspect, each of R$^{90a}$, R$^{90b}$, and R$^{90c}$ is independently selected from hydrogen, —F, methyl, —CF$_3$, —OH, —OCH$_3$, —OCF$_3$, —NH$_2$, —NHCH$_3$, and —N(CH$_3$)$_2$.

In a further aspect, each of R$^{90a}$, R$^{90b}$, and R$^{90c}$ is independently selected from hydrogen, halogen, C1-C3 alkyl, C1-C3 monohaloalkyl, C1-C3 polyhaloalkyl, and cyclopropyl. In an even further aspect, each of R$^{90a}$, R$^{90b}$, and R$^{90c}$ is independently selected from hydrogen, —F, —Cl, methyl, ethyl, —CH$_2$F, —CH$_2$CH$_2$F, —CHF$_2$, —CF$_3$, and cyclopropyl. In a yet further aspect, each of R$^{90a}$, R$^{90b}$, and R$^{90c}$ is independently selected from hydrogen, —F, methyl, —CH$_2$F, —CHF$_2$, —CF$_3$, and cyclopropyl. In an even further aspect, each of R$^{90a}$, R$^{90b}$, and R$^{90c}$ is independently selected from hydrogen, —F, methyl, —CF$_3$, and cyclopropyl.

In a further aspect, each of R$^{90a}$, R$^{90b}$, and R$^{90c}$ is independently selected from hydrogen, halogen, C1-C3 alkyl, C1-C3 monohaloalkyl, and C1-C3 polyhaloalkyl. In a still further aspect, each of R$^{90a}$, R$^{90b}$, and R$^{90c}$ is independently selected from hydrogen, —F, —Cl, methyl, ethyl, —CH$_2$F, —CH$_2$CH$_2$F, —CHF$_2$, and —CF$_3$. In an even further aspect, each of R$^{90a}$, R$^{90b}$, and R$^{90c}$ is independently selected from hydrogen, —F, methyl, —CH$_2$F, —CHF$_2$, and —CF$_3$. In yet a further aspect, each of R$^{90a}$, R$^{90b}$, and R$^{90c}$ is independently selected from hydrogen, —F, —Cl, methyl, and —CF$_3$. In an even further aspect, each of R$^{90a}$, R$^{90b}$, and R$^{90c}$ is independently selected from hydrogen, —F, methyl, and —CF$_3$.

In a further aspect, each of R$^{90a}$, R$^{90b}$, and R$^{90c}$ is independently selected from hydrogen, halogen, and C1-C3 alkyl. In a still further aspect, each of R$^{90a}$, R$^{90b}$, and R$^{90c}$ is independently selected from hydrogen, —F, —Cl, methyl, and ethyl. In an even further aspect, each of R$^{90a}$, R$^{90b}$, and R$^{90c}$ is independently selected from hydrogen, —F, —Cl, and methyl. In a yet further aspect, each of R$^{90a}$, R$^{90b}$, and R$^{90c}$ is independently selected from hydrogen, —F, and methyl.

In a further aspect, each of R$^{90a}$, R$^{90b}$, and R$^{90c}$ is independently selected from hydrogen and C1-C3 alkyl. In still further aspect, each of R$^{90a}$, R$^{90b}$, and R$^{90c}$ is independently selected from hydrogen, methyl, and ethyl. In an even further aspect, each of R$^{90a}$, R$^{90b}$, and R$^{90c}$ is independently selected from hydrogen and methyl. In a still further aspect, each of R$^{90a}$, R$^{90b}$, and R$^{90c}$ is hydrogen.

cc. R$^{100a}$ and R$^{100b}$ Groups

In one aspect, each of R$^{100a}$ and R$^{100b}$ is independently selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$. In a further aspect, each of R$^{100a}$ and R$^{100b}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In a still further aspect, each of R$^{100a}$ and R$^{100b}$ is independently selected from hydrogen, —F, —Cl, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a yet further aspect, each of R$^{100a}$ and R$^{100b}$ is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, each of R$^{100a}$ and R$^{100b}$ is independently selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, each of R$^{100a}$ and R$^{100b}$ is independently selected from halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$. In a yet further aspect, each of R$^{100a}$ and R$^{100b}$ is independently selected from —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$CH$_2$F, —(C=O)CHF$_2$, —(C=O)CF$_3$, —(C=O)NH$_2$, —(C=O)NHCH$_3$, and —(C=O)N(CH$_3$)$_2$. In an even further aspect, each of R$^{100a}$ and R$^{100b}$ is independently selected from —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a still further aspect, each of R$^{100a}$ and R$^{100b}$ is independently selected from —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, each of R$^{100a}$ and R$^{100b}$ is independently selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, and —SO$_2$R$^{32}$. In a yet further aspect, each of R$^{100a}$ and R$^{100b}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —CH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In an even further aspect, each of R$^{100a}$ and R$^{100b}$ is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{100a}$ and R$^{100b}$ is independently selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{100a}$ and R$^{100b}$ is independently selected from hydrogen, halogen, C1-C3 alkyl, C1-C3 monohaloalkyl, C1-C3 polyhaloalkyl, cyclopropyl, —OR$^{30}$, —NR$^{31a}$R$^{31b}$, and —SO$_2$R$^{32}$. In a still further aspect, each of R$^{100a}$ and R$^{100b}$ is independently selected from hydrogen, —F, —Cl, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In an even further aspect, each of R$^{100a}$ and R$^{100b}$ is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a yet further aspect, each of R$^{100a}$ and R$^{100b}$ is independently selected from hydrogen, —F, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{100a}$ and R$^{100b}$ is independently selected from hydrogen, halogen, C1-C3 alkyl, C1-C3 monohaloalkyl, C1-C3 polyhaloalkyl, —OR$^{30}$, —NR$^{31a}$R$^{31b}$, and —SO$_2$R$^{32}$. In yet further aspect, each of R$^{100a}$ and R$^{100b}$ is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$—NH$_2$, —SO$_2$—NHCH$_3$, and —SO$_2$—N(CH$_3$)$_2$. In a still further aspect, each of R$^{100a}$ and R$^{100b}$ is independently selected from hydrogen, —F, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{100a}$ and R$^{100b}$ is independently selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, each of R$^{100a}$ and R$^{100b}$ is independently selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, each of R$^{100a}$ and R$^{100b}$ is independently selected from hydrogen, halogen, —CN, C1-C3 alkyl, C1-C3 monohaloalkyl, C1-C3 polyhaloalkyl, cyclopropyl, —OR$^{30}$, and —NR$^{31a}$R$^{31b}$. In a yet further aspect, each of R$^{100a}$ and R$^{100b}$ is independently selected from hydrogen, —F, —Cl, —CN, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a still further aspect, each of R$^{100a}$ and R$^{100b}$ is independently selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In an even further aspect, each of R$^{100a}$ and R$^{100b}$ is independently selected from hydrogen, —F, —CN, methyl, —CF$_3$, cyclopropyl, —OH, —OCH$_3$, —OCF$_3$, —NH$_2$, —NHCH$_3$, and —N(CH$_3$)$_2$.

In a further aspect, each of R$^{100a}$ and R$^{100b}$ is independently selected from hydrogen, halogen, C1-C3 alkyl, C1-C3 monohaloalkyl, C1-C3 polyhaloalkyl, cyclopropyl, —OR$^{30}$, and —NR$^{31a}$R$^{31b}$. In yet further aspect, each of R$^{100a}$ and R$^{100b}$ is independently selected from hydrogen, —F, —Cl, methyl, ethyl, —CH$_2$F, —CH$_2$CH$_2$F, —CHF$_2$, —CF$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In an even further aspect, each of R$^{100a}$ and R$^{100b}$ is independently selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, each of R$^{100a}$ and R$^{100b}$ is independently selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, each of R$^{100a}$ and R$^{100b}$ is independently selected from hydrogen, halogen, C1-C3 alkyl, C1-C3 monohaloalkyl, C1-C3 polyhaloalkyl, —OR$^{30}$, and —NR$^{31a}$R$^{31b}$. In an even further aspect, each of R$^{100a}$ and R$^{100b}$ is independently selected from hydrogen, —F, —Cl, methyl, ethyl, —CH$_2$F, —CH$_2$CH$_2$F, —CHF$_2$, —CF$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, each of R$^{100a}$ and R$^{100b}$ is independently selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In an even further aspect, each of R$^{100a}$ and R$^{100b}$ is independently selected from hydrogen, —F, —C, methyl, —CF$_3$, —OH, —OCH$_3$, —OCF$_3$, —NH$_2$, —NHCH$_3$, and —N(CH$_3$)$_2$. In a yet further aspect, each of R$^{100a}$ and R$^{100b}$ is independently selected from hydrogen, —F, methyl, —CF$_3$, —OH, —OCH$_3$, —OCF$_3$, —NH$_2$, —NHCH$_3$, and —N(CH$_3$)$_2$.

In a further aspect, each of R$^{100a}$ and R$^{100b}$ is independently selected from hydrogen, halogen, C1-C3 alkyl, C1-C3 monohaloalkyl, C1-C3 polyhaloalkyl, and cyclopropyl. In an even further aspect, each of R$^{100a}$ and R$^{100b}$ is independently selected from hydrogen, —F, —Cl, methyl, ethyl, —CH$_2$F, —CH$_2$CH$_2$F, —CHF$_2$, —CF$_3$, and cyclopropyl. In a yet further aspect, each of R$^{100a}$ and R$^{100b}$ is independently selected from hydrogen, —F, methyl, —CH$_2$F, —CHF$_2$, —CF$_3$, and cyclopropyl. In an even further aspect, each of R$^{100a}$ and R$^{100b}$ is independently selected from hydrogen, —F, methyl, —CF$_3$, and cyclopropyl.

In a further aspect, each of R$^{100a}$ and R$^{100b}$ is independently selected from hydrogen, halogen, C1-C3 alkyl, C1-C3 monohaloalkyl, and C1-C3 polyhaloalkyl. In a still further aspect, each of R$^{100a}$ and R$^{100b}$ is independently selected from hydrogen, —F, —Cl, methyl, ethyl, —CH$_2$F, —CH$_2$CH$_2$F, —CHF$_2$, and —CF$_3$. In an even further aspect, each of R$^{100a}$ and R$^{100b}$ is independently selected from hydrogen, —F, methyl, —CH$_2$F, —CHF$_2$, and —CF$_3$. In a still further aspect, each of R$^{100a}$ and R$^{100b}$ is independently selected from hydrogen, —F, —Cl, methyl, and —CF$_3$. In an even further aspect, each of R$^{100a}$ and R$^{100b}$ is independently selected from hydrogen, —F, methyl, and —CF$_3$.

In a further aspect, each of R$^{100a}$ and R$^{100b}$ is independently selected from hydrogen, halogen, and C1-C3 alkyl. In a still further aspect, each of R$^{100a}$ and R$^{100b}$ is independently selected from hydrogen, —F, —Cl, methyl, and ethyl. In an even further aspect, each of R$^{100a}$ and R$^{100b}$ is independently selected from hydrogen, —F, —Cl, and methyl. In a yet further aspect, each of R$^{100a}$ and R$^{100b}$ is independently selected from hydrogen, —F, and methyl.

In a further aspect, each of R$^{100a}$ and R$^{100b}$ is independently selected from hydrogen and C1-C3 alkyl. In still further aspect, each of R$^{100a}$ and R$^{100b}$ is independently selected from hydrogen, methyl, and ethyl. In an even further aspect, each of R$^{100a}$ and R$^{100b}$ is independently selected from hydrogen and methyl.

In a further aspect, each of R$^{100a}$ and R$^{100b}$ is —F. In a still further aspect, each of R$^{100a}$ and R$^{100b}$ is —Cl. In an even further aspect, each of R$^{100a}$ and R$^{100b}$ is methyl. In a still further aspect, each of R$^{100a}$ and R$^{100b}$ is —CF$_3$. In a yet further aspect, each of R$^{100a}$ and R$^{100b}$ is hydrogen.

dd. R$^{110a}$ and R$^{110b}$ Groups

In one aspect, each of R$^{110a}$ and R$^{110b}$, when present, is independently selected from hydrogen and C1-C8 alkyl; or R$^{110a}$ and R$^{110b}$, when present, are optionally covalently bonded and, together with the oxygen atoms to which they are attached, comprise a 4- to 6-membered heterocycle.

In a further aspect, each of R$^{110a}$ and R$^{110b}$, when present, is independently selected from hydrogen and C1-C8 alkyl. In a still further aspect, each of R$^{110a}$ and R$^{110b}$, when present, is independently selected from hydrogen and C1-C4 alkyl. In yet a further aspect, each of R$^{110a}$ and R$^{110b}$, when present, is hydrogen.

In a further aspect, each of R$^{110a}$ and R$^{110b}$, when present, is independently selected from hydrogen, methyl, ethyl, n-propyl, iso-propyl, n-butyl, sec-butyl, iso-butyl, and t-butyl. In a still further aspect, each of R$^{110a}$ and R$^{110b}$, when present, is independently selected from hydrogen, methyl, ethyl, n-propyl, and iso-propyl. In yet a further aspect, each of R$^{110a}$ and R$^{110b}$, when present, is independently selected from hydrogen, methyl, and ethyl. In an even further aspect, each of R$^{110a}$ and R$^{110b}$, when present, is independently selected from hydrogen and ethyl. In a still further aspect, each of R$^{110a}$ and R$^{110b}$, when present, is independently selected from hydrogen and methyl.

In a further aspect, R$^{110a}$ and R$^{110b}$, when present, are optionally covalently bonded and, together with the oxygen atoms to which they are attached, comprise a 4- to 6-membered heterocycle. In a still further aspect, R$^{110a}$ and R$^{110b}$, when present, are optionally covalently bonded and, together with the oxygen atoms to which they are attached, comprise a 5-membered heterocycle having a structure represented by a formula selected from:

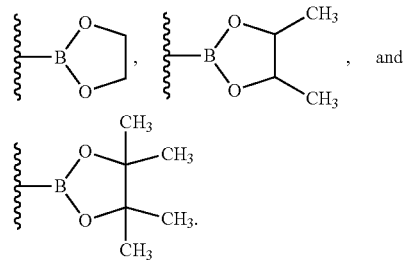

In a further aspect, R$^{110a}$ and R$^{110b}$, when present, are optionally covalently bonded and, together with the oxygen atoms to which they are attached, comprise a 5-membered heterocycle having a structure represented by a formula:

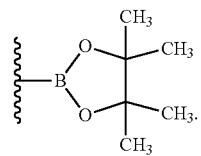

ee. AR$^1$ Groups

In one aspect, Ar$^1$ is selected from aryl and heteroaryl, and Ar$^1$ is substituted with 0, 1, 2, or 3 groups independently selected from halogen, —CN, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a further aspect, Ar$^1$ is selected from aryl and heteroaryl, and Ar$^1$ is unsubstituted.

In a further aspect, Ar$^1$ is selected from aryl and heteroaryl, and Ar$^1$ is substituted with 0, 1, 2, or 3 groups independently selected from —F, —Cl, methyl, ethyl, propyl, isopropyl, —CH$_2$F, —CH$_2$CH$_2$F, —CH$_2$)$_2$CH$_2$F, —CHF$_2$, —CF$_3$, —CHBr$_2$, —CBr$_3$, —CHI$_2$, —CI$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is aryl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is heteroaryl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is phenyl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is pyridinyl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, ad cyclopropyl.

In a further aspect, Ar$^1$ is pyrazolyl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is pyrimidinyl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is indazolyl substituted with 0, 1, 2, or 3 groups independently selected from —F, —Cl, methyl, ethyl, propyl, isopropyl, —CH$_2$F, —CH$_2$CH$_2$F, —(CH$_2$)$_2$CH$_2$F, —CHF$_2$, —CF$_3$, —CH$_2$CHF$_2$, —CH$_2$CF$_3$, —(CH$_2$)$_2$CHF$_2$, —(CH$_2$)$_2$CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is selected from aryl and heteroaryl, and Ar$^1$ is substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is selected from aryl and heteroaryl, and Ar$^1$ is substituted with 0, 1, 2, or 3 groups independently selected from —F, —C, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, and cyclopropyl. In yet a further aspect, Ar$^1$ is selected from aryl and heteroaryl, and Ar$^1$ is substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is aryl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is aryl substituted with 0, 1, 2, or 3 groups independently selected from —F, —Cl, methyl, ethyl, —CH$_2$F—CHF$_2$, —CF$_3$, —OR$^{30}$, —NR$^{31a}$R$^{31b}$, —SO$_2$R$^{32}$, —(C=O)R$^{33}$, cyclopropyl. In yet a further aspect, Ar$^1$ is aryl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is heteroaryl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is heteroaryl substituted with 0, 1, 2, or 3 groups independently selected from —F, —Cl, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, and cyclopropyl. In yet a further aspect, Ar$^1$ is heteroaryl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is phenyl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In yet a further aspect, Ar$^1$ is phenyl substituted with 0, 1, 2, or 3 groups independently selected from —F, —Cl, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, and cyclopropyl. In yet a further aspect, Ar$^1$ is phenyl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is pyridinyl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is pyridinyl substituted with 0, 1, 2, or 3 groups independently selected from —F, —Cl, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, and cyclopropyl. In yet a further aspect, Ar$^1$ is pyridinyl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is pyrazolyl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is pyrazolyl substituted with 0, 1, 2, or 3 groups independently selected from —F, —Cl, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, ad cyclopropyl. In yet a further aspect, Ar$^1$ is pyrazolyl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is pyrimidinyl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is pyrimidinyl substituted with 0, 1, 2, or 3 groups independently selected from —F, —Cl, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, ad cyclopropyl. In yet a further aspect, Ar$^1$ is pyrimidinyl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is indazolyl substituted with 0, 1, 2, or 3 groups independently selected from —F, —Cl, methyl, ethyl, propyl, isopropyl, —CH$_2$F, —CH$_2$CH$_2$F, —CHF$_2$, —CF$_3$, —CH$_2$CHF$_2$, —CH$_2$CF$_3$, —OR$^{30}$, —NR$^{31a}$R$^{31b}$, —SO$_2$R$^{32}$, —(C=O)R$^{33}$, and cyclopropyl. In a still further aspect, Ar$^1$ is indazolyl substituted with 0, 1, 2, or 3 groups independently selected from —F, —Cl, methyl, ethyl, —CH$_2$F, —CHF$_2$, —CF$_3$, —OR$^{30}$, —NR$^{31a}$R$^{31b}$, —SO$_2$R$^{32}$, —(C=O)R$^{33}$, ad cyclopropyl. In yet a further aspect, Ar$^1$ is indazolyl substituted with 0, 1, 2, or 3 groups independently selected from —F, —Cl, methyl, —CF$_3$, —OR$^{30}$, —NR$^{31a}$R$^{31b}$, —SO$_2$R$^{32}$, —(C=O)R$^{33}$, and cyclopropyl.

In a further aspect, Ar$^1$ is selected from aryl and heteroaryl, and Ar$^1$ is substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is selected from aryl and heteroaryl, and Ar$^1$ is substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In yet a further aspect, Ar$^1$ is selected from aryl and heteroaryl, and Ar$^1$ is monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl.

In a further aspect, Ar$^1$ is aryl substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is aryl substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In yet a further aspect, Ar$^1$ is aryl monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In an even further aspect, Ar$^1$ is unsubstituted aryl.

In a further aspect, Ar$^1$ is heteroaryl substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is heteroaryl substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In yet a further aspect, Ar$^1$ is heteroaryl monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In an even further aspect, Ar$^1$ is unsubstituted heteroaryl.

In a further aspect, Ar$^1$ is pyridinyl substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is pyridinyl substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In yet a further aspect, Ar$^1$ is pyridinyl monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In an even further aspect, Ar$^1$ is unsubstituted pyridinyl.

In a further aspect, Ar$^1$ is pyrazolyl substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is pyrazolyl substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, cyclopropyl. In yet a further aspect, Ar$^1$ is pyrazolyl monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In an even further aspect, Ar$^1$ is unsubstituted pyrazolyl.

In a further aspect, Ar$^1$ is pyrimidinyl substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is pyrimidinyl substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In yet a further aspect, Ar$^1$ is pyrimidinyl monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In an even further aspect, Ar$^1$ is unsubstituted pyrimidinyl.

In a further aspect, Ar$^1$ is indazolyl substituted with 0, 1, or 2 groups independently selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In a still further aspect, Ar$^1$ is indazolyl substituted with 0 or 1 group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In yet a further aspect, Ar$^1$ is indazolyl monosubstituted with a group selected from halogen, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl. In an even further aspect, Ar$^1$ is unsubstituted indazolyl.

2. Compound Examples

In one aspect, a compound can be present as:

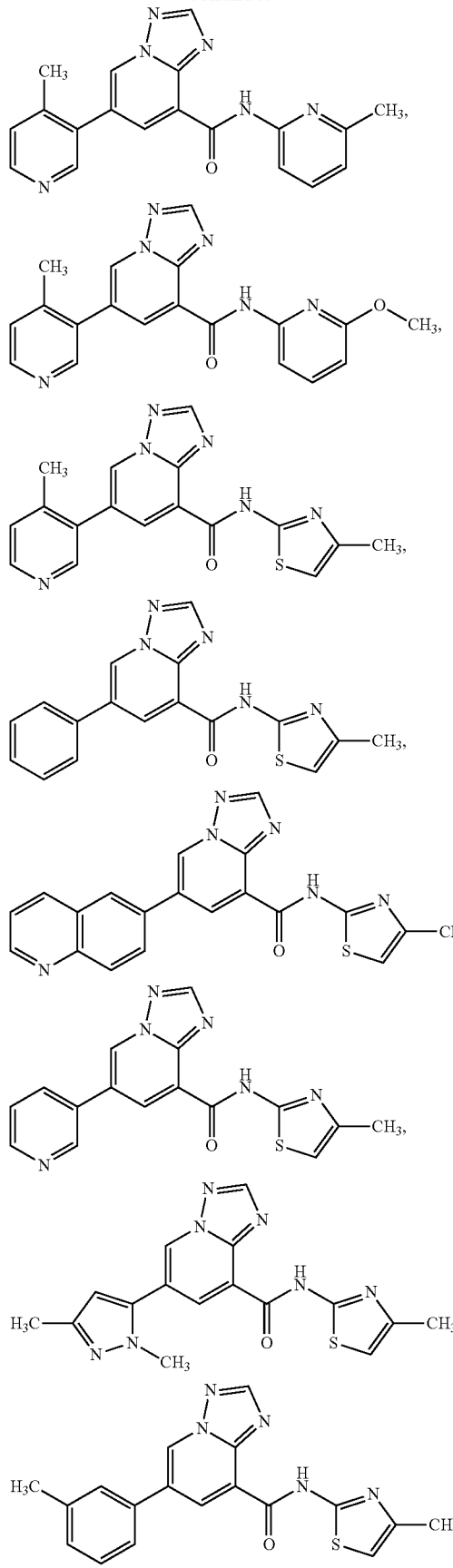
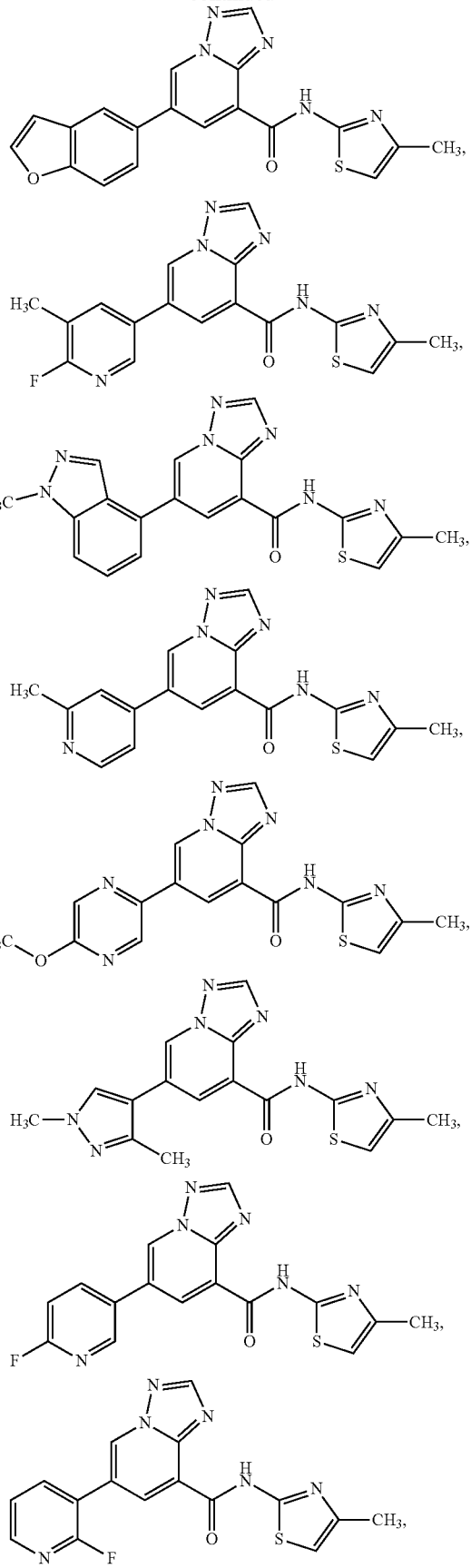

-continued
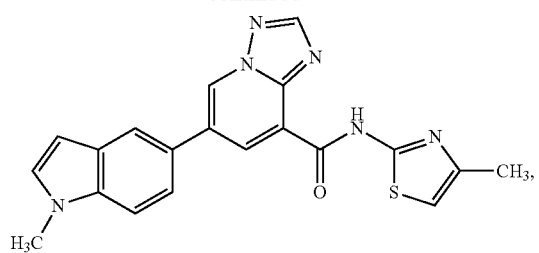
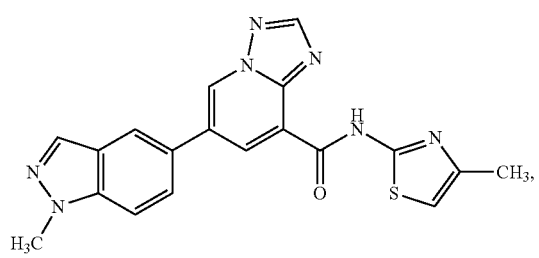
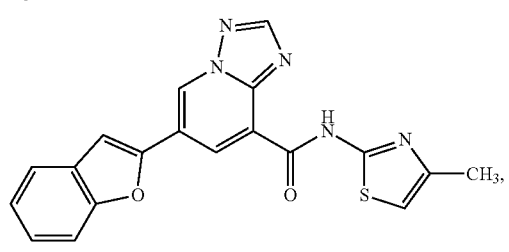
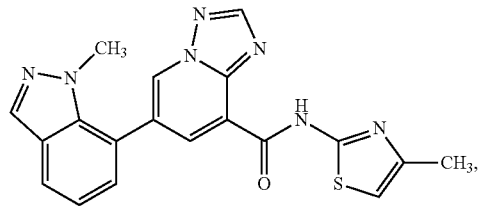
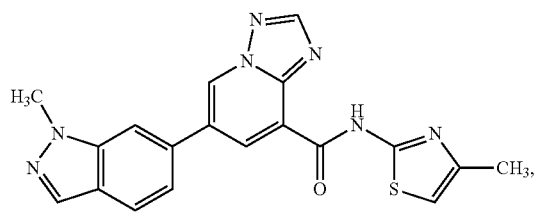
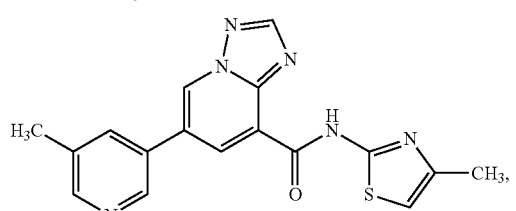
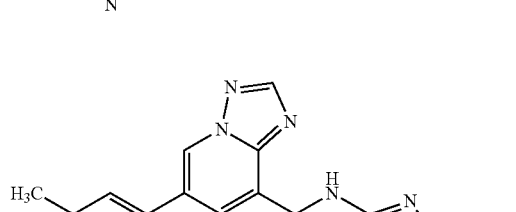
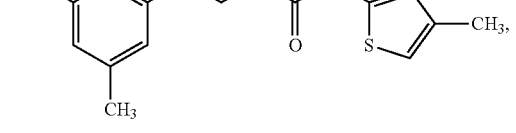
-continued
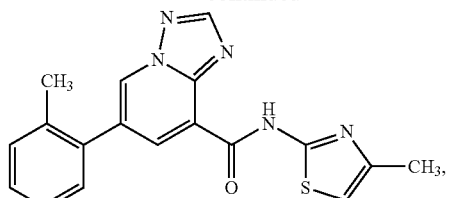
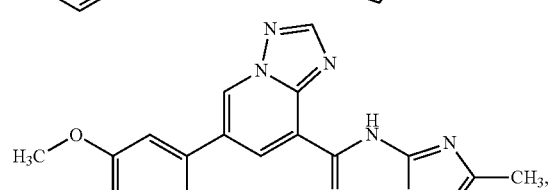
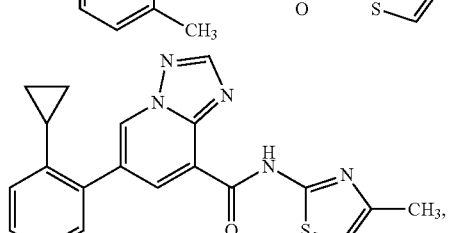
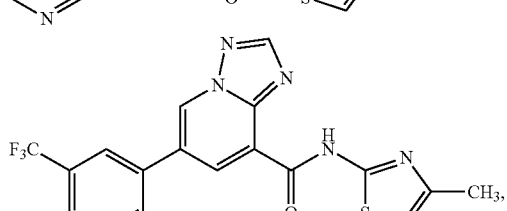
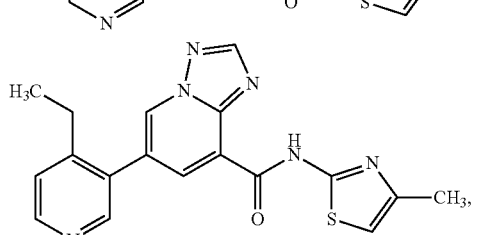
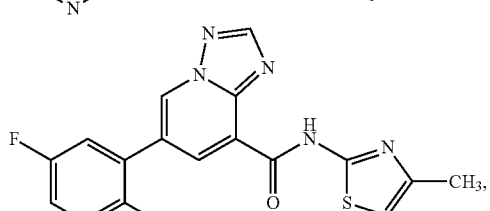
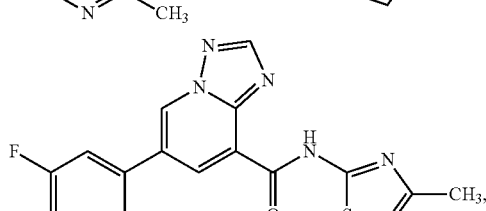
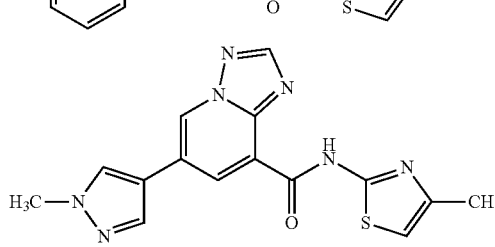

-continued
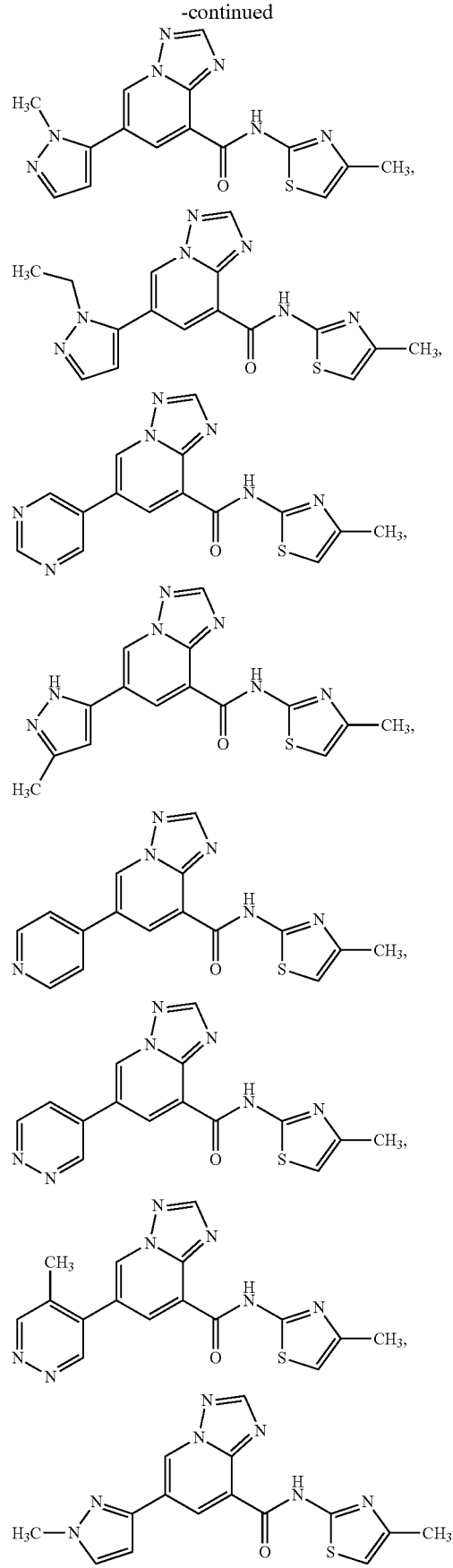
-continued
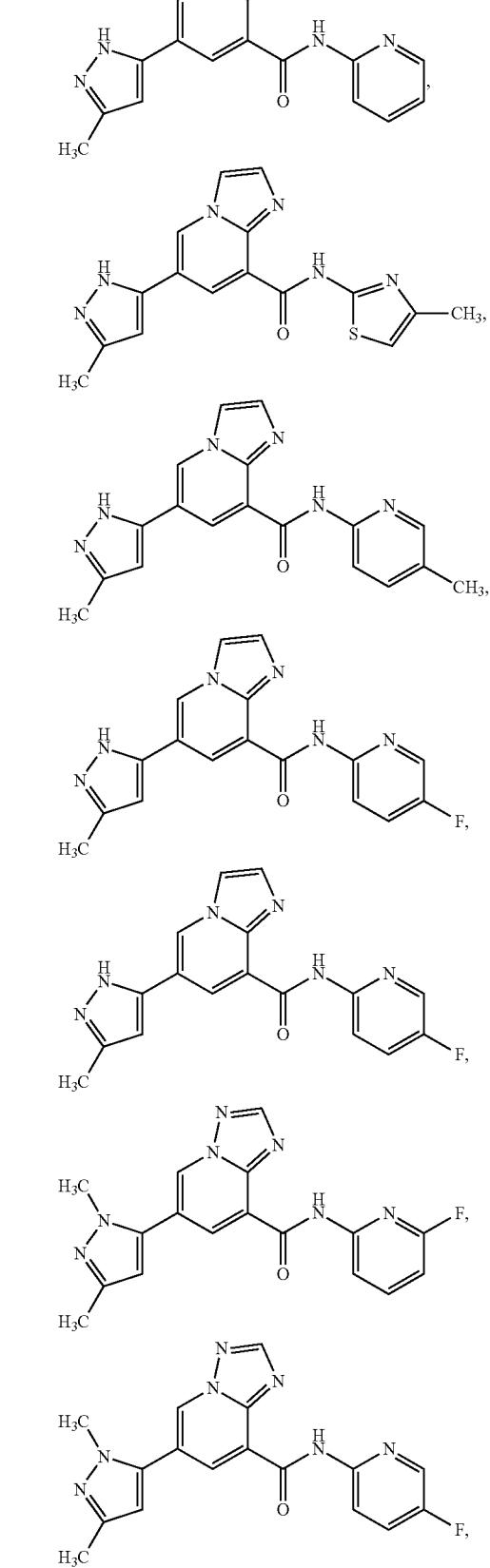

117
-continued
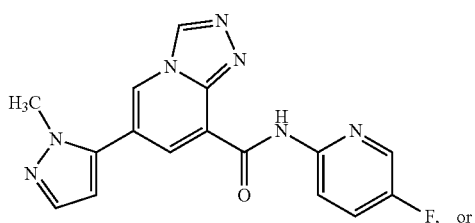
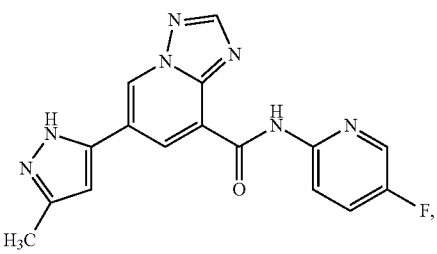
or subgroup thereof.
In one aspect, a compound can be present as:
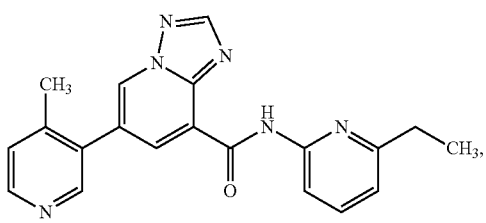
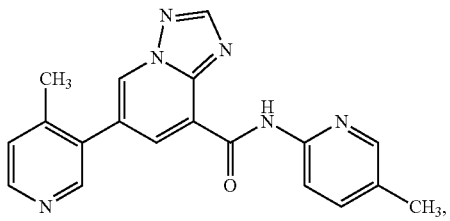
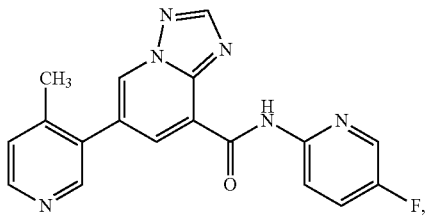
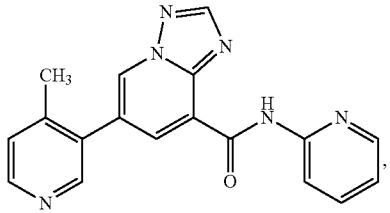
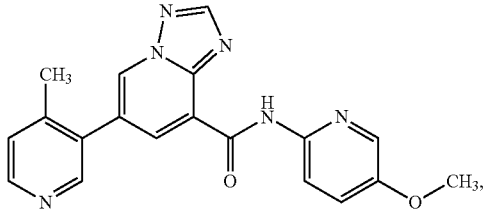
118
-continued
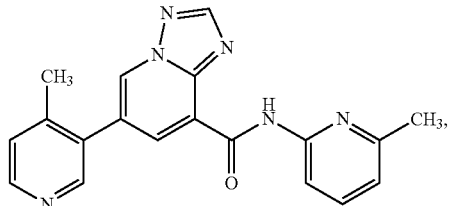
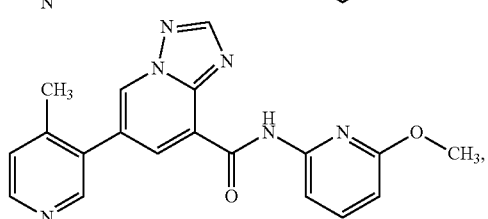
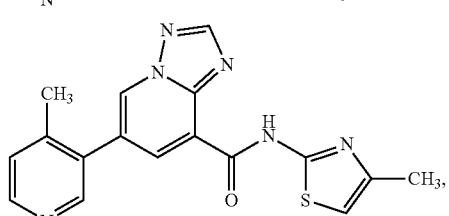
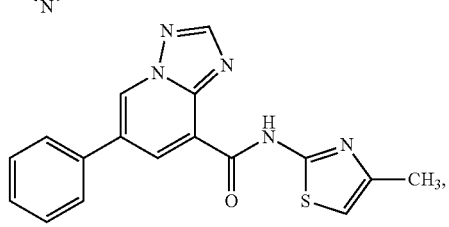
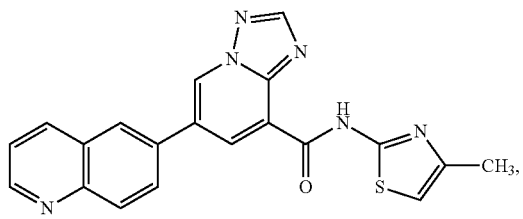
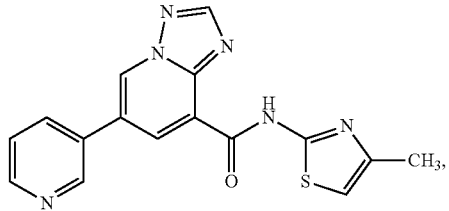
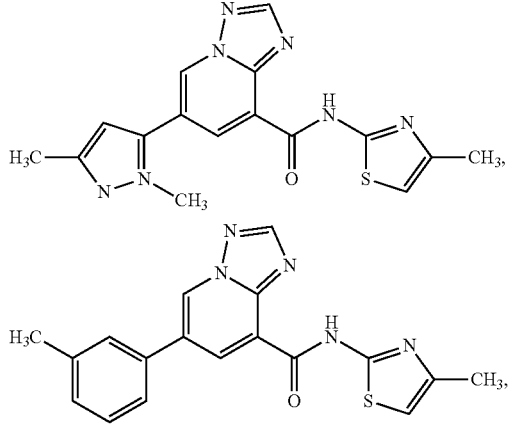

-continued
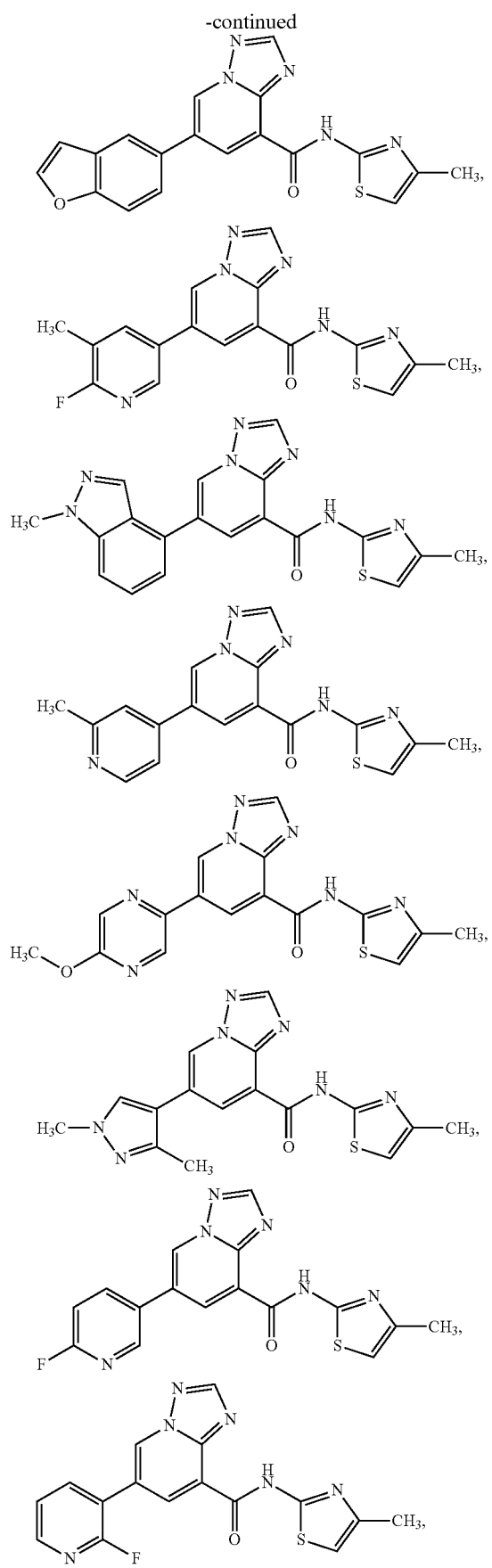
-continued
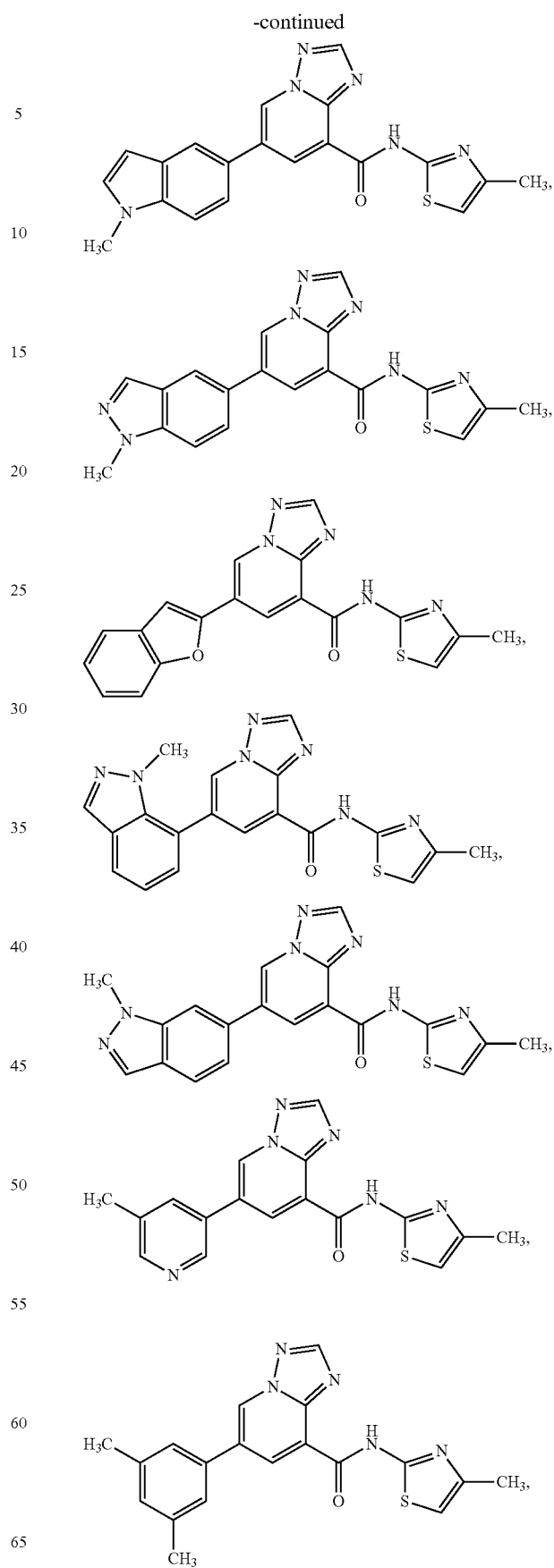

121
-continued
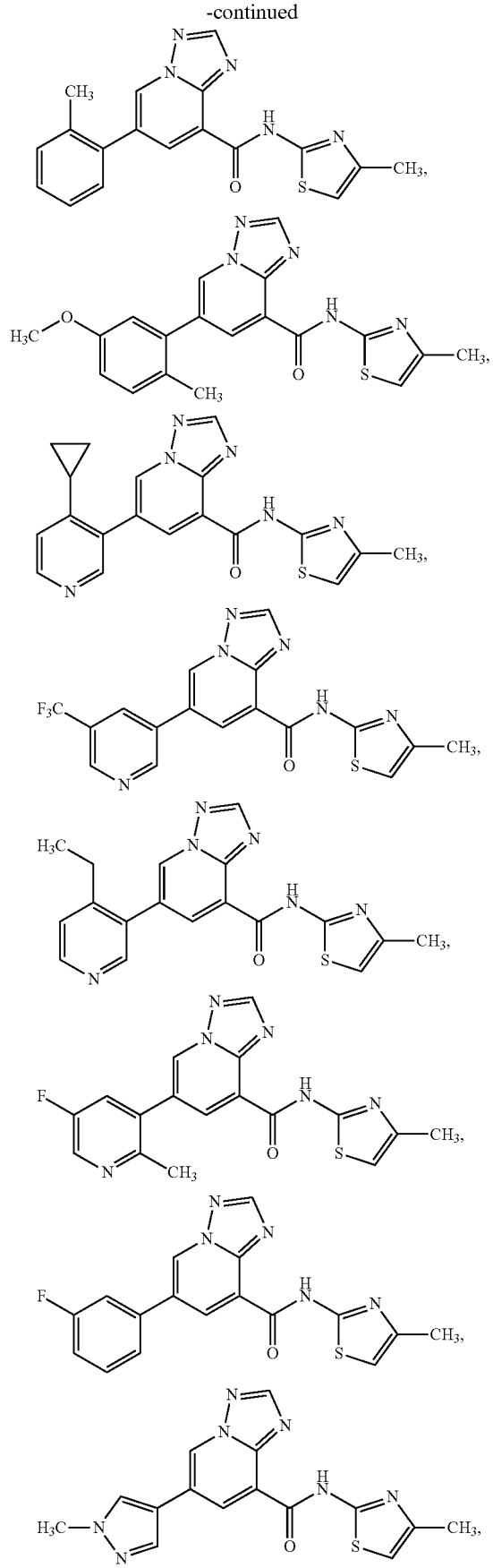
122
-continued
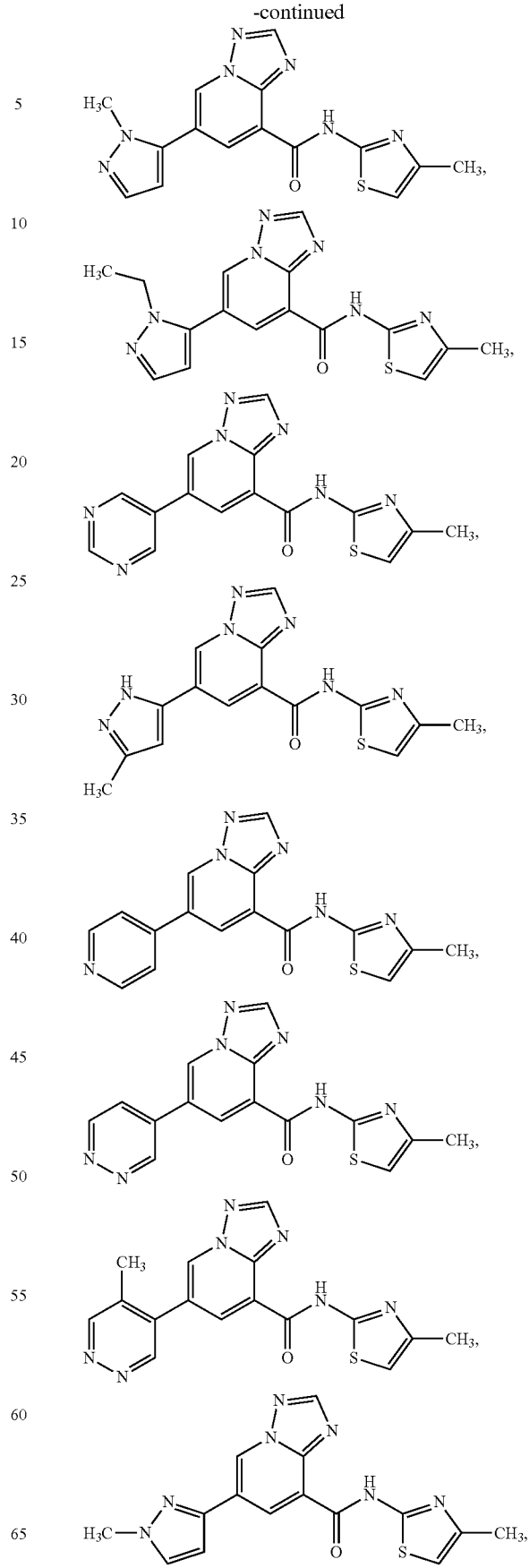

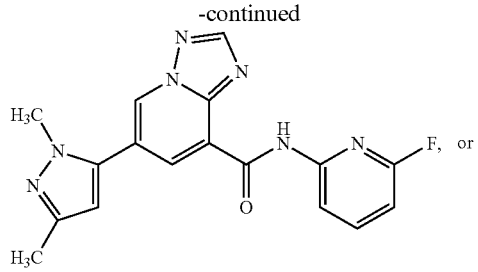
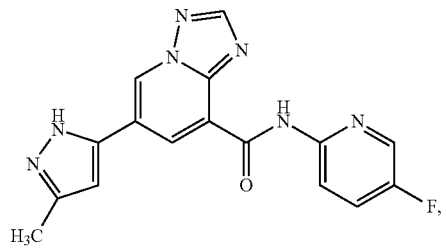
or a subgroup thereof.
In further aspect, a compound can be present as:
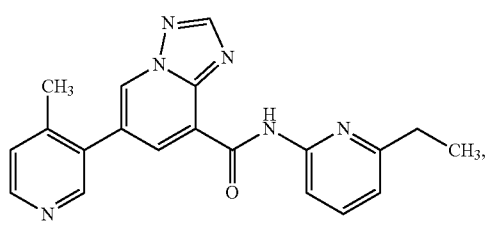
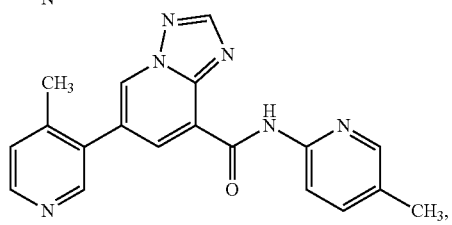
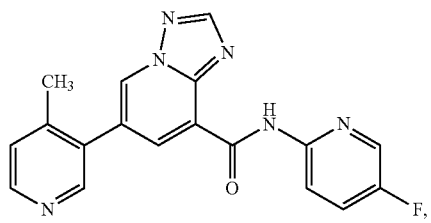
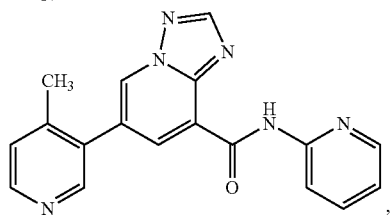
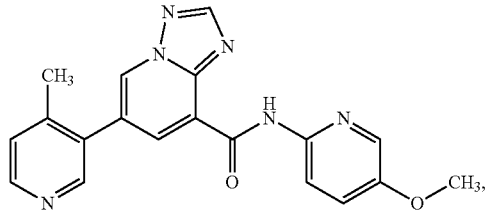
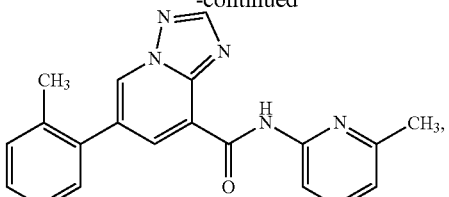
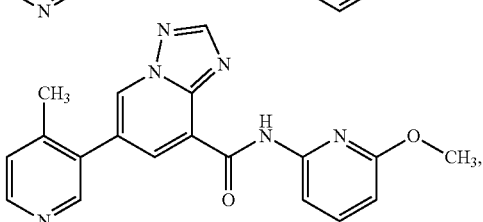
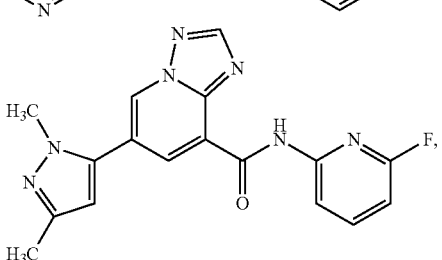
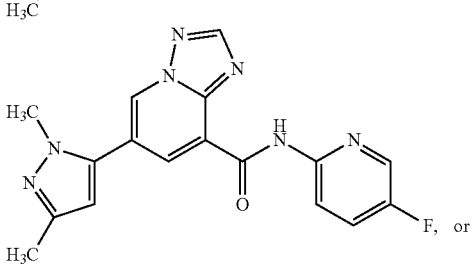
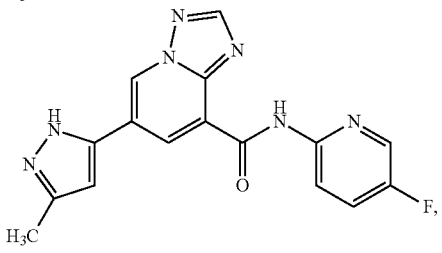
or a subgroup thereof.
In a still further aspect, a compound can be present as:
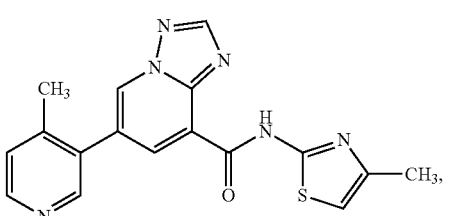
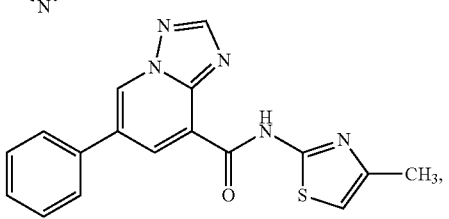

125 126
-continued -continued
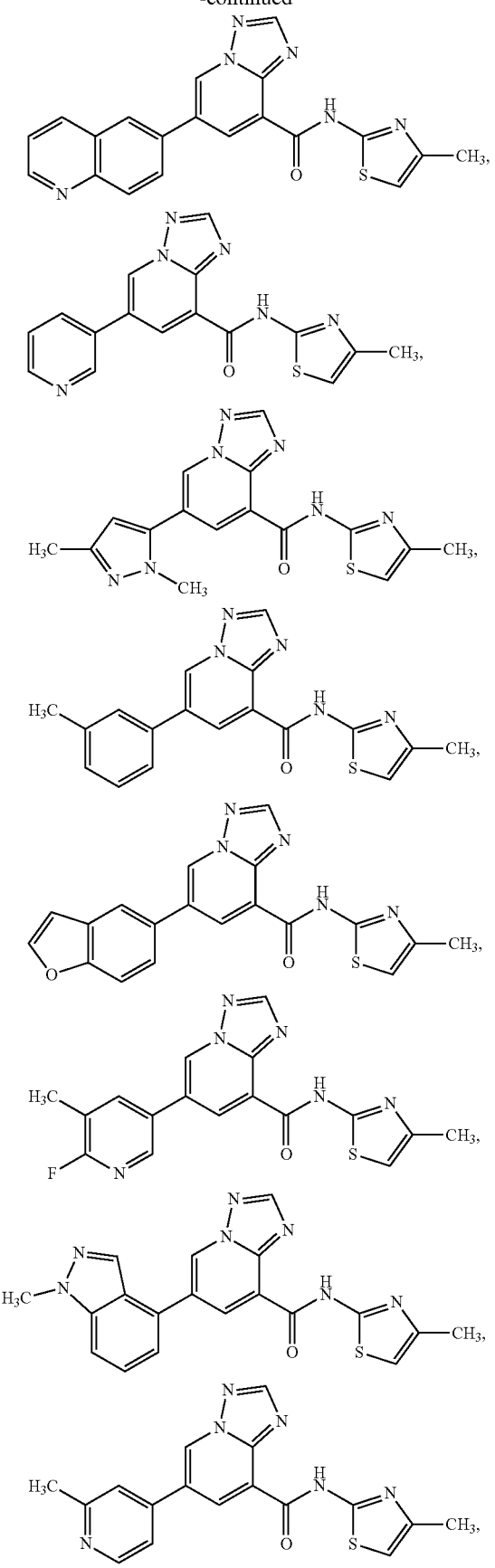
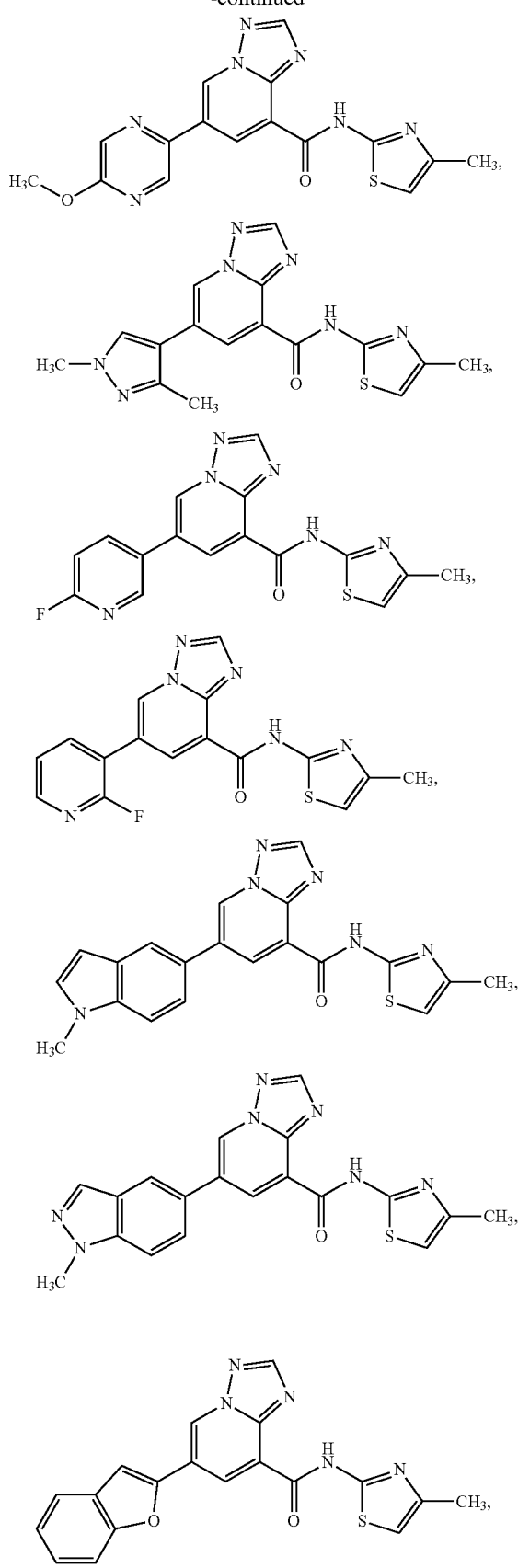

127
-continued
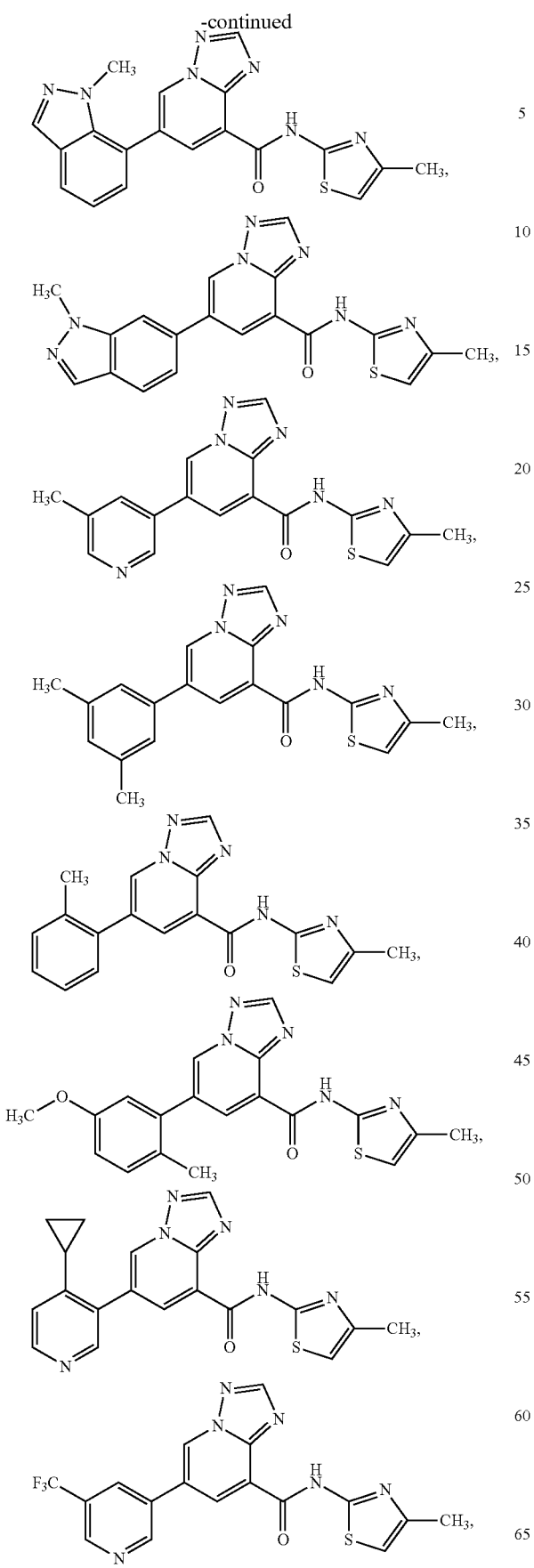
128
-continued
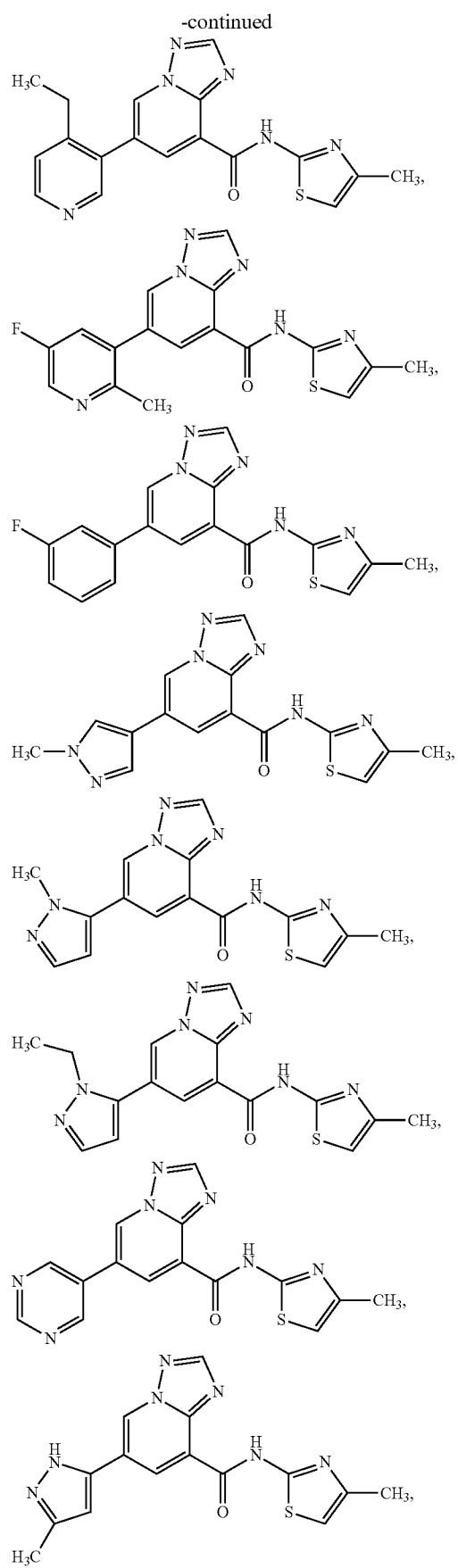

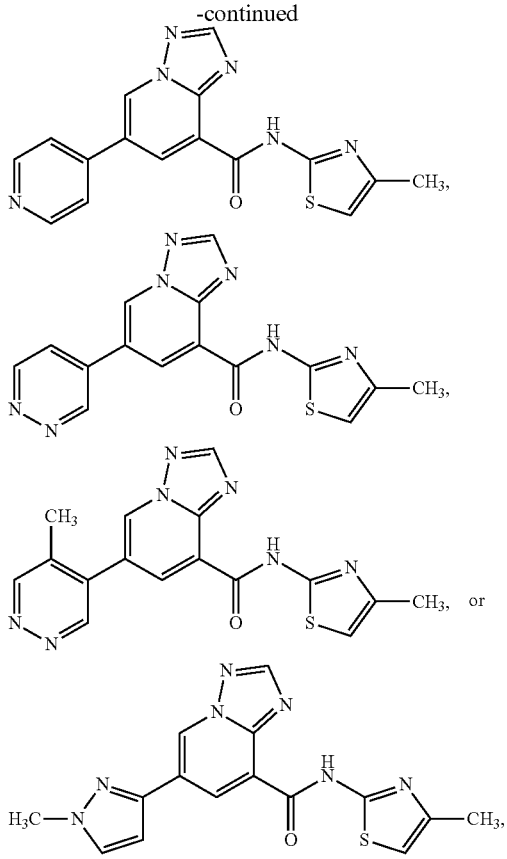
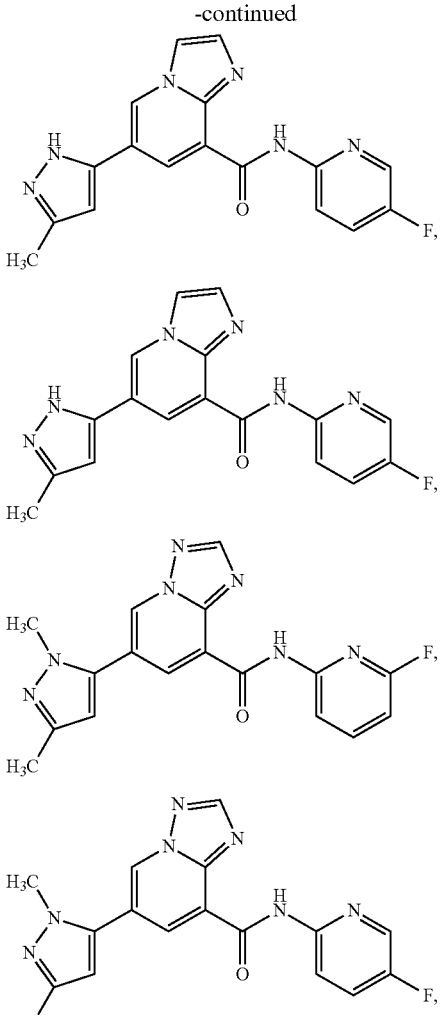
or subgroup thereof.
In one aspect, a compound can be present as:
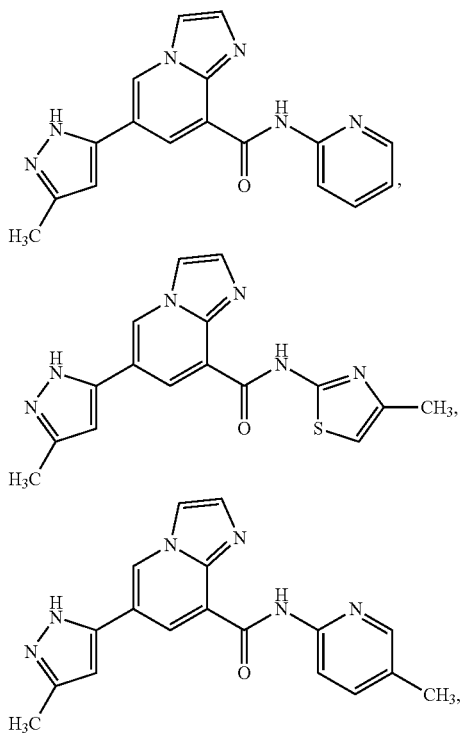
or a subgroup thereof.
In a further aspect, a compound can be present as:
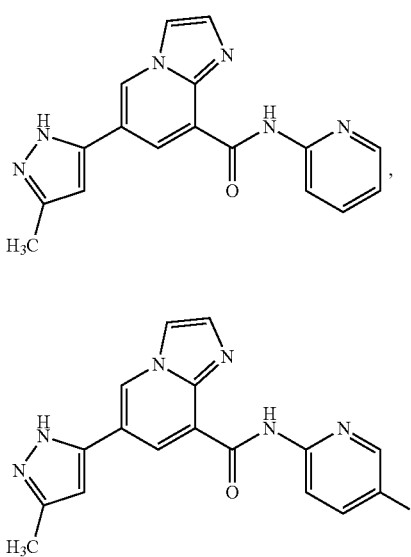

-continued

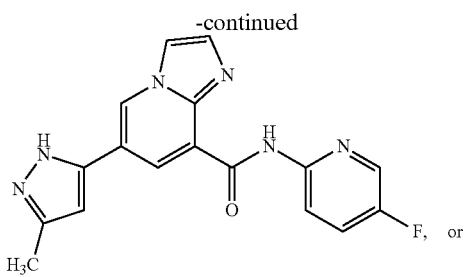

F, or

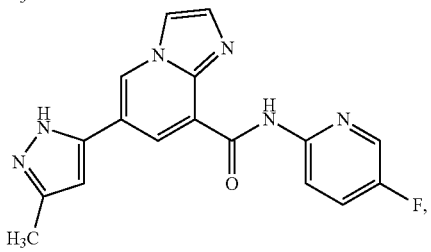

F, or a subgroup thereof.

In a further aspect, a compound can be present as:

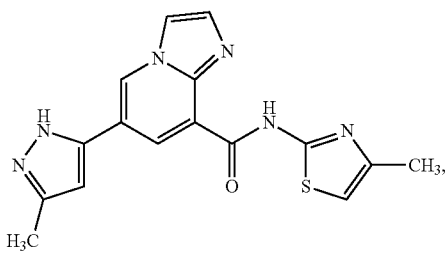 [SMILES: Cc1cc(-c2cc(C(=O)Nc3nc(C)cs3)c3nccn3c2)[nH]n1]

or a subgroup thereof.

In one aspect, a compound can be present as:

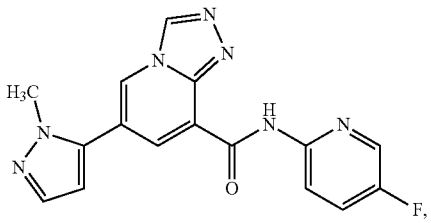 [SMILES: Cn1nccc1-c1cc(C(=O)Nc2ccc(F)cn2)c2nncn2c1]

F, or a subgroup thereof.

In yet a further aspect, the compound exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound exhibits negative allosteric modulation of mGluR5 after contacting a cell expressing mGluR5.

In a further aspect, the compound produced exhibits partial or total inhibition of mGluR5 after contacting a cell expressing mGluR5.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits noncompetitive antagonism. In a still further aspect, the compound exhibits negative allosteric modulation. In a yet further aspect, the compound exhibits noncompetitive inhibition. In an even further aspect, the compound exhibits allosteric antagonism.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15 \times 10^{-7}$ M. In a still further aspect, the compounds exhibit negative allosteric modulation with an $IC_{50}$ of less than about $10 \times 10^{-7}$ M. In yet a further aspect, the compounds exhibit negative allosteric modulation with an $IC_{50}$ of less than about $5 \times 10^{-7}$ M. In an even further aspect, the compounds exhibit negative allosteric modulation with an $IC_{50}$ of less than about $1 \times 10^{-7}$ M.

In a further aspect, a pharmaceutical composition comprising a therapeutically effective amount of the compound and a pharmaceutically acceptable carrier.

It is contemplated that one or more example structures can be optionally omitted from the disclosed invention.

3. Prophetic Compound Examples

The following compound examples are prophetic, and can be prepared using the synthesis methods described herein above and other general methods as needed as would be known to one skilled in the art. It is anticipated that the prophetic compounds would be active as negative allosteric modulators of mGluR5 response, and such activity can be determined using the assay methods described herein below.

In one aspect, a compound can be selected from:

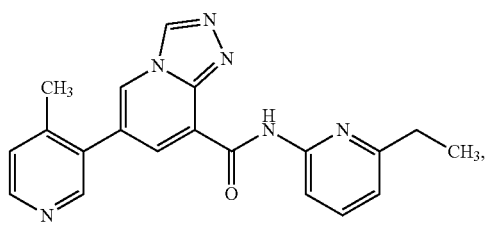

-continued
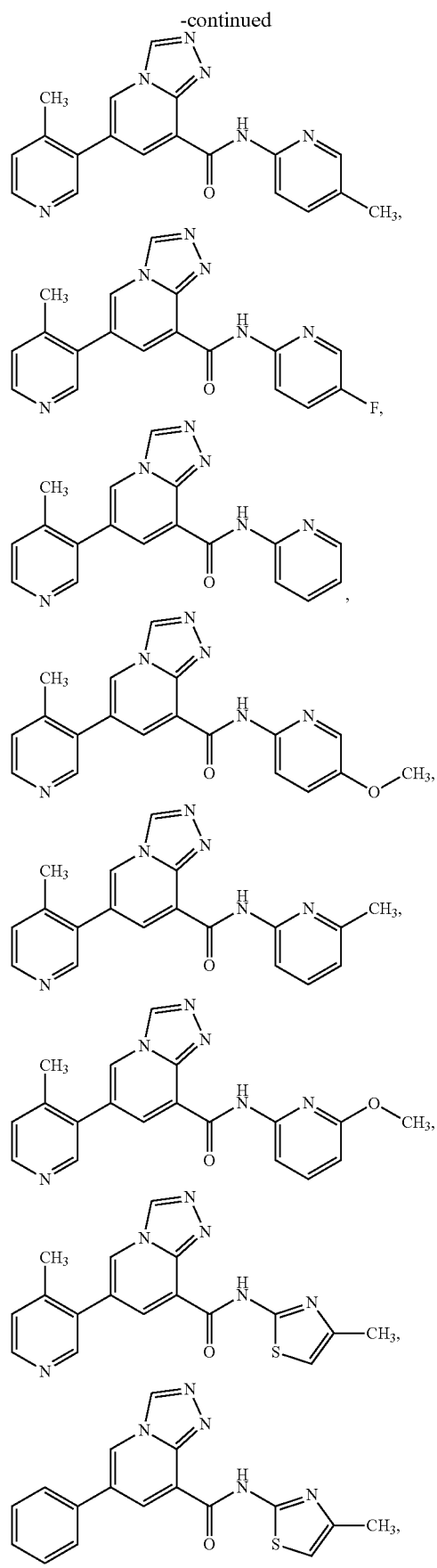
-continued
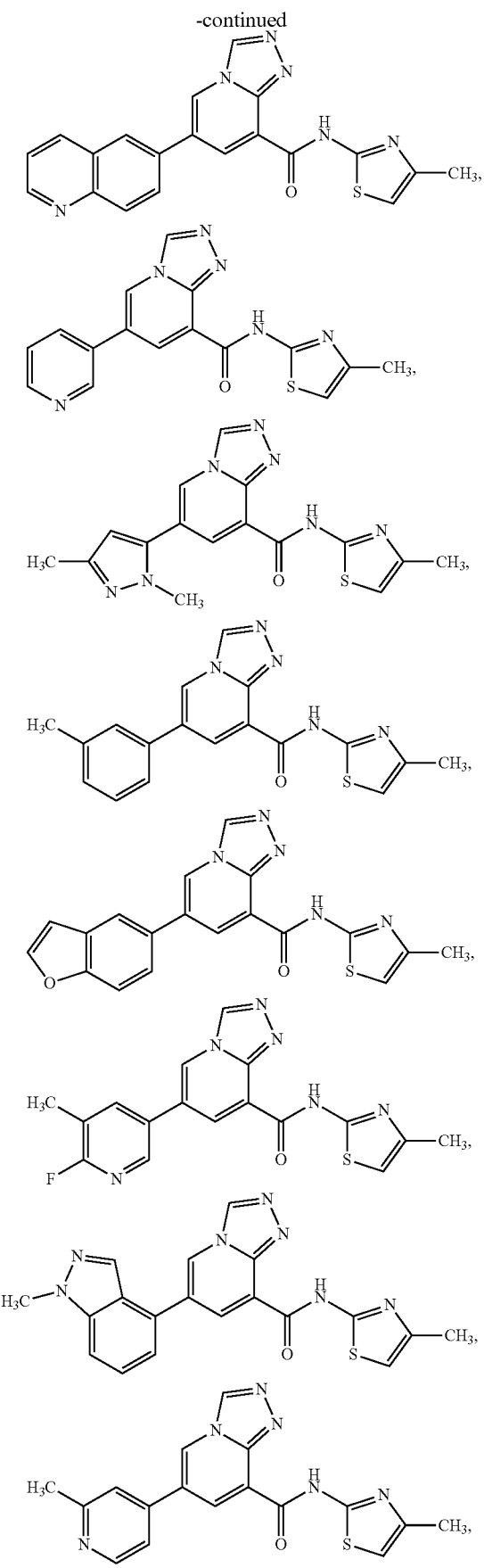

-continued
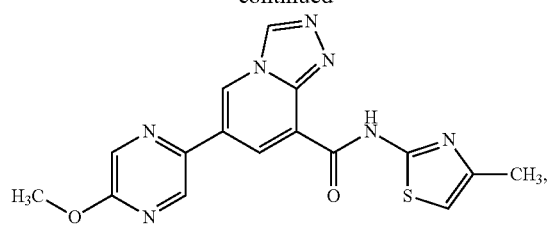
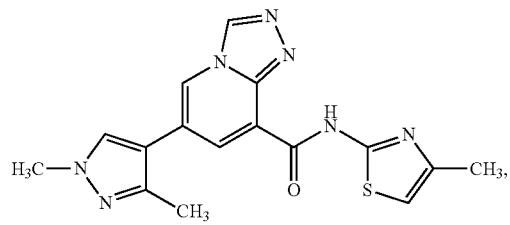
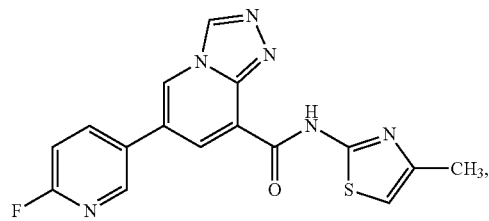
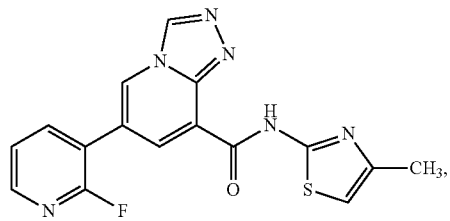
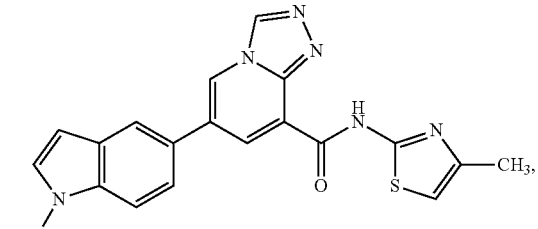
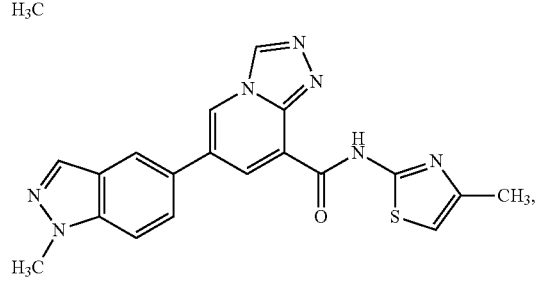
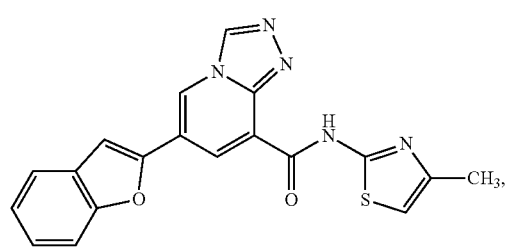
-continued
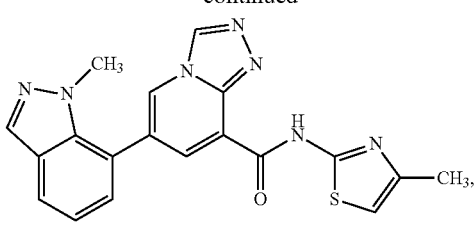
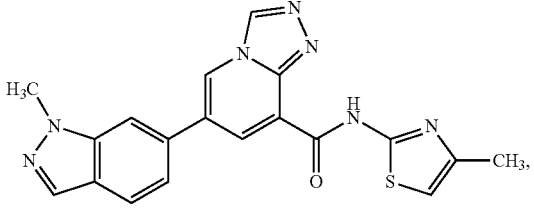
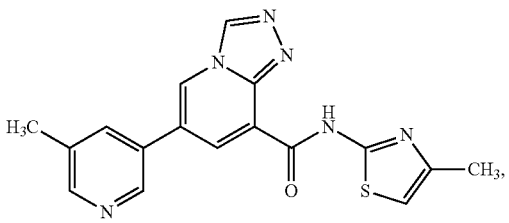
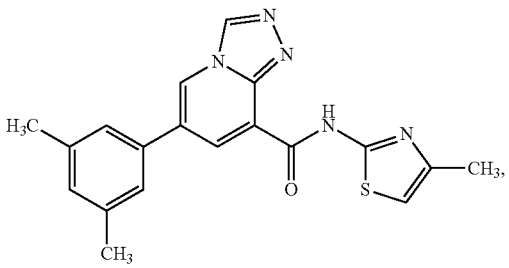
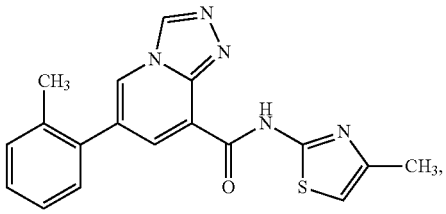
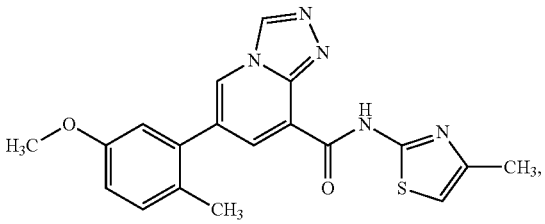
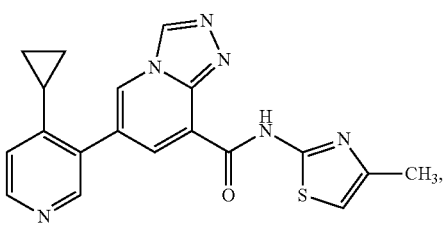

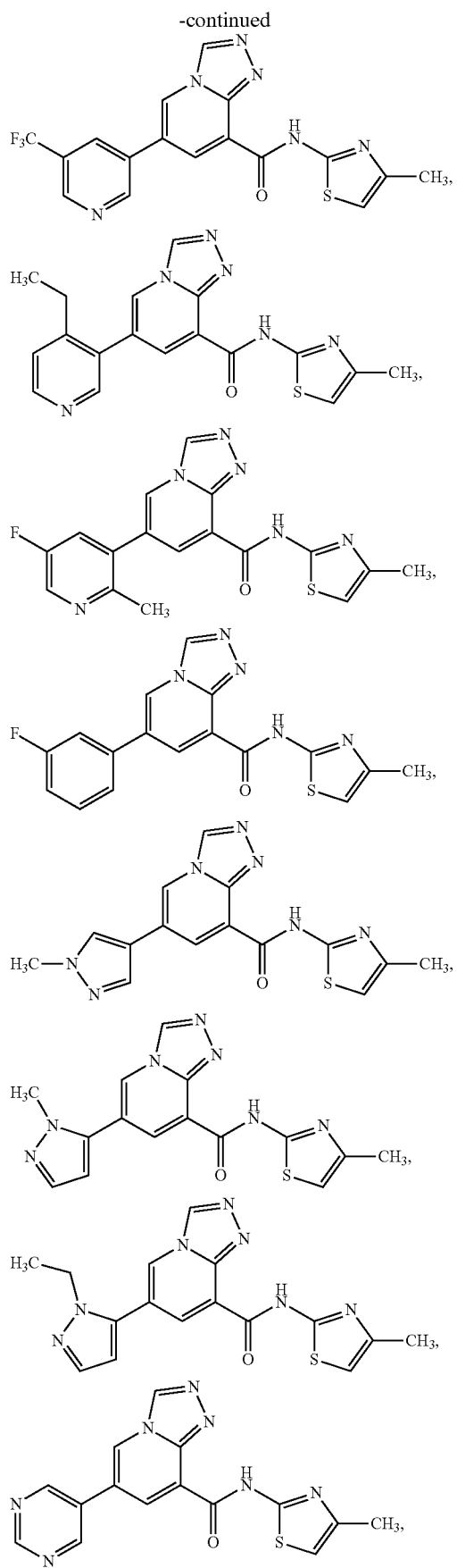
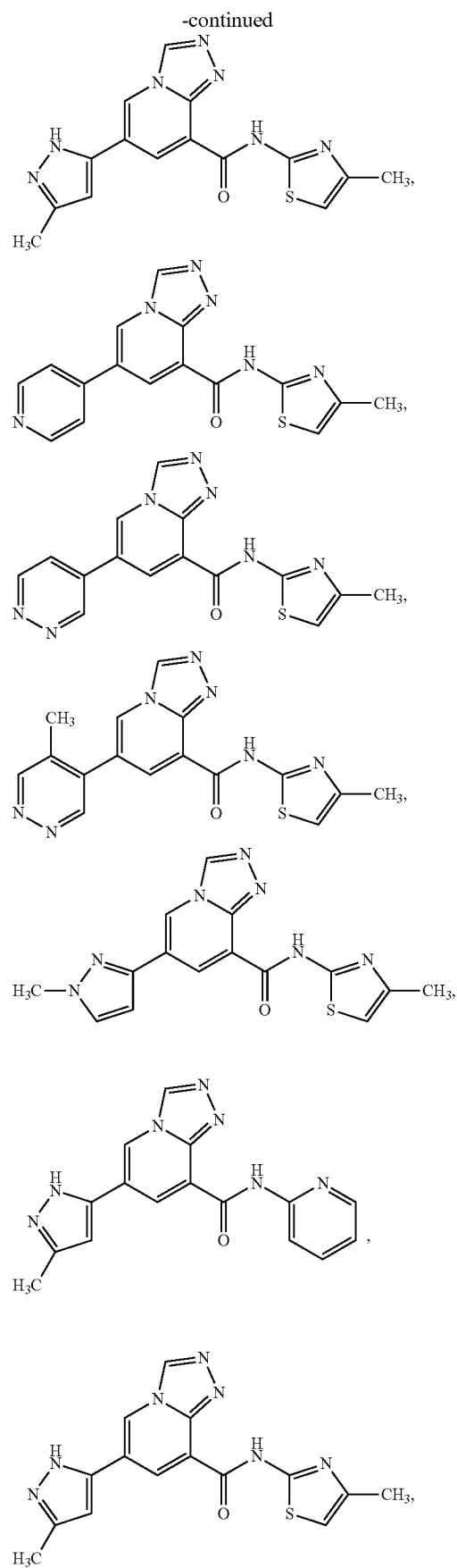

-continued
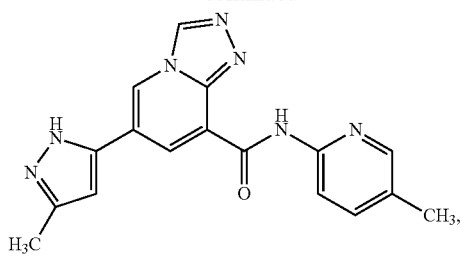
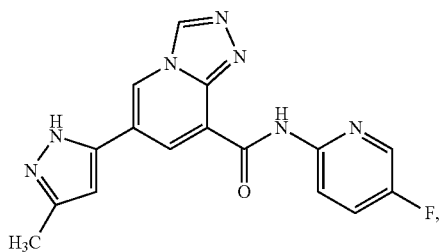
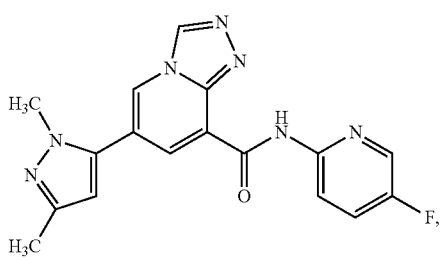 [SMILES: Cc1cc(-c2cc(C(=O)Nc3ccc(F)cn3)c3nncn3c2)n(C)n1]
or a subgroup thereof.
In one aspect, a compound can be selected from:
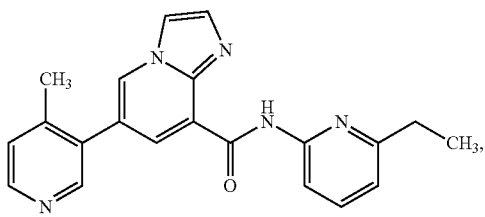
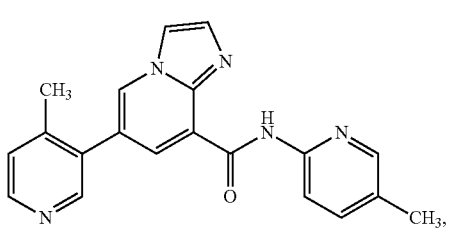
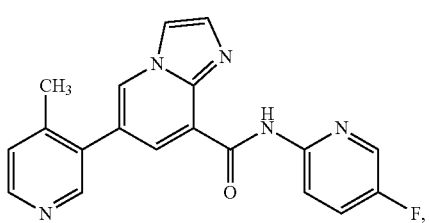
-continued
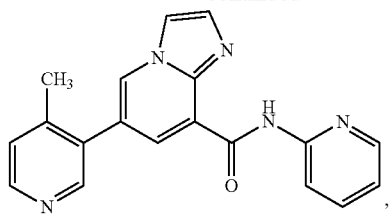
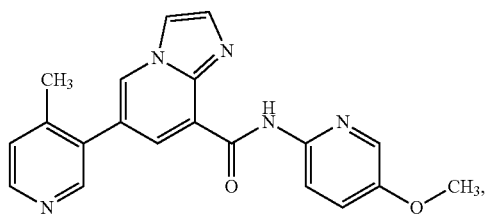
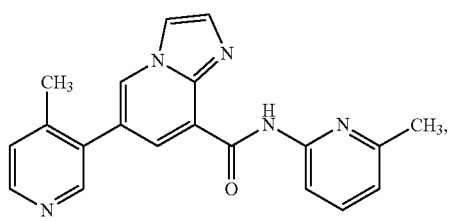
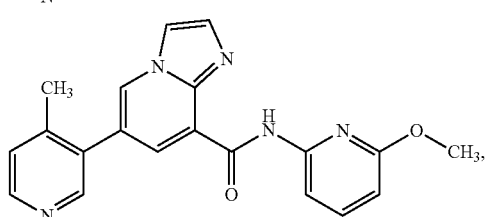
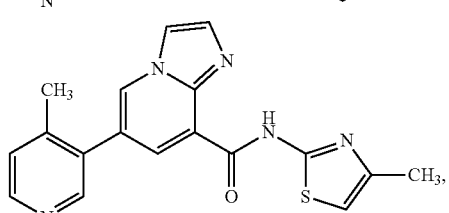
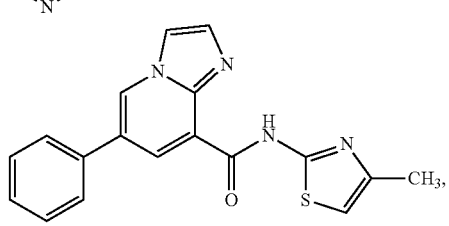
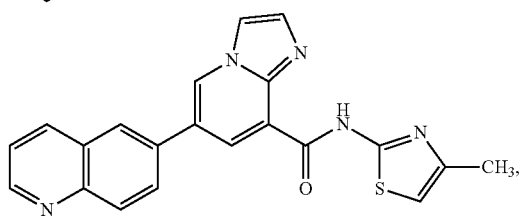
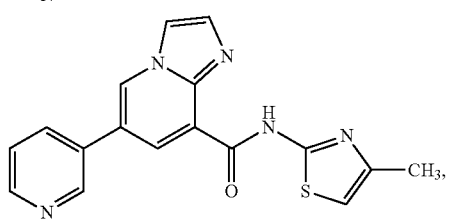

141
-continued
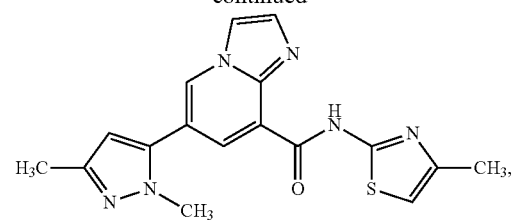
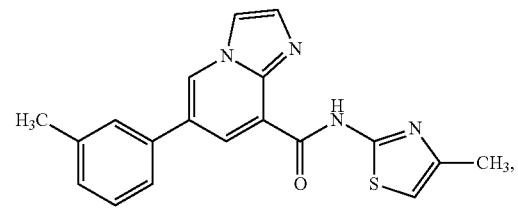
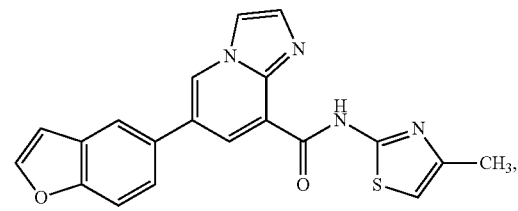
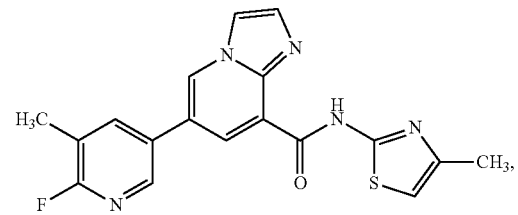
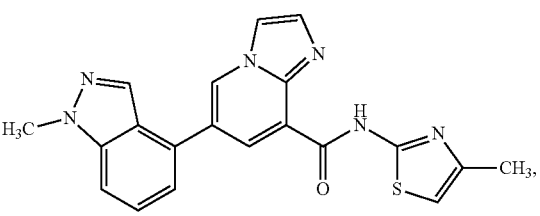
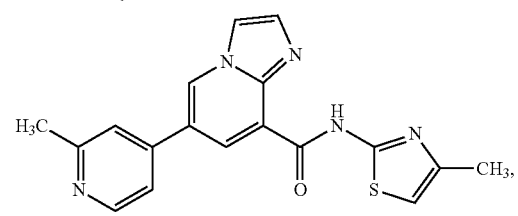
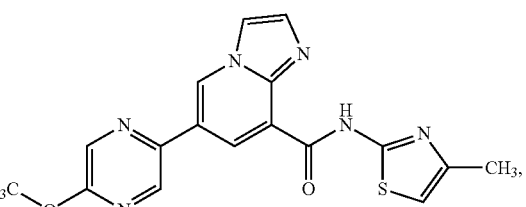
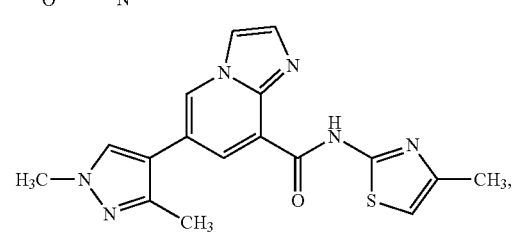
142
-continued
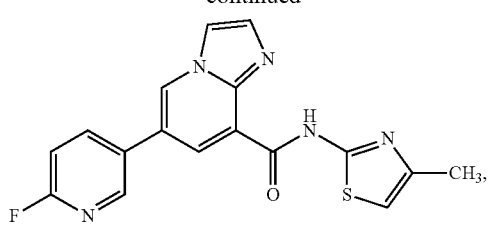
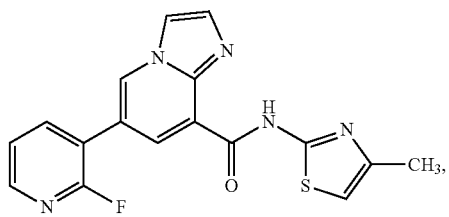
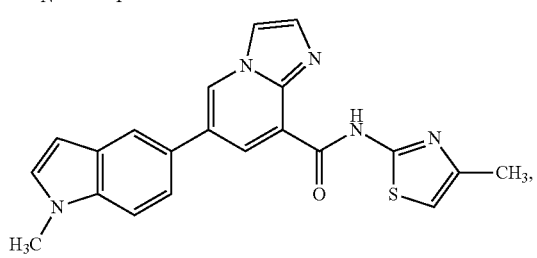
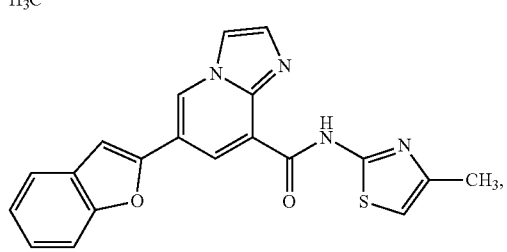
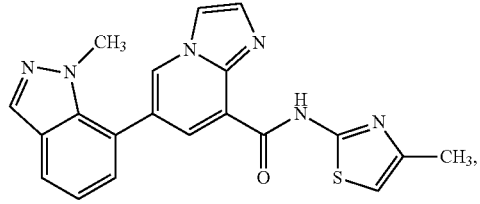
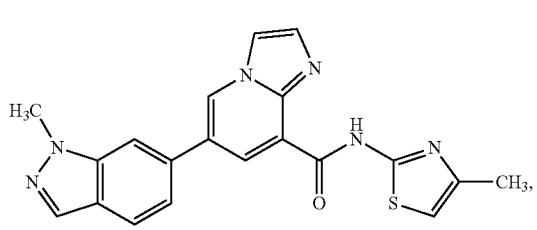

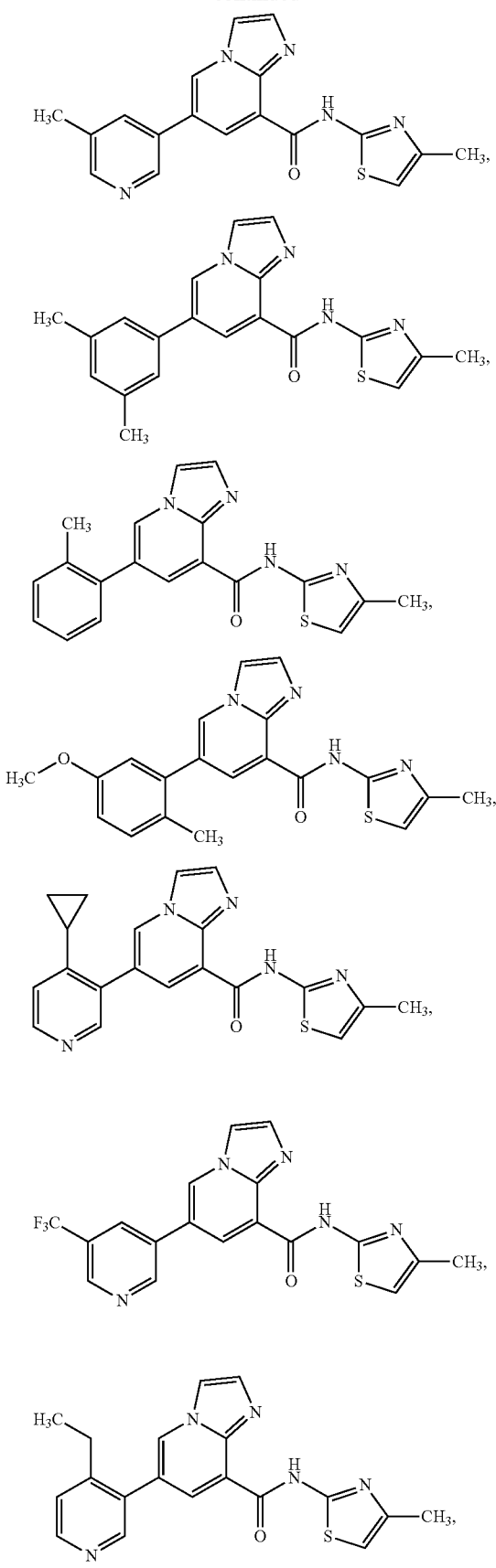
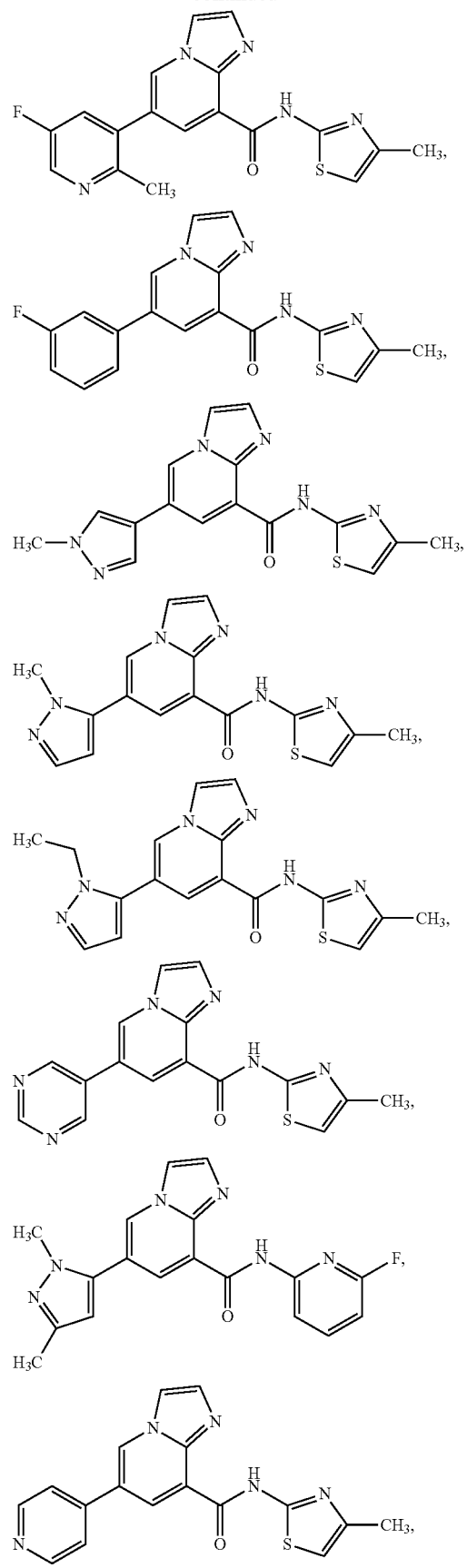

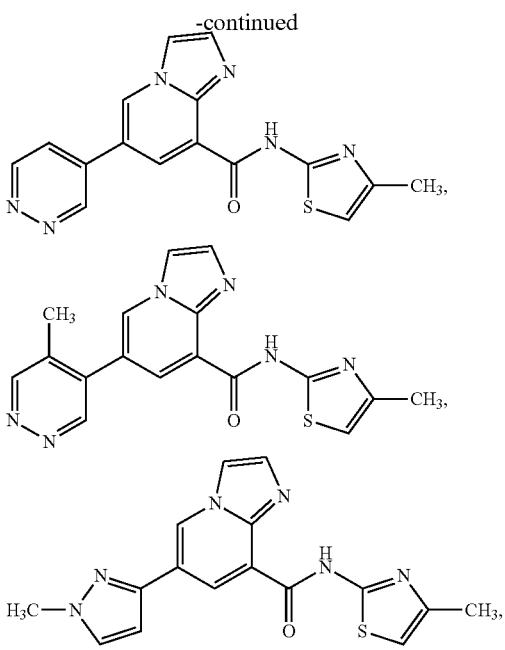

or a subgroup thereof.

In on aspect, a compound can be selected from:

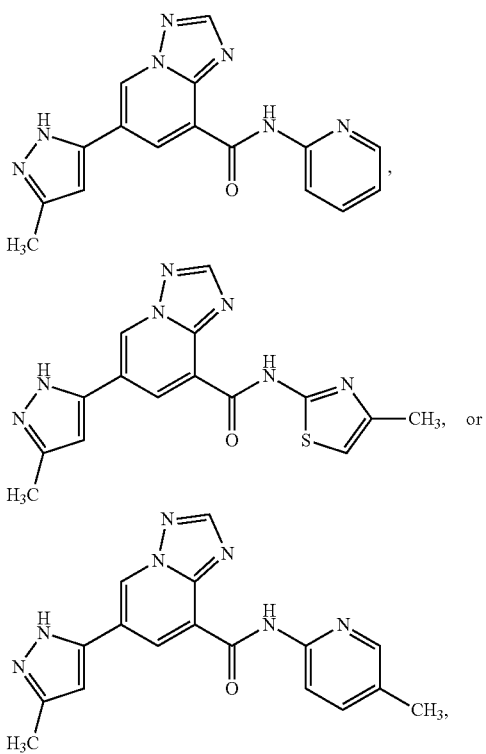

or a subgroup thereof.

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

4. Negative Allosteric Modulation of mGluR5 Response

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits noncompetitive antagonism. In a still further aspect, the compound exhibits negative allosteric modulation. In a yet further aspect, the compound exhibits noncompetitive inhibition. In an even further aspect, the compound exhibits allosteric antagonism.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15 \times 10^{-7}$ M. In a still further aspect, the compounds exhibit negative allosteric modulation with an $IC_{50}$ of less than about $10 \times 10^{-7}$ M. In yet a further aspect, the compounds exhibit negative allosteric modulation with an $IC_{50}$ of less than about $5 \times 10^{-7}$ M. In an even further aspect, the compounds exhibit negative allosteric modulation with an $IC_{50}$ of less than about $1 \times 10^{-7}$ M.

C. Metabotropic Glutamate Receptor Activity

The utility of the compounds in accordance with the present invention as negative allosteric modulators of metabotropic glutamate receptor activity, in particular mGluR5 activity, can be demonstrated by methodology known in the art. HEK 293A cells stably expressing either rat or human mGluR5 were plated in black-walled, clear-bottomed, poly-D-lysine coated 384-well plates in 20 μL of assay medium (DMEM containing 10% dialyzed FBS, 20 mM HEPES, 100 units/mL penicillin/streptomycin plus 250 ng/mL Fungizone® (amphotericin B), and 1 mM sodium pyruvate) at a density of 20,000 cells/well. The cells were grown overnight at 37° C. in the presence of 5% $CO_2$. The next day, medium was removed and the cells incubated with 20 μL of 2.3 μM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 µL of assay buffer was added, and the plate was incubated for 5 minutes at room temperature.

Ca$^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an EC$_{20}$ concentration of the mGluR5 receptor agonist glutamate was added to the cells, and the response of the cells was measured for 1.9 minutes; an EC$_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Antagonism of the agonist response of the mGluR5 receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function (F/F$_0$) for each measurement of the total 360 values per well divided by each well's initial value. Data were then reduced to peak amplitudes (Max–Initial Min) using a time range that starts approximately 3 seconds prior to the glutamate EC$_{20}$/EC$_{80}$ addition and continues for approximately 90-120 seconds. This is sufficient time to capture the peak amplitude of the cellular calcium response. Individual amplitudes were expressed as % E$_{Max}$ by multiplying each amplitude by 100 and then dividing the product by the mean of the amplitudes derived from the glutamate EC$_{Max}$-treated wells. IC$_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a negative allosteric modulator (NAM) if the compound showed a concentration-dependent decrease in the glutamate EC$_{80}$ addition. For NAMs with a CRC that plateaus at a Glu Max (i.e., the amplitude of response in the presence of compound as a percentage of the maximal response to glutamate) below 10%, IC$_{50}$ values are reported. For NAMs with a CRC that plateaus above 10% Glu Max, the IC$_{50}$ values are reported, the compound is designated a "partial NAM" and the % Glu Max is reported. For NAMs that show a decrease in the EC$_{80}$ response, but do not hit a plateau, the average of the Glu Max at a single concentration (30 µM) was determined (% Glu Max), reported, and IC$_{50}$ values are reported as ">10,000 nM". Compounds without measurable activity are designated as ">30,000 nM" since the top concentration of compound tested in the assay is 30 µM. Exemplary data are provided in Table 1 herein below.

In particular, the disclosed compounds had activity in modulating the mGluR5 receptor in the aforementioned assays, generally with an IC$_{50}$ for modulation of less than about 30 µM. Preferred compounds within the present invention had activity in modulating the mGluR5 receptor with an IC$_{50}$ for negative allosteric modulation of less than about 500 nM. Preferred compounds reduced the response to an EC$_{80}$ concentration of glutamate to less than 50% of the maximal response and also induced a rightward and downward shift of the glutamate concentration response curve. These compounds are negative allosteric modulators of human and rat mGluR5 and were selective for mGluR5 compared to the other six subtypes of metabotropic glutamate receptors.

D. Methods of Making the Compounds

In one aspect, the invention relates to methods of making compounds useful as negative allosteric modulators of the metabotropic glutamate receptor subtype 5 (mGluR5), which can be useful in the treatment neurological and psychiatric disorders associated with glutamate dysfunction and other diseases in which metabotropic glutamate receptors are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In a further aspect, the compound produced exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

1. Intermediate Route I

In one aspect, silyl ether intermediates can be prepared as shown below.

SCHEME 1A.

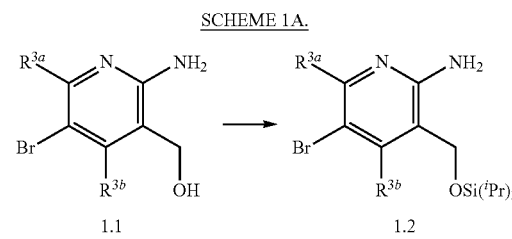

Compounds are represented in generic form, with substituents as noted in compound descriptions elsewhere herein. A more specific example is set forth below.

SCHEME 1B.

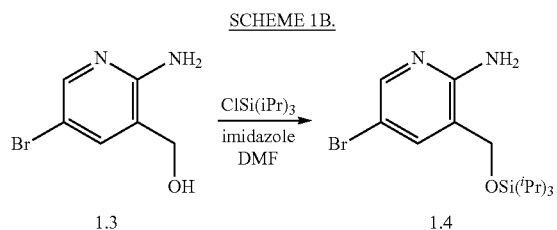

In one aspect, compounds of type 1.2, and similar compounds, can be prepared according to reaction Scheme 1B above. Thus, compounds of type 1.4 can be prepared by a protection of an appropriate alcohol, e.g., 1.3 as shown above. Appropriate alcohols are commercially available or prepared by methods known to one skilled in the art. The protection is carried out in the presence of an appropriate electrophile, e.g., triisopropylsilyl chloride, and an appropriate base, e.g., imidazole as shown above, in an appropriate solvent, e.g., dimethylformamide (DMF). Additional examples of suitable bases include, but are not limited to, triethylamine, diisopropylethylamine, and 4-dimethylaminopyridine. It will be appreciated by one skilled in the art that other protecting groups may also function suitably for the purposes outlined herein (see Greene, T. W. and Wuts, P. G. M. *Protecting Groups in Organic Synthesis*, 3$^{rd}$ Ed. New York: John Wiley & Sons, Inc. 1999). As can be appreciated by one skilled in the art, the above reaction provides an example of a generalized approach wherein compounds similar in structure to the specific reactants above (compounds similar to compounds of type 1.1), can be substituted in the reaction to provide silyl ether intermediates similar to Formula 1.2.

Thus, in one aspect, the invention relates to a method of making a compound, the method comprising the step of reacting a compound having a structure represented by a formula:

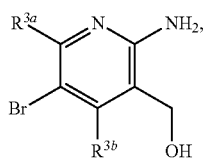

wherein each of R$^{3a}$ and R$^{3b}$ is independently selected from hydrogen and fluoro; with triisopropylsilyl chloride in the presence of a suitable base, thereby forming a silyl ether intermediate, having a structure represented by a formula:

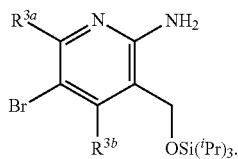

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Intermediate Route II

In one aspect, 6-bromotriazolopyridine intermediates can be prepared as shown below.

SCHEME 2A.

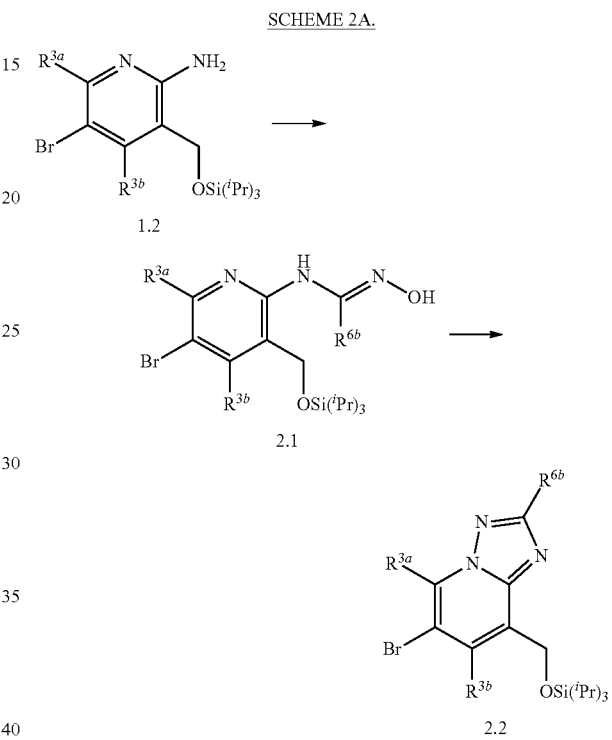

Compounds are represented in generic form, with substituents as noted in compound descriptions elsewhere herein. A more specific example is set forth below.

SCHEME 2B.

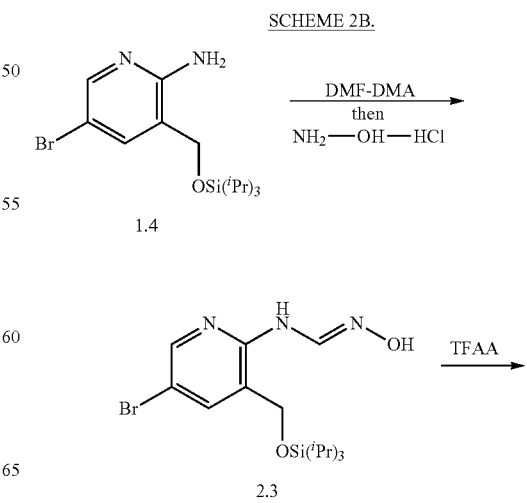

-continued

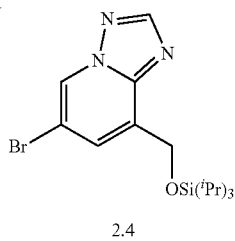

2.4

In one aspect, compounds of type 2.2, and similar compounds, can be prepared according to reaction Scheme 2B above. Thus, compounds of type 2.3 can be prepared by formation of an amideoxime from an appropriate amine, e.g., 1.4 as shown above. The formation of the amideoxime is carried out in the presence of an appropriate acetal, e.g., dimethylformamide dimethyl acetal (DMF-DMA), and an appropriate hydroxylamine, e.g., hydroxylamine hydrochloride as shown above, with optional heating. Compounds of type 2.4 can be prepared by cyclization of an appropriate amideoxime, e.g., 2.3 as shown above. The cyclization is carried out in the presence of an appropriate acid anhydride, e.g., trifluoroacetic anhydride (TFAA). As can be appreciated by one skilled in the art, the above reaction provides an example of a generalized approach wherein compounds similar in structure to the specific reactants above (compounds similar to compounds of type 1.2 and 2.1), can be substituted in the reaction to provide 6-bromotriazolopyridine intermediates similar to Formula 2.2.

Thus, in one aspect, the invention relates to a method of making a compound, the method comprising the step of reacting a compound having a structure represented by a formula:

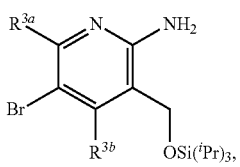

wherein each of $R^{3a}$ and $R^{3b}$ is independently selected from hydrogen and fluoro; with an appropriate acetal and subsequently hydroxylamine thereby forming an amideoxime intermediate having a structure represented by a formula:

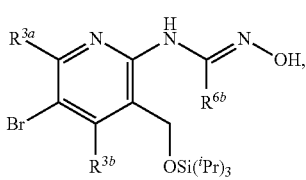

wherein $R^{6b}$ is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$, wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with the nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with the nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with the nitrogen atom to which they are attached, comprise a 3- to 6-membered heterocycle.

In a further aspect, the method comprises the step of reacting the amideoxime intermediate with trifluoroacetic anhydride, thereby forming a 6-bromotriazolopyridine intermediate, having a structure represented by a formula:

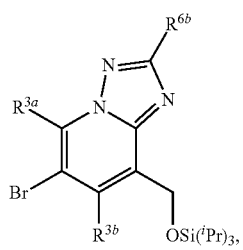

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

3. Intermediate Route III

In one aspect, 6-bromoimidazopyridine intermediates can be prepared as shown below.

SCHEME 3A.

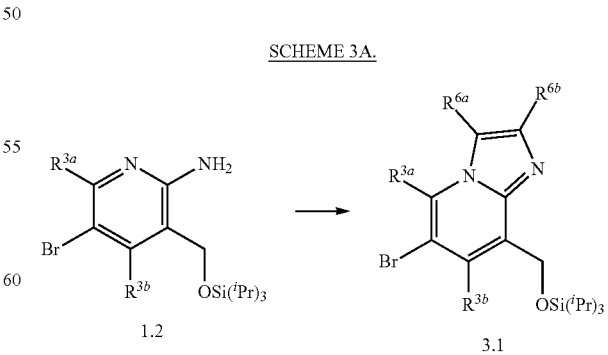

Compounds are represented in generic form, with substituents as noted in compound descriptions elsewhere herein. A more specific example is set forth below.

SCHEME 3B.

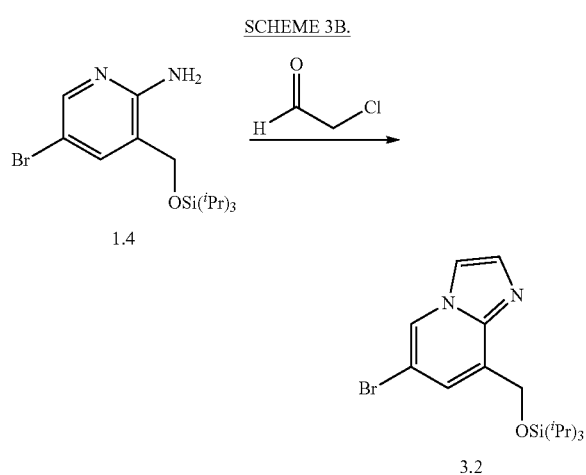
1.4

3.2

In one aspect, compounds of type 3.1, and similar compounds, can be prepared according to reaction Scheme 3B above. Thus, compounds of type 3.2 can be prepared by cyclization of an appropriate amine, e.g., 1.4 as shown above. The cyclization is carried out in the presence of an appropriate cyclizing agent, e.g., chloroacetaldehyde. A mild base may optionally be added to the reaction. Examples of suitable mild bases included but are not limited to sodium hydrogen carbonate, sodium carbonate, and potassium carbonate. It will be appreciated that the cyclization reaction may be optionally heated, either conventionally or with microwave irradiation. As can be appreciated by one skilled in the art, the above reaction provides an example of a generalized approach wherein compounds similar in structure to the specific reactants above (compounds similar to compounds of type 1.2), can be substituted in the reaction to provide 6-bromoimidazopyridine intermediates similar to Formula 3.1.

Thus, in one aspect, the invention relates to a method of making a compound, the method comprising the step of reacting a compound having a structure represented by a formula:

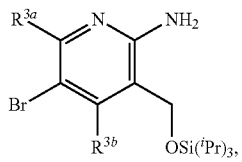

wherein each of $R^{3a}$ and $R^{3b}$ is independently selected from hydrogen and fluoro; with an α-halo aldehyde or ketone, or its equivalent, thereby forming a -bromo imidazopyridine intermediate having a structure represented by a formula:

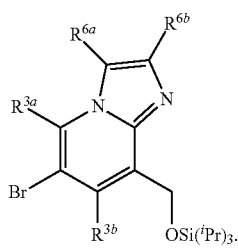

wherein each of $R^{6a}$ and $R^{6b}$ is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$ wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Intermediate Route IV

In one aspect, alcohol intermediates can be prepared as shown below.

SCHEME 4A.

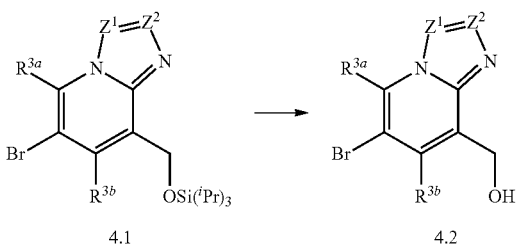

Compounds are represented in generic form, with substituents as noted in compound descriptions elsewhere herein. A more specific example is set forth below.

SCHEME 4B.

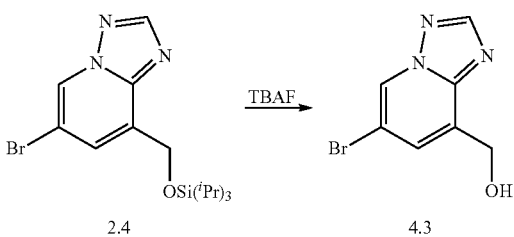

In one aspect, compounds of type 4.2, and similar compounds, can be prepared according to reaction Scheme 4B above. Thus, compounds of type 4.3 can be prepared by deprotection of an appropriate ether, e.g., 2.4 as shown above. The deprotection is carried out in the presence of an appropriate deprotecting agent, e.g., tetrabutylammonium fluoride (TBAF). It will be appreciate by one skilled in the art that other reagents may be effective agents for cleavage of the silyl ether protecting group. Examples of such reagents include but are not limited to potassium fluoride, HF, HF.pyridine, and HCl. As can be appreciated by one skilled in the art, the above reaction provides an example of a generalized approach wherein compounds similar in structure to the specific reactants above (compounds similar to compounds of type 4.1), can be substituted in the reaction to provide alcohol intermediates similar to Formula 4.2.

Thus, in one aspect, the invention relates to a method of making a compound, the method comprising the step of reacting a compound having a structure represented by a formula:

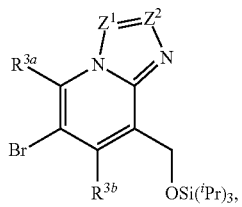

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$ wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein each of $R^{3a}$ and $R^{3b}$ is independently selected from hydrogen and fluoro; with tetrabutylammonium fluoride, or other suitable deprotecting agent, thereby forming an alcohol intermediate having a structure represented by a formula:

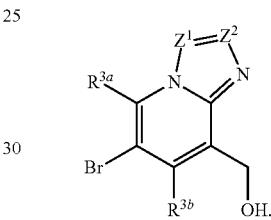

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

5. Intermediate Route V

In one aspect, alcohol intermediates can be prepared as shown below.

SCHEME 5A.

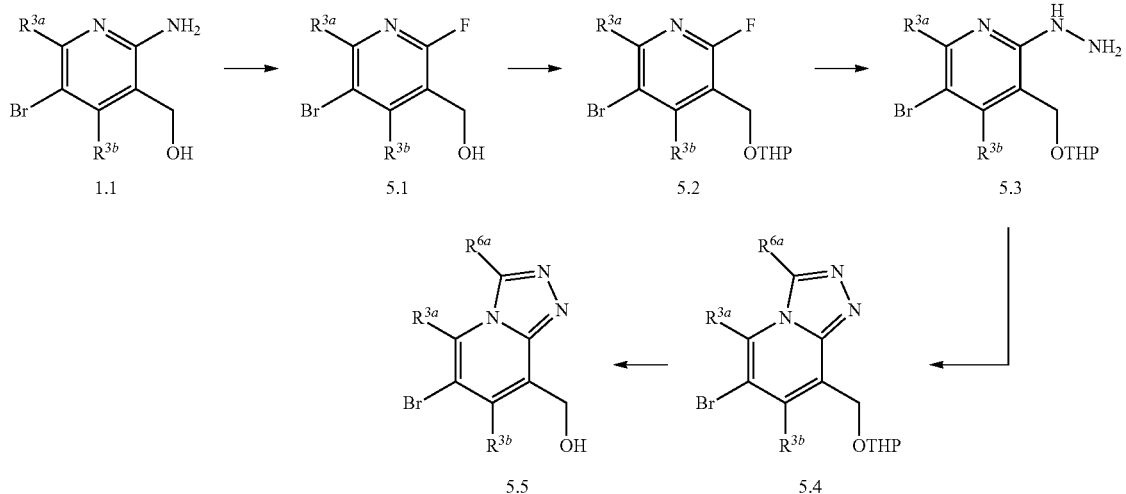

Compounds are represented in generic form, with substituents as noted in compound descriptions elsewhere herein. A more specific example is set forth below.

SCHEME 5B.

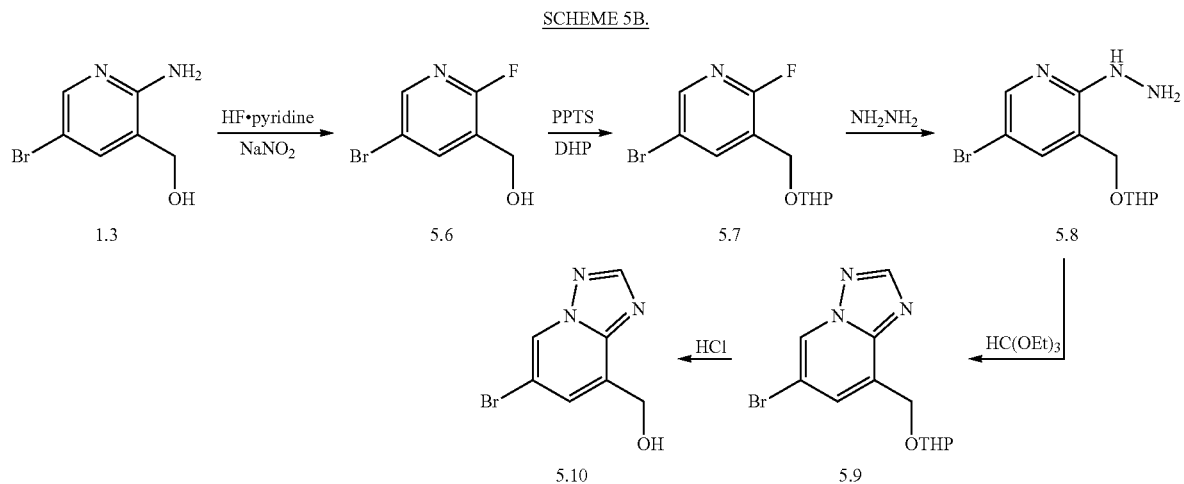

In one aspect, compounds of type 5.5, and similar compounds, can be prepared according to reaction Scheme 5B above. Thus, compounds of type 5.6 can be prepared by substitution reaction of an appropriate aminopyridine, e.g., 1.3 as shown above. The substitution reaction is carried out in the presence of an appropriate nucleophile, e.g., hydrogen fluoride-pyridine complex, and an appropriate salt, e.g., sodium nitrite. Compounds of type 5.7 can be prepared by protection of an appropriate alcohol, e.g., 5.8 as shown above. The protection is carried out in the presence of an appropriate protecting group, e.g., 3,4-dihydro-2H-pyran (DHP), an appropriate protic acid. It will be appreciated by one skilled in the art that a variety of protic acids may be suitable for this transformation, including but not limited to pyridinium p-toluenesulfonate (PPTS) and p-toluenesulfonic acid (PTSA). It will further be appreciated by one skilled in the art that other protecting groups may also function suitably for the purposes outlined herein (see Greene, T. W. and Wuts, P. G. M. Protecting Groups in Organic Synthesis, 3$^{rd}$ Ed. New York: John Wiley & Sons, Inc. 1999). Compounds of type 5.8 can be prepared by nucleophilic aromatic substitution of an appropriate aryl halide, e.g., 5.7 as shown above. The nucleophilic aromatic substitution is carried out in the presence of an appropriate nucleophile, e.g., hydrazine. It will be appreciated by one skilled in the art that the S$_N$Ar reaction may be optionally heated, either conventionally or with microwave irradiation. Compounds of type 5.9 can be prepared by cyclization of an appropriate hydrazinyl pyridine, e.g., 5.8 as shown above. The cyclization is carried out in the presence of an appropriate cyclizing agent, e.g., triethylorthoformate as shown above. It will be appreciated by one skilled in the art that the cyclization reaction may be optionally heated, either conventionally or with microwave irradiation. Compounds of type 5.10 can be prepared by deprotection of an appropriate protected alcohol, e.g., 5.9 as shown above. The deprotection is carried out in the presence of an appropriate acid, e.g., hydrochloric acid (HCl), in an appropriate protic solvent, e.g., methanol. It will be appreciated by one skilled in the art that a variety of acids may be suitable for this transformation, including but not limited to HCl, PTSA, and trifluoroacetic acid. It will further be appreciated that a variety of protic solvents may be used, including but not limited to water, methanol, and ethanol. As can be appreciated by one skilled in the art, the above reaction provides an example of a generalized approach wherein compounds similar in structure to the specific reactants above (compounds similar to compounds of type 1.1, 5.1, 5.2, 5.3, and 5.4), can be substituted in the reaction to provide alcohol intermediates similar to Formula 5.5.

Thus, in one aspect, the invention relates to a method of making a compound, the method comprising the step of reacting a compound having a structure represented by a formula:

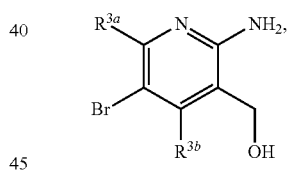

wherein each of R$^{3a}$ and R$^{3b}$ is independently selected from hydrogen and fluoro; with hydrogen fluoride-pyridine complex and sodium nitrite, thereby forming a 2-fluoropyridine intermediate having a structure represented by a formula:

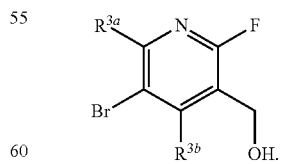

In a further aspect, the method comprises the step of reacting the alcohol intermediate with 3,4-dihydro-2H-pyran in the presence of a protic acid, thereby forming a tetrahydropyranyl ether intermediate having a structure represented by a formula:

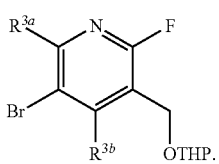

In a further aspect, the method comprises the step of reacting the 2-fluoropyridine intermediate with hydrazine, thereby forming a 2-hydrazinylpyridine intermediate, having a structure represented by a formula:

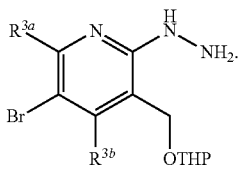

In a further aspect, the method comprises the step of reacting the 2-hydrazinylpyridine intermediate with an appropriate orthoester, or its equivalent, thereby forming a triazolopyridine intermediate, having a structure represented by a formula:

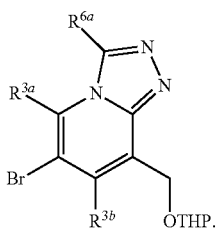

wherein $R^{6a}$ is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$ wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle.

In a further aspect, the method comprises the step of reacting the tetrahydropyranyl ether intermediate with acid thereby forming an alcohol intermediate, having a structure represented by a formula:

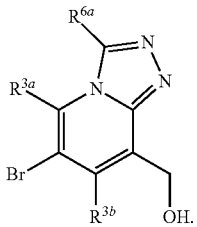

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

6. Intermediate Route VI

In one aspect, amide intermediates can be prepared as shown below.

SCHEME 6A.

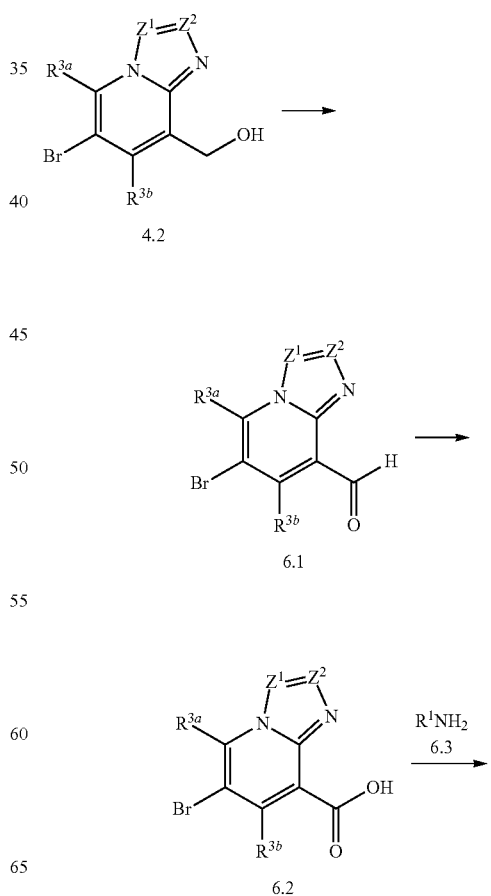

-continued

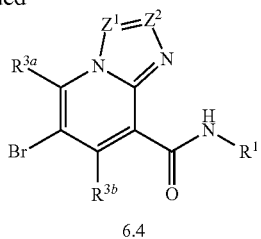

6.4

Compounds are represented in generic form, with substituents as noted in compound descriptions elsewhere herein. A more specific example is set forth below.

SCHEME 6B.

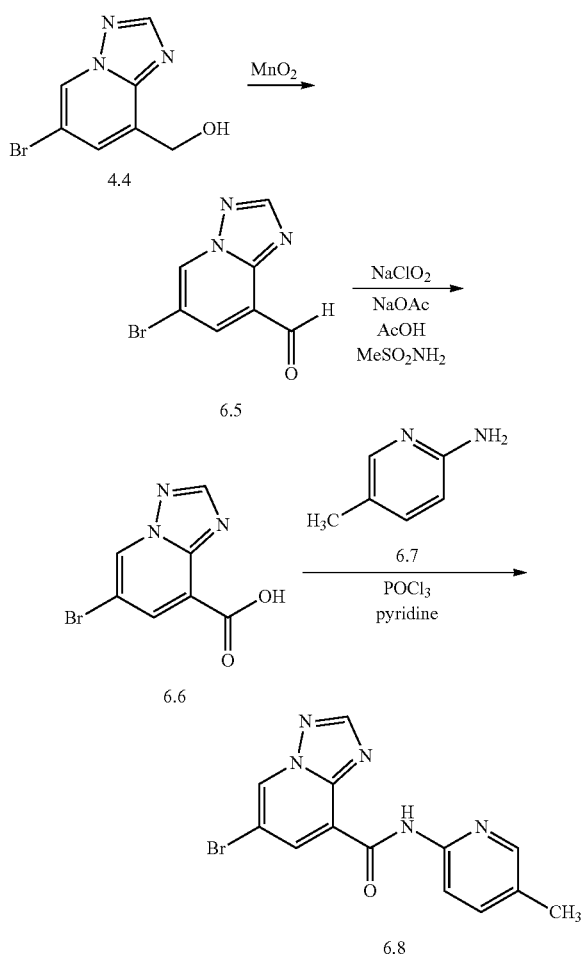

In one aspect, compounds of type 6.4, and similar compounds, can be prepared according to reaction Scheme 6B above. Thus, compounds of type 6.5 can be prepared by oxidation of an appropriate alcohol, e.g., 4.4 as shown above. The oxidation is carried out in the presence of an appropriate oxidizing agent. It will be appreciated by one skilled in the art that a variety of oxidizing agents may be effective for this transformation, including but not limited to manganese dioxide, Dess-Martin reagent, and sulfur trioxide-pyridine. Compounds of type 6.6 can be prepared by oxidation of an appropriate aldehyde, e.g., 6.5 as shown above. The oxidation is carried out in the presence of an appropriate oxidizing agent. It will be appreciated by one skilled in the art that a variety of oxidizing agents may be useful for this transformation, including but not limited to sodium chlorite, oxone, and Jones reagent. Compounds of type 6.8 can be prepared by coupling reaction of an appropriate carboxylic acid, e.g., 6.6 as shown above. The coupling reaction is carried out in the presence of an appropriate heteroaryl amine, e.g., 6.7, and an appropriate activating agent, e.g., phosphorous oxychloride. Such aryl or heteroaryl amines are commercially available or readily prepared by one skilled in the art. Such coupling reactions are generally well known. For example, carboxylic acids can be treated with activating reagents such as 2-(1H-7-azabenzotriazol-1-yl)-1,1,3,3-tetramethyl uronium hexafluoro-phosphate methanaminium (HATU), Ghosez's Reagent (1-chloro-N,N,2-trimethyl-1-propenylamine), and phosphorous oxychloride/pyridine including mixtures thereof, and then reacted with the amine. As can be appreciated by one skilled in the art, the above reaction provides an example of a generalized approach wherein compounds similar in structure to the specific reactants above (compounds similar to compounds of type 4.2, 6.1, 6.2 and 6.3), can be substituted in the reaction to provide amide intermediates similar to Formula 6.4.

Thus, in one aspect, the invention relates to a method of making a compound, the method comprising the step of reacting a compound having a structure represented by a formula:

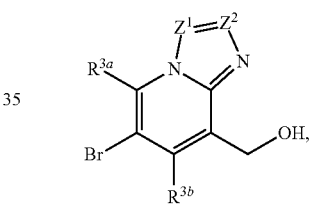

wherein $Z^1$ is selected from N and $CR^{6a}$, wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with the nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with the nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein each of $R^{3a}$ and $R^{3b}$ is independently selected from hydrogen and fluoro; with an oxidizing agent, thereby forming an aldehyde intermediate having a structure represented by a formula:

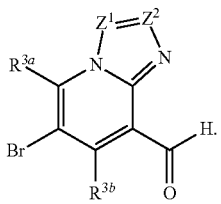

In a further aspect, the method comprises the step of reacting the aldehyde intermediate with a suitable oxidizing agent, thereby forming a carboxylic acid intermediate having a structure represented by a formula:

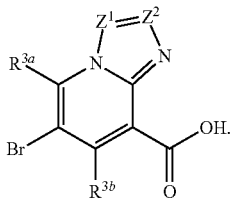

In a further aspect, the method comprises the step of reacting the carboxylic acid intermediate in a coupling reaction with a heteroaryl amine having a structure represented by a formula:

$R^1NH_2$, wherein $R^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein each occurrence of $R^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl an —$NR^{64a}R^{64b}$; wherein each occurrence of each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; thereby forming an amide having a structure represented by a formula:

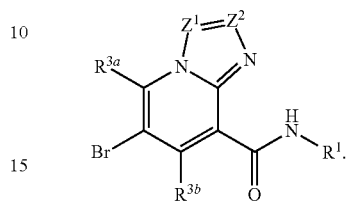

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

7. Intermediate Route VII

In one aspect, carboxylic acid intermediates can be prepared as shown below.

SCHEME 7A.

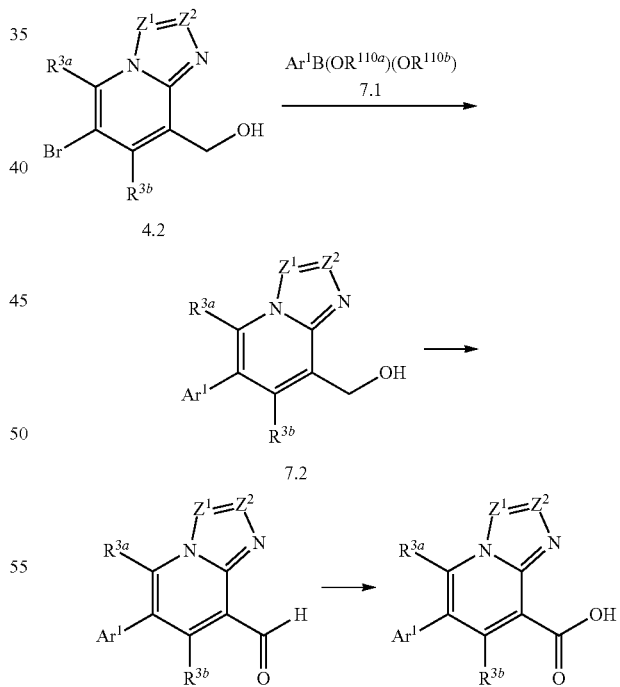

Compounds are represented in generic form, with substituents as noted in compound descriptions elsewhere herein. A more specific example is set forth below.

SCHEME 7B.

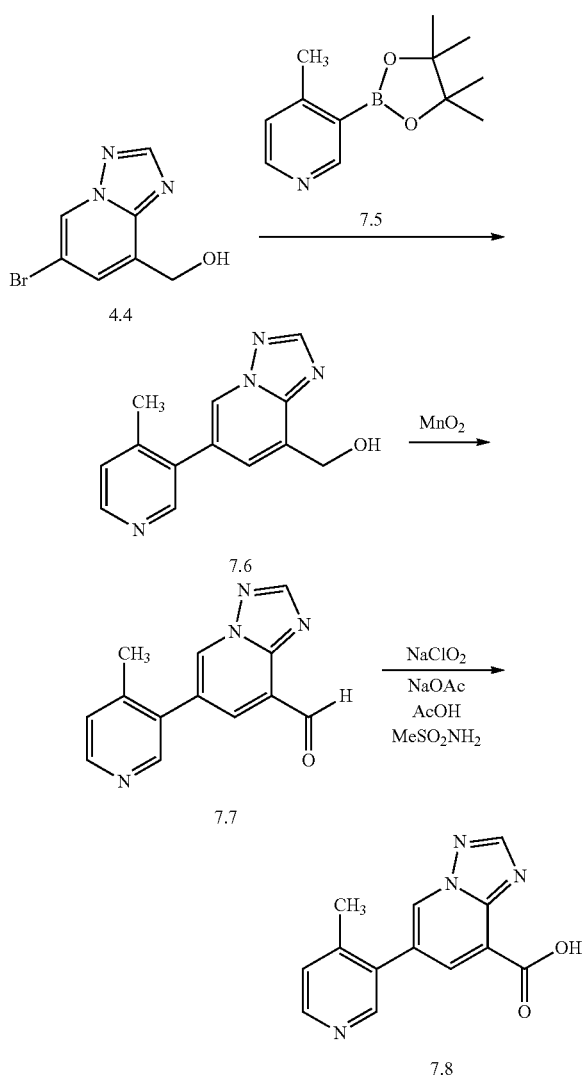

In one aspect, compounds of type 7.4, and similar compounds, can be prepared according to reaction Scheme 7B above. Thus, compounds of type 7.6 can be prepared by a coupling reaction of an appropriate aryl halide, e.g., 4.4 as shown above. The coupling reaction is carried out in the presence of an appropriate coupling agent, e.g., a boronic acid or a boronic acid pinacol ester (7.5), in the presence of an appropriate palladium catalyst. Such a palladium catalyzed coupling is commonly referred to as a "Suzuki coupling" and is well described in the literature (see Miyaura, N; Suzuki, A. *Chem. Rev.* 1995, 95, 2457-83 and *J. Organomet. Chem.* 1999, 576, 147-68). Examples of suitable Suzuki conditions include but are not limited to Pd(PtBu$_3$)$_2$, Cs$_2$CO$_3$, H$_2$O, THF, microwave, 150° C.; Pd(PPh$_3$), K$_2$CO$_3$, dioxane, H$_2$O, microwave, 150° C.; and PdCl$_2$(dppf) .CH$_2$Cl$_2$, DME, Na$_2$CO$_3$, H$_2$O, 100° C. It will be appreciated by one skilled in the art that the biaryl intermediate may or may not contain functional groups that require temporary protecting groups for compatibility with further chemistry (see Greene, T. W. and Wuts, P. G. M. *Protecting Groups in Organic Synthesis*, 3$^{rd}$ Ed. New York: John Wiley & Sons, Inc. 1999). It will be further appreciated that certain steps in the sequence may be rearranged. For example, the palladium coupling may be carried out on compounds containing a silyl ether protecting group (as described in Intermediate Routes II and III). In such a case, the cleavage of the silyl ether protecting group as described in Intermediate Route IV would be carried out after the palladium coupling to afford the desired alcohol intermediate. Compounds of type 7.7 can be prepared by an oxidation reaction of an appropriate alcohol, e.g., 7.6 as shown above. The oxidation is carried out in the presence of an appropriate oxidizing agent. It will be appreciated by one skilled in the art that a variety of oxidizing agents may be effective for this transformation, including but not limited to manganese dioxide, Dess-Martin reagent, and sulfur trioxide-pyridine. Compounds of type 7.8 can be prepared by an oxidation reaction of an appropriate aldehyde, e.g., 7.7 as shown above. The oxidation is carried out in the presence of an appropriate oxidizing agent. It will be appreciated by one skilled in the art that a variety of oxidizing agents may be useful for this transformation, including but not limited to sodium chlorite, oxone, and Jones reagent. As can be appreciated by one skilled in the art, the above reaction provides an example of a generalized approach wherein compounds similar in structure to the specific reactants above (compounds similar to compounds of type 4.2, 7.1, 7.2, and 7.3), can be substituted in the reaction to provide carboxylic acid intermediates similar to Formula 7.4.

Thus, in one aspect, the invention relates to a method of making a compound, the method comprising the step of reacting a compound having a structure represented by a formula:

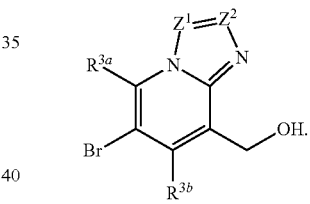

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with the nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with the nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with the nitrogen atom to which they are attached, comprise a 3- to 6-membered heterocycle; wherein each of R$^{3a}$ and R$^{3b}$ is independently selected from hydrogen and fluoro; in a palladium catalyzed coupling reaction with a second compound having the formula:

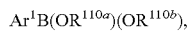

Ar$^1$B(OR$^{110a}$)(OR$^{110b}$), wherein Ar$^1$ is selected from aryl and heteroaryl, and wherein Ar$^1$ is substituted with 0, 1, 2, or 3 groups independently selected from halogen, —CN, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C=O)R$^{33}$, and cyclopropyl; wherein each occurrence of R$^{30}$, when present, is independently selected from hydrogen, C1-C3 alkyl, C1-C3 monohaloalkyl, C1-C3 polyhaloalkyl, and cyclopropyl; wherein each occurrence of each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with the nitrogen atom to which they are attached, comprise a 3- to 6-membered heterocycle; wherein each occurrence of R$^{32}$, when present, is independently selected from C1-C3 alkyl, C1-C3 monohaloalkyl, C1-C3 polyhaloalkyl, cyclopropyl, and —NR$^{34a}$R$^{34b}$; wherein each occurrence of each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R34 and R$^{34b}$, when present, are optionally covalently bonded and, together with the nitrogen atom to which they are attached, comprise a 3- to 6-membered heterocycle; wherein each occurrence of R$^{33}$, when present, is independently from C1-C3 alkyl, C1-C3 monohaloalkyl, C1-C3 polyhaloalkyl, cyclopropyl, and —NR$^{35a}$R$^{35b}$; wherein each occurrence of each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; and wherein each of R$^{110a}$ and R$^{110b}$ when present, is independently selected from hydrogen and C1-C8 alkyl; or R$^{110a}$ and R$^{110b}$ when present, are optionally covalently bonded and, together with the oxygen atoms to which they are attached, comprise a 4- to 6-membered heterocycle; thereby forming an intermediate having a structure represented by a formula:

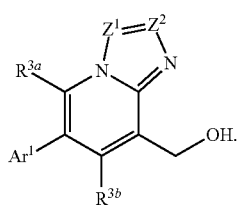

In a further aspect, the method comprises the step of reacting the alcohol intermediate with an oxidizing agent, thereby forming an aldehyde intermediate having a structure represented by a formula:

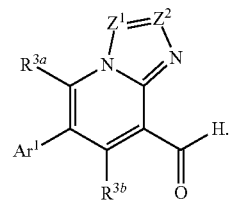

In a further aspect, the method comprises the step of reacting the aldehyde intermediate with a suitable oxidizing agent thereby forming a carboxylic acid intermediate having a structure represented by a formula:

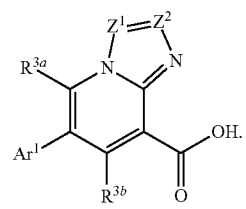

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

8. Analog Route I

In one aspect, triazolopyridine and imidazopyridine analogs can be prepared as shown below.

SCHEME 8A.

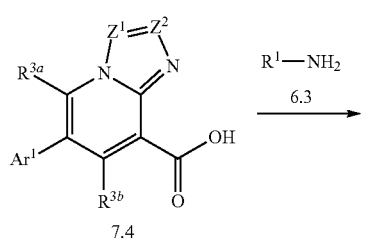

7.4

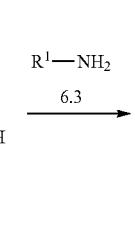

8.1

Compounds are represented in generic form, with substituents as noted in compound descriptions elsewhere herein. A more specific example is set forth below.

SCHEME 8B.

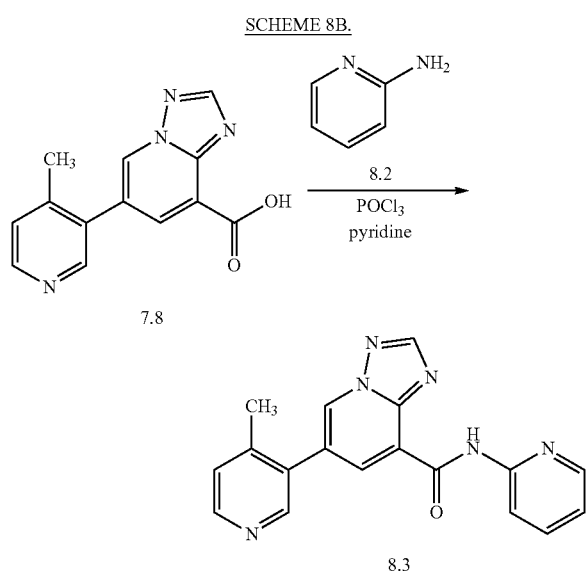

In one aspect, compounds of type 8.1, and similar compounds, can be prepared according to reaction Scheme 8B above. Thus, compounds of type 8.3 can be prepared by a coupling reaction of an appropriate carboxylic acid, e.g., 7.8 as shown above. The coupling reaction is carried out in the presence of an appropriate heteroaryl amine, e.g., 8.2, and an appropriate activating agent, e.g., phosphorous oxychloride. Such aryl or heteroaryl amines are commercially available or readily prepared by one skilled in the art. Such coupling reactions are generally well known. For example, carboxylic acids can be treated with activating reagents such as 2-(1H-7-azabenzotriazol-1-yl)-1,1,3,3-tetramethyl uronium hexafluoro-phosphate methanaminium (HATU), Ghosez's Reagent (1-chloro-N,N,2-trimethyl-1-propenylamine), and phosphorous oxychloride/pyridine including mixtures thereof, and then reacted with the amine. As can be appreciated by one skilled in the art, the above reaction provides an example of a generalized approach wherein compounds similar in structure to the specific reactants above (compounds similar to compounds of type 7.4 and 6.3), can be substituted in the reaction to provide triazolopyridine and imidazopyridine analogs similar to Formula 8.1.

Thus, in one aspect, the invention relates to a method of making a compound comprising the step of reacting a compound having a structure represented by a formula:

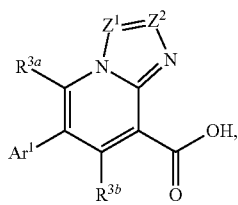

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C═O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with the nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with the nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with the nitrogen atom to which they are attached, comprise a 3- to 6-membered heterocycle; wherein each of R$^{3a}$ and R$^{3b}$ is independently selected from hydrogen and fluoro; wherein Ar$^1$ is selected from aryl and heteroaryl, and wherein Ar$^1$ is substituted with 0, 1, 2, or 3 groups independently selected from halogen, —CN, C1-C3 alkyl, C1-C3 monohaloalkyl, C1-C3 polyhaloalkyl, —OR$^{30}$, —NR$^{31a}$R$^{31b}$, —SO$_2$R$^{32}$, —(C═O)R$^{33}$, and cyclopropyl; wherein each occurrence of R$^{30}$, when present, is independently selected from hydrogen, C1-C3 alkyl, C1-C3 monohaloalkyl, C1-C3 polyhaloalkyl, and cyclopropyl; wherein each occurrence of each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with the nitrogen atom to which they are attached, comprise a 3- to 6-membered heterocycle; wherein each occurrence of R$^{32}$, when present, is independently selected from C1-C3 alkyl, C1-C3 monohaloalkyl, C1-C3 polyhaloalkyl, cyclopropyl, and —NR$^{34a}$R$^{34b}$; wherein each occurrence of each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with the nitrogen atom to which they are attached, comprise a 3- to 6-membered heterocycle; wherein each occurrence of R$^{33}$, when present, is independently from C1-C3 alkyl, C1-C3 monohaloalkyl, C1-C3 polyhaloalkyl, cyclopropyl, and —NR$^{35a}$R$^{35b}$; wherein each occurrence of each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; in a coupling reaction with a second compound having the formula:

$R^1$—NH$_2$, wherein R$^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C═O)R$^{63}$; wherein each occurrence of R$^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl, and —$NR^{64a}R^{64b}$; wherein each occurrence of each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; thereby forming an amide.

In a further aspect, the compound produced has a structure represented by a formula:

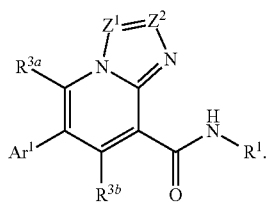

In a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

In a further aspect, the compound produced exhibits noncompetitive antagonism. In a yet further aspect, the compound produced exhibits noncompetitive inhibition. In an even further aspect, the compound produced exhibits allosteric antagonism.

In a further aspect, a compound produced is a component in a pharmaceutical composition. In a still further aspect, a pharmaceutical composition comprises a therapeutically effective amount of a compound produced and a pharmaceutically acceptable carrier. In a still further aspect, a compound produced is a component is used in the manufacture of a medicament comprising combining at least one compound produced with a pharmaceutically acceptable carrier or diluent.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

9. Analog Route II

In one aspect, triazolopyridine and imidazopyridine analogs can be prepared as shown below.

SCHEME 9A.

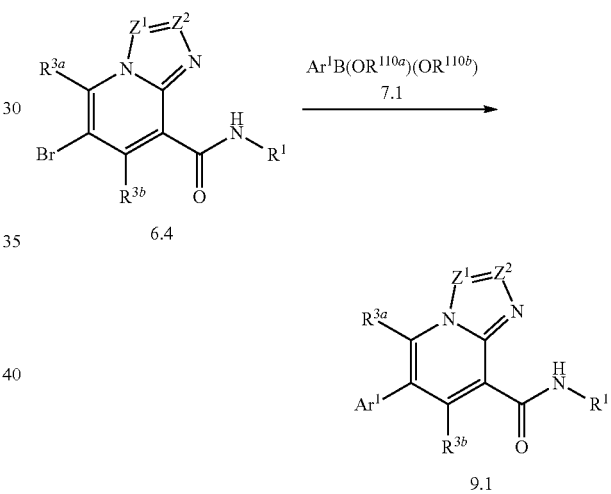

Compounds are represented in generic form, with substituents as noted in compound descriptions elsewhere herein. A more specific example is set forth below.

SCHEME 9B.

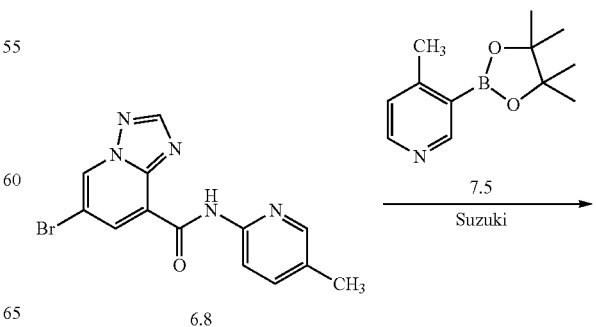

-continued

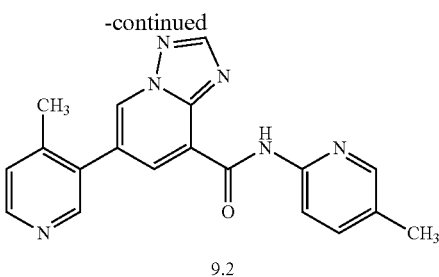

9.2

In one aspect, compounds of type 9.1, and similar compounds, can be prepared according to reaction Scheme 9B above. Thus, compounds of type 9.2 can be prepared by a coupling reaction of an appropriate aryl halide, e.g., 6.8 as shown above. The coupling reaction is carried out in the presence of an appropriate coupling agent, e.g., a boronic acid or a boronic acid pinacol ester (7.5, in the presence of an appropriate palladium catalyst. Such a palladium catalyzed coupling is commonly referred to as a "Suzuki coupling" and is well described in the literature (see Miyaura, N; Suzuki, A. Chem. Rev. 1995, 95, 2457-83 and J. Orgamomet. Chem. 1999, 576, 147-68). Examples of suitable Suzuki conditions include but are not limited to $Pd(PtBu_3)_2$, $Cs_2CO_3$, $H_2O$, THF, microwave, 150° C.; $Pd(PPh_3)$, $K_2CO_3$, dioxane, $H_2O$, microwave, 150° C.; and $PdCl_2(dppf).CH_2Cl_2$, DME, $Na_2CO_3$, $H_2O$, 100° C. As can be appreciated by one skilled in the art, the above reaction provides an example of a generalized approach wherein compounds similar in structure to the specific reactants above (compounds similar to compounds of type 6.4 and 7.1), can be substituted in the reaction to provide carboxylic acid intermediates similar to Formula 9.1.

Thus, in one aspect, the invention relates to a method of making a compound comprising the step of reacting a compound having a structure represented by a formula:

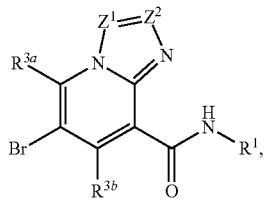

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein each of $R^{3a}$ and $R^{3b}$ is independently selected from hydrogen and fluoro; wherein $R^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$; wherein each occurrence of $R^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl, and —$NR^{64a}R^{64b}$; wherein each occurrence of each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; in a palladium catalyzed coupling reaction with a second compound having the formula:

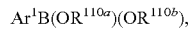

$Ar^1B(OR^{110a})(OR^{110b})$, wherein $Ar^1$ is selected from aryl and heteroaryl, and wherein $Ar^1$ is substituted with 0, 1, 2, or 3 groups independently selected from halogen, —CN, C1-C3 alkyl, C1-C3 monohaloalkyl, C1-C3 polyhaloalkyl, —$OR^{30}$, —$NR^{31a}R^{31b}$, —$SO_2R^{32}$, —$(C=O)R^{33}$, and cyclopropyl; wherein each occurrence of $R^{30}$, when present, is independently selected from hydrogen, C1-C3 alkyl, C1-C3 monohaloalkyl, C1-C3 polyhaloalkyl, and cyclopropyl; wherein each occurrence of each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$ when present, are optionally covalently bonded and, together with the nitrogen atom to which they are attached, comprise a 3- to 6-membered heterocycle; wherein each occurrence of $R^{32}$, when present, is independently selected from C1-C3 alkyl, C1-C3 monohaloalkyl, C1-C3 polyhaloalkyl, cyclopropyl, and —$NR^{34a}R^{34b}$; wherein each occurrence of each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with the nitrogen atom to which they are attached, comprise a 3- to 6-membered heterocycle; wherein each occurrence of $R^{33}$, when present, is independently from C1-C3 alkyl, C1-C3 monohaloalkyl, C1-C3 polyhaloalkyl, cyclopropyl, and —$NR^{35a}R^{35b}$; wherein each occurrence of each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; thereby forming a biaryl analog; and wherein each of $R^{110a}$ and $R^{110b}$, when present, is independently selected from hydrogen and C1-C8 alkyl; or $R^{110a}$ and $R^{110b}$, when present, are optionally covalently bonded and, together with the oxygen atoms to which they are attached, comprise a 4- to 6-membered heterocycle.

In a further aspect, the compound produced has a structure represented by a formula:

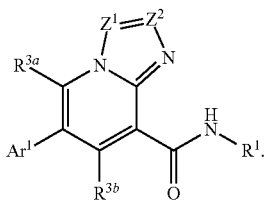

In a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

In a further aspect, the compound produced exhibits noncompetitive antagonism. In a yet further aspect, the compound produced exhibits noncompetitive inhibition. In an even further aspect, the compound produced exhibits allosteric antagonism.

In a further aspect, a compound produced is a component in a pharmaceutical composition. In a still further aspect, a pharmaceutical composition comprises a therapeutically effective amount of a compound produced and a pharmaceutically acceptable carrier. In a still further aspect, a compound produced is a component is used in the manufacture of a medicament comprising combining at least one compound produced with a pharmaceutically acceptable carrier or diluent.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

E. Pharmaceutical Compositions

In one aspect, the invention relates to pharmaceutical compositions comprising the disclosed compounds. That is, a pharmaceutical composition can be provided comprising a therapeutically effective amount of at least one disclosed compound, at least one product of a disclosed method of making a compound, or a pharmaceutically acceptable salt, solvate, hydrate, or polymorph thereof, and a pharmaceutically acceptable carrier.

In one aspect, the invention relates to pharmaceutical compositions comprising a pharmaceutically acceptable carrier and an effective amount of a disclosed compound or a product of a disclosed compound, or a pharmaceutically acceptable salt, solvate, or polymorph thereof.

In a further aspect, the effective amount is a therapeutically effective amount. In a still further aspect, the effective amount is a prophylactically effective amount.

In a further aspect, the pharmaceutical composition comprises a disclosed compound. In a yet further aspect, the pharmaceutical composition comprises a product of a disclosed method of making.

In a further aspect, the pharmaceutical composition comprises a compound that exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, the human embryonic kidney cells are transfected with rat mGluR5. In a yet further aspect, the human embryonic kidney cells are transfected with human mGluR5.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), iron (-ic and -ous), lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorgamisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. Methods of Using the Compounds and Compositions

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as an agonist for all three receptor subtypes, selective ligands have been discovered that activate each subtype. The ionotropic glutamate receptors are named after their respective selective ligands: kainate receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through $G\alpha q/11$ to increase inositol phosphate and metabolism and resultant increases in intracellular calcium. Group I mGluRs are primarily located post-synaptically and have a modulatory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to $G\alpha i$ and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et al., *J. Neurosci.* (2001) 21:5925-5934). Therefore, modulation of mGluRs is an approach to modulating glutamatergic transmission. Numerous reports indicate that mGluR5 plays a role in a number of disease states including anxiety (Spooren et al., *J. Pharmacol. Exp. Therapeut.* (2000) 295:1267-1275, Tatarczynska et al., *Br. J. Pharmacol.* (2001) 132:1423-1430), addiction to cocaine (Chiamulera et al., *Nature Neurosci.* (2001) 4:873-874), Parkinson's disease (Awad et al., *J. Neurosci.* 20:7871-7879 (2000), Ossowska et al., *Neuropharmacol.* (2001) 41: 413-420), pain (Salt and Binns, *Neurosci.* 100:375-380 (2001)), Fragile X syndrome ("FXS", see de Vrij et al. *Neurobiol Disease* (2008) 31(1): 127-132; Yan et al. *Neuropharmacol* (2005) 49(7): 1053-1066), GERD (Jensen et al. *Eur. J. Pharmacol.* (2005) 519, 154-157), nicotine addiction (Tronci et al. *Psychopharmacology* (2010) 211, 33-42), morphine addiction (Kotlinska, J. and Bochenski, M. *Eur. J.*

Pharmacol. (2007) 558, 113-118), methamphetamine addiction (Gass et al. *Neuropsychopharmacology* (2009) 34, 820-833), alcohol addiction (Lominac et al. Drug Alcohol Depend. 85, 142-156), depression (Hughes et al. Neuropharmacology (2013)66, 202-214), and Alzheimer's disease (Hamilton et al. Molecular Brain (2014)7:40).

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of neurological and psychiatric disorders associated with glutamate dysfunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more neurological and/or psychiatric disorders associated with glutamate dysfunction in a subject comprising the step of administering to the subject at least one disclosed compound; at least one disclosed pharmaceutical composition; and/or at least one disclosed product in a dosage and amount effective to treat the disorder in the subject.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Also provided is a method for treating or preventing anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder, and anxiety disorder not otherwise specified.

Further disorders that can be treated or prevented by the compositions disclosed herein include autism spectrum disorders, which are neuropsychiatric conditions characterized by widespread abnormalities of social interactions and communication, as well as severely restricted interests and highly repetitive behavior. Autism spectrum disorders include Autism, Asperger syndrome, Childhood Disintegrative Disorders, Pervasive Developmental Disorder Not Otherwise Specified (PDD-NOS), sometimes called atypical autism, and Rett Syndrome. Fragile X syndrome (FXS) is a single gene disorder almost universally associated with symptoms of autism spectrum disorder, the most common form of inherited mental retardation, and the most common known cause of autism, affecting 1 in 6,000 births. Therapeutic agents for treatment of patients with FXS are among the most critical of unmet medical needs, and there are very few proven effective treatment strategies for this patient population. Again, without wishing to be bound by theory, increasing evidence has identified a connection between the fragile X phenotype and mGluR signaling Compounds of the invention can be used, for example, for the treatment of fragile X syndrome and autism spectrum disorders in a manner that can improve symptoms (e.g., reduce anxiety and irritability; increase cognitive function, communication and/or social interaction). Thus, the methods of the invention can provide an effective manner to treat a subject having fragile X syndrome or autism spectrum disorder.

a. Treating a Disorder Associated with Metabotropic Glutamate Receptor Activity

In one aspect, the invention relates to a method for the treatment of a disorder associated with metabotropic glutamate receptor activity in a subject, the method comprising the step of administering to the subject an effective amount of at least one disclosed compound, at least one product of a disclosed method of making a compound, at least one disclosed compound in a pharmaceutical dosage form, or at least one product of a disclosed method of making a compound in a pharmaceutical dosage form, or a pharmaceutically acceptable salt thereof, thereby treating the disorder associated with metabotropic glutamate receptor activity in the subject. In a further aspect, the metabotropic glutamate receptor is mGluR5.

In a further aspect, the subject is a mammal. In a still further aspect, the mammal is a human.

In a further aspect, the compound exhibits partial inhibition of mGluR5 response. In a still further aspect, the compound exhibits total inhibition of mGluR5 response.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15 \times 10^{-7}$ M. In a still further aspect, the compounds exhibit negative allosteric modulation with an $IC_{50}$ of less than about $10 \times 10^{-7}$ M. In yet a further aspect, the compounds exhibit negative allosteric modulation with an $IC_{50}$ of less than about $5 \times 10^{-7}$ M. In an even further aspect, the compounds exhibit negative allosteric modulation with an $IC_{50}$ of less than about $1 \times 10^{-7}$ M.

In a further aspect, the subject has been diagnosed with a need for treatment of the disorder prior to the administering step. In a still further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the disorder is a neurological and/or psychiatric disorder. In a still further aspect, the neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpetic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

b. Decreasing Metabotropic Glutamate Receptor Activity

In one aspect, the invention relates to a method for decreasing metabotropic glutamate receptor activity in a subject, the method comprising the step of administering to the subject an effective amount of at least one disclosed compound, at least one product of a disclosed method of making a compound, at least one disclosed compound in a pharmaceutical dosage form, or at least one product of a disclosed method of making a compound in a pharmaceutical dosage form, or a pharmaceutically acceptable salt thereof, thereby decreasing metabotropic glutamate receptor activity in the subject. In a further aspect, the metabotropic glutamate receptor is mGluR5.

In a further aspect, the subject is a mammal. In a still further aspect, the mammal is a human.

In a further aspect, the compound exhibits partial inhibition of mGluR5 response. In a still further aspect, the compound exhibits total inhibition of mGluR5 response.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15\times10^{-7}$ M. In a still further aspect, the compounds exhibit negative allosteric modulation with an $IC_{50}$ of less than about $10\times10^{-7}$ M. In yet a further aspect, the compounds exhibit negative allosteric modulation with an $IC_{50}$ of less than about $5\times10^{-7}$ M. In an even further aspect, the compounds exhibit negative allosteric modulation with an $IC_{50}$ of less than about $1\times10^{-7}$ M.

In a further aspect, the subject has been diagnosed with a need for treatment of the disorder prior to the administering step. In a still further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the disorder is a neurological and/or psychiatric disorder. In a still further aspect, the neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

c. Inhibiting Metabotropic Glutamate Receptor Activity

In one aspect, the invention relates to a method for inhibiting metabotropic glutamate receptor activity in a subject, the method comprising the step of administering to the subject an effective amount of at least one disclosed compound, at least one product of a disclosed method of making a compound, at least one disclosed compound in a pharmaceutical dosage form, or at least one product of a disclosed method of making a compound in a pharmaceutical dosage form, or a pharmaceutically acceptable salt thereof, thereby inhibiting metabotropic glutamate receptor activity in the subject. In a further aspect, the metabotropic glutamate receptor is mGluR5.

In a further aspect, the subject is a mammal. In a still further aspect, the mammal is a human.

In a further aspect, the compound exhibits noncompetitive antagonism of metabotropic glutamate receptor activity. In a yet further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism of metabotropic glutamate receptor activity.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compounds exhibit negative allosteric modulation with an $IC_{50}$ of less than about $30\times10^{-6}$ M. In a still further aspect, the compounds exhibit negative allosteric modulation with an $IC_{50}$ of less than about $25\times10^{-6}$ M. In yet a further aspect, the compounds exhibit negative allosteric modulation with an $IC_{50}$ of less than about $20\times10^{-6}$ M. In an even further aspect, the compounds exhibit negative allosteric modulation with an $IC_{50}$ of less than about $15\times10^{-6}$ M. In a still further aspect, the compounds exhibit negative allosteric modulation with an $IC_{50}$ of less than about $10\times10^{-6}$ M. In yet a further aspect, the compounds exhibit negative allosteric modulation with an $IC_{50}$ of less than about $5\times10^{-6}$ M. In an even further aspect, the compounds exhibit negative allosteric modulation with an $IC_{50}$ of less than about $1\times10^{-6}$ M.

In a further aspect, the compounds exhibit negative allosteric modulation with an $IC_{50}$ of less than about $30\times10^{-7}$ M. In a still further aspect, the compounds exhibit negative allosteric modulation with an $IC_{50}$ of less than about $25\times10^{-7}$ M. In yet a further aspect, the compounds exhibit negative allosteric modulation with an $IC_{50}$ of less than about $20\times10^{-7}$ M. In an even further aspect, the compounds exhibit negative allosteric modulation with an $IC_{50}$ of less than about $15\times10^{-7}$ M. In a still further aspect, the compounds exhibit negative allosteric modulation with an $IC_{50}$ of less than about $10\times10^{-7}$ M. In yet a further aspect, the compounds exhibit negative allosteric modulation with an $IC_{50}$ of less than about $5\times10^{-7}$ M. In an even further aspect, the compounds exhibit negative allosteric modulation with an $IC_{50}$ of less than about $1\times10^{-7}$ M.

In a further aspect, the subject has been diagnosed with a need for treatment of the disorder prior to the administering step. In a still further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the disorder is a neurological and/or psychiatric disorder. In a still further aspect, the neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

d. Negative Allosteric Modulation of Metabotropic Glutamate Receptor Activity

In one aspect, the invention relates to a method for negative allosteric modulation of metabotropic glutamate receptor activity in a subject, the method comprising the step of administering to the subject an effective amount of at least one disclosed compound, at least one product of a disclosed method of making a compound, at least one disclosed compound in a pharmaceutical dosage form, or at least one product of a disclosed method of making a compound in a pharmaceutical dosage form, or a pharmaceutically acceptable salt thereof, thereby negatively allosterically modulating the metabotropic glutamate receptor activity in the subject. In a further aspect, the metabotropic glutamate receptor is mGluR5.

In a further aspect, the subject is a mammal. In a still further aspect, the mammal is a human.

In a further aspect, the compound exhibits partial inhibition of mGluR5 response. In a still further aspect, the compound exhibits total inhibition of mGluR5 response.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15 \times 10^{-7}$ M. In a still further aspect, the compounds exhibit negative allosteric modulation with an $IC_{50}$ of less than about $10 \times 10^{-7}$ M. In yet a further aspect, the compounds exhibit negative allosteric modulation with an $IC_{50}$ of less than about $5 \times 10^{-7}$ M. In an even further aspect, the compounds exhibit negative allosteric modulation with an $IC_{50}$ of less than about $1 \times 10^{-7}$ M.

In a further aspect, the subject has been diagnosed with a need for treatment of the disorder prior to the administering step. In a still further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the disorder is a neurological and/or psychiatric disorder. In a still further aspect, the neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, e. Partial Antagonism of Metabotropic Glutamate Receptor Activity

In one aspect, the invention relates to a method for partial antagonism of metabotropic glutamate receptor activity in a subject, the method comprising the step of administering to the subject an effective amount of at least one disclosed compound, at least one product of a disclosed method of making a compound, at least one disclosed compound in a pharmaceutical dosage form, or at least one product of a disclosed method of making a compound in a pharmaceutical dosage form, or a pharmaceutically acceptable salt thereof, thereby partially antagonizing the metabotropic glutamate receptor activity in the subject. In a further aspect, the metabotropic glutamate receptor is mGluR5.

In a further aspect, the subject is a mammal. In a still further aspect, the mammal is a human.

In a further aspect, the compound exhibits partial inhibition of mGluR5 response. In a still further aspect, the compound exhibits total inhibition of mGluR5 response.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15 \times 10^{-7}$ M. In a still further aspect, the compounds exhibit negative allosteric modulation with an $IC_{50}$ of less than about $10 \times 10^{-7}$ M. In yet a further aspect, the compounds exhibit negative allosteric modulation with an $IC_{50}$ of less than about $5 \times 10^{-7}$ M. In an even further aspect, the compounds exhibit negative allosteric modulation with an $IC_{50}$ of less than about $1 \times 10^{-7}$ M.

In a further aspect, the subject has been diagnosed with a need for treatment of the disorder prior to the administering step. In a still further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the disorder is a neurological and/or psychiatric disorder. In a still further aspect, the neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

f. Modulating Metabotropic Glutamate Receptor Activity

In one aspect, the invention relates to a method for modulating metabotropic glutamate receptor activity in a subject, the method comprising the step of administering to the subject an effective amount of at least one disclosed compound, at least one product of a disclosed method of making a compound, at least one disclosed compound in a pharmaceutical dosage form, or at least one product of a disclosed method of making a compound in a pharmaceutical dosage form, or a pharmaceutically acceptable salt thereof, thereby modulating the metabotropic glutamate receptor activity in the subject. In a further aspect, the metabotropic glutamate receptor is mGluR5.

In a further aspect, the subject is a mammal. In a still further aspect, the mammal is a human.

In a further aspect, modulating is decreasing. In a still further aspect, modulating is inhibition. In yet a further aspect, modulating is noncompetitive inhibition. In an even further aspect, modulating is noncompetitive antagonism. In a still further aspect, modulating is negative allosteric modulation. In yet a further aspect, modulating is partial antagonism.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10\times10^{-6}$ M. In yet a further aspect, the compounds exhibit negative allosteric modulation with an $IC_{50}$ of less than about $5\times10^{-6}$ M. In an even further aspect, the compounds exhibit negative allosteric modulation with an $IC_{50}$ of less than about $1\times10^{-6}$ M.

In a further aspect, the compounds exhibit negative allosteric modulation with an $IC_{50}$ of less than about $30\times10^{-7}$ M. In a still further aspect, the compounds exhibit negative allosteric modulation with an $IC_{50}$ of less than about $25\times10^{-7}$ M. In yet a further aspect, the compounds exhibit negative allosteric modulation with an $IC_{50}$ of less than about $20\times10^{-7}$ M. In an even further aspect, the compounds exhibit negative allosteric modulation with an $IC_{50}$ of less than about $15\times10^{-7}$ M. In a still further aspect, the compounds exhibit negative allosteric modulation with an $IC_{50}$ of less than about $10\times10^{-7}$ M. In yet a further aspect, the compounds exhibit negative allosteric modulation with an $IC_{50}$ of less than about $5\times10^{-7}$ M. In an even further aspect, the compounds exhibit negative allosteric modulation with an $IC_{50}$ of less than about $1\times10^{-7}$ M.

In a further aspect, the subject has been diagnosed with a need for treatment of the disorder prior to the administering step. In a still further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the disorder is a neurological and/or psychiatric disorder. In a still further aspect, the neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

g. Modulating Metabotropic Glutamate Receptor Activity in Cell

In one aspect, the invention relates to a method for modulating metabotropic glutamate receptor activity in at least one cell, the method comprising the step of contacting the at least one cell with an effective amount of at least one disclosed compound, at least one product of a disclosed method of making a compound, at least one disclosed compound in a pharmaceutical dosage form, at least one product of a disclosed method of making a compound in a pharmaceutical dosage form, or a pharmaceutically acceptable salt thereof, thereby modulating the metabotropic glutamate receptor activity in the at least one cell. In a further aspect, the metabotropic glutamate receptor is mGluR5.

In a further aspect, the cell is mammalian. In a still further aspect, the cell is human.

In a further aspect, modulating is decreasing. In a still further aspect, modulating is inhibition. In yet a further aspect, modulating is noncompetitive inhibition. In an even further aspect, modulating is noncompetitive antagonism. In a still further aspect, modulating is negative allosteric modulation. In yet a further aspect, modulating is partial antagonism.

In a further aspect, the compounds exhibit negative allosteric modulation with an $IC_{50}$ of less than about $30\times10^{-6}$ M. In a still further aspect, the compounds exhibit negative allosteric modulation with an $IC_{50}$ of less than about $25\times10^{-6}$ M. In yet a further aspect, the compounds exhibit negative allosteric modulation with an $IC_{50}$ of less than about $20\times10^{-6}$ M. In an even further aspect, the compounds exhibit negative allosteric modulation with an $IC_{50}$ of less than about $15\times10^{-6}$ M. In a still further aspect, the compounds exhibit negative allosteric modulation with an $IC_{50}$ of less than about $10\times10^{-6}$ M. In yet a further aspect, the compounds exhibit negative allosteric modulation with an $IC_{50}$ of less than about $5\times10^{-6}$ M. In an even further aspect, the compounds exhibit negative allosteric modulation with an $IC_{50}$ of less than about $1\times10^{-6}$ M.

In a further aspect, the compounds exhibit negative allosteric modulation with an $IC_{50}$ of less than about $30\times10^{-7}$ M. In a still further aspect, the compounds exhibit negative allosteric modulation with an $IC_{50}$ of less than about $25\times10^{-7}$ M. In yet a further aspect, the compounds exhibit negative allosteric modulation with an $IC_{50}$ of less than about $20\times10^{-7}$ M. In an even further aspect, the compounds exhibit negative allosteric modulation with an $IC_{50}$ of less than about $15\times10^{-7}$ M. In a still further aspect, the compounds exhibit negative allosteric modulation with an $IC_{50}$ of less than about $10\times10^{-7}$ M. In yet a further aspect, the compounds exhibit negative allosteric modulation with an $IC_{50}$ of less than about $5\times10^{-7}$ M.

In an even further aspect, the compounds exhibit negative allosteric modulation with an $IC_{50}$ of less than about $1\times10^{-7}$ M.

In a further aspect, the cell has been isolated from a mammal prior to the contacting step. In a still further aspect, contacting is via administration to a mammal.

In a further aspect, the mammal has been diagnosed with a need for modulation of metabotropic glutamate receptor activity prior to the administering step. In a still further aspect, the method further comprises the step of identifying a mammal in need of modulation of metabotropic glutamate receptor activity.

In a further aspect, the mammal has been diagnosed with a need for treatment of a disorder related to metabotropic glutamate receptor activity prior to the administering step.

In a still further aspect, the disorder related to metabotropic glutamate receptor activity is a neurological and/or psychiatric disorder associated with glutamate dysfunction. In yet a further aspect, neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In an even further aspect, the neurological and/or psychiatric disorder is selected from addiction, anxiety disorders, depression, dystonia, fragile x syndrome, and Parkinson's disease. In a still further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

h. Inhibiting Metabotropic Glutamate Receptor Activity in Cell

In one aspect, the invention relates to a method for inhibiting metabotropic glutamate receptor activity in at least one cell, the method comprising the step of contacting the at least one cell with an effective amount of at least one disclosed compound, at least one product of a disclosed method of making a compound, at least one disclosed compound in a pharmaceutical dosage form, at least one product of a disclosed method of making a compound in a pharmaceutical dosage form, or a pharmaceutically acceptable salt thereof, thereby inhibiting the metabotropic glutamate receptor activity in the at least one cell. In a further aspect, the metabotropic glutamate receptor is mGluR5.

In a further aspect, the cell is mammalian. In a still further aspect, the cell is human.

In a further aspect, inhibiting is antagonism. In a still further aspect, inhibiting is noncompetitive antagonism. In yet a further aspect, inhibiting is negative allosteric modulation.

In a further aspect, the compounds exhibit negative allosteric modulation with an $IC_{50}$ of less than about $30 \times 10^{-6}$ M. In a still further aspect, the compounds exhibit negative allosteric modulation with an $IC_{50}$ of less than about $25 \times 10^{-6}$ M. In yet a further aspect, the compounds exhibit negative allosteric modulation with an $IC_{50}$ of less than about $20 \times 10^{-6}$ M. In an even further aspect, the compounds exhibit negative allosteric modulation with an $IC_{50}$ of less than about $15 \times 10^{-6}$ M. In a still further aspect, the compounds exhibit negative allosteric modulation with an $IC_{50}$ of less than about $10 \times 10^{-6}$ M. In yet a further aspect, the compounds exhibit negative allosteric modulation with an $IC_{50}$ of less than about $5 \times 10^{-6}$ M. In an even further aspect, the compounds exhibit negative allosteric modulation with an $IC_{50}$ of less than about $1 \times 10^{-6}$ M.

In a further aspect, the compounds exhibit negative allosteric modulation with an $IC_{50}$ of less than about $30 \times 10^{-7}$ M. In a still further aspect, the compounds exhibit negative allosteric modulation with an $IC_{50}$ of less than about $25 \times 10^{-7}$ M. In yet a further aspect, the compounds exhibit negative allosteric modulation with an $IC_{50}$ of less than about $20 \times 10^{-7}$ M. In an even further aspect, the compounds exhibit negative allosteric modulation with an $IC_{50}$ of less than about $15 \times 10^{-7}$ M. In a still further aspect, the compounds exhibit negative allosteric modulation with an $IC_{50}$ of less than about $10 \times 10^{-7}$ M. In yet a further aspect, the compounds exhibit negative allosteric modulation with an $IC_{50}$ of less than about $5 \times 10^{-7}$ M. In an even further aspect, the compounds exhibit negative allosteric modulation with an $IC_{50}$ of less than about $1 \times 10^{-7}$ M.

In a further aspect, the cell has been isolated from a mammal prior to the contacting step. In a still further aspect, contacting is via administration to a mammal.

In a further aspect, the mammal has been diagnosed with a need for modulation of metabotropic glutamate receptor activity prior to the administering step. In a still further aspect, the method further comprises the step of identifying a mammal in need of modulation of metabotropic glutamate receptor activity.

In a further aspect, the mammal has been diagnosed with a need for treatment of a disorder related to metabotropic glutamate receptor activity prior to the administering step. In a still further aspect, the disorder related to metabotropic glutamate receptor activity is a neurological and/or psychiatric disorder associated with glutamate dysfunction. In yet a further aspect, neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In an even further aspect, the neurological and/or psychiatric disorder is selected from addiction, anxiety disorders, depression, dystonia, fragile x syndrome, and Parkinson's disease. In a still further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In yet a further aspect, the disease of uncontrolled cellular proliferation is selected from breast cancer, renal cancer, gastric cancer, and colorectal cancer. In an even further aspect, the disease if uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

2. Use of Compounds

Also provided are the uses of the disclosed compounds and products. In one aspect, the use relates to a treatment of a disorder in a mammal. In a further aspect, the use is characterized in that the mammal is a human. In a further aspect, the use is characterized in that the disorder is a neurological and/or psychiatric disorder. In a yet further aspect, the neurological and/or psychiatric disorder is associated with glutamate dysfunction. In one aspect, the use relates to negative allosteric modulation of metabotropic glutamate receptor activity in a mammal.

In one aspect, the use is of a disclosed compound or product of a disclosed method of making, or a pharmaceutical salt thereof, and the use relates to a treatment of a disorder in a mammal, wherein the disorder is a neurological and/or psychiatric disorder. In a further aspect, the use is of a disclosed compound or product of a disclosed method of making, or a pharmaceutical salt thereof, and the use relates to a treatment of a disorder in a mammal, wherein the disorder is a neurological disorder. In a further aspect, the use is of a disclosed compound or product of a disclosed method of making, or a pharmaceutical salt thereof, and the use relates to a treatment of a disorder in a mammal, wherein the disorder is a psychiatric disorder.

In one aspect, the use is of a disclosed compound or product of a disclosed method of making, or a pharmaceutical salt thereof, wherein the compound or product of a disclosed method of making is in a pharmaceutical dosage form; and the use relates to a treatment of a disorder in a mammal, wherein the disorder is a neurological and/or psychiatric disorder. In a further aspect, the use is of a disclosed compound or product of a disclosed method of making, or a pharmaceutical salt thereof, wherein the compound or product of a disclosed method of making is in a pharmaceutical dosage form; and the use relates to a treatment of a disorder in a mammal, wherein the disorder is a neurological disorder. In a further aspect, the use is of a disclosed compound or product of a disclosed method of making, or a pharmaceutical salt thereof, wherein the compound or product of a disclosed method of making is in a pharmaceutical dosage form; and the use relates to a treatment of a disorder in a mammal, wherein the disorder is a psychiatric disorder.

In one aspect, the invention relates to use of a disclosed compound or a product of a disclosed method of making, or a pharmaceutically acceptable salt, solvate, or polymorph thereof.

In a further aspect, compound exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, the human embryonic kidney cells are transfected with rat mGluR5. In a yet further aspect, the human embryonic kidney cells are transfected with human mGluR5.

In a further aspect, the compound treats a neurological and/or psychiatric disorder associated with glutamate dysfunction. In a still further aspect, neurological and/or psychiatric disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the neurological and/or psychiatric disorder is selected from addiction, anxiety disorders, depression, dystonia, fragile x syndrome, and Parkinson's disease. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the compound treats a disease of uncontrolled cellular proliferation. In a still further aspect, disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

In a further aspect, the invention relates to the use of a disclosed compound or a disclosed product in the manufacture of a medicament for the treatment of a disorder associated with glutamate dysfunction in a mammal. In a still further aspect, the disorder is a neurological and/or psychiatric disorder. In a yet further aspect, the disorder is a disease of uncontrolled cellular proliferation.

3. Manufacture of a Medicament

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

In various aspects, the present invention is further directed to a method for the manufacture of a medicament for treatment of one or more neurological and/or psychiatric disorder in mammals (e.g., humans) comprising combining one or more disclosed compounds, products, or compositions with a pharmaceutically acceptable carrier or diluent.

In one aspect, the present invention is further directed to a method for the manufacture of a medicament for treatment of one or more neurological and/or psychiatric disorder in mammals (e.g., humans) comprising combining one or more disclosed compounds, or pharmaceutical salt thereof, with a pharmaceutically acceptable carrier or diluent. In a further aspect, the present invention is further directed to a method for the manufacture of a medicament for treatment of one or more neurological disorder in mammals (e.g., humans) comprising combining one or more disclosed compounds, or pharmaceutical salt thereof, with a pharmaceutically acceptable carrier or diluent. In a still further aspect, the present invention is further directed to a method for the manufacture of a medicament for treatment of one or more psychiatric disorder in mammals (e.g., humans) comprising combining one or more disclosed compounds, or pharmaceutical salt thereof, with a pharmaceutically acceptable carrier or diluent.

In one aspect, the present invention is further directed to a method for the manufacture of a medicament for treatment of one or more neurological and/or psychiatric disorder in mammals (e.g., humans) comprising combining one or more products of a disclosed method of making, or pharmaceutical salt thereof, with a pharmaceutically acceptable carrier or diluent. In a further aspect, the present invention is further directed to a method for the manufacture of a medicament for treatment of one or more neurological disorder in mammals (e.g., humans) comprising combining one or more products of a disclosed method of making, or pharmaceutical salt thereof, with a pharmaceutically acceptable carrier or diluent. In a still further aspect, the present invention is further directed to a method for the manufacture of a medicament for treatment of one or more psychiatric disorder in mammals (e.g., humans) comprising combining one or more products of a disclosed method of making, or pharmaceutical salt thereof, with a pharmaceutically acceptable carrier or diluent.

In one aspect, the present invention is further directed to a method for the manufacture of a medicament for treatment of one or more neurological and/or psychiatric disorder in mammals (e.g., humans) comprising combining one or more disclosed compounds, or pharmaceutical salt thereof, in a pharmaceutical dosage form. In a further aspect, the present invention is further directed to a method for the manufacture of a medicament for treatment of one or more neurological disorder in mammals (e.g., humans) comprising combining one or more disclosed compounds, or pharmaceutical salt thereof, in a pharmaceutical dosage form. In a still further aspect, the present invention is further directed to a method for the manufacture of a medicament for treatment of one or more psychiatric disorder in mammals (e.g., humans) comprising combining one or more disclosed compounds, or pharmaceutical salt thereof, in a pharmaceutical dosage form.

In one aspect, the present invention is further directed to a method for the manufacture of a medicament for treatment of one or more neurological and/or psychiatric disorder in mammals (e.g., humans) comprising combining one or more products of a disclosed method of making, or pharmaceutical salt thereof, in a pharmaceutical dosage form. In a further aspect, the present invention is further directed to a method for the manufacture of a medicament for treatment of one or more neurological disorder in mammals (e.g., humans) comprising combining one or more products of a disclosed method of making, or pharmaceutical salt thereof, in a pharmaceutical dosage form. In a still further aspect, the present invention is further directed to a method for the manufacture of a medicament for treatment of one or more psychiatric disorder in mammals (e.g., humans) comprising combining one or more products of a disclosed method of making, or pharmaceutical salt thereof, in a pharmaceutical dosage form.

In various aspects, the present invention is further directed to a method for the manufacture of a medicament for treatment of one or more neurological and/or psychiatric disorder associated with glutamate dysfunction in mammals (e.g., humans) comprising combining one or more disclosed compounds, products, or compositions with a pharmaceutically acceptable carrier or diluent.

In one aspect, the present invention is further directed to a method for the manufacture of a medicament for treatment of one or more neurological and/or psychiatric disorder associated with glutamate dysfunction in mammals (e.g., humans) comprising combining one or more disclosed compounds, or pharmaceutical salt thereof, with a pharmaceutically acceptable carrier or diluent. In a further aspect, the present invention is further directed to a method for the manufacture of a medicament for treatment of one or more neurological disorder associated with glutamate dysfunction in mammals (e.g., humans) comprising combining one or more disclosed compounds, or pharmaceutical salt thereof, with a pharmaceutically acceptable carrier or diluent. In a still further aspect, the present invention is further directed to a method for the manufacture of a medicament for treatment of one or more psychiatric disorder associated with glutamate dysfunction in mammals (e.g., humans) comprising combining one or more disclosed compounds, or pharmaceutical salt thereof, with a pharmaceutically acceptable carrier or diluent.

In one aspect, the present invention is further directed to a method for the manufacture of a medicament for treatment of one or more neurological and/or psychiatric disorder associated with glutamate dysfunction in mammals (e.g., humans) comprising combining one or more products of a disclosed method of making, or pharmaceutical salt thereof, with a pharmaceutically acceptable carrier or diluent. In a further aspect, the present invention is further directed to a method for the manufacture of a medicament for treatment of one or more neurological disorder associated with glutamate dysfunction in mammals (e.g., humans) comprising combining one or more products of a disclosed method of making, or pharmaceutical salt thereof, with a pharmaceutically acceptable carrier or diluent. In a still further aspect, the present invention is further directed to a method for the manufacture of a medicament for treatment of one or more psychiatric disorder associated with glutamate dysfunction in mammals (e.g., humans) comprising combining one or more products of a disclosed method of making, or pharmaceutical salt thereof, with a pharmaceutically acceptable carrier or diluent.

In one aspect, the present invention is further directed to a method for the manufacture of a medicament for treatment of one or more neurological and/or psychiatric disorder associated with glutamate dysfunction in mammals (e.g., humans) comprising combining one or more disclosed compounds, or pharmaceutical salt thereof, in a pharmaceutical dosage form. In a further aspect, the present invention is further directed to a method for the manufacture of a medicament for treatment of one or more neurological disorder associated with glutamate dysfunction in mammals (e.g., humans) comprising combining one or more disclosed compounds, or pharmaceutical salt thereof, in a pharmaceutical dosage form. In a still further aspect, the present invention is further directed to a method for the manufacture of a medicament for treatment of one or more psychiatric disorder associated with glutamate dysfunction in mammals (e.g., humans) comprising combining one or more disclosed compounds, or pharmaceutical salt thereof, in a pharmaceutical dosage form.

In one aspect, the present invention is further directed to a method for the manufacture of a medicament for treatment of one or more neurological and/or psychiatric disorder associated with glutamate dysfunction in mammals (e.g., humans) comprising combining one or more products of a disclosed method of making, or pharmaceutical salt thereof, in a pharmaceutical dosage form. In a further aspect, the present invention is further directed to a method for the manufacture of a medicament for treatment of one or more neurological disorder associated with glutamate dysfunction in mammals (e.g., humans) comprising combining one or more products of a disclosed method of making, or pharmaceutical salt thereof, in a pharmaceutical dosage form. In a still further aspect, the present invention is further directed to a method for the manufacture of a medicament for treatment of one or more psychiatric disorder associated with glutamate dysfunction in mammals (e.g., humans) comprising combining one or more products of a disclosed method of making, or pharmaceutical salt thereof, in a pharmaceutical dosage form.

In a further aspect, the compound is present in an effective amount. In a still further aspect, the effective amount is a therapeutically effective amount. In yet a further aspect, the effective amount is a prophylactically effective amount.

In a further aspect, the compound exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, the human embryonic kidney cells are transfected with rat mGluR5. In a yet further aspect, the human embryonic kidney cells are transfected with human mGluR5.

In a further aspect, the disorder is a neurological and/or psychiatric disorder. In a still further aspect, the disorder is selected from addiction, affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, fragile x syndrome, Huntington's-related chorea, gastroesophageal reflux disease (GERD), levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression. In yet a further aspect, the disorder is selected from autism, addiction, anxiety, fragile x syndrome, gastroesophageal reflux disease (GERD), Parkinson's disease, and pain. In an even further aspect, the neurological and/or psychiatric disorder is selected from major depressive disorder, obsessive compulsive disorder, addiction, aggression, and levodopa-induced dyskinesia in Parkinson's disease ("PD-LID").

In a further aspect, the disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the medicament is for the treatment of a disease of uncontrolled cellular proliferation. In a still further aspect, the disease of uncontrolled cellular proliferation is cancer. In yet a further aspect, the cancer is selected from breast cancer, renal cancer, gastric cancer, and colorectal cancer. In an even further aspect, the cancer is selected from lymphoma, cancers of the brain, genitourinary tract cancer, lymphatic system cancer, stomach cancer, larynx cancer, lung, pancreatic cancer, breast cancer, and malignant melanoma.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

4. Kits

In one aspect, the invention relates to a kit comprising at least one disclosed compound or at least one disclosed product and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction. In a further aspect, the at least one compound or the at least one product and the at least one agent are co-formulated. In a further aspect, the at least one compound or the at least one product and the at least one agent are co-packaged.

In one aspect, the invention relates to a kit comprising at least one disclosed compound or at least one product of a disclosed method of making, or a pharmaceutically acceptable salt thereof, and one or more of:
  (a) at least one agent known to increase mGluR5 activity;
  (b) at least one agent known to decrease mGluR5 activity;
  (c) at least one agent known to treat a neurological and/or psychiatric disorder; or
  (d) instructions for treating a disorder associated with glutamate dysfunction.

In a further aspect, the compound exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, the human embryonic kidney cells are transfected with rat mGluR5. In a yet further aspect, the human embryonic kidney cells are transfected with human mGluR5.

In a further aspect, the at least one agent is selected from an antipsychotic, a selective serotonin reuptake inhibitor, a central sympathomimetic, an imidazoline receptor agonists, a proprionic acid derivative, a benzodiazepine, sympathomimetics, a fatty acid derivative, a vitamin or multivitamin (with or without minerals), a piperazine derivative, an anilide, a lipid modifying agent, an aminoalkyl ether analogue, a macrolide, a melatonin receptor agonist, a penicillin derivative, a tetracycline analogue, an expectorant, an antihistamine, an azaspirodecanedione derivative, a central acting agent, a carboxamide, an opium alkaloid or derivative, an antidepressant, an antiepileptic, a beta blocker, a psychostimulant, a proton pump inhibitor, a 5HT3 antagonist, a vitamin D analogue, a diazepine, an indole derivative, an HMG CoA reductase inhibitor, a topical antibiotic, a progesterone analogue, an estrogen analogue, an angiotensin-converting enzyme inhibitor, an anesthetic, an antifungal, an antidiarrheal, an oxazepine, a thiazepine, a vaccine, a sulfonamide, a leukotriene receptor antagonist, a lincosamide, a neuroamidase inhibitor, a non-selective monoamine reuptake inhibitor, and a salicylic acid analogue.

In a further aspect, the at least one agent is selected from aripiprazole, acetaminophen, acetylcarnitine, acetylsalicylic acid, alprazolam, amitryptyline, amoxicillin, augmentin, azithromycin, baclofen, benzylpenicllin, bupropion, buspirone, carbamazepine, cetirizine, cimetidine, ciprofoxacin, citalopram, clonidine, clozapine, dexamfetamine, dexmethylphenidate, dextromethorphan, diazepam, dimetapp, diphenhydramine, donepezil, drospirenone with ethinylestradiol, ergocalciferol, escitalopram, fish oil, fuoxetine, fuvoxamine, guaifenesin, guanfacine, haloperidol, ibuprofen, imipramine, lamotrigine, lansoprazole, levoceterizine, lisdexamfetamine, loratadine, lorazepam, melatonin, methylphenidate, midazolam, minocycline, modafinil, mupirocin, naproxen, obetrol, olanzapine, omega-3 TG, omeprazole, ondansetron, oxcarbazepine, paliperidone, paracetamol, phenobarbital, phenylephrine, phenytoin, promethazine with codeine, propranolol, pseudoephedrine, risperidone, sertraline, simvastatin, a statin, topiramate, trazodone, tricyclic AD, valproate, venlafaxine, ziprasidone, and zonisamide.

In a further aspect, the at least one compound and the at least one agent are co-formulated. In a still further aspect, the at least one agent is selected from an antipsychotic, a selective serotonin reuptake inhibitor, a central sympathomimetic, an imidazoline receptor agonists, a proprionic acid derivative, a benzodiazepine, sympathomimetics, a fatty acid derivative, a vitamin or multivitamin (with or without minerals), a piperazine derivative, an anilide, a lipid modifying agent, an aminoalkyl ether analogue, a macrolide, a melatonin receptor agonist, a penicillin derivative, a tetracycline analogue, an expectorant, an antihistamine, an azaspirodecanedione derivative, a central acting agent, a carboxamide, an opium alkaloid or derivative, an antidepressant, an antiepileptic, a beta blocker, a psychostimulant, a proton pump inhibitor, a 5HT3 antagonist, a vitamin D analogue, a diazepine, an indole derivative, an HMG CoA reductase inhibitor, a topical antibiotic, a progesterone analogue, an estrogen analogue, an angiotensin-converting enzyme inhibitor, an anesthetic, an antifungal, an antidiarrheal, an oxazepine, a thiazepine, a vaccine, a sulfonamide, a leukotriene receptor antagonist, a lincosamide, a neuroamidase inhibitor, a non-selective monoamine reuptake inhibitor, and a salicylic acid analogue. In yet a further aspect, the at least one agent is selected from aripiprazole, acetaminophen, acetylcarnitine, acetylsalicylic acid, alprazolam, amitryptyline, amoxicillin, augmentin, azithromycin, baclofen, benzylpenicllin, bupropion, buspirone, carbamazepine, cetirizine, cimetidine, ciprofoxacin, citalopram, clonidine, clozapine, dexamfetamine, dexmethylphenidate, dextromethorphan, diazepam, dimetapp, diphenhydramine, donepezil, drospirenone with ethinylestradiol, ergocalciferol, escitalopram, fish oil, fuoxetine, fluvoxamine, guaifenesin, guanfacine, haloperidol, ibuprofen, imipramine, lamotrigine, lansoprazole, levoceterizine, lisdexamfetamine, loratadine, lorazepam, melatonin, methylphenidate, midazolam, minocycline, modafinil, mupirocin, naproxen, obetrol, olanzapine, omega-3 TG, omeprazole, ondansetron, oxcarbazepine, paliperidone, paracetamol, phenobarbital, phenylephrine, phenytoin, promethazine with codeine, propranolol, pseudoephedrine, risperidone, sertraline, simvastatin, a statin, topiramate, trazodone, tricyclic AD, valproate, venlafaxine, ziprasidone, and zonisamide.

In a further aspect, the at least one compound and the at least one agent are co-packaged. In a still further aspect, the at least one agent is selected from an antipsychotic, a selective serotonin reuptake inhibitor, a central sympathomimetic, an imidazoline receptor agonists, a proprionic acid derivative, a benzodiazepine, sympathomimetics, a fatty acid derivative, a vitamin or multivitamin (with or without minerals), a piperazine derivative, an anilide, a lipid modifying agent, an aminoalkyl ether analogue, a macrolide, a melatonin receptor agonist, a penicillin derivative, a tetracycline analogue, an expectorant, an antihistamine, an azaspirodecanedione derivative, a central acting agent, a carboxamide, an opium alkaloid or derivative, an antidepressant, an antiepileptic, a beta blocker, a psychostimulant, a proton pump inhibitor, a 5HT3 antagonist, a vitamin D analogue, a diazepine, an indole derivative, an HMG CoA reductase inhibitor, a topical antibiotic, a progesterone analogue, an estrogen analogue, an angiotensin-converting enzyme inhibitor, an anesthetic, an antifungal, an antidiarrheal, an oxazepine, a thiazepine, a vaccine, a sulfonamide, a leukotriene receptor antagonist, a lincosamide, a neuroamidase inhibitor, a non-selective monoamine reuptake inhibitor, and a salicylic acid analogue. In yet a further aspect, the at least one agent is selected from aripiprazole, acetaminophen, acetylcarnitine, acetylsalicylic acid, alprazolam, amitryptyline, amoxicillin, augmentin, azithromycin, baclofen, benzylpenicllin, bupropion, buspirone, carbamazepine, cetirizine, cimetidine, ciprofoxacin, citalopram, clonidine, clozapine, dexamfetamine, dexmethylphenidate, dextromethorphan, diazepam, dimetapp, diphenhydramine, donepezil, drospirenone with ethinylestradiol, ergocalciferol, escitalopram, fish oil, fuoxetine, fluvoxamine, guaifenesin, guanfacine, haloperidol, ibuprofen, imipramine, lamotrigine, lansoprazole, levoceterizine, lisdexamfetamine, loratadine, lorazepam, melatonin, methylphenidate, midazolam, minocycline, modafinil, mupirocin, naproxen, obetrol, olanzapine, omega-3 TG, omeprazole, ondansetron, oxcarbazepine, paliperidone, paracetamol, phenobarbital, phenylephrine, phenytoin, promethazine with codeine, propranolol, pseudoephedrine, risperidone, sertraline, simvastatin, a statin, topiramate, trazodone, tricyclic AD, valproate, venlafaxine, ziprasidone, and zonisamide.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of modulators of mGluR related activity in laboratory animals such as cats, dogs, rabbits, monkeys, rats and mice, as part of the search for new therapeutic agents of mGluR. In a further aspect, the invention relates to the use of a disclosed compound or a disclosed product as pharmacological tools in the development and standardization of in vitro and in vivo test systems for the evaluation of the effects of modulators of mGluR5 related activity in laboratory animals such as cats, dogs, rabbits, monkeys, rats and mice, as part of the search for new therapeutic agents of mGluR5.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following examples. Starting materials and the requisite intermediates are in some cases commercially available, or can be prepared according to literature procedures or as illustrated herein. All $^1$H NMR spectra were obtained on instrumentation at a field strength of 300 to 500 MHz.

1. Intermediate Route I a. Preparation of 5-bromo-3-(((triisopropylsilyl)oxy)methyl)pyridin-2-amine (1)

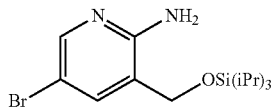

Triisopropylsilyl chloride (2.11 mL, 9.85 mmol, 1.0 eq) was added to (2-amino-5-bromopyridin-3-yl)methanol (2.00 g, 9.85 mmol, 1.0 eq) and imidazole (1.48 g, 21.7 mmol, 2.2 eq) dissolved in DMF (49 mL). The reaction was stirred for 4 hours at room temperature at which point it was diluted with ethyl acetate and washed with water (2×). The aqueous phase was back extracted with ethyl acetate and the combined organics were dried (MgSO$_4$), filtered and concentrated in vacuo. Purification by flash chromatography on silica gel afforded 2.43 g (69%) of the title compound as a pale yellow solid. $^1$H NMR (400 MHz, DMSO-d$_6$) δ 7.90 (d, J=2.4 Hz, 1H), 7.57-7.55 (m, 1H), 5.94 (s, 2H), 4.56 (s, 2H), 1.21-1.10 (m, 3H), 1.04 (d, J=6.9 Hz, 18H); ES-MS [M+1]$^+$: 359.2.

2. Intermediate Route II a. Preparation of N-(5-bromo-3-(((triisopropylsilyl)oxy)methyl)pyridin-2-yl)-N'-hydroxyformimidamide (2)

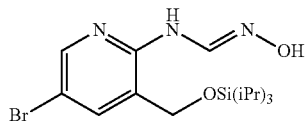

Compound 1 (10.2 g, 25.4 mmol, 1.0 eq) was dissolved in isopropanol (90 mL) and DMF-DMA (4.39 mL, 33.0 mmol, 1.3 eq) was added. The reaction was heated to reflux for 3 hours at which point it was cooled to 50° C. and hydroxylamine hydrochloride (2.29 g, 33.0 mmol, 1.3 eq) was added. After an additional 2 hours at 50° C. the reaction was cooled and concentrated to afford the title compound as a yellow solid that was used without further purification.

b. Preparation of 6-bromo-8-(((triisopropylsilyl)oxy)methyl) [1,2,4]triazolo[1,5-a]pyridine (3)

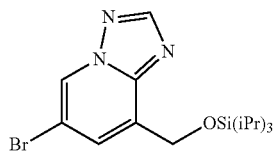

To a solution of the compound 2 (10.2 g, 25.4 mmol, 1.0 eq) in THF (130 mL) at 0° C. was added trifluoroacetic anhydride (5.3 mL, 38 mmol, 1.5 eq) dropwise. The reaction was allowed to warm to room temperature. After 2.5 hours, the reaction was quenched with saturated sodium bicarbonate solution and extracted with EtOAc (3×), dried (MgSO$_4$), filtered and concentrated in vacuo. Purification by flash chromatography on silica gel afforded 7.67 g (79%) of the title compound: $^1$H NMR (400 MHz, DMSO-d$_6$) δ 9.32 (dt, J=15.7, 0.88 Hz, 1H), 8.52 (d, J=7.9 Hz, 1H), 7.69-7.67 (m, 1H), 5.13 (s, 2H), 1.24-1.18 (m, 3H), 1.08 (s, 18H); ES-MS [M+1]$^+$: 385.2.

3. Intermediate Route III a. Preparation of 6-bromo-8-(((triisopropylsilyl)oxy)methyl)imidazo[1,2-a]pyridine (4)

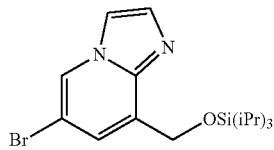

Compound 1 (750 mg, 2.09 mmol, 1.0 eq), chloroacetaldehyde solution (1.55 mL, ~50% wt. in H$_2$O), potassium carbonate (577 mg, 4.17 mmol, 2.0 eq) and isopropanol (10.4 mL) were added to a microwave vial and heated in a microwave reactor at 170° C. for 20 minutes. The reaction was filtered and washed with 5% MeOH/DCM. The filtrate was concentrated and purified by flash chromatography on silica gel to afford 630 mg (79%) of the title compound as a brown solid: $^1$H NMR (400 MHz, DMSO-d$_6$) δ 8.82 (s, 1H), 7.93 (d, J=1.07 Hz, 1H), 7.54 (d, J=1.0 Hz, 1H), 7.27 (d, J=1.6 Hz, 1H), 5.11 (s, 2H), 1.25-1.13 (m, 3H), 1.06 (d, J=7.1 Hz, 18H); ES-MS [M+1]$^+$: 383.2.

4. Intermediate Route IV a. Preparation of (6-bromo-[1,2,4]triazolo[1,5-a]pyridin-8-yl)methanol (5)

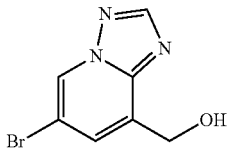 [SMILES: OCc1cc(Br)cn2ncnc12]

To a solution of compound 3 (750 mg, 1.95 mmol, 1.0 eq) in THF (10 mL) was added tetrabutylammonium fluoride (2.34 mL, 1.0 M in THF, 2.34 mmol, 1.2 eq). After 30 minutes the reaction was concentrated to dryness. Purification by flash chromatography on silica gel afforded 445 mg (100%) of the title compound: $^1$H NMR (400 MHz, DMSO-d$_6$) δ 9.28 (t, J=0.88 Hz, 1H), 8.5 (s, 1H), 7.69 (q, J=1.4 Hz, 1H), 5.69 (t, J=5.8 Hz, 1H), 4.86 (d, J=5.7 Hz, 2H); ES-MS [M+1]$^+$: 228.0.

5. Intermediate Route V a. Preparation of (5-bromo-2-fluoropyridin-3-yl)methanol (6)

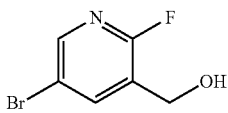

(2-amino-5-bromopyridin-3-yl)methanol (1.00 g, 4.93 mmol, 1.0 eq) was dissolved in HF-pyridine (15.4 mL) in a HDPE vessel. The reaction was cooled to 0° C. and sodium nitrite (510 mg, 7.39 mmol, 1.5 eq) was added in portions. After 5 minutes at 0° C. the reaction was poured onto ice and made basic with saturated NaHCO$_3$. The reaction was extracted with ethyl acetate (1×) and 3:1 CHCl$_3$/IPA (2×). The combined organics were dried (MgSO$_4$), filtered and concentrated in vacuo. Purification by flash chromatography on silica gel afforded 849 mg (84%) of the title compound as a pale yellow solid: $^1$H NMR (400 MHz, DMSO-d$_6$) δ 8.27-8.25 (m, 1H), 8.13-8.09 (m, 1H), 5.54 (t, J=5.8 Hz, 1H), 4.52 (d, J=5.7 Hz, 2H); ES-MS [M+1]$^+$: 206.0.

b. Preparation of 5-bromo-2-fluoro-3-(((tetrahydro-2H-pyran-2-yl)oxy)methyl)pyridine (7)

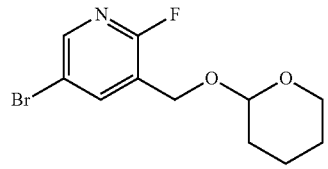 [SMILES: Fc1ncc(Br)cc1COC1CCCCO1]

Compound 6 (1.41 g, 6.84 mmol, 1.0 eq), 3,4-dihydro-2H-pyran (1.31 mL, 14.4 mmol, 2.1 eq) and pyridinium p-toluenesulfonate (1.72 g, 6.84 mmol, 1.0 eq) were dissolved in dichloromethane in a round-bottom flask and stirred at room temperature for 16 hours. The reaction was washed with saturated sodium bicarbonate, dried (MgSO$_4$), filtered and concentrated in vacuo to afford 2.06 g of the title compound as a clear oil that was used without further purification. ES-MS [M+1]$^+$: 290.1.

c. Preparation of 5-bromo-2-hydrazinyl-3-(((tetrahydro-2H-pyran-2-yl)oxy)methyl)pyridine (8)

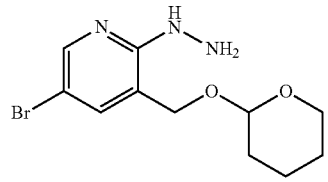 [SMILES: NNc1ncc(Br)cc1COC1CCCCO1]

Compound 7 (519 mg, 1.79 mmol, 1.0 eq), hydrazine (0.562 mL, 17.9 mmol, 10 eq) and ethanol (4.5 mL) were added to a microwave vial and heated in a microwave reactor at 150° C. for 30 minutes. The reaction was concentrated in vacuo and purification by flash chromatography on silica gel afforded 436 mg (81%) of the title compound as a brown oil: 1H NMR (400 MHz, DMSO-d$_6$) δ 8.10 (d, J=2.3 Hz, 1H), 7.55 (d, J=2.4 Hz, 1H), 7.24 (s, 1H), 4.67 (t, J=3.5 Hz, 1H), 4.51 (d, J=13.3 Hz, 1H), 4.33 (d, J=13.3 Hz, 1H), 4.17 (s, 2H), 3.80-3.72 (m, 1H), 3.51-3.43 (m, 1H), 1.78-1.60 (m, 2H), 1.55-1.41 (m, 4H); ES-MS [M+1]$^+$: 302.2.

d. Preparation of 6-bromo-8-(((tetrahydro-2H-pyran-2-yl)oxy)methyl)-[1,2,4]triazolo[4,3-a]pyridine (9)

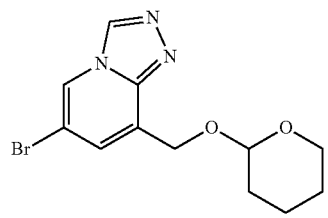 [SMILES: Brc1cc(COC2CCCCO2)c2nncn2c1]

Compound 8 (381 mg, 1.26 mmol, 1.0 eq) and triethylorthoformate (3.1 mL) were added to a microwave vial and heated in a microwave reactor at 180° C. for 30 minutes. The reaction was concentrated in vacuo and purified by flash chromatography on silica gel to provide 347 mg (88%) of the title compound as a white solid: $^1$H NMR (400 MHz, DMSO-d$_6$) δ 9.20 (s, 1H), 8.87-8.85 (m, 1H), 7.38 (d, J=1.5 Hz, 1H), 5.00 (d, J=14.4 Hz, 1H), 4.87-4.80 (m, 2H), 3.86-3.78 (m, 1H), 3.54-3.47 (m, 1H), 1.82-1.65 (m, 2H), 1.63-1.42 (m, 4H); ES-MS [M+1]$^+$: 312.0.

e. Preparation of (6-bromo-[1,2,4]triazolo[4,3-a]pyridin-8-yl)methanol (10)

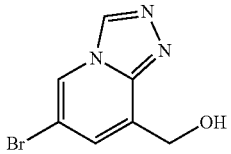 [SMILES: OCc1cc(Br)cn2cnnc12]

Compound 9 (892 mg, 2.86 mmol, 1.0 eq) was dissolved in methanol (14.3 mL) and 4N HCl in dioxane (1.43 mL, 5.72 mmol, 2.00 eq) was added. The reaction was stirred for 16 hours at which point it was neutralized to pH 4-5 with saturated sodium bicarbonate. The mixture was extracted with 3:1 CHCl$_3$/IPA (3×), dried (MgSO$_4$), filtered and concentrated in vacuo. Purification by flash chromatography on silica gel afforded 547 mg (84%) of the title compound as an off white solid: $^1$H NMR (400 MHz, DMSO-d$_6$) δ 9.18 (s, 1H), 8.82-8.80 (m, 1H), 7.34 (q, J=1.6 Hz, 1H), 4.86 (s, 2H); ES-MS [M+1]$^+$: 228.0.

6. Intermediate Route VI a. Preparation of 6-bromo-[1,2,4]triazolo[1,5-a]pyridine-8-carbaldehyde (11)

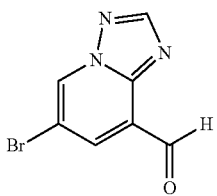 [SMILES: O=Cc1cc(Br)cn2ncnc12]

To a solution of compound 5 (100 mg, 0.44 mmol) in DCM (4.4 mL) that was cooled to 0° C. was added Dess-Martin periodinane (223 mg, 0.53 mmol, 1.2 eq). The reaction was allowed to warm to room temperature and after two hours was quenched with saturated sodium bicarbonate solution and extracted with 3:1 CHCl$_3$/IPA (2×). The organics were concentrated in vacuo to give 100 mg (100%) of the title compound that was used without further purification: $^1$H NMR (400 MHz, DMSO-d$_6$) δ 10.4 (s, 1H), 9.76 (d, J=1.9 Hz, 1H), 8.73 (s, 1H), 8.33 (d, J=1.8 Hz, 1H); ES-MS [M+1]$^+$: 228.0.

b. Preparation of 6-bromo-[1,2,4]triazolo[1,5-a]pyridine-8-carboxylic acid (12)

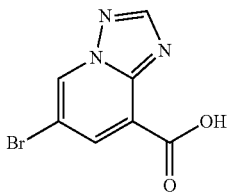 [SMILES: O=C(O)c1cc(Br)cn2ncnc12]

To a solution of compound 11 (100 mg, 0.44 mmol, 1.0 eq) in dioxane (9.2 mL) was added sodium acetate (127 mg, 1.55 mmol, 3.5 eq) in acetic acid (4.4 mL) and water (4.4 mL), sodium chlorite (105 mg, 0.93 mmol, 2.1 eq) in water (6.32 mL) and sulfamic acid (90.2 mg, 0.930 mmol, 2.1 eq) in water (8.2 mL). After two hours the reaction was concentrated to one-third volume in vacuo and extracted with 3:1 CHCl$_3$/IPA (5×). The organics were concentrated to dryness, taken up in 10% MeOH/DCM, sodium salts filtered and concentrated in vacuo to give 105 mg (98%) of the title compound that was used without further purification. ES-MS [M+1]$^+$: 244.0.

c. Preparation of 6-bromo-N-(4-methylthiazol-2-yl)-[1,2,4]triazolo[1,5-a]pyridine-8-carboxamide (13)

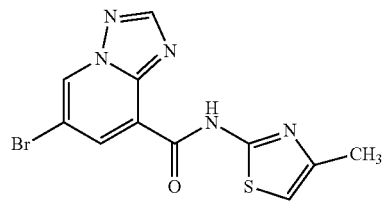 [SMILES: Cc1csc(NC(=O)c2cc(Br)cn3ncnc23)n1]

To a solution of compound 12 (105 mg, 0.44 mmol, 1.0 eq) and 2-amino-4-methylthiazole (104 mg, 0.91 mmol, 2.1 eq) in pyridine (2 mL) cooled to −15° C. was added phosphorus oxychloride (85 μL, 0.91 mmol, 2.1 eq) dropwise while keeping the temperature below −15° C. After stirring at −15° C. for one hour, the reaction was quenched with ice-water, neutralized with 10% K$_2$CO$_3$, and allowed to warm to room temperature. The reaction was extracted with EtOAc (2×), dried (MgSO$_4$), filtered, and concentrated in vacuo. Purification by flash chromatography on silica gel afforded 110 mg (75%) of the title compound: 1H NMR (400 MHz, DMSO-d$_6$) δ 9.79 (d, J=1.8 Hz, 1H), 8.87 (s, 1H), 8.48 (d, J=1.8 Hz, 1H), 6.97 (s, 1H), 5.76 (s, 1H), 2.33 (d, J=0.96 Hz, 3H); ES-MS [M+1]$^+$: 338.0.

7. Intermediate Route VII a. Preparation of (6-(3-methyl-1H-pyrazol-5-yl)-[1,2,4]triazolo[1,5-a]pyridin-8-yl)methanol (14)

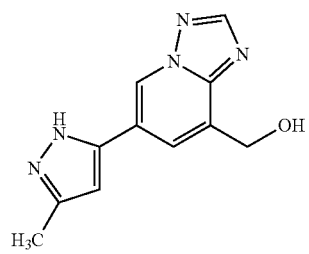 [SMILES: Cc1cc(-c2cc(CO)c3ncnn3c2)[nH]n1]

Compound 5 (450 mg, 1.97 mmol, 1.0 eq), (2-tert-butoxycarbonyl-5-methyl-pyrazol-3-yl)boronic acid (937 mg, 4.14 mmol, 2.1 eq), Pd(dppf)Cl$_2$.CH$_2$Cl$_2$ (144 mg, 0.197 mmol, 0.10 eq), 1 M sodium carbonate solution (1.97 mL, 1.97 mmol, 1 eq) and DME (10 mL) were added to a large microwave vial. The vial was capped and stirred overnight at 100° C. The reaction was washed with water and brine and extracted with EtOAc (2×). The organics were combined, dried (MgSO$_4$), and concentrated to dryness. Purification by flash chromatography on silica gel afforded 330 mg (73%) of the title compound: $^1$H NMR (400 MHz, DMSO-d$_6$) δ 9.15 (s, 1H), 8.45 (s, 1H), 8.16 (s, 1H), 6.63 (s, 1H), 5.62 (s, 1H), 4.88 (d, J=3.3 Hz, 2H), 2.28 (s, 3H); ES-MS [M+1]$^+$: 230.2.

b. Preparation of 6-(3-methyl-1H-pyrazol-5-yl)-[1,2,4]triazolo[1,5-a]pyridine-8-carbaldehyde (15)

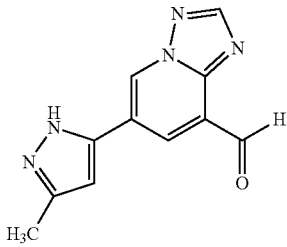 [SMILES: Cc1cc(-c2cc(C=O)c3ncnn3c2)[nH]n1]

To a solution of compound 14 (330 mg, 1.44 mmol, 1.0 eq) in DCM (7.2 mL) cooled to 0° C. was added Dess-Martin periodinane (733 mg, 1.73 mmol, 1.2 eq). The reaction was allowed to warm to room temperature and after two hours the reaction was quenched with saturated sodium bicarbonate solution and extracted with 3:1 CHCl$_3$/IPA (2×). The organics were concentrated in vacuo and purification by flash chromatography to give 250 mg (76%) of the title compound: $^1$H NMR (400 MHz, DMSO-d$_6$) δ 10.5 (s, 1H), 9.63 (d, J=1.4 Hz, 1H), 8.7 (s, 1H), 8.66 (s, 1H), 6.76 (s, 1H), 2.31 (s, 3H); ES-MS [M+1]$^+$: 228.2.

c. Preparation of 6-(3-methyl-1H-pyrazol-5-yl)-[1,2,4]triazolo[1,5-a]pyridine-8-carboxylicacid (16)

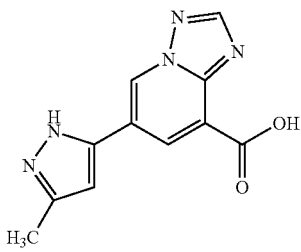 [SMILES: Cc1cc(-c2cc(C(=O)O)c3ncnn3c2)[nH]n1]

To a solution of compound 15 (250 mg, 1.1 mmol) in dioxane (23 mL) was added sodium acetate (316 mg, 3.85 mmol, 3.5 eq) in acetic acid (11 mL) and water (11 mL), sodium chlorite (261 mg, 2.31 mmol, 2.1 eq) in water (20.4 mL) and sulfamic acid (224 mg, 2.31 mmol, 2.1 eq) in water (15.7 mL). After two hours the reaction was concentrated to one-third volume in vacuo and extracted with 3:1 CHCl$_3$/IPA (5×). The organics were concentrated to dryness, taken up in 10% MeOH/DCM, sodium salts filtered and concentrated in vacuo to give 260 mg (97%) of the title compound that was used without further purification: $^1$H NMR (400 MHz, DMSO-d$_6$) δ 9.18 (d, J=1.3 Hz, 1H), 8.54 (s, 1H), 8.45 (s, 1H), 6.63 (s, 1H), 4.26 (s, 1H), 2.28 (s, 3H); ES-MS [M+1]$^+$: 244.2.

8. Analog Route I a. Preparation of N-(5-fluoropyridin-2-yl)-6-(3-methyl-1H-pyrazol-5yl)-[1,2,4]triazolo[1,5-a]pyridine-8-carboxamide (17)

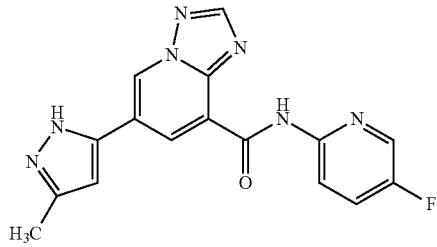 [SMILES: Cc1cc(-c2cc(C(=O)Nc3ccc(F)cn3)c3ncnn3c2)[nH]n1]

To a solution of compound 16 (20 mg, 0.082 mmol, 1.0 eq) and 2-amino-5-fluoropyridine (19.4 mg, 0.17 mmol, 2.1 eq) in pyridine (1 mL) cooled to −15° C. was added phosphorus oxychloride (16.1 μL, 0.17 mmol, 2.1 eq) dropwise while keeping the temperature below −15° C. After stirring at −15° C. for one hour, the reaction was quenched with ice-water, neutralized with 10% K$_2$CO$_3$, and allowed to warm to room temperature. The reaction was extracted with EtOAc (2×), dried (MgSO$_4$), filtered, and concentrated in vacuo. Purification by flash chromatography on silica gel afforded 3.3 mg (12%) of the title compound: $^1$H NMR (400 MHz, DMSO-d$_6$) δ 9.62 (d, J=1.6 Hz, 1H), 8.95 (d, J=1.6 Hz, 1H), 8.81 (s, 1H), 8.59 (s, 1H), 8.44 (dd, J=3, 7.8 Hz, 2H), 8.04 (s, 1H), 7.92-7.87 (m, 1H), 6.77 (s, 1H), 2.32 (s, 3H); ES-MS [M+1]$^+$: 337.9.

9. Analog Route II a. Preparation of 6-(4-methylpyrimidin-5-yl)-N-(4-methylthiazol 2-yl)-[1,2,4]triazolo[1,5-a]pyridine-8-carboxamide (1)

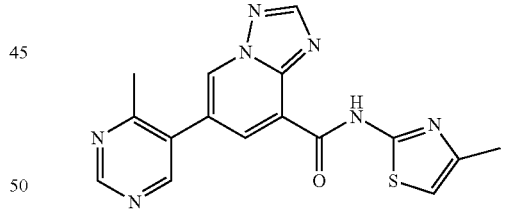

Compound 13 (25 mg, 0.08 mmol, 1.0 eq), 4-methyl-5-(4,4,5,5-tetramethyl-1,3,2-dioxaborolan-2-yl)pyrimidine (35.5 mg, 0.16 mmol, 2.1 eq), Pd(dppf)Cl$_2$.CH$_2$Cl$_2$ (5.6 mg, 0.008 mmol, 0.1 eq), 1 M sodium carbonate solution (384 μL, 0.38 mmol, 5 eq) and DME (384 μL) were added to a small microwave vial. The vial was capped and stirred overnight at 100° C. The reaction was washed with water and brine and extracted with EtOAc (2×). The organics were combined, dried (MgSO$_4$), and concentrated to dryness. Purification by reverse phase HPLC afforded 3.4 mg (13%) of the title compound: $^1$H NMR (400 MHz, DMSO-d$_6$) δ 9.24 (s, 1H), 8.84.8.82 (m, 1H), 8.67 (d, J=1.5 Hz, 1H), 8.61-8.57 (m, 2H), 8.50 (s, 1H), 6.68 (d, J=1.0 Hz, 1H), 2.63 (d, J=3.2 Hz, 3H), 2.47 (dd, J=0.88, 5.3 Hz, 3H); ES-MS [M+1]$^+$: 352.2.

10. Characterization of Exemplary Compounds

Table 1 below lists specific compounds as well as a preferred route for its synthesis, experimentally determined molecular mass, and mGluR5 activity determined in a cell-based assay. The mGluR5 activity was determined using the calcium mobilization assays in human embryonic kidney cells as described herein below, wherein the human embryonic kidney cells were transfected with rat mGluR5. The mGluR5 activity data for some compounds are shown as the average of at least three experiments with the standard error in these cases. If no error is indicated for the mGluR5 activity, the values given represent the results from a single experiment or the average of two experiments. The compounds in Table 1 were synthesized with methods identical or analogous to those shown herein. The requisite starting materials were commercially available, described in the literature, or readily synthesized by one skilled in the art of organic synthesis.

Unless otherwise stated, the GluMax values for analogs with an $IC_{50}$ value below 10,000 nM are below 10%. GluMax is the amplitude of response in the presence of 30 µM test compound as a percentage of maximal response (100 µM glutamate). Partial antagonists display concentration-response curves (CRCs) that plateau above 10%. In the table below, compounds that behave as partial antagonists are noted as such and their respective GluMax values are specified. Analogs with $IC_{50}$ values specified as ">10,000 nM" display CRCs that do not plateau.

TABLE 1

| Structure | mGluR5 $IC_{50}$ (nM) | Intermediate Route Reference | Analog Route Reference | $[M + H]^+$ |
|---|---|---|---|---|
| 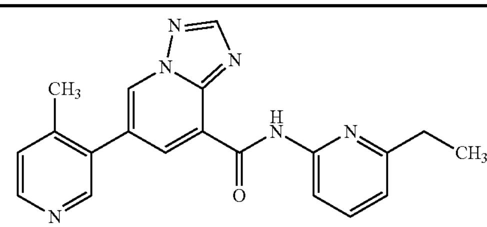 | 1760 | I, II, IV VII | I | 358.9 |
| 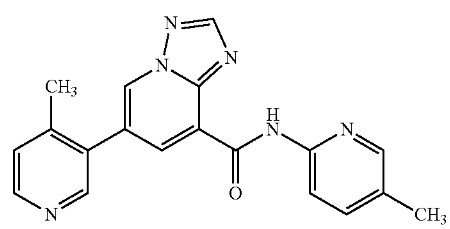 [SMILES: Cc1ccc(NC(=O)c2cc(-c3cnccc3C)cn3ncnc23)nc1] | 325 | I, II, IV VII | I | 344.9 |
| 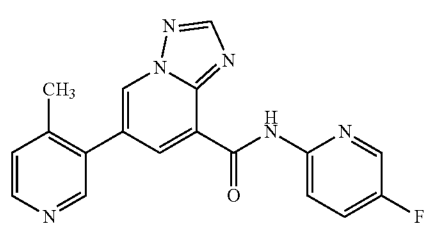 [SMILES: Cc1ccncc1-c1cc(C(=O)Nc2ccc(F)cn2)c2ncnn2c1] | >10,000 (52% Glu Max) | I, II, IV VII | I | 348.9 |
| 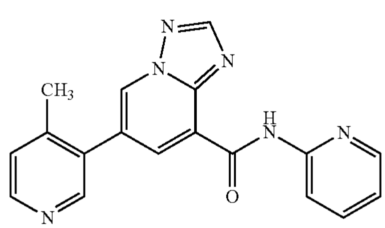 [SMILES: Cc1ccncc1-c1cc(C(=O)Nc2ccccn2)c2ncnn2c1] | 358 | I, II, IV VII | I | 330.9 |
| 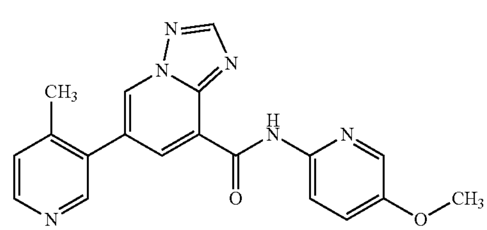 [SMILES: COc1ccc(NC(=O)c2cc(-c3cnccc3C)cn3ncnc23)nc1] | 1310 | I, II, IV VII | I | 360.9 |

TABLE 1-continued

| Structure | mGluR5 IC$_{50}$ (nM) | Intermediate Route Reference | Analog Route Reference | [M + H]$^+$ |
|---|---|---|---|---|
| 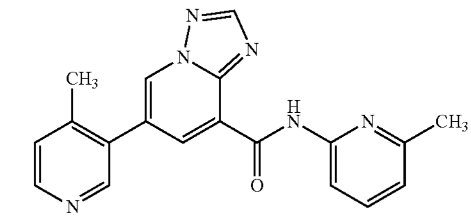 [SMILES: Cc1cccc(NC(=O)c2cc(-c3cnccc3C)cn3ncnc23)n1] | 793 | I, II, IV VII | I | 344.9 |
| 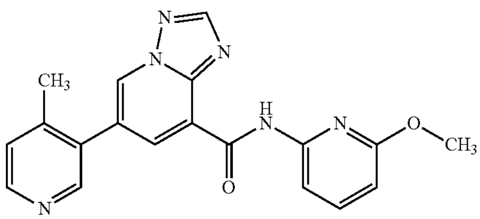 [SMILES: COc1cccc(NC(=O)c2cc(-c3cnccc3C)cn3ncnc23)n1] | >10,000 (31% Glu Max) | I, II, IV VII | I | 360.9 |
| 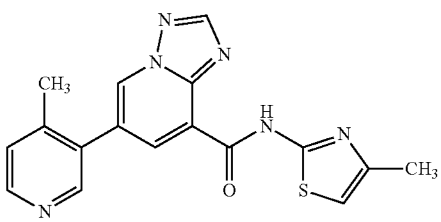 [SMILES: Cc1csc(NC(=O)c2cc(-c3cnccc3C)cn3ncnc23)n1] | 170 | I, II, IV VII | I | 350.8 |
| 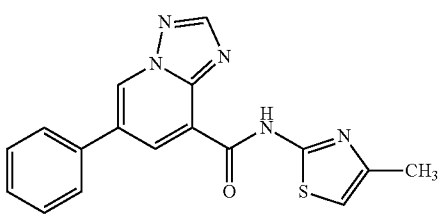 [SMILES: Cc1csc(NC(=O)c2cc(-c3ccccc3)cn3ncnc23)n1] | 385 | I, II, IV, VI | II | 335.9 |
| 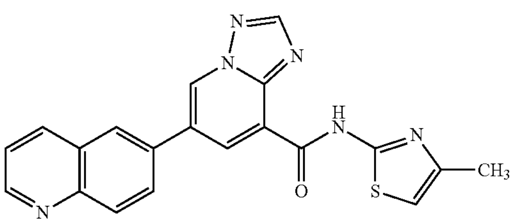 [SMILES: Cc1csc(NC(=O)c2cc(-c3ccc4ncccc4c3)cn3ncnc23)n1] | >10,000 (74% Glu Max) | I, II, IV, VI | II | 387.1 |
| 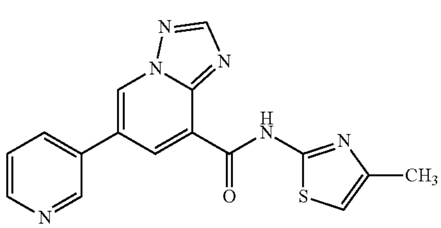 [SMILES: Cc1csc(NC(=O)c2cc(-c3cccnc3)cn3ncnc23)n1] | 587 | I, II, IV, VI | II | 337.1 |
| 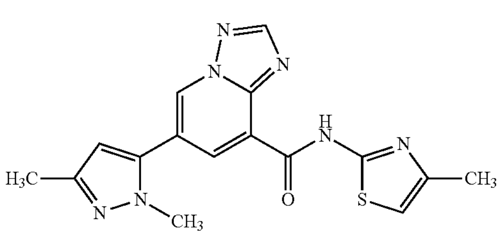 | 690 | I, II, IV, VI | II | 354.1 |

TABLE 1-continued

| Structure | mGluR5 IC$_{50}$ (nM) | Intermediate Route Reference | Analog Route Reference | [M + H]$^+$ |
|---|---|---|---|---|
| 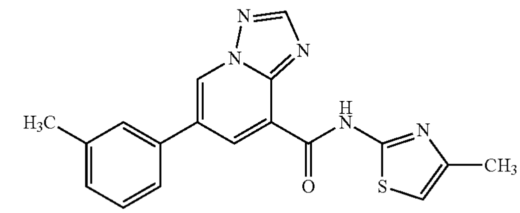 | 4770 | I, II, IV, VI | II | 350.1 |
| 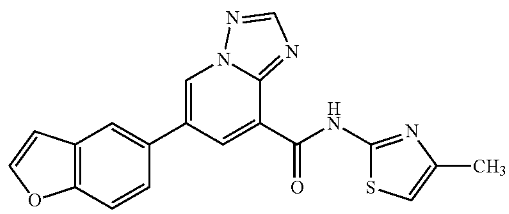 [SMILES: Cc1csc(NC(=O)c2cc(-c3ccc4occc4c3)cn3ncnc23)n1] | >30,000 | I, II, IV, VI | II | 376.1 |
| 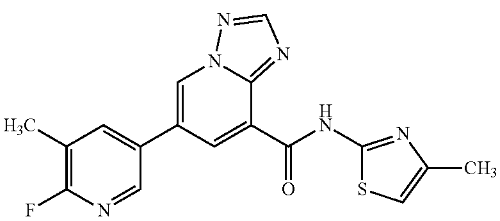 [SMILES: Cc1csc(NC(=O)c2cc(-c3cnc(F)c(C)c3)cn3ncnc23)n1] | 2810 | I, II, IV, VI | II | 369.1 |
| 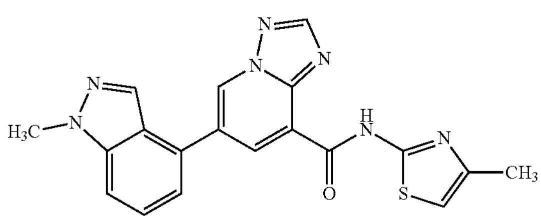 | 7020 | I, II, IV, VI | II | 390.1 |
| 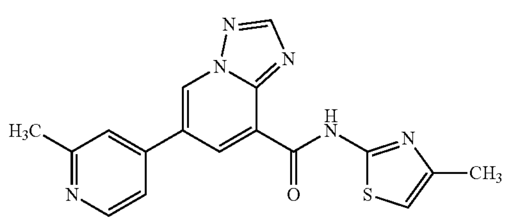 | 10,000 | I, II, IV, VI | II | 351.1 |
| 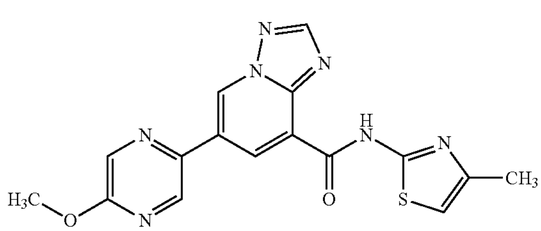 | >10,000 (71% Glu Max) | I, II, IV, VI | II | 368.1 |
| 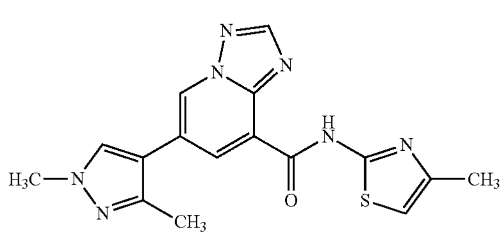 | 2160 | I, II, IV, VI | II | 354.1 |

TABLE 1-continued

| Structure | mGluR5 IC$_{50}$ (nM) | Intermediate Route Reference | Analog Route Reference | [M + H]$^+$ |
|---|---|---|---|---|
| 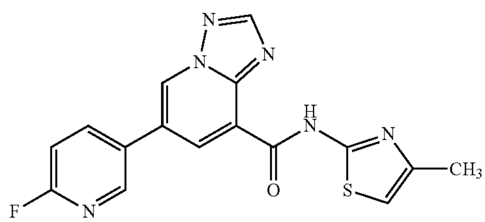 [SMILES: Cc1csc(NC(=O)c2cc(-c3ccc(F)nc3)cn3ncnc23)n1] | 4930 | I, II, IV, VI | II | 355.1 |
| 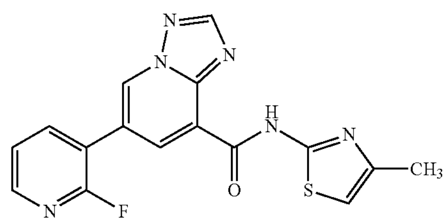 [SMILES: Cc1csc(NC(=O)c2cc(-c3cccnc3F)cn3ncnc23)n1] | 978 | I, II, IV, VI | II | 355.1 |
| 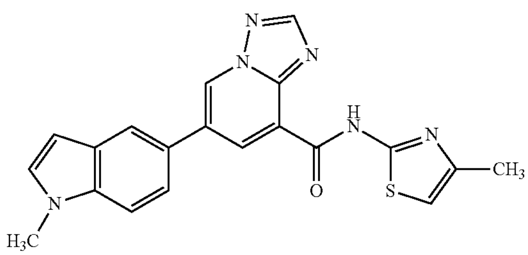 | >10,000 (27% Glu Max) | I, II, IV, VI | II | 389.1 |
| 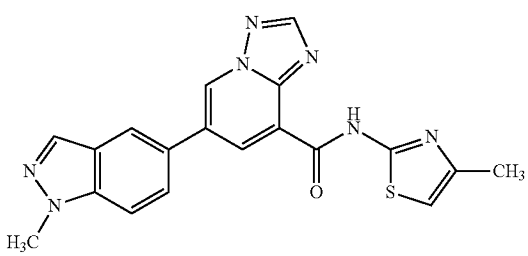 [SMILES: Cc1csc(NC(=O)c2cc(-c3ccc4c(cnn4C)c3)cn3ncnc23)n1] | >10,000 (53% Glu Max) | I, II, IV, VI | II | 390.1 |
| 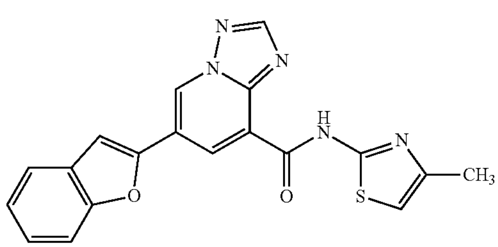 [SMILES: Cc1csc(NC(=O)c2cc(-c3cc4ccccc4o3)cn3ncnc23)n1] | >10,000 (39% Glu Max) | I, II, IV, VI | II | 376.1 |
| 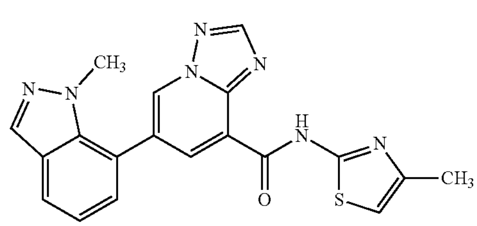 [SMILES: Cc1csc(NC(=O)c2cc(-c3cccc4cnn(C)c34)cn3ncnc23)n1] | 10,200 | I, II, IV, VI | II | 390.1 |

TABLE 1-continued

| Structure | mGluR5 IC$_{50}$ (nM) | Intermediate Route Reference | Analog Route Reference | [M + H]$^+$ |
|---|---|---|---|---|
| 6-(1-methyl-1H-indazol-6-yl)-N-(4-methylthiazol-2-yl)-[1,2,4]triazolo[1,5-a]pyridine-8-carboxamide | >10,000 (30% Glu Max) | I, II, IV, VI | II | 390.1 |
| 6-(5-methylpyridin-3-yl)-N-(4-methylthiazol-2-yl)-[1,2,4]triazolo[1,5-a]pyridine-8-carboxamide | 1500 | I, II, IV, VI | II | 351.1 |
| 6-(3,5-dimethylphenyl)-N-(4-methylthiazol-2-yl)-[1,2,4]triazolo[1,5-a]pyridine-8-carboxamide | >10,000 (57% Glu Max) | I, II, IV, VI | II | 364.2 |
| N-(4-methylthiazol-2-yl)-6-(o-tolyl)-[1,2,4]triazolo[1,5-a]pyridine-8-carboxamide | 7940 (n = 2) | I, II, IV, VI | II | 350.1 |
| 6-(5-methoxy-2-methylphenyl)-N-(4-methylthiazol-2-yl)-[1,2,4]triazolo[1,5-a]pyridine-8-carboxamide | 7100 | I, II, IV, VI | II | 380.1 |
| 6-(4-cyclopropylpyridin-3-yl)-N-(4-methylthiazol-2-yl)-[1,2,4]triazolo[1,5-a]pyridine-8-carboxamide | 1010 | I, II, IV, VI | II | 377.2 |

TABLE 1-continued

| Structure | mGluR5 IC$_{50}$ (nM) | Intermediate Route Reference | Analog Route Reference | [M + H]$^+$ |
|---|---|---|---|---|
| 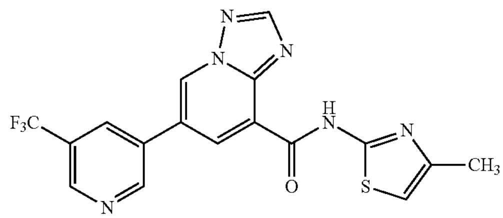 [SMILES: Cc1csc(NC(=O)c2cc(-c3cncc(C(F)(F)F)c3)cn3ncnc23)n1] | >10,000 (64% Glu Max) | I, II, IV, VI | II | 404.1 |
| 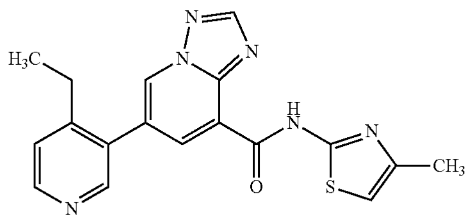 [SMILES: CCc1ccncc1-c1cc(C(=O)Nc2nc(C)cs2)c2ncnn2c1] | 984 | I, II, IV, VI | II | 365.2 |
| 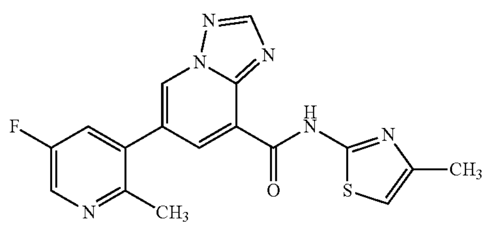 [SMILES: Cc1csc(NC(=O)c2cc(-c3cc(F)cnc3C)cn3ncnc23)n1] | 3700 | I, II, IV, VI | II | 368.1 |
| 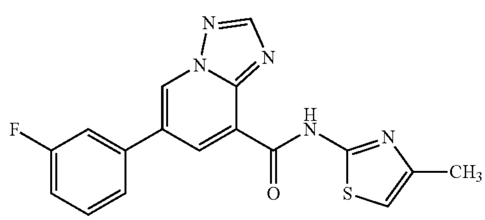 [SMILES: Cc1csc(NC(=O)c2cc(-c3cccc(F)c3)cn3ncnc23)n1] | 788 | I, II, IV, VI | II | 354.1 |
| 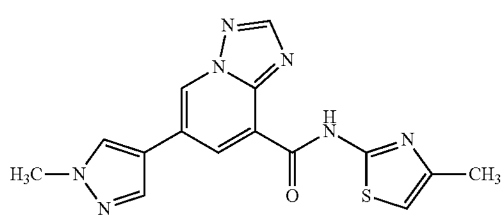 | >10,000 (30% Glu Max) | I, II, IV, VI | II | 340.2 |
| 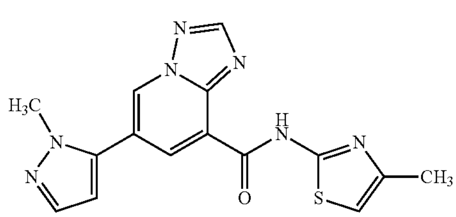 [SMILES: Cc1csc(NC(=O)c2cc(-c3ccnn3C)cn3ncnc23)n1] | 378 ± 17 | I, II, IV, VI | II | 340.2 |
| 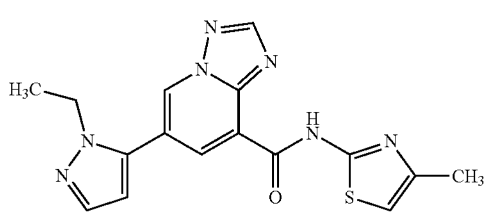 [SMILES: CCn1nccc1-c1cc(C(=O)Nc2nc(C)cs2)c2ncnn2c1] | 3920 | I, II, IV, VI | II | 354.1 |

TABLE 1-continued

| Structure | mGluR5 IC$_{50}$ (nM) | Intermediate Route Reference | Analog Route Reference | [M + H]$^+$ |
|---|---|---|---|---|
| (6-pyrimidin-5-yl-[1,2,4]triazolo[1,5-a]pyridine-8-carboxylic acid (4-methyl-thiazol-2-yl)-amide) | 758 ± 280 | I, II, IV, VI | II | 338.1 |
| (6-(5-methyl-1H-pyrazol-3-yl)-[1,2,4]triazolo[1,5-a]pyridine-8-carboxylic acid (4-methyl-thiazol-2-yl)-amide) | 60 ± 8 | I, II, IV, VI | II | 340.0 |
| (6-pyridin-4-yl-[1,2,4]triazolo[1,5-a]pyridine-8-carboxylic acid (4-methyl-thiazol-2-yl)-amide) | 8070 | I, II, IV, VI | II | 337.0 |
| (6-pyridazin-4-yl-[1,2,4]triazolo[1,5-a]pyridine-8-carboxylic acid (4-methyl-thiazol-2-yl)-amide) | >10,000 (27% Glu Max) | I, II, IV, VI | II | 338.0 |
| (6-(5-methyl-pyridazin-4-yl)-[1,2,4]triazolo[1,5-a]pyridine-8-carboxylic acid (4-methyl-thiazol-2-yl)-amide) | 2910 | I, II, IV, VI | II | 352.2 |
| (6-(1-methyl-1H-pyrazol-3-yl)-[1,2,4]triazolo[1,5-a]pyridine-8-carboxylic acid (4-methyl-thiazol-2-yl)-amide) | >10,000 (70% Glu Max) | I, II, IV, VI | II | 340.2 |

TABLE 1-continued

| Structure | mGluR5 IC$_{50}$ (nM) | Intermediate Route Reference | Analog Route Reference | [M + H]$^+$ |
|---|---|---|---|---|
| 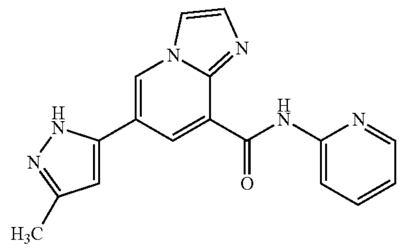 | 1140 | I, III, IV, VII | I | 319.2 |
| 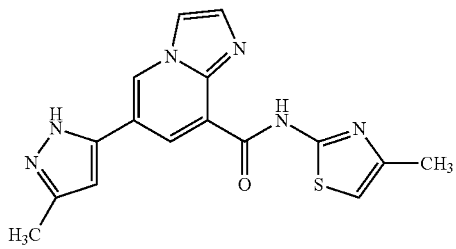 [SMILES: Cc1cc(-c2cc(C(=O)Nc3nc(C)cs3)c3ncnn3c2)[nH]n1] | 1410 | I, III, IV, VII | I | 339.2 |
| 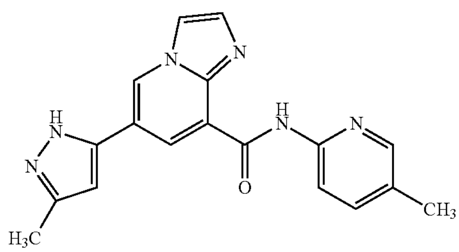 [SMILES: Cc1ccc(NC(=O)c2cc(-c3cc(C)n[nH]3)cn3ccnc23)nc1] | 5110 | I, III, IV, VII | I | 333.2 |
| 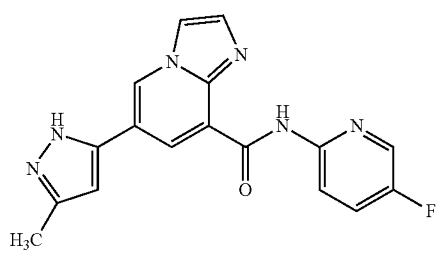 | 3930 | I, III, IV, VII | I | 337.2 |
| 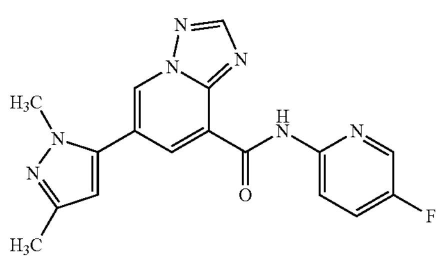 [SMILES: Cc1cc(-c2cc(C(=O)Nc3ccc(F)cn3)c3ncnn3c2)n(C)n1] | 2130 | I, II, IV VII | I | 352.2 |
| 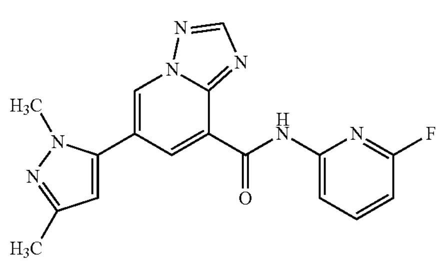 [SMILES: Cc1cc(-c2cc(C(=O)Nc3cccc(F)n3)c3ncnn3c2)n(C)n1] | 835 | I, II, IV VII | I | 352.2 |

TABLE 1-continued

| Structure | mGluR5 IC$_{50}$ (nM) | Intermediate Route Reference | Analog Route Reference | [M + H]$^+$ |
|---|---|---|---|---|
| (structure) | 1450 | V, VI | II | 338.2 |
| (structure) | >30,000 | I, II, IV VII | I | 338.2 |

11. Generation of mGluR5 Stable Cell Line

Typically, the mGluR5 activity of the disclosed compounds is determined a stable cell line transfected with rat mGluR5. The preparation of rat mGluR5 stable cell-lines is as previously described (e.g., see Romano et al. (1996) *J Biol. Chem.* 271: 28612-28616). Data generated using this cell-line in the mGluR5 assay (described below) are shown in Table 1.

mGluR5 activity of the disclosed cell-lines can also be determined using a stable cell-line transfected with human mGluR5. Briefly, human mGluR5a cDNA in pCMV6-XL6 mammalian expression plasmid was purchased from OriGene Technologies, Inc. (catalogue number SC326357) and subcloned into pcDNA3.1(−). Human embryonic kidney (HEK)293A cells were then transfected with human mGluR5a pcDNA3.1(−) using Lipofectamine® 2000 (Invitrogen) and monoclones were selected and tested for functional response using a Ca$^{2+}$ mobilization assay. Monoclones were named for the species ("H" for human) plus the location on the plate (e.g., "10H").

12. Metabotropic Glutamate Receptor Activity

Calcium Mobilization Assay

HEK 293A cells stably expressing either rat or human mGluR5 were plated in black-walled, clear-bottomed, poly-D-lysine coated 384-well plates in 20 µL of assay medium (DMEM containing 10% dialyzed FBS, 20 mM HEPES, 100 units/mL penicillin/streptomycin plus 250 ng/mL Fungizone, and 1 mM sodium pyruvate) at a density of 20,000 cells/well. The cells were grown overnight at 37° C. in the presence of 5% CO$_2$. The next day, medium was removed and the cells incubated with 20 µL of 2.3 µM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 µL of assay buffer was added, and the plate was incubated for 5 minutes at room temperature.

Ca$^{2+}$ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an EC$_{20}$ concentration of the mGluR5 receptor agonist glutamate was added to the cells, and the response of the cells was measured for 1.9 minutes; an EC$_{80}$ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Antagonism of the agonist response of the mGluR5 receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function (F/F$_0$) for each measurement of the total 360 values per well divided by each well's initial value. Data were then reduced to peak amplitudes (Max–Initial Min) using a time range that starts approximately 3 seconds prior to the glutamate EC$_{20}$/EC$_{80}$ addition and continues for approximately 90-120 seconds. This is sufficient time to capture the peak amplitude of the cellular calcium response. Individual amplitudes were expressed as % E$_{Max}$ by multiplying each amplitude by 100 and then dividing the product by the mean of the amplitudes derived from the glutamate EC$_{Max}$-treated wells. IC$_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a negative allosteric modulator (NAM) if the compound showed a concentration-dependent decrease in the glutamate $EC_{80}$ addition. For NAMs with a CRC that plateaus at a Glu Max (i.e. the amplitude of response in the presence of compound as a percentage of the maximal response to glutamate) below 10%, $IC_{50}$ values are reported. For NAMs with a CRC that plateaus above 10% Glu Max, the $IC_{50}$ values are reported, the compound is designated a "partial NAM" and the % Glu Max is reported. For NAMs that show a decrease in the $EC_{80}$ response, but do not hit a plateau, the average of the Glu Max at a single concentration (30 µM) was determined (% Glu Max), reported, and $IC_{50}$ values are reported as ">10,000 nM". Compounds without measurable activity are designated as ">30,000 nM" since the top concentration of compound tested in the assay is 30 µM.

13. Prophetic metabotropic Glutamate Receptor Activity

Radioligand Binding Assay

The following examples of the in vitro effects of the disclosed compounds are prophetic. An example of an in vitro assay method for assessing the receptor ligand binding activity of the disclosed compounds is given below. Competition binding studies can be performed with the allosteric antagonist [$^3$H]methoxyPEPy to determine if the disclosed compounds interact with the well-characterized allosteric binding site for the mGluR5 NAM MPEP.

The allosteric antagonist MPEP analog [$^3$H]methoxyPEPy is used to evaluate the ability of test compounds to interact with the MPEP site on mGluR5 (Cosford et al., *Bioorg. Med. Chem. Lett.* 2003, 13, 351). Membranes are prepared from rat mGluR5 HEK293 cells (Rodriguez et al., *Mol. Pharmacol.* 2005, 68, 1793). Compounds are diluted in assay buffer (50 mM Tris/0.9% NaCl, pH 7.4) to a 5× stock and 100 µL test compound is added to each well of a 96 deep-well assay plate. 300 µL aliquots of membranes diluted in assay buffer (40 µg/well) are added to each well. 100 µL [$^3$H]methoxyPEPy (2 nM final concentration) is added and the reaction is incubated at room temperature for 1 hour with shaking. After the incubation period, the membrane-bound ligand is separated from free ligand by filtration through glass-fiber 96 well filter plates (Unifilter-96, GF/B, PerkinElmer Life and Analytical Sciences, Boston, Mass.). The contents of each well are transferred simultaneously to the filter plate and washed 3-4 times with assay buffer using a cell harvester (Brandel Cell Harvester, Brandel Inc., Gaithersburg, Md.). 40 µL scintillation fluid is added to each well and the membrane-bound radioactivity determined by scintillation counting (TopCount, PerkinElmer Life and Analytical Sciences). Non-specific binding is estimated using 5 µM MPEP. Concentration response curves were generated using a four parameter logistical equation in GraphPad Prism (GraphPad Software, Inc., La Jolla, Calif.).

14. Prophetic metabotropic Glutamate Receptor Activity

Selectivity Assays

The following examples of the in vitro effects of the disclosed compounds are prophetic. Typical examples of in vitro assay methods for assessing the receptor selectivity of the disclosed compounds are given below.

a. Rat mGluR1 Assay

Compound activity at the group I mGluRs can be assessed in the assay described herein. HEK293 cells stably expressing rat mGluR1 are cultured and assayed as described above for mGluR5-expressing cells. For these assays, after establishment of a fluorescence baseline for about 3 seconds, the compounds of the present invention are added to the cells at 2× final concentration, and the response in cells is measured. 2.3 min later the appropriate concentration of agonist is added at 5× the final concentration and readings taken for an additional 2.6 minutes. Data are analyzed as described for mGluR5 assays.

b. Rat mGlu Receptors 2, 3, 4, 7, and 8, and Human mGluR6 Assays

Compound activity at the group II and group III mGluRs can be assessed using thallium flux through G-protein-coupled inwardly rectifying potassium (GIRK) channels, a method that has been described in detail (Niswender et al. (2008) Mol. Pharmacol. 73, 1213-1224). These cell lines are grown in growth media containing 45% DMEM, 45% F-12, 10% FBS, 20 mM HEPES, 2 mM L-glutamine, antibiotic/antimycotic, nonessential amino acids, 700 µg/mL G418, and 0.6 µg/mL puromycin at 37° C. in the presence of 5% $CO_2$. Briefly, HEK/GIRK cells expressing the mGluR subtype 2, 3, 4, 6, 7, or 8 are plated into 384 well, black-walled, clear-bottom poly-D-lysine coated plates at a density of 15,000 cells/20 µL/well in assay medium and incubated overnight at 37° C. in the presence of 5% $CO_2$. The following day, the medium from the cells and 20 µL/well of 1.7 µM concentration of the indicator dye BTC-AM (Invitrogen, Carlsbad, Calif.) in assay buffer is added. Cells are incubated for 1 hour at room temperature and the dye is replaced with 20 µL/well of assay buffer. After establishment of a fluorescence baseline for about 3 seconds, the compounds of the present invention are added to the cells at 2× final concentration, and the response in cells is measured. 2.3 min later the appropriate concentration of agonist is added and readings taken for an additional 2.6 minutes. Agonists are diluted in thallium buffer (125 mM sodium bicarbonate, 1 mM magnesium sulfate, 1.8 mM calcium sulfate, 5 mM glucose, 12 mM thallium sulfate, 10 mM HEPES) at 5× the final concentration to be assayed. Data are analyzed as described in Niswender et al. 2008.

c. Prophetic Activity of the Disclosed Compounds and Products of the Disclosed Methods of Making In one aspect, the disclosed compounds are anticipated to show at least about 1.5 fold greater selectivity for rat mGluR5 compared rat mGlu receptors R1, R2, R3, R4, R7, and R8, and Human mGluR6 based on $IC_{50}$. In a further aspect, the disclosed compounds are anticipated to show about at least 5 fold greater selectivity for rat mGluR5 compared rat mGlu receptors R1, R2, R3, R4, R7, and R8, and Human mGluR6 based on $IC_{50}$. In a still further aspect, the disclosed compounds are anticipated to show at least about 10 fold greater selectivity for rat mGluR5 compared rat mGlu receptors R1, R2, R3, R4, R7, and R8, and Human mGluR6 based on $IC_{50}$. In an even further aspect, the disclosed compounds are anticipated to show at least about 50 fold greater selectivity for rat mGluR5 compared rat mGlu receptors R1, R2, R3, R4, R7, and R8, and Human mGluR6 based on $IC_{50}$. In a still further aspect, the disclosed compounds are anticipated to show at least about 100 fold greater selectivity for rat mGluR5 compared rat mGlu receptors R1, R2, R3, R4, R7, and R8, and Human mGluR6 based on $IC_{50}$. Moreover, compounds prepared using the disclosed synthetic methods are also expected to show such effects.

15. Prophetic In Vivo Effects

The following examples of the in vivo effects of the disclosed compounds are prophetic. Typical examples of study methods for assessing the in vivo effects of the disclosed compounds are given below.

Generally clinically relevant antipsychotic agents (both typical and atypical) display efficacy in preclinical behavior challenge models. In vivo effects of the compounds described in the preceding examples are expected to be shown in various animal models of disorders associated with metabotropic glutamate receptor dysfunction known to a person skilled in the art, such as models of stress and anxiety (e.g. the marble burying assay as described herein; or alternatively, elevated plus maze, shock probe burying, social interaction, passive avoidance, open field behavior, elevated plus maze, Y-maze, Hole-Board and stress-induced hyperthermia models in rodent; for example, see Lindsley et al., *ACS Chem. Neurosci.* 2011, 2, 47; Nicolas et al., *Eur. J. Pharmacol.* 2006, 547, 106; Pietraszek et al., *Eur. J. Pharmacol.* 2005, 514, 25; Busse et al., *Neuropsychopharmacology* 2004, 29, 1971; Klodzinska et al., *Neuropharmacology* 2004, 47, 342; Spooren et al., *Pharmacol. Exp. Ther.* 2000, 295, 1267), models of gastroesophageal disease ("GERD"; e.g. transient lower esophageal sphincter relaxations and measurement of gastric pressure; for example, see Jensen et al., *Eur. J. Pharmacol.* 2005, 519, 154; Frisby et al., *Gastroenterology* 2005, 129, 995), models of Parkinson's disease levodopa induced dyskinesia ("PD-LID"; e.g. dyskinetic response, locomotor response, and Parkinsonian score in monkeys; for example, see Morin et al., *Neuropharmacology* 2010, 58, 981), models of autism spectrum disorders (e.g. models of social behavior, self-grooming and vertical jumping in mice; for example, see Silverman et al., *Sci. Transl. Med.* 2012, 4, 131ra51; Silverman et al., *Neuropsychopharmacology* 2010, 35, 976), models of depression (e.g. tail suspension and forced swim; for example, see Hughes et al., *Neuropharmacology* 2013, 66, 202), models of addictive behavior (e.g. reinstatement of ethanol-seeking behavior by drug-associated cues in rat or the alcohol deprivation effect in long-term ethanol-consuming rat; for example, see Amato et al., *ACS Chem. Neurosci.* 2013, 4, 1217; Martin-Fardon et al., *J. Pharmacol. Exp. Ther.* 2009, 329, 1084; Kumaresan et al., *Behav. Brain Res.* 2009, 202, 238; Tronci et al., *Psychopharmacology* 2010, 211, 33; Gass et al., *Neuropsychopharmacology* 2009, 34, 820; Kotlinska, J.; Bochenski, M. *Eur. J. Pharmacol.* 2007, 558, 113; Adams et al., *Br. J. Pharmacol.* 2010, 159, 534; Besheer et al., *J. Neurosci.* 2009, 29, 9582) and reversal or amelioration of Fragile X phenotypes in FMR1 knockout mice or FMR1 transgenic mice (e.g. susceptibility to audiogenic seizures, learning deficits, and growth abnormalities of dendritic spine; for example, see Michalon et al., *Neuron* 2012, 74, 49; de Vrij et al., *Neurobiol. Dis.* 2008, 31, 127; Yan et al., *Neuropharmacology* 2005, 49, 1053). These models are typically conducted in rodent, such as rat or mouse, but may be conducted in other animal species as is convenient to the study goals.

Compounds, products, and compositions disclosed herein are expected to show in vivo effects in various animal models of disorders associated with metabotropic glutamate receptor dysfunction known to the skilled person, such as those described herein above, including models of stress and anxiety (e.g. the marble burying assay as described herein; or alternatively, elevated plus maze, shock probe burying, social interaction, passive avoidance, open field behavior, elevated plus maze, Y-maze, Hole-Board and stress-induced hyperthermia models in rodent), models of gastroesophageal disease ("GERD"; e.g. transient lower esophageal sphincter relaxations and measurement of gastric pressure), models of Parkinson's disease levodopa induced dyskinesia ("PD-LID"; e.g. dyskinetic response, locomotor response, and Parkinsonian score in monkeys), models of autism spectrum disorders (e.g. models of social behavior, self-grooming and vertical jumping in mice), models of depression (e.g. tail suspension and forced swim), models of addictive behavior (e.g. reinstatement of ethanol-seeking behavior by drug-associated cues in rat or the alcohol deprivation effect in long-term ethanol-consuming rat) and reversal or amelioration of Fragile X phenotypes in FMR1 knockout mice or FMR1 transgenic mice (e.g. susceptibility to audiogenic seizures, learning deficits, and growth abnormalities of dendritic spine). These models are typically conducted in rodent, such as rat or mouse, but may be conducted in other animal species as is convenient to the study goals.

For example, compounds having a structure represented by a formula:

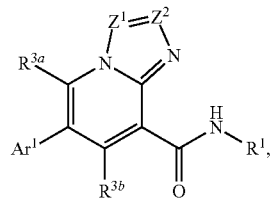

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C═O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein R44 and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein $R^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C═O)$R^{63}$; wherein each occurrence of $R^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl, and —$NR^{64a}R^{64b}$; wherein each occurrence of each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{3a}$ and $R^{3b}$ is independently selected from hydrogen and fluoro; wherein $Ar^1$ is selected from aryl and heteroaryl, and wherein $Ar^1$ is substituted with 0, 1, 2, or 3 groups independently selected from halogen, —CN, C1-C3 alkyl, C1-C3 monohaloalkyl, C1-C3 polyhaloalkyl, —$OR^{30}$, —$NR^{31a}R^{31b}$, —$SO_2R^{32}$, —$(C=O)R^{33}$, and cyclopropyl; wherein each occurrence of $R^{30}$, when present, is independently selected from hydrogen, C1-C3 alkyl, C1-C3 monohaloalkyl, C1-C3 polyhaloalkyl, and cyclopropyl; wherein each occurrence of each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with the nitrogen atom to which they are attached, comprise a 3- to 6-membered heterocycle; wherein each occurrence of $R^{32}$, when present, is independently selected from C1-C3 alkyl, C1-C3 monohaloalkyl, C1-C3 polyhaloalkyl, cyclopropyl, and —$NR^{34a}R^{34b}$; wherein each occurrence of each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with the nitrogen atom to which they are attached, comprise a 3- to 6-membered heterocycle; wherein each occurrence of $R^{33}$, when present, is independently from C1-C3 alkyl, C1-C3 monohaloalkyl, C1-C3 polyhaloalkyl, cyclopropyl, and —$NR^{35a}R^{35b}$; wherein each occurrence of each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; or a pharmaceutically acceptable salt thereof.

16. Prophetic Pharmaceutical Composition Examples

"Active ingredient" as used throughout these examples relates to one or more compounds having a structure represented by a formula:

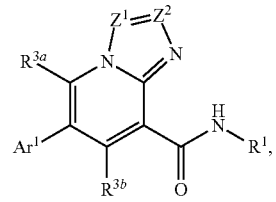

wherein $Z^1$ is selected from N and $CR^{6a}$; wherein $Z^2$ is selected from N and $CR^{6b}$; and wherein $Z^1$ and $Z^2$ are not simultaneously N; wherein each of $R^{6a}$ and $R^{6b}$, when present, is independently selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with the nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with the nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with the nitrogen atom to which they are attached, comprise a 3- to 6-membered heterocycle; wherein $R^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$; wherein each occurrence of $R^{60}$, when present, is independently selected from hydrogen, C1-C3 alkyl, C1-C3 monohaloalkyl, C1-C3 polyhaloalkyl, and cyclopropyl; wherein each occurrence of each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with the nitrogen atom to which they are attached, comprise a 3- to 6-membered heterocycle; wherein each occurrence of $R^{62}$, when present, is independently selected from C1-C3 alkyl, C1-C3 monohaloalkyl, C1-C3 polyhaloalkyl, cyclopropyl and —$NR^{64a}R^{64b}$; wherein each occurrence of each of $R^{64a}R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with the nitrogen atom to which they are attached, comprise a 3- to 6-membered heterocycle; wherein each occurrence of $R^{63}$, when present, is independently from C1-C3 alkyl, C1-C3 monohaloalkyl, C1-C3 polyhaloalkyl, cyclopropyl, and —$NR^{65a}R^{65b}$; wherein each occurrence of each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{3a}$ and $R^{3b}$ is independently selected from hydrogen and fluoro; wherein $Ar^1$ is selected from aryl and heteroaryl, and wherein $Ar^1$ is substituted with 0, 1, 2, or 3 groups independently selected from halogen, —CN, C1-C3 alkyl, C1-C3 monohaloalkyl, C1-C3 polyhaloalkyl, —$OR^{30}$, —$NR^{31a}R^{31b}$, —$SO_2R^{32}$, —(C=O)$R^{33}$, and cyclopropyl; wherein each occurrence of $R^{30}$, when present, is independently selected from hydrogen, C1-C3 alkyl, C1-C3 monohaloalkyl, C1-C3 polyhaloalkyl, and cyclopropyl; wherein each occurrence of each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with the nitrogen atom to which they are attached, comprise a 3- to 6-membered heterocycle; wherein each occurrence of $R^{32}$, when present, is independently selected from C1-C3 alkyl, C1-C3 monohaloalkyl, C1-C3 polyhaloalkyl, cyclopropyl, and —$NR^{34a}R^{34b}$; wherein each occurrence of each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with the nitrogen atom to which they are attached, comprise a 3- to 6-membered heterocycle; wherein each occurrence of $R^{33}$, when present, is independently from C1-C3 alkyl, C1-C3 monohaloalkyl, C1-C3 polyhaloalkyl, cyclopropyl, and —$NR^{35a}R^{35b}$; wherein each occurrence of each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; or a pharmaceutically acceptable salt thereof.

The following examples of the formulation of the disclosed compounds of the present invention in tablets, suspension, injectables and ointments are prophetic. Typical examples of recipes for the formulation of the invention are as given below.

a. Tablets

A tablet can be prepared as follows:

| Component | Amount |
| --- | --- |
| Active ingredient | 5 to 50 mg |
| Di-calcium phosphate | 20 mg |
| Lactose | 30 mg |
| Talcum | 10 mg |
| Magnesium stearate | 5 |
| Potato starch | add to make total weight 200 mg |

In this Example, active ingredient can be replaced with the same amount of any of the compounds according to the present invention, in particular by the same amount of any of the exemplified compounds.

b. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and 1 mL of water.

c. Injectable

A parenteral composition is prepared by stirring 1.5% by weight of active ingredient of the invention in 10% by volume propylene glycol in water.

d. Ointment

An ointment can be prepared as follows:

| Component | Amount |
| --- | --- |
| Active ingredient | 5 to 1000 mg |
| Stearyl alcohol | 3 g |
| Lanoline | 5 g |
| White petroleum | 15 g |
| Water | add to make total weight 100 g |

In this Example, active ingredient can be replaced with the same amount of any of the compounds according to the present invention, in particular by the same amount of any of the exemplified compounds.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a formula:

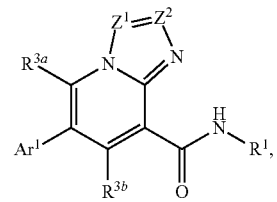

wherein $Z^1$ is selected from N and $CR^{6a}$; wherein $Z^2$ is selected from N and $CR^{6b}$; and wherein $Z^1$ and $Z^2$ are not simultaneously N;
wherein each of $R^{6a}$ and $R^{6b}$ is hydrogen;
wherein $R^1$ is heteroaryl substituted with 0, 1, 2, or 3 groups independently selected from alkyl, alkoxy, and halogen;
wherein each of $R^{3a}$ and $R^{3b}$ is independently selected from hydrogen and fluoro;
wherein $Ar^1$ is selected from aryl and heteroaryl, and wherein $Ar^1$ is substituted with 0, 1, 2, or 3 groups independently selected from alkyl, alkoxy, halogen, trifluoroalkyl, and cycloalkyl;
or a pharmaceutically acceptable salt thereof.

2. The compound of claim 1, wherein $R^1$ is pyridinyl monosubstituted with a group selected from alkyl, alkoxy, and halogen.

3. The compound of claim 1, wherein $R^1$ is thiazolyl monosubstituted with a group selected from alkyl, alkoxy, and halogen.

4. The compound of claim 1, wherein each of $R^{3a}$ and $R^{3b}$ is hydrogen.

5. The compound of claim 1, wherein $Ar^1$ is phenyl substituted with 0, 1, 2, or 3 groups independently selected from alkyl, alkoxy, halogen, trifluoroalkyl, and cycloalkyl.

6. The compound of claim 1, wherein $Ar^1$ is pyridinyl substituted with 0, 1, 2, or 3 groups independently selected from alkyl, alkoxy, halogen, trifluoroalkyl, and cycloalkyl.

7. The compound of claim 1, wherein $Ar^1$ is pyrazolyl substituted with 0, 1, 2, or 3 groups independently selected from alkyl, alkoxy, halogen, trifluoroalkyl, and cycloalkyl.

8. The compound of claim 1, wherein $Z^1$ is N and $Z^2$ is $CR^{6b}$.

9. The compound of claim 1, wherein $Z^1$ is $CR^{6a}$ and $Z^2$ is $CR^{6b}$.

10. The compound of claim 1, wherein the compound has a formula:

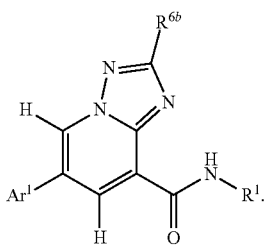

11. The compound of claim 1, wherein the compound has a formula:

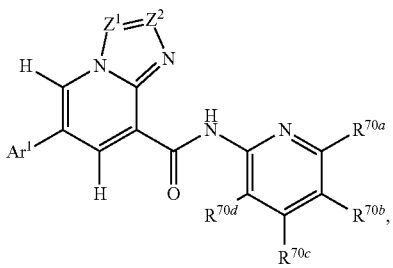

wherein each of $R^{70a}$, $R^{70b}$, $R^{70c}$, and $R^{70d}$ is independently selected from hydrogen, alkyl, alkoxy, and halogen, provided that at least one of $R^{70a}$, $R^{70b}$, $R^{70c}$, and $R^{70d}$ is hydrogen.

12. The compound of claim 1, wherein the compound has a formula:

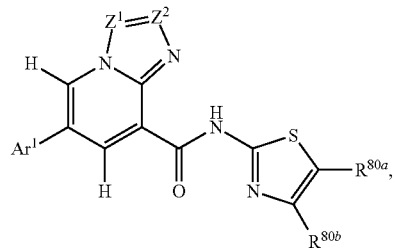

wherein each of $R^{80a}$ and $R^{80b}$ is independently selected from hydrogen, alkyl, alkoxy, halogen, trifluoroalkyl, and cycloalkyl.

13. A pharmaceutical composition comprising an effective amount of at least one compound of claim 1, or a pharmaceutically acceptable salt thereof, and a pharmaceutically acceptable carrier.

14. The compound of claim 1, having a formula:

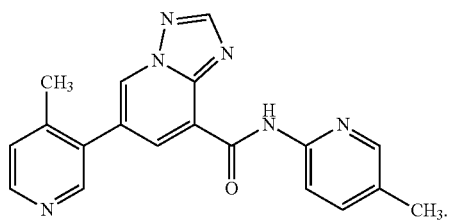 [SMILES: Cc1ccc(NC(=O)c2cc(-c3cnccc3C)cn3ncnc23)nc1]

* * * * *

UNITED STATES PATENT AND TRADEMARK OFFICE
CERTIFICATE OF CORRECTION

PATENT NO. : 9,550,778 B2
APPLICATION NO. : 14/873869
DATED : January 24, 2017
INVENTOR(S) : Kyle A. Emmitte et al.

It is certified that error appears in the above-identified patent and that said Letters Patent is hereby corrected as shown below:

In the Specification

In Column 1, Lines 16-26, please replace:
"This invention was made with government support under Grant no. 2R01-MH062646-12 awarded by the National Institute of Mental Health (NIMH), under Grant no. 5R01-MH073676-04 awarded by the National Institute of Mental Health (NIMH), under Grant no. 5R01-NS031373-15 awarded by the National Institute of Neurological Disorders and Stroke (NINDS), under Grant no. 1R0-DA023947-01 awarded by the National Institute of Drug Abuse (NIDA), and under Grant no. 1U19-MH097056-01 awarded by the National Institute of Mental Health (NIMH). The United States government has certain rights in the Invention,"

With:
--This invention was made with government support under grant numbers MH062646, MH073676, NS031373, DA023947, and MH097056 awarded by the National Institutes of Health. The government has certain rights in the invention.--

Signed and Sealed this
Twenty-ninth Day of October, 2019

Andrei Iancu
*Director of the United States Patent and Trademark Office*